United States Patent
Jeanmart et al.

(10) Patent No.: US 8,946,453 B2
(45) Date of Patent: Feb. 3, 2015

(54) CHEMICAL COMPOUNDS

(75) Inventors: Stephane Andre Marie Jeanmart, Stein (CH); Long Lu, Shanghai (CN); Yaming Wu, Shanghai (CN); Lisheng Mao, Shanghai (CN); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/978,493

(22) PCT Filed: Dec. 30, 2011

(86) PCT No.: PCT/CN2011/085024
§ 371 (c)(1),
(2), (4) Date: Sep. 11, 2013

(87) PCT Pub. No.: WO2012/092827
PCT Pub. Date: Jul. 12, 2012

(65) Prior Publication Data
US 2014/0011845 A1    Jan. 9, 2014

(30) Foreign Application Priority Data

Jan. 5, 2011 (CN) .................. PCT/CN2011/000023
Apr. 7, 2011 (CN) .................. PCT/CN2011/000603

(51) Int. Cl.
| | |
|---|---|
| C07D 307/00 | (2006.01) |
| C07D 333/00 | (2006.01) |
| C07D 207/00 | (2006.01) |
| C07D 401/06 | (2006.01) |
| A01N 43/16 | (2006.01) |
| A01N 47/06 | (2006.01) |
| A01N 47/40 | (2006.01) |
| C07D 211/26 | (2006.01) |
| C07D 211/94 | (2006.01) |
| C07D 309/06 | (2006.01) |
| C07D 335/02 | (2006.01) |
| C07D 405/06 | (2006.01) |
| C07D 407/06 | (2006.01) |
| C07D 409/06 | (2006.01) |
| A01N 43/36 | (2006.01) |
| A01N 43/40 | (2006.01) |
| C07D 211/34 | (2006.01) |
| C07D 403/06 | (2006.01) |

(52) U.S. Cl.
CPC .............. *C07D 401/06* (2013.01); *A01N 43/16* (2013.01); *A01N 47/06* (2013.01); *A01N 47/40* (2013.01); *C07D 211/26* (2013.01); *C07D 211/94* (2013.01); *C07D 309/06* (2013.01); *C07D 335/02* (2013.01); *C07D 405/06* (2013.01); *C07D 407/06* (2013.01); *C07D 409/06* (2013.01); *A01N 43/36* (2013.01); *A01N 43/40* (2013.01); *C07D 211/34* (2013.01); *C07D 403/06* (2013.01)
USPC .............................. 549/313; 549/9; 548/544

(58) Field of Classification Search
USPC ....................... 549/313, 6; 548/544
See application file for complete search history.

(56) References Cited

FOREIGN PATENT DOCUMENTS

WO    98/25928    6/1998
WO    2007/121868    11/2007

OTHER PUBLICATIONS

Dorwald F. A. Side Reactions in Organic Synthesis, 2005, Wiley: VCH, Weinheim p. IX of Preface p. 1-15.*
International Search Report, International Application No. PCT/CN2011/085024, completion date: Feb. 19, 2012.

* cited by examiner

Primary Examiner — Nizal Chandrakumar
(74) Attorney, Agent, or Firm — R. Kody Jones

(57) ABSTRACT

Disclosed are cyclic dione derivatives represented by formula (I), wherein the substituents are as defined in the description. The preparation method, intermediate and use thereof are also provided.

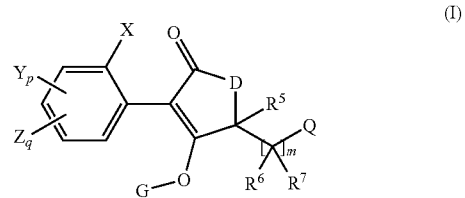

(I)

19 Claims, No Drawings

CHEMICAL COMPOUNDS

This application is a 371 of International Application No. PCT/CN2011/085024 filed Dec. 30, 2011, which claims priority to PCT/CN2011/000023, filed Jan. 5, 2011 and PCT/CN2011/000603, filed Apr. 7, 2011, the contents of which are incorporated herein by reference.

The present invention relates to new substituted cyclic dione derivatives, to processes for preparing them, to pesticidal, in particular insecticidal, acaricidal, molluscicidal and nematicidal compositions comprising them and to methods of using them to combat and control pests such as insect, acarine, mollusc and nematode pests.

It has now surprisingly been found that certain new substituted cyclic dione derivatives have good insecticidal properties.

The present invention therefore provides compounds of the formula I

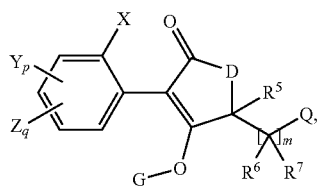

(I)

wherein

X, Y and Z independently of each other are $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl, halogen, phenyl or phenyl substituted by $C_{1-4}$alkyl, $C_{1-4}$haloalkyl, halogen or cyano;

p and q, independently of each other, are 0, 1, 2 or 3, where p+q is 0, 1, 2 or 3;

G is hydrogen, a metal, ammonium, sulfonium or a latentiating group;

D is O, S, $NR^1$ or $NOR^1$, wherein $R^1$ is hydrogen, $C_{1-6}$alkyl, $C_{1-6}$haloalkyl, $C_{3-6}$cycloalkyl or $C_{3-6}$cycloalkyl, wherein a methylene group is replaced by O, S or $NR^{00}$, where $R^{00}$ is $C_{1-6}$alkyl or $C_{1-6}$alkoxy, or $R^1$ is $C_{3-6}$cycloalkyl($C_{1-4}$)alkyl or $C_{3-6}$cycloalkyl($C_{1-4}$)alkyl, where in the cycloalkyl moiety a methylene group is replaced by O, S or $NR^{01}$, where $R^{01}$ is $C_{1-6}$alkyl or $C_{1-6}$alkoxy, or $R^1$ is $C_{2-6}$alkenyl, $C_{2-6}$haloalkenyl, $C_{3-6}$alkynyl, $C_{1-6}$cyanoalkyl, benzyl, furanyl-($C_{1-4}$)alkyl, $C_{1-4}$alkoxy($C_{1-4}$)alkyl, $C_{1-4}$alkoxy($C_{1-4}$)alkoxy($C_{1-4}$)alkyl, $C_{1-4}$alkylthio($C_{1-4}$)alkyl, $C_{1-4}$alkylsulfinyl($C_{1-4}$)alkyl or $C_{1-4}$alkylsulfonyl($C_{1-4}$)alkyl;

$R^5$, $R^6$ and $R^7$, independently of each other, are hydrogen, halogen, $C_1$-$C_6$alkyl, $C_1$-$C_6$haloalkyl, $C_1$-$C_6$alkoxy, $C_1$-$C_6$haloalkoxy, $C_{1-4}$alkoxy($C_{1-4}$)alkyl, $C_{3-6}$cycloalkyl or $C_{3-6}$cycloalkyl, wherein a ring or chain methylene group is replaced by O or S, or $C_{3-6}$cycloalkyl($C_{1-4}$)alkyl or $C_{3-6}$cycloalkyl($C_{1-4}$)alkyl, wherein a ring or chain methylene group is replaced by O or S, or $R^6$ and $R^7$ together with the carbon atoms to which they are attached form an optionally substituted 3- to 8-membered ring, optionally containing O, S or $NR^{02}$, where $R^{02}$ is $C_{1-6}$alkyl or $C_{1-6}$alkoxy, or $R^5$ and $R^6$ together form a bond;

Q is a saturated or mono-unsaturated $C_{3-8}$heterocyclyl containing at least one heteroatom selected from O, N and S, which heterocyclyl is unsubstituted or substituted by a residue of formula $=O$, $=N$—$R^{03}$, $C_{1-4}$alkyl, $C_{1-4}$haloalkyl, $C_{1-4}$alkoxy$C_{1-2}$alkyl, $C_{3-6}$cycloalkyl, $C_{1-4}$alkoxy, phenyl or phenyl substituted by $C_{1-4}$alkyl, $C_{1-3}$haloalkyl, $C_{1-3}$alkoxy, $C_{1-3}$haloalkoxy, cyano, nitro, halogen, $C_{1-3}$alkylthio, $C_{1-3}$alkylsulfinyl or $C_{1-3}$alkylsulfonyl, where $R^{03}$ is $C_{1-6}$alkyl, $C_{1-6}$haloalkyl, $C_{3-7}$cycloalkyl, $C_{1-6}$alkoxy, $C_{1-6}$haloalkoxy, $C_{1-6}$alkylsulfinyl, $C_{1-6}$alkylsulfonyl, $C_{1-6}$alkylcarbonyl, $C_{1-6}$haloalkylcarbonyl, $C_{1-6}$alkoxycarbonyl, $C_{1-6}$alkylaminocarbonyl, $C_{2-8}$dialkylaminocarbonyl, cyano, $C_{1-6}$haloalkylsulfinyl or $C_{1-6}$haloalkylsulfonyl; and m is 0, 1, 2 or 3, where, when m is 0, Q is directly attached to the —C(D)$R^5$— moiety through a bond, and where, when m is 2 or 3, each group —C($R^6R^7$)— can have a different meaning;

or an agrochemically acceptable salt or an N-oxide thereof, and where the compounds of 2H-Pyrrol-2-one, 3-(2-bromo-6-ethyl-4-methylphenyl)-1,5-dihydro-4-hydroxy-5-methyl-5-(tetrahydro-3-furanyl)- and 2H-Pyrrol-2-one, 3-(4-bromo-2-ethyl-6-methylphenyl)-1,5-dihydro-4-hydroxy-5-methyl-5-(tetrahydro-3-furanyl)- are excluded.

In the compounds of the formula I, each alkyl moiety either alone or as part of a larger group is a straight or branched chain and is, for example, methyl, ethyl, n-propyl, n-butyl, iso-propyl, sec-butyl, iso-butyl, tert-butyl, n-pentyl, iso-pentyl and n-hexyl.

Alkoxy groups have a preferred chain length of from 1 to 6, in particular 1 to 4 carbon atoms. Alkoxy is, for example, methoxy, ethoxy, propoxy, i-propoxy, n-butoxy, isobutoxy, sec-butoxy or tert-butoxy. Such groups can be part of a larger group such as alkoxyalkyl and alkoxyalkoxyalkyl. Alkoxyalkyl is, for example, methoxymethyl, methoxyethyl, ethoxymethyl, ethoxyethyl, n-propoxymethyl, n-propoxyethyl or isopropoxymethyl. In alkylthioalkyl groups, oxygen is replaced by sulphur.

Halogen is generally fluorine, chlorine, bromine or iodine.

Haloalkyl groups preferably have a chain length of from 1 to 6, in particular 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

The preferred alkenyl and alkynyl radicals having 2 to 6 carbon atoms can be straight or branched and can contain more than one double or triple bond. Examples are vinyl, (E)- or (Z)-propenyl, 2-methyl-propenyl, allyl, 3-methyl-but-2-enyl, ethynyl, prop-1-ynyl, propargyl, butenyl, butynyl, pentenyl and pentynyl.

The cycloalkyl and cycloalkylalkyl groups preferably have from 3 to 6 ring carbon atoms, for example cyclopropyl, cyclobutyl, cyclopentyl and cyclohexyl. In these rings, a methylene group can be replaced by a heteroatom such as oxygen, sulphur, or nitrogen in form of a group $NR_0$, where $R_0$ is $C_{1-6}$alkyl or $C_{1-6}$alkoxy, which leads, for example, to oxetan-3-yl, tetrahydrofuran-2-yl, tetrahydropyran-2-yl, tetrahydrofuran-3-yl, tetrahydropyran-3-yl, tetrahydropyran-4-yl, tetrahydro-thiofuranyl, tetrahydro-thiopyranyl, N—($C_{1-4}$)alkyl-piperidinyl or N—($C_{1-4}$)alkoxy-piperidinyl rings. Cycloalkylalkyl and furanylalkyl groups preferably have a chain length of 1 to 4 carbon atoms. Cycloalkylalkyl is, for example, cyclopropylmethyl, cyclobutylmethyl, cyclopentylmethyl, or cyclohexylmethyl. Furanylalkyl is, for example, furan-2-ylmethyl or furan-3-ylmethyl. The same apply when a methylene group in the cycloalkyl moiety is replaced by O, S or $NR_0$, where $R_0$ is $C_{1-6}$alkyl or $C_{1-6}$alkoxy, to form groups such as, for example, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl or tetrahydro-thiopyran-4-ylmethyl.

Phenyl, also as part of a substituent such as benzyl, may be substituted, preferably by alkyl, haloalkyl, halogen or cyano groups. In this case, the substituents can be in ortho, meta and/or para position. The preferred substituent positions are the ortho and para positions, especially the ortho position to the ring attachment point.

The term "heterocyclyl" preferably refers to a non-aromatic, preferably monocyclic or bicyclic ring systems containing up to 8 atoms including at least one (preferably one or two) heteroatoms selected from O, S and N. Examples of such rings include 1,3-dithiane, 1,3-dioxane, 1,4-dioxane, morpholine, thiomorpholine, piperazine, tetrahydropyran, piperidine, thiane, 1,3-dioxolane, tetrahydrofuran, tetrahydrothiophene, pyrrolidine, imidazoline, azetidine, oxetane, thietane, aziridine, epoxide and thiirane.

Preferred examples of heterocyclic radicals include 1,3-dioxane, morpholine, thiomorpholine, tetrahydropyran, 1,3-dioxolane, tetrahydrofuran and tetrahydrothiophene.

For substituted heterocyclyl groups such as the rings formed by $R^6$ and $R^7$, it is preferred that one or more substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $C_1$-$C_6$alkyl groups. When heterocyclic rings are formed by joining two groups on an N atom, the resulting rings are suitably pyrrolidine, piperidine, thiomorpholine and morpholine each of which may be substituted by one or two independently selected $C_1$-$C_6$alkyl groups.

The term "latentiating group" as used for the moiety G are well known to the person skilled in the art of making compounds suitable for use in plant protection products such as insecticidal, acaricidal, molluscicidal and nematocidal compounds. Such latentiating groups G are selected to allow its removal by one or a combination of biochemical, chemical or physical processes to afford compounds of formula I where G is hydrogen before, during or following application to the treated pests, locus of the pests or plants. Examples of these processes include enzymatic cleavage, chemical hydrolysis and photoysis. Compounds bearing such groups G may offer certain advantages, such as improved penetration of the cuticula of the plants treated, increased tolerance of crops, improved compatibility or stability in formulated mixtures containing other insecticides, herbicide safeners, plant growth regulators, herbicides or fungicides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^e)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro, heteroaryl or heteroaryl substituted by $C_1$-$C_3$ alkyl, $C_{1-3}$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-

$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is also preferred that G is hydrogen, an alkali metal or alkaline earth metal, or an ammonium or sulfonium group, where hydrogen is especially preferred.

The excluded compounds 2H-Pyrrol-2-one, 3-(2-bromo-6-ethyl-4-methylphenyl)-1,5-dihydro-4-hydroxy-5-methyl-5-(tetrahydro-3-furanyl)- and 2H-Pyrrol-2-one, 3-(4-bromo-2-ethyl-6-methylphenyl)-1,5-dihydro-4-hydroxy-5-methyl-5-(tetrahydro-3-furanyl)- have been cited as compounds no. I-a-15 and I-a-16 on page 98 of WO07/121,868.

Depending on the nature of the substituents, compounds of formula I may exist in different isomeric forms. When G is hydrogen, for example, compounds of formula I may exist in different tautomeric forms:

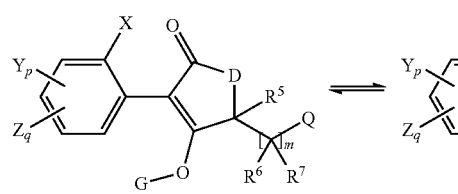 ⇌ 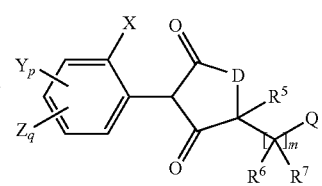 ⇌ 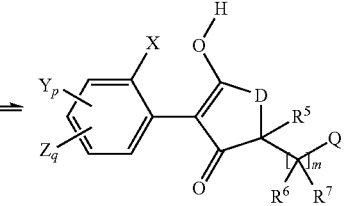

This invention covers all such isomers and tautomers and mixtures thereof in all proportions. Also, when substituents contain double bonds, cis- and trans-isomers can exist. These isomers, too, are within the scope of the claimed compounds of the formula I.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula $[N(R_{a1}R_{b1}R_{c1}R_{d1})]OH$, wherein $R_{a1}$, $R_{b1}$, $R_{c1}$ and $R_{d1}$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_{e1}R_{f1}R_{g1}]OH$, wherein $R_{e1}$, $R_{f1}$ and $R_{g1}$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C═C—C═O unit.

The compounds of formula I according to the invention also include hydrates which may be formed during the salt formation.

The preferred values of $R^5$, $R^6$, $R^7$, m, Q, D, X, Y, Z, p and q in the compounds of formula I in any combination thereof are set out below, and can be combined with any values of G, in particular with any preferred values of G, as defined above.

Preferably, D is O or S, and even more preferably, D is O.

Preferably, D is $NR^1$ or $NOR^1$, wherein $R^1$ is hydrogen, $C_{1-6}$alkyl, $C_{1-6}$haloalkyl, $C_{3-6}$cycloalkyl or $C_{3-6}$cycloalkyl, wherein a methylene group is replaced by O, S or $NR^{00}$, where $R^{00}$ is $C_{1-6}$alkyl or $C_{1-6}$alkoxy, or $R^1$ is $C_{3-6}$cycloalkyl $(C_{1-4})$alkyl or $C_{3-6}$cycloalkyl$(C_{1-4})$alkyl, where in the cycloalkyl moiety a methylene group is replaced by O, S or $NR^{01}$, where $R^{01}$ is $C_{1-6}$alkyl or $C_{1-6}$alkoxy, or $R^1$ is $C_{2-6}$alkenyl, $C_{2-6}$haloalkenyl, $C_{3-6}$alkynyl, $C_{1-6}$cyanoalkyl, benzyl, furanyl-$(C_{1-4})$alkyl, $C_{1-4}$alkoxy$(C_{1-4})$alkyl, $C_{1-4}$alkoxy$(C_{1-4})$alkoxy$(C_{1-4})$alkyl, $C_{1-4}$alkylthio$(C_{1-4})$alkyl, $C_{1-4}$alkylsulfinyl$(C_{1-4})$alkyl or $C_{1-4}$alkylsulfonyl$(C_{1-4})$alkyl, in particular hydrogen, methyl, ethyl, isopropyl, trifluoromethyl, 2,2,2-trifluoroethyl, 2,2-difluoroethyl, 2-fluoroethyl, cyclopropyl, cyclobutyl, cyclopentyl, cyclohexyl, cyclopropylmethyl, cyclobutyl-methyl, cyclopentylmethyl, cyclohexylmethyl, allyl, propargyl, benzyl, methoxymethyl, ethoxymethyl, methoxyethyl, methoxypropyl, methoxyethoxymethyl, methoxymethoxyethyl, oxetan-3-yl, tetrahydrofuran-2-yl, tetrahydropyran-2-yl, tetrahydrofuran-3-yl, tetrahydropyran-4-yl, tetrahydrothiopyran-4-yl, 1-methoxy-piperidin-4-yl, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, methylthioethyl, 2-methanesulfinyl-ethyl, 2-methanesulfonyl-ethyl, furan-2-ylmethyl, furan-3-ylmethyl or tetrahydro-thiopyran-4-ylmethyl.

Preferably, X, Y and Z denote $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl or halogen, in particular methyl, ethyl, isopropyl, cyclopropyl, trifluoromethyl, methoxy, vinyl, ethynyl, fluoro, bromo, iodo or chloro.

Preferably, p+q is 1-3, in particular, p+q is 1-2.

Alternatively, Y and Z, independently of each other, denote $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl, halogen, phenyl or phenyl substituted by $C_{1-4}$alkyl, $C_{1-4}$haloalkyl or halogen, in particular, Y and Z, independently of each other, denote methyl, ethyl, isopropyl, cyclopropyl, trifluoromethyl, methoxy, vinyl, ethynyl, fluoro, chloro, bromo, iodo, phenyl or phenyl substituted with methyl, trifluoromethyl or halogen (in particular fluorophenyl or chlorophenyl and especially 4-chlorophenyl or 4-fluorophenyl).

In another preferred group of the compounds of the formula (I), $R^5$ is hydrogen, halogen, $C_1$-$C_6$alkyl, $C_1$-$C_6$haloalkyl, $C_1$-$C_6$alkoxy, $C_1$-$C_6$haloalkoxy or $C_{1-4}$alkoxy$(C_{1-4})$alkyl, and, more preferably, $R^5$ is hydrogen or methyl.

Preferably, in the compounds of the formula (I) for use in the invention, $R^6$ and $R^7$, independently of each other, are hydrogen, halogen, $C_1$-$C_6$alkyl, $C_1$-$C_6$haloalkyl, $C_1$-$C_6$alkoxy, $C_1$-$C_6$haloalkoxy or $C_{1-4}$alkoxy$(C_{1-4})$alkyl, and, more preferably, $R^6$ and $R^7$ independently of each other, are hydrogen or methyl.

Preferred saturated or mono-unsaturated rings Q are those of the formula

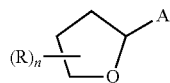 $Q_1$

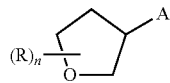 $Q_2$

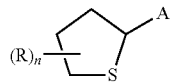 $Q_3$

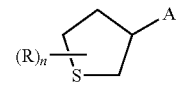 $Q_4$

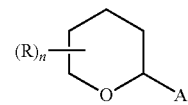 $Q_5$

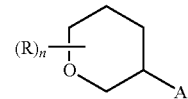 $Q_6$

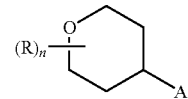 $Q_7$

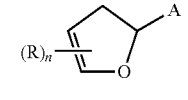 $Q_8$

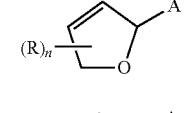 $Q_9$

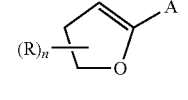 $Q_{10}$

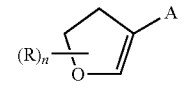 $Q_{11}$

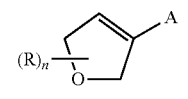 $Q_{12}$

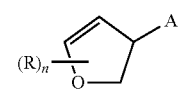 $Q_{13}$

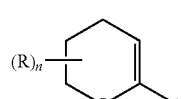 $Q_{14}$

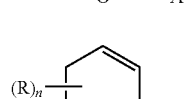 $Q_{15}$

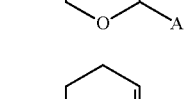 $Q_{16}$

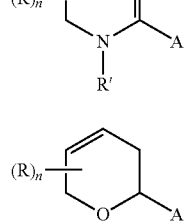 $Q_{17}$

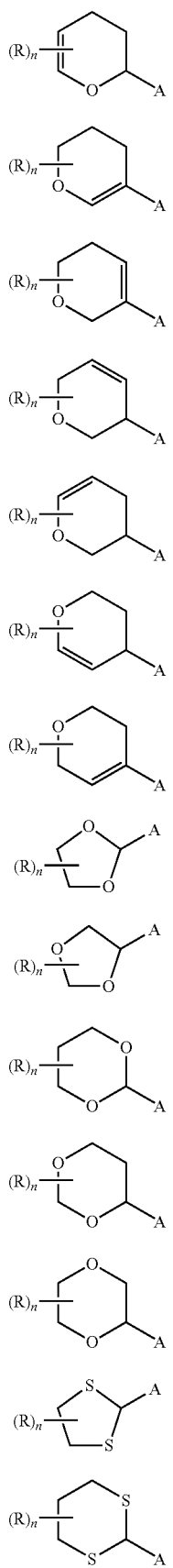
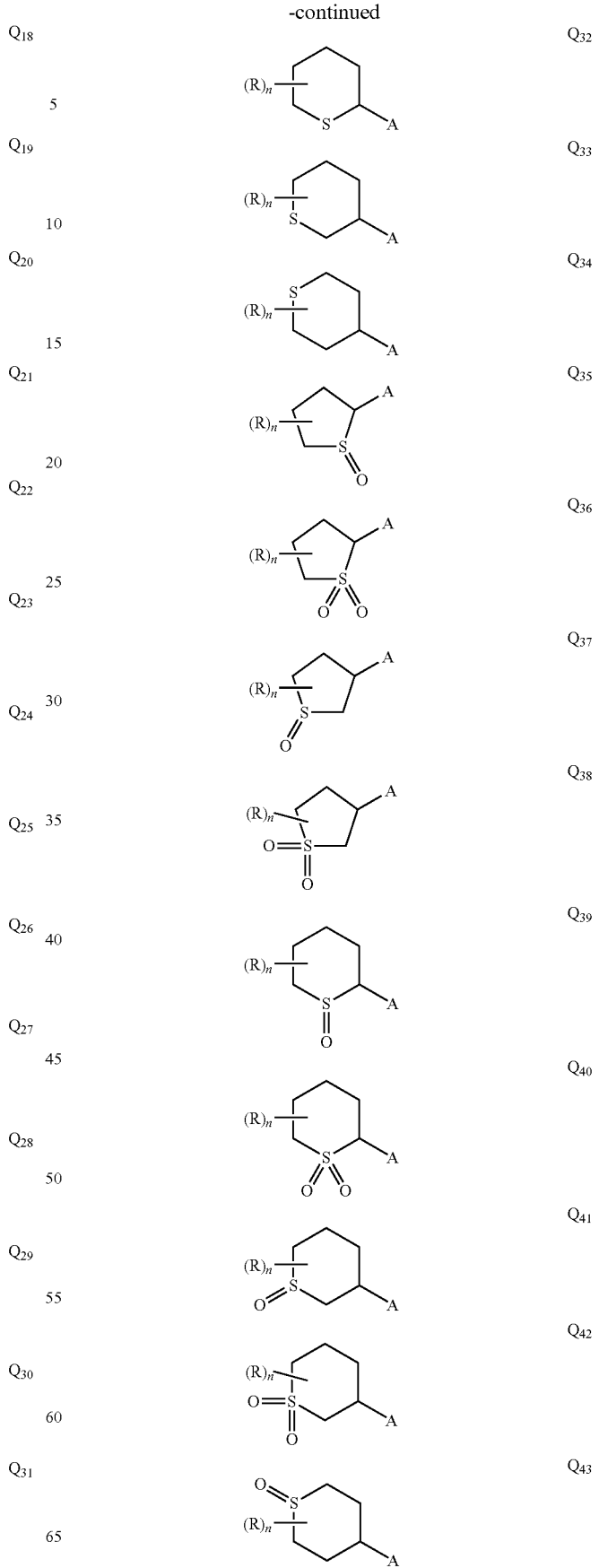

-continued
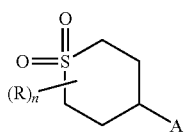 Q44
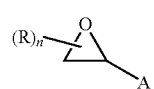 Q45
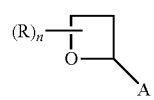 Q46
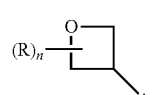 Q47
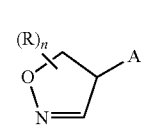 Q48
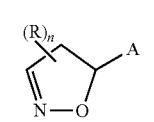 Q49
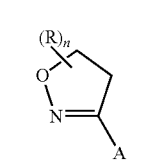 Q50
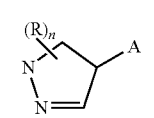 Q51
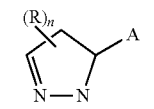 Q52
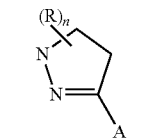 Q53
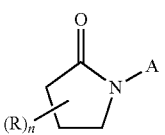 Q54
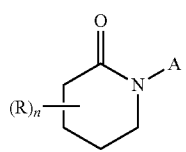 Q55
-continued
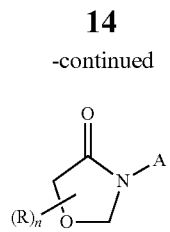 Q56
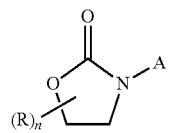 Q57
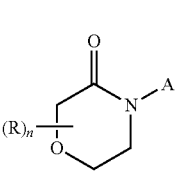 Q58
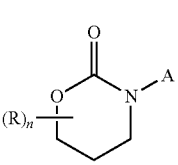 Q59
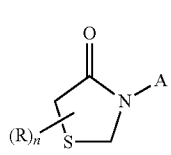 Q60
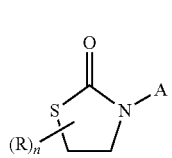 Q61
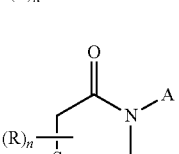 Q62
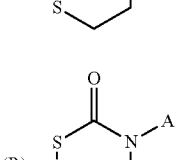 Q63
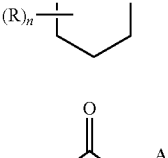 Q64
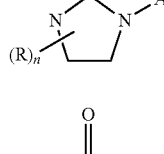 Q65

-continued
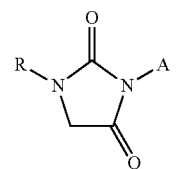 Q66
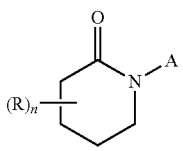 Q67
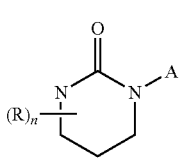 Q68
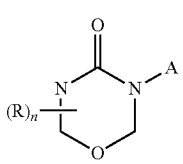 Q69
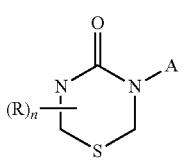 Q70
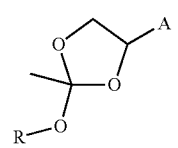 Q71
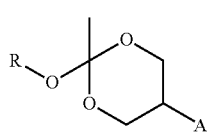 Q72
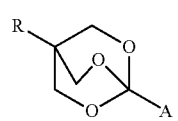 Q73
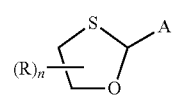 Q74
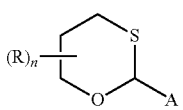 Q75
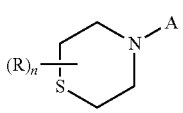 Q76
-continued
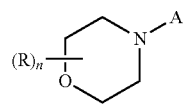 Q77
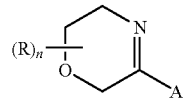 Q78
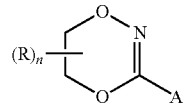 Q79
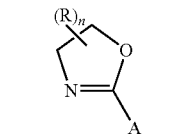 Q80
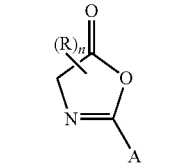 Q81
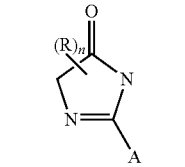 Q82
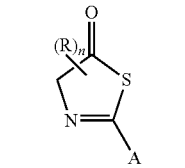 Q83
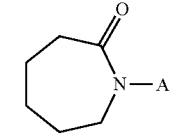 Q84
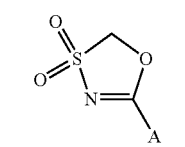 Q85
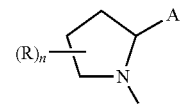 Q86
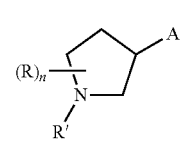 Q87

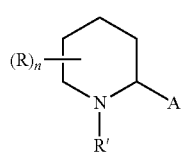 Q88
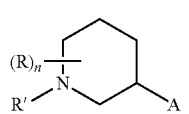 Q89
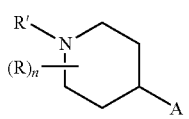 Q90
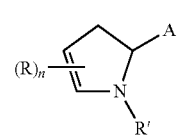 Q91
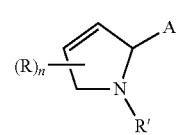 Q92
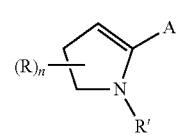 Q93
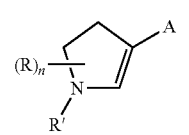 Q94
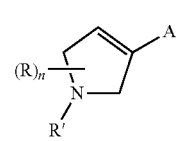 Q95
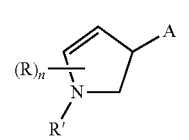 Q96
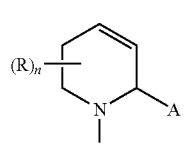 Q97
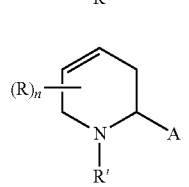 Q98
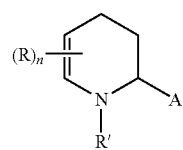 Q100
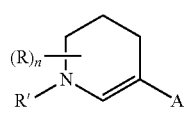 Q101
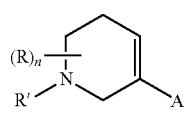 Q102
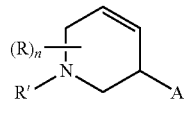 Q103
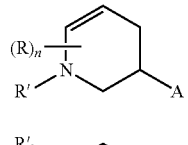 Q104
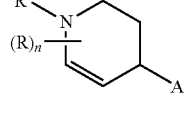 Q105
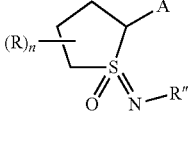 Q106
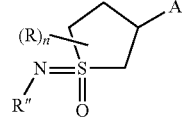 Q107
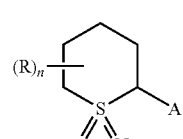 Q108
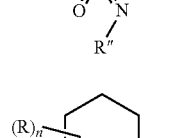 Q109
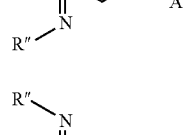 Q110
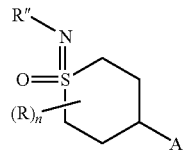

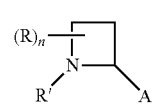
$Q_{111}$

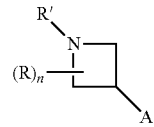
$Q_{112}$

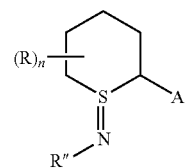
$Q_{113}$

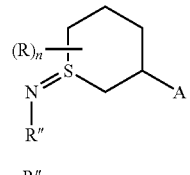
$Q_{114}$

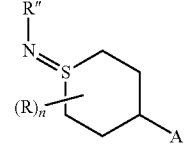
$Q_{115}$ wherein

R is hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, R' is hydrogen, hydroxy, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_{2-6}$alkenyloxy, $C_{2-6}$haloalkenyloxy, $C_3$-$C_6$alkynyloxy, benzyloxy, $C_{1-4}$alkoxy($C_{1-4}$)alkyoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_6$-$C_{10}$arylsulfonyl, $C_6$-$C_{10}$arylcarbonyl, $C_6$-$C_{10}$arylaminocarbonyl, $C_7$-$C_{16}$arylalkylaminocarbonyl, $C_1$-$C_9$hetarylsulfonyl, $C_1$-$C_9$hetarylcarbonyl, $C_1$-$C_9$hetarylaminocarbonyl, $C_2$-$C_{15}$hetarylalkylaminocarbonyl, R" is hydrogen, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_1$-$C_6$haloalkylsulfinyl, $C_1$-$C_6$haloalkylsulfonyl, cyano or nitro, n is 0, 1, 2, 3 or 4, and A denotes the position of attachment to the —$(CR^6R^7)_m$— moiety in the compounds of formula (I).

Groups $Q_1$, $Q_2$, $Q_3$, $Q_4$, $Q_5$, $Q_6$, $Q_7$, $Q_{25}$, $Q_{26}$, $Q_{27}$, $Q_{28}$, $Q_{29}$, $Q_{34}$, $Q_{43}$, $Q_{44}$, $Q_{86}$, $Q_{87}$, $Q_{88}$, $Q_{89}$, $Q_{90}$, $Q_{110}$, $Q_{115}$ are more preferred, and groups $Q_1$ to $Q_7$, $Q_{34}$, $Q_{43}$, $Q_{44}$, $Q_{90}$, $Q_{110}$ and $Q_{115}$ are particularly preferred.

Preferably, R and R', independently of each other, are hydrogen, $C_1$-$C_4$alkyl, $C_1$-$C_4$haloalkyl, $C_1$-$C_4$alkoxy or $C_1$-$C_4$haloalkoxy, and R" is hydrogen, $C_1$-$C_4$alkyl, $C_1$-$C_4$haloalkyl, $C_1$-$C_4$alkoxy, $C_1$-$C_4$haloalkoxy, $C_1$-$C_6$haloalkylcarbonyl or cyano.

Preferably, in the compounds of the formula (I) with group $Q_{90}$, the substituent R' is hydroxy, methyl, methoxy, ethoxy, propoxy, isopropoxy, 2,2,2-trifluoroethoxy, allyloxy, propargyloxy, benzyloxy, methoxymethoxy, ethoxymethoxy or methoxyethoxy.

Preferably, n is 0, 1 and 2.

Preferably, in the compounds of the formula (I), m is 0, 1 or 2, more preferably m is 0 or 1, and most preferably m is 1.

The preferred groups of $R^5$, $R^6$, $R^7$, m, Q, D, X, Y, Z, G, p and q in the compounds of formula I defined above can be combined in any way.

In a preferred group of the compounds of the formula (I), X, Y and Z are $C_{1-4}$alkyl, in particular methyl, p and q, independently of each other, are 1 or 2; G is hydrogen or a latentiating group, in particular a group —$C(X^b)$—$X^c$—$R^b$, wherein the meanings of $X^b$, $X^c$ and $R^b$ are as defined above, in particular $X^b$ is O, $X^c$ is O and $R^b$ is ethyl; D is O or, in particular, NH or $NCH_3$; $R^5$, $R^6$ and $R^7$ are hydrogen; Q is a saturated or mono-unsaturated $C_{3-8}$hetero-cyclyl, in particular a saturated $C_6$-heterocyclyl, containing at least one heteroatom selected from O, N and S, which O,N,S-heterocyclyl is unsubstituted or substituted at a carbon, S or N atom by a residue of formula =O, =N—$R^{03}$, $C_1$-$C_4$alkyl or $C_1$-$C_4$alkoxy, in particular methyl or methoxy, where $R^{03}$ is $C_1$-$C_6$haloalkylcarbonyl or cyano; and m is 0 or 1.

In another preferred group of the compounds of the formula (I), X is $C_{1-4}$alkyl, in particular methyl; Y and Z are $C_{1-4}$alkyl or halogen, in particular methyl or chloro; p and q, independently of each other, are 1 or 2; G is hydrogen or a latentiating group, in particular a group —$C(X^b)$—$X^c$—$R^b$, wherein the meanings of $X^b$, $X^c$ and $R^b$ are as defined above, in particular $X^b$ is O, $X^c$ is O and $R^b$ is ethyl; D is O or, in particular, NH or $NCH_3$; $R^5$, $R^6$ and $R^7$ are hydrogen; Q is a saturated or mono-unsaturated $C_{3-8}$hetero-cyclyl, in particular a saturated $C_6$-heterocyclyl, containing at least one heteroatom selected from O, N and S, which O,N,S-heterocyclyl is unsubstituted or substituted at a carbon, S or N atom by a residue of formula =O, =N—$R^{03}$, $C_1$-$C_4$alkyl or $C_1$-$C_4$alkoxy, in particular methyl or methoxy, where $R^{03}$ is $C_1$-$C_6$haloalkylcarbonyl or cyano; and m is 0 or 1.

Certain compounds of formula (I) are alkenes, and as such undergo further reactions typical of alkenes to give additional compounds of formula (I) according to known procedures. Example of such reaction include, but are not restricted to, halogenation or hydrogenation

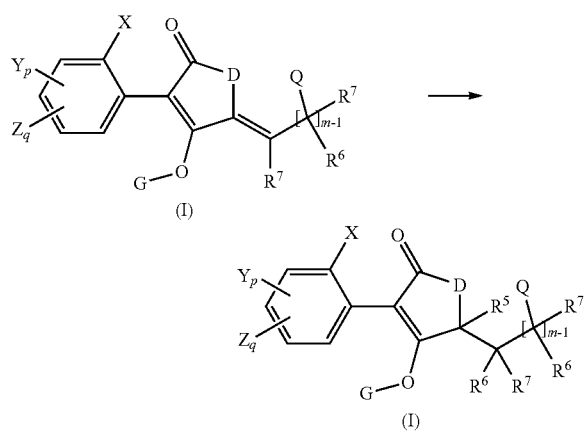

wherein $R^5$ and $R^6$ form a bond

Compounds of formula (I) wherein $R^5$ and $R^6$ form a bond and $R^7$ is halogen (preferably chloride or bromide) or $R^7$ is $C_1$-$C_6$alkylsulfonate (preferably mesylate) or $C_1$-$C_6$haloalkylsulfonate (preferably triflate) or an arylsulfonate (preferable tosylate) may undergo a cross-coupling reaction with a suitable coupling partner under conditions described in the literature for Suzuki-Miyaura, Sonogashira and related cross-coupling reactions to give additional compounds of formula (I) (see, for example, O'Brien, C. J. and Organ, M. G. Angew. Chem. Int. Ed. (2007), 46, 2768-2813; Suzuki, A. Journal of Organometallic Chemistry (2002), 653, 83; Miyaura N. and Suzuki, A. Chem. Rev. (1995), 95, 2457-2483).

The invention covers also salts of the compounds of the formula I with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_{a2}R_{b2}R_{c2}R_{d2})]OH$ wherein $R_{a2}$, $R_{b2}$, $R_{c2}$ and $R_{d2}$ are each independently of the others $C_1$-$C_4$alkyl. Further suitable tetraalkylammonium bases with other anions can be obtained, for example, by anion exchange reactions.

The compounds of the invention may be made by a variety of methods. For example, the compounds of formula I, wherein the substituents have the meanings assigned to them above, can be prepared by means of processes known per se, e.g. by treating compounds of formula II with an alkylating, acylating, phosphorylating or sulfonylating agent G-LG in the presence of at least one equivalent of a base, where G is the alkyl, acyl, phosphoryl or sulfonyl group to be incorporated and LG is a nucleofuge:

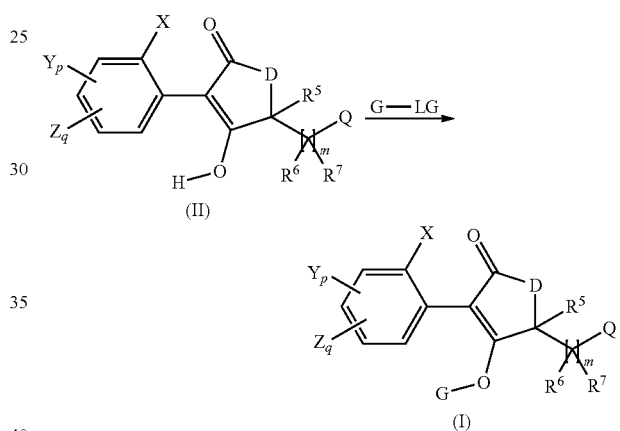

Compounds of formula I, in which X, Y, Z, $R^5$, $R^6$, $R^7$, Q, m, p, q and D are as defined above and wherein G is a latentiating group of the formula —$C(X^a)$—$R^a$, $C(X^b)$—$X^c$—$R^b$ or —$C(X^d)$—$NR^cR^d$ may be prepared by procedures known in the art, described for example in WO 09/049,851. Typically, compounds of formula II, in which X, Y, Z, $R^5$, $R^6$, $R^7$, Q, m, p, q and D are as defined above, are treated with an acylating agent such as an acid halide (especially acid chloride), acid anhydride, haloformate (especially chloroformate), halothioformate (especially chlorothioformate), isocyanate, isothiocycanate, carbamoyl halide (especially carbamoyl chloride) or thiocarbamoyl halide (especially thiocarbamoyl chloride) in the presence of at least one equivalent of a suitable base, optionally in the presence of a suitable solvent. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases, where the acylating agent is a carboxylic acid, acylation is preferably effected in the presence of a coupling agent such as 2-chloro-1-methylpyridinium iodide, N,N'-dicyclohexycarbodiimide, 1-(3-dimethylaminopropyl)-3-ethylcarbodiimide and N,N'-carbodiimidazole, and a base such as triethylamine or pyridine in a suitable solvent such as tetrahydrofuran, dichloromethane and acetonitrile.

Compounds of formula I, in which X, Y, Z, $R^5$, $R^6$, $R^7$, Q, m, p, q and D are as defined above and wherein G is a latentiating group of the formula $C(X^b)$—$X^c$—$R^b$ or —$C(X^d)$—$NR^cR^d$, may be also be prepared by treating compounds of formula II, in which X, Y, Z, $R^5$, $R^6$, $R^7$, Q, m, p, q and D are as defined above, with phosgene or a phosgene equivalent, optionally in the presence of a solvent such as toluene or ethyl acetate, and a base and reacting the resultant chloroformate, or equivalent, with an alcohol, thiol or amine under known conditions, as described, for example, in U.S. Pat. No. 6,774,133, U.S. Pat. No. 6,555,567 and U.S. Pat. No. 6,479,489.

Compounds of formula I, in which X, Y, Z, $R^5$, $R^6$, $R^7$, Q, m, p, q and D are as defined above and wherein G is a latentiating group of the formula —$P(X^e)R^fR^g$, may be prepared from compounds of formula II, in which X, Y, Z, $R^5$, $R^6$, $R^7$, Q, m, p, q and D are as defined above, using procedures described, for example, in U.S. Pat. No. 6,774,133, U.S. Pat. No. 6,555,567 and U.S. Pat. No. 6,479,489.

Compounds of formula I, in which X, Y, Z, $R^5$, $R^6$, $R^7$, Q, m, p, q and D are as defined above and wherein G is a latentiating group of the formula —$SO_2R^e$, may be prepared by reaction of compounds of formula II, in which X, Y, Z, $R^5$, $R^6$, $R^7$, Q, m, p, q and D are as defined above, with an alkyl or aryl sulfonyl halide, preferably in the presence of at least one equivalent of base.

Compounds of formula I, in which X, Y, Z, $R^5$, $R^6$, $R^7$, Q, m, p, q and D are as defined above and wherein G is $C_1$-$C_6$alkyl, $C_2$-$C_6$alkenyl, $C_3$-$C_6$alkynyl or a latentiating group of the formula $CH_2$—$X^f$—$R^h$, may be prepared by treatment of a compound of formula II, in which X, Y, Z, $R^5$, $R^6$, $R^7$, Q, m, p, q and D are as defined above, with a compound of formula G-$Y_{LG}$ wherein $Y_{LG}$ is a halogen (especially bromine or iodine), sulfonate (especially mesylate or tosylate) or a sulfate preferably in the presence of a base, under known conditions.

Compounds of formula III, in which X, Y, Z, p, q, D, m, $R^5$, $R^6$, $R^7$ and G are as defined above and in which GR is hydrogen,

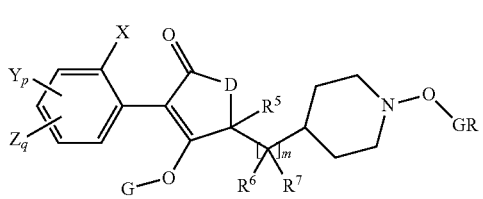

(III)

can be obtained by catalytic hydrogenation of compounds of formula III, in which GR is represented by a benzyl group.

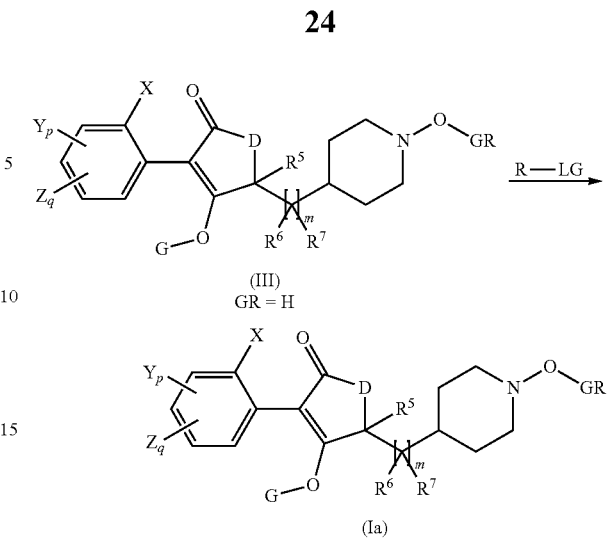

GR = methoxy, ethoxy, propoxy, isopropoxy, 2,2,2-trifluoroethoxy, allyloxy, propargyloxy, benzyloxy, methoxymethoxy, ethoxymethox or methoxyethoxy Compounds of formula Ia, a sub-group of compounds of formula I where the element Q is $Q_{90}$, n is 0 and R' is preferably methoxy, ethoxy, propoxy, isopropoxy, 2,2,2-trifluoroethoxy, allyloxy, propargyloxy, benzyloxy, methoxymethoxy, ethoxymethoxy or methoxyethoxy, and in which X, Y, Z, p, q, D, m, $R^5$, $R^6$, $R^7$ and G are as defined above, can be obtained by treating compounds of formula III, in which in which GR is hydrogen, with an alkylating agent R-LG, wherein R represents the alkyl group (methyl, ethyl, propyl, isopropyl, 2,2,2-trifluoroethyl, allyl, propargyl, benzyl, methoxymethyl, ethoxymethyl or methoxyethyl) to be incorporated and LG represents a nucleofuge, in the presence of at least one equivalent of a base, and optionally in the presence of a suitable solvent.

Compounds of formula II may be prepared via the cyclisation of compounds of formula IV,

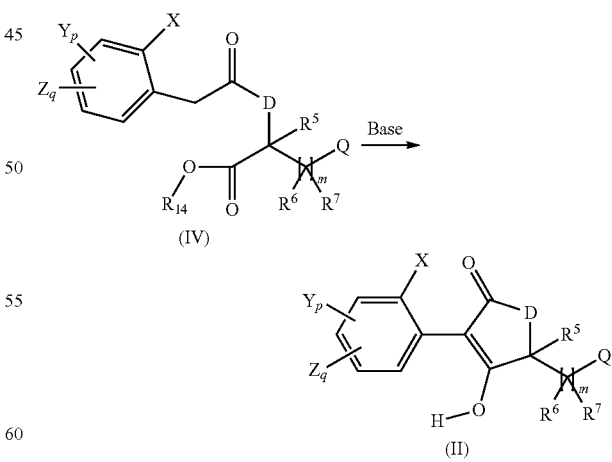

wherein $R_{14}$ is $C_{1-6}$alkyl, preferably in the presence of base, and optionally in the presence of a suitable solvent, by known methods described, for example, in WO 09/049, 851.

X, Y, Z, $R^5$, $R^6$, $R^7$, Q, m, p, q and D are as defined above.

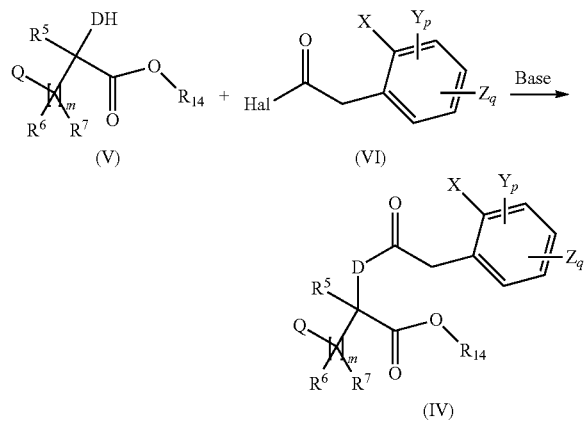

Compounds of formula IV, which are novel and thus constitute another subject of the invention, may be prepared by reacting derivatives of formula V with phenylacetyl halides of formula VI, preferably in the presence of base in a suitable solvent by known methods described, for example, in WO 09/049,851. X, Y, Z, $R^5$, $R^6$, $R^7$, Q, m, p, q and D are as defined above. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. In the situation wherein D is NOH, acylation methods of α-hydroxylamino acid derivatives of formula V are of extreme advantage where N-acylation selectivity can be achieved according, for example, to Vallée and Blandin, Organic & Biomolecular Chemistry, 4, 3125-3141, (2006) or to WO 1996/35714, and whereby the use of transition metal, alkali metal, and alkaline earth metal bases is preferred. The use of a mild base, especially bicarbonates and carbonates of lithium, sodium, potassium and cesium, and more particularly lithium, sodium, potassium and cesium hydrogen carbonate, and even more particularly sodium and potassium hydrogen carbonate in solvents like dichloromethane, tetrahydrofuran, dioxane or mixtures thereof are preferred reaction conditions. The solvent system for these mild basic acylation conditions may also be aqueous biphasic employing, for example, ethyl acetate (or dichloromethane, or any related organic solvent) and water, as described, for example, by Ito et al., Heterocycles, 57, 881-894, (2002).

Phenylacetyl halides of formula VI, wherein Hal is F, Cl or Br and in which X, Y, Z, p, q are as defined above, are known compounds or can be prepared by known methods, described for example in WO 09/049,851.

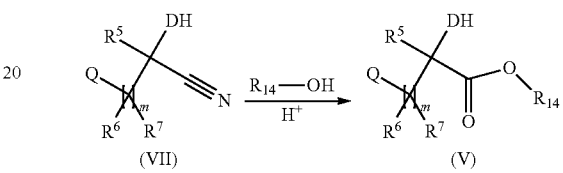

Compounds of the formula V, wherein $R_{14}$ is $C_1$-$C_6$alkyl, may be prepared by reacting nitriles of the formula VII with an alcohol of the formula $R_{14}OH$, wherein $R_{14}$ is $C_1$-$C_6$alkyl, preferably in the presence of a strong acid (especially sulfuric acid or hydrochloric acid), under known conditions. For the particular situation where $R_{14}$ is methyl, a compound of the formula VII may also be treated with acetyl chloride in methanol.

Derivatives of the formula V, wherein $R_{14}$ is $C_1$-$C_6$alkyl, can also be prepared by known methods from acids of formula VIII. Esterification of VIII with an alcohol of the formula $R_{14}OH$, wherein $R_{14}$ is $C_1$-$C_6$alkyl, under thionyl chloride activation is a typical example for the preparation of esters V, as described for example in WO09/049,851, but other known esterification methods may also be applied, like for example treatment of a compound of the formula VIII with an alcohol of the formula $R_{14}OH$ under acidic conditions (typically $H_2SO_4$ or HCl). For the particular situation where $R_{14}$ is methyl, a compound of the formula VIII may also be treated with diazomethane or trimethylsilyldiazomethane, or with acetyl chloride in methanol. The compounds VIII, VII and V can be reacted and/or isolated as free amines or amine salts (eg a hydrohalide salt, more specifically a hydrochloride or hydrobromide salt, or any other equivalent salt).

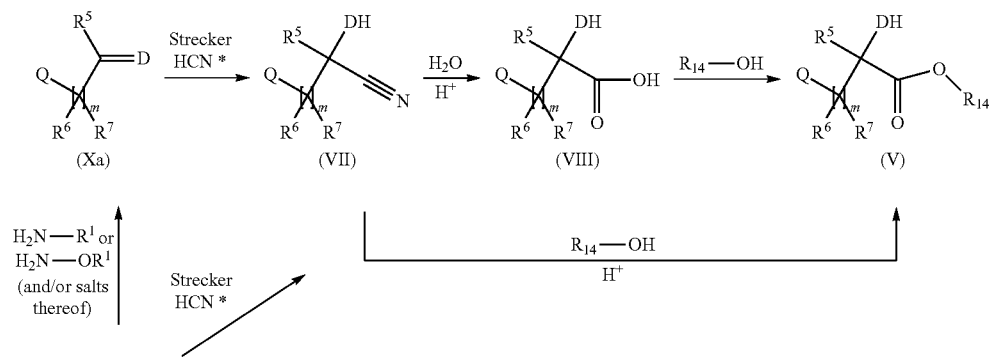

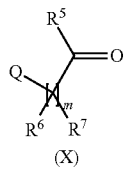

(X)

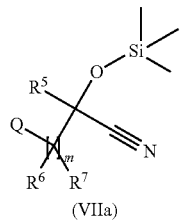

(VIIa)

* or other sources of cyanide (see text)

Hydrolysis of nitriles of the formula VII into acids of formula VIII is typically performed with water under acidic conditions, for example in presence of hydrochloric or sulfuric acid.

Compounds of the formula VIII or V can be prepared from ketones of the formula X by means of Strecker-type chemistry via nitrile compounds of the formula VII. Compounds of the formula VII (D=O) can be prepared from ketones of the formula X by a number of methods, for example by treatment with hydrocyanic acid, in analogy to, for example, B. V. Unkovskii et al., Khimiya Geterotsiklicheskikh Soedinenii (1990), (10), 1359-63. Other sources of cyanide are, for example, potassium or sodium cyanide, optionally in presence of for example ammonium chloride (in analogy to, for example, I. Iriepa et al., Trends in Heterocyclic Chemistry (1999), 6, 87-95) or sodium hydrogen sulphite $NaHSO_3$ (in analogy to, for example, R. A. Y. Jones et al., J. Chem. Soc. (B), 1971, 1302-1307), or trimethylsilyl cyanide TMS-CN, acetone cyanohydrin (in analogy to, for example, A. I. Kuznetsov et al., Khimiya Geterotsiklicheskikh Soedinenii (1992), (5), 648-52) or diethylaluminum cyanide, optionally in presence of a Lewis acid, like for example, zinc chloride, zinc iodide, titanium chloride, titanium isopropoxide, ytterbium isopropoxide, magnesium bromide, boron trifluoride ethyl etherate, tetrachlorosilane or equivalents thereof. In case of treatment of ketones of formula X with trimethylsilyl cyanide TMS-CN, one may isolate the silylated cyanohydrins of the formula VIIIa and subject them to hydrolysis, typically performed with water under acidic conditions, for example in presence of hydrochloric acid or sulfuric acid, in order to isolate compounds of formula VII. This path from a compound of the formula X to a derivative of the formula VII via a trimethylsilyl ether cyanohydrin intermediate VIIa can be performed in analogy to P. G. Gassman, J. J. Talley, Tetrahedron Lett. (1978), 40, 3773-3776.

Compounds of the formula VII (D=NR$^1$ or NOR$^1$) can be prepared directly from ketones of the formula X by means of the well described one-pot three components coupling involving, besides ketones X, hydrogen cyanide HCN or various alkali cyanides (eg KCN, NaCN, etc.) in buffered aqueous media or trimethylsilyl cyanide TMSCN, optionally in presence of a catalytic amount of a Lewis acid, for example $ZnI_2$, and a N-substituted amine of the formula $H_2N-R^1$ or an O-substituted hydroxyl-amine of the formula $H_2N-OR^1$, both $H_2N-R^1$ or $H_2N-OR^1$ either as free amine or amine salt (eg a hydrohalide salt, more specifically a hydrochloride or hydrobromide salt, or any other equivalent salt of the amine $H_2N-R^1$ or $H_2N-OR^1$). An appropriate source of cyanide (eg HCN) may also be added to a preformed ketimine (or iminium salt), oxime or oxime ether (or salts thereof) of the formula Xa. Particularly advantageous is the mild method using a cyanide source (especially sodium or potassium cyanide) in an aqueous phosphate buffer according, for example, to Porter and Hellerman, J. Am. Chem. Soc. 66, 1652-55, (1944) and J. Am. Chem. Soc. 61, 754, (1939).

Compounds of the formula Xa may be obtained from reaction of ketones of the formula X with a N-substituted amine $H_2N-R^1$ or an O-substituted hydroxyl-amine of the formula $H_2N-OR^1$, or a salts thereof, by known methods. A summary on the scope of the Strecker reaction may be found, for example, in L. Kürti, B. Czakó, 'Strategic Applications of Named Reactions in Organic Synthesis', Elsevier Academic Press, 2005, pp. 446-447 and 690-691. Typical reaction conditions for the Strecker reaction may be found also, for example, in M. M. Mehrotra et al., J. Med. Chem. (2004), 47, 2037-2061, or B. J. Mavunkel et al., J. Med. Chem. (1996), 39, 3169-3173, or P. L. Feldman et al., J. Org. Chem. (1990), 55, 4207-4209, or in J. L. Marco et al., Tetrahedron (1999), 55, 7625-7644.

Compounds of the formula P1 and of the formula P2, wherein D is O, S or NR$^1$, and wherein R$^1$ is hydrogen or methyl, R$^\#$ is cyano, methoxycarbonyl or ethoxycarbonyl, and W is O, N—R$^{03}$ or S, SO, SO$_2$, S=N—R$^{04}$ or S(O)=N—R$^{04}$, wherein R$^{03}$ and R$^{04}$, independently of each other, are hydrogen, methyl, methoxy, trifluoromethylcarbonyl or cyano, form a particular subset of compounds of the formula V and of the formula VII, in which m, R$^5$, R$^6$, R$^7$ and Q have the meanings assigned to them above:

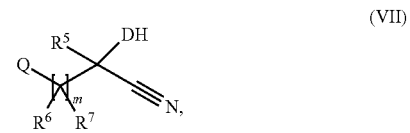

(VII)

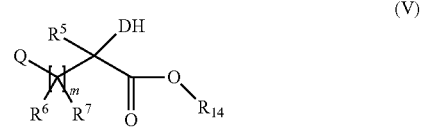

(V)

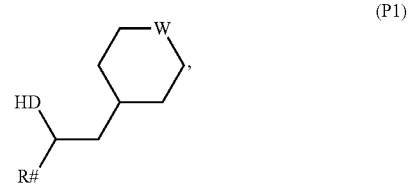

(P1)

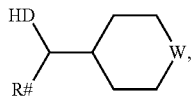

(P2)

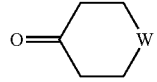

(P3)

Compounds of the formula P1 and P2 may be prepared from a common starting material of the formula P3 by means of homologation-type reactions.

The preparation of aldehyde P4, wherein W is as defined above, from ketone P3 in a typical 3- to 4-steps homologation sequence is outlined in scheme 1, and may be performed in analogy to R. Kitbunnadaj et al, Bioorganic & Medicinal Chemistry (2005), 13, 6309-6323. Intermediates of the formula $PI_1$ may be prepared from ketones of the formula P3 through a Wittig, Wittig-Horner or Horner-Emmons-Wadsworth type olefination reaction involving, for example, a Horner-Emmons-Wadsworth reagent RE1, wherein $R_{14}$ is $C_{1-6}$alkyl, like trimethyl or triethyl phosphonoacetate. Typical bases and solvents for such a reaction are for example: sodium hydride (NaH), potassium-, sodium-, or lithium-hexamethyldisilazane (KHMDS, NaHMDS, LiHMDS), potassium tert-butoxide (KO-t-Bu) in benzene, toluene, tetrahydrofuran (THF) or dioxane. Intermediates of the formula $PI_2$ may be prepared from compounds of the formula $PI_1$ by means of a hydrogenation reaction. Treatment of $PI_1$ with hydrogen ($H_2$, 1-100 bars pressure) and catalytic amounts of palladium (for example palladium on carbon 1-30 wt. %, Pd/C) in solvents like methanol ($CH_3OH$), ethyl acetate (EtOAc) or tetrahydrofuran, optionally further containing water or acids like HCl, at 0-100° C. are typical reaction conditions for such a hydrogenation. Intermediates of the formula $PI_3$ may be prepared from compounds of the formula $PI_2$ by means of a reduction step, involving a reducing agent, such as, for example, sodium borohydride, lithium aluminium hydride (LiAlH$_4$) or other metallic hydrides, in solvents, such as, for example, methanol, ethanol, isopropanol, tetrahydrofuran (THF) or ethers, under conditions known and described in the literature. Aldehydes of the formula P4 may be prepared from compounds of the formula $PI_3$ by means of an oxidation step, involving, for example, Swern (oxalyl chloride, trifluoroacetic anhydride (TFAA) or dimethyl sulfoxide (DMSO), triethylamine), Jones (CrO$_3$, or $Cr_2O_7^{2-}$ with acetic acid or sulphuric acid and water), pyridinium chlorochromate (PCC) or pyridinium dichromate (PDC) oxidation conditions, in solvents such as, for example, dichloromethane ($CH_2Cl_2$) or acetone. Aldehydes of the formula P4 may also be prepared directly from compounds of the formula $PI_2$ by means of a reduction involving diisobutylaluminum hydride (DIBAL-H), in solvents such as, for example, hexane or toluene, and performed in analogy to T. Sato et al., Heterocycles (2001), 54, 747-755.

Scheme 1

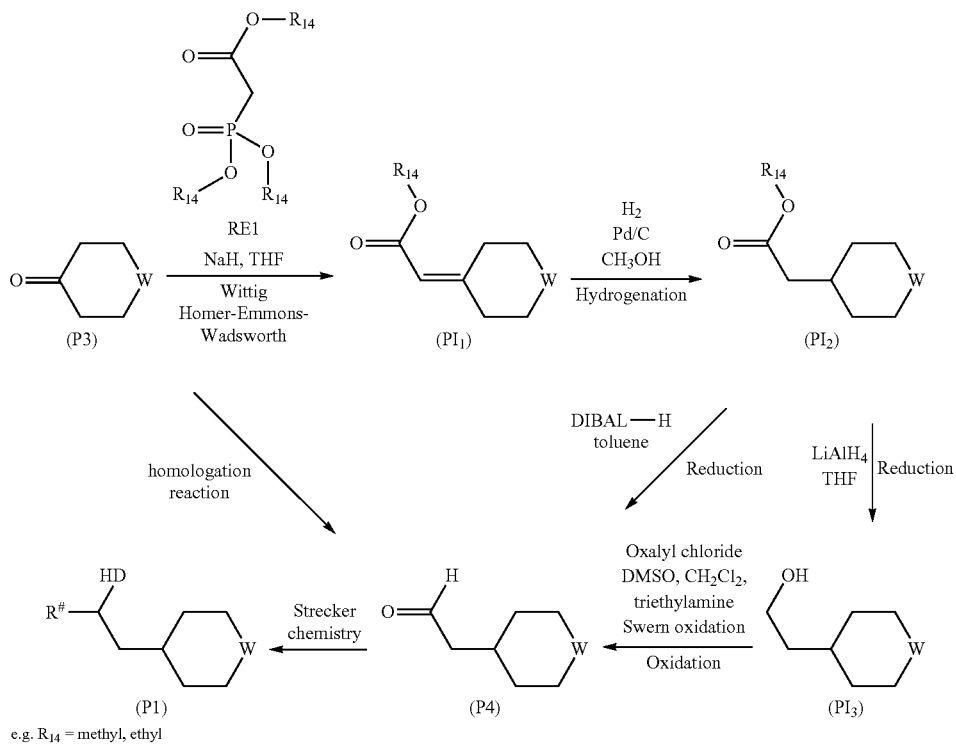

Compounds of the formula P4, wherein W is O, N—$R^{03}$ or S, SO, SO$_2$, S=N—$R^{04}$ or S(O)=N—$R^{04}$, wherein $R^{03}$ and $R^{04}$, independently of each other, are hydrogen, methyl, methoxy, trifluoromethylcarbonyl or cyano, form a particular subset of compounds of the formula X, in which m, $R^5$, $R^6$, $R^7$ and Q have the meanings assigned to them above. Subjecting compounds of the formula P4 to Strecker-type chemistry, using reaction conditions described above for the transformation of compounds of the formula X into compounds of the formula VII (possibly via compounds of the formula Xa), allow the preparation of the desired compounds of the formula P1, in which D is O, S or NR$^1$, and wherein R$^1$ is hydrogen or methyl, R$^\#$ is cyano, methoxycarbonyl or ethoxycarbonyl, and W is O, N—R$^{03}$ or S, SO, SO$_2$, S=N—R$^{04}$ or S(O)=N—R$^{04}$, wherein R$^{03}$ and R$^{04}$, independently of each other, are hydrogen, methyl, methoxy, trifluoromethylcarbonyl or cyano.

The preparation of aldehyde P5, wherein W is as defined above, from ketone P3 in a typical 2-steps homologation sequence is outlined in scheme 2, and may be performed in analogy to V. Balannik et al., Biochemistry (2009), 48, 11872-11882. Intermediates of the formula PI$_4$ may be prepared from ketones of the formula P3 through a Wittig, Wittig-Horner or Horner-Emmons-Wadsworth type olefination reaction involving, for example, a phosphonium salt reagent RE2, wherein R$_{14}$ is C$_{1-6}$alkyl, like (methoxymethyl)triphenylphosphonium chloride. Typical bases and solvents for such a reaction are for example: sodium hydride (NaH), potassium-, sodium-, or lithium-hexamethyldisilazane (KHMDS, NaHMDS, LiHMDS), lithium diisopropylamide (LDA), potassium tert-butoxide (KO-t-Bu), alkyl- or aryllithiums (n- or sec-butyllithium (n-BuLi, s-BuLi), phenyllithium) in benzene, toluene, tetrahydrofuran (THF) or dioxane. Aldehydes of the formula P5 may be prepared from compounds of the formula PI$_4$ by means of hydrolysis of the enol ether functionality, under typical reaction conditions known in the literature, such as, for example, treatment of PI$_4$ with aqueous acid (hydrochloric acid (HCl) or sulfuric acid) in solvents like, for example, tetrahydrofuran (THF), dioxane or ethyl acetate (EtOAc).

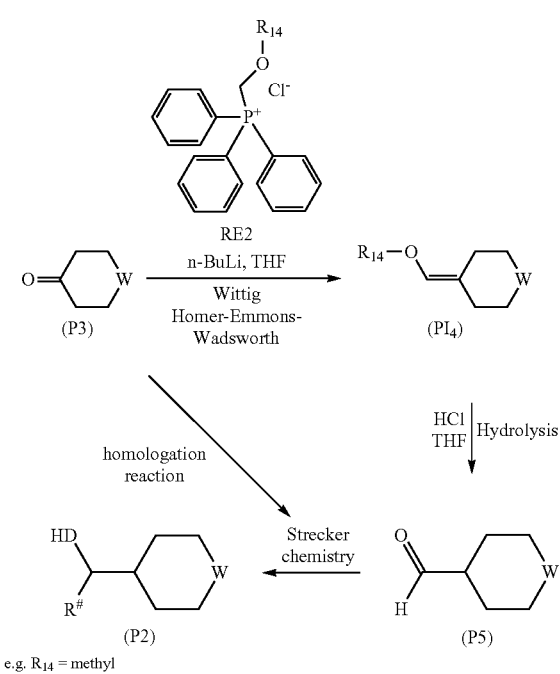

Compounds of the formula P5, wherein W is O, N—R$^{03}$ or S, SO, SO$_2$, S=N—R$^{04}$ or S(O)=N—R$^{04}$, wherein R$^{03}$ and R$^{04}$, independently of each other, are hydrogen, methyl, methoxy, trifluoromethylcarbonyl or cyano, form a particular subset of compounds of the formula X, in which m, R$^5$, R$^6$, R$^7$ and Q have the meanings assigned to them above. Subjecting compounds of the formula P5 to Strecker-type chemistry, using reaction conditions described above for the transformation of compounds of the formula X into compounds of the formula VII (possibly via compounds of the formula Xa), allow the preparation of the desired compounds of the formula P2, in which D is O, S or NR$^1$, and wherein R$^1$ is hydrogen or methyl, R$^\#$ is cyano, methoxycarbonyl or ethoxycarbonyl, and W is O, N—R$^{03}$ or S, SO, SO$_2$, S=N—R$^{04}$ or S(O)=N—R$^{04}$, wherein R$^{03}$ and R$^{04}$, independently of each other, are hydrogen, methyl, methoxy, trifluoromethylcarbonyl or cyano.

Compounds of the formula P3, wherein W is as defined above, are known compounds or can be prepared by known methods, described for example in Major and Dursch, Journal of Organic Chemistry (1962), 26, 1867-74 or D. E. Ward et al., Synthesis (2007), (10), 1584-6.

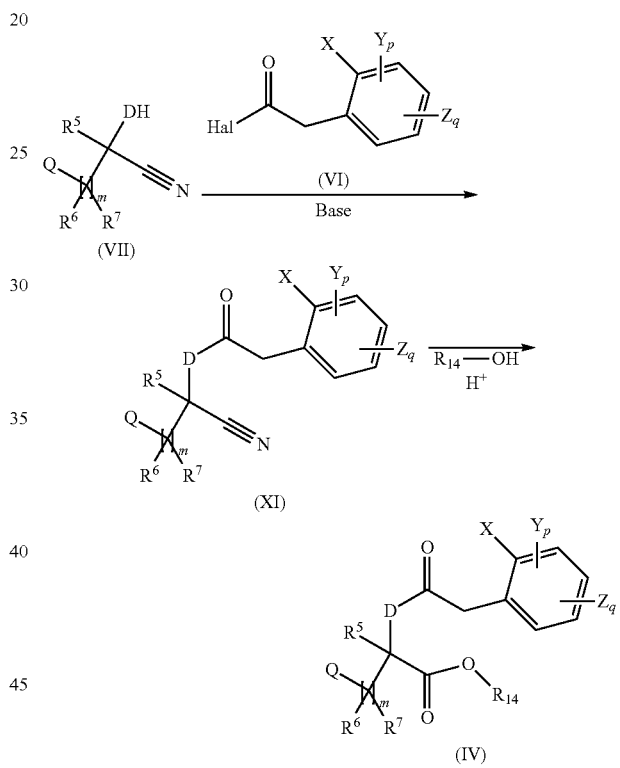

Alternatively, compounds of formula IV wherein R$_{14}$ is C$_1$-C$_6$alkyl, may be prepared by subjecting nitrile derivatives of formula XI to alcoholysis with R$_{14}$OH, preferably in acidic media (especially sulfuric acid or hydrochloric acid) by known methods described, for example, in WO 09/049,851. X, Y, Z, R$^5$, R$^6$, R$^7$, Q, m, p, q and D are as defined above. Nitrile compounds of formula XI may be themselves prepared by reacting compounds of formula VII with phenylacetyl halides of formula VI, preferably in the presence of base in a suitable solvent by known methods described, for example, in WO 09/049,851. X, Y, Z, R$^5$, R$^6$, R$^7$, Q, m, p, q and D are as defined above. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent.

A further process for the preparation of compounds of formula II involves catalytic hydrogenation of compounds of formula XIII having an enol benzyl ether functionality, in which the benzyl group might be optionally substituted with T, wherein T is for example 4-methoxy or 3,4-dimethoxy. Treatment of XIII with hydrogen (1-100 bars pressure) and catalytic amounts of palladium (for example palladium on carbon 1-30 wt. %) in solvents like methanol or tetrahydrofuran, optionally further containing water or acids like HCl, at 0-100° C. are typical reaction conditions for the hydrogenolytic debenzylation. A representative procedure can be found, for example, according to Schobert et al., Organic & Biomolecular Chemistry 2004, 2, 3524-3529. Other mild reaction conditions to remove the benzyl group make use of triethylsilane and a catalytic amount of palladium(II) acetate in presence of a base according, for example, to Paintner et al., Synlett 2003, 627-30.

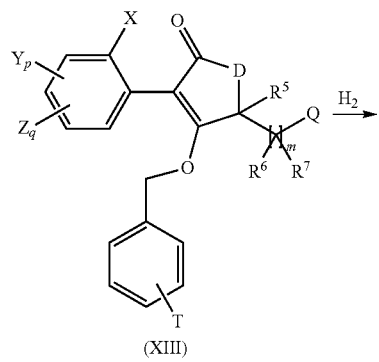

(XIII)

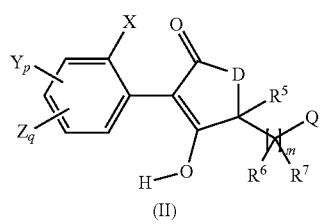

(II)

Compounds of formula XIII may be prepared by treatment of an analog of compound of formula II with a benzyl halide, which may be optionally substituted by T, wherein T is defined as above, in presence of a base, under known conditions, for example in analogy to R. Labruere et al., Synthesis (2006), (24), 4163-4166 or Y. Bourdreux et al., Tetrahedron (2008), 64(37), 8930-8937. Suitable reaction conditions for the formation of XIII are, for example, the same as described above for the conversion of compounds of formula II to compounds of formula I.

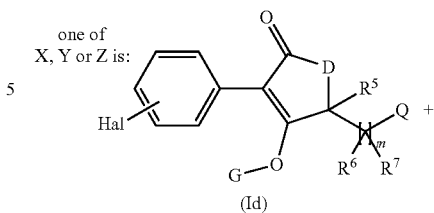

(Id)

Hal is chlorine, bromine or iodine, or a pseudohalogen such as triflate

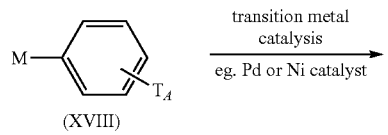

(XVIII)

M is B, Sn, Mg, Zn, etc.. together with ligands and/or substituents

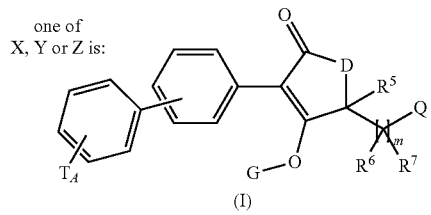

(I)

$T_A$ is $C_{1-4}$alkyl, $C_{1-4}$haloalkyl, halogen or cyano

Compounds of the formula I, wherein X, Y or Z is phenyl or phenyl substituted by $C_{1-4}$alkyl, $C_{1-4}$haloalkyl, halogen or cyano, may be prepared by reacting a corresponding halogen precursor of the formula Id, wherein Hal is chlorine, bromine, iodine or a pseudohalogen such as $C_{1-4}$haloalkylsulfonate, especially triflate, with an appropriate organometallic phenyl species of the formula XVIII, wherein $T_A$ is $C_{1-4}$alkyl, $C_{1-4}$haloalkyl, halogen or cyano and M is for example B, Sn, Si, Mg or Zn holding further ligands and/or substituents, by means of a transition metal-catalyzed reaction. The organometallic species of the formula XVIII is for example an aryl boronic acid $T_A$-Phenyl-B(OH)$_2$, or a suitable salt or ester thereof, which will react with a compound of the formula Id under palladium- or nickel-catalyzed conditions, such as for example the Suzuki-Miyaura conditions. A variety of metals, catalysts and ligands may be used in this reaction type. Reaction conditions and catalytic systems for such a transformation have been described, for example, in WO08/071,405. G, m, $R^5$, $R^6$, $R^7$, Q and D are as defined above.

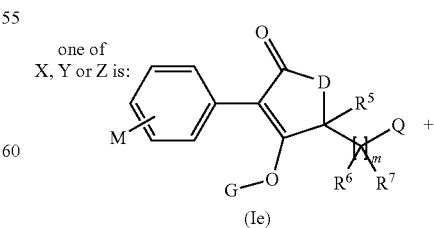

(Ie)

M is B, Sn, Mg, Zn, etc.. together with ligands and/or substituents

-continued

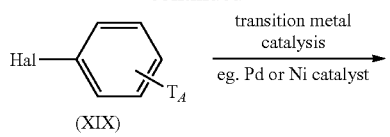

(XIX)

Hal is chlorine, bromine or iodine, or a pseudohalogen such as triflate one of X, Y or Z is:

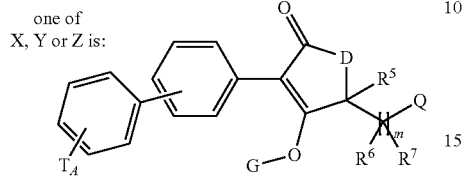

(I)

$T_A$ is $C_{1-4}$alkyl, $C_{1-4}$haloalkyl, halogen or cyano

One person skilled in the art will recognize that the polarity at the two reacting centers in this cross-coupling process may be reversed. Compounds of the formula I, wherein X, Y or Z is phenyl or phenyl substituted by $C_{1-4}$alkyl, $C_{1-4}$haloalkyl, halogen or cyano, may be also prepared by reacting a corresponding organometallic species of the formula Ie, wherein M is for example B, Sn, Si, Mg or Zn holding further ligands and/or substituents, with an aryl halide of the formula XIX, wherein Hal is chlorine, bromine, iodine or a pseudohalogen such as $C_{1-4}$haloalkylsulfonate, especially triflate, by means of a transition metal-catalyzed reaction and under similar conditions as described above. G, m, $R^5$, $R^6$, $R^7$, Q and D are as defined above.

The sulfur oxidation state of compounds of the formula I, II, IV and XI, and of intermediates of the formula V, VII and VIII, wherein A is incorporating such a S atom, like for example when D is either $NR^1$ or $NOR^1$ wherein $R^1$ is $C_{1-4}$alkylthio($C_{1-4}$)alkyl, may be easily adapted from the sulfide oxidation state into the sulfoxide or sulfone level by means of an oxidation reaction involving reagents such as, for example, m-chloroperbenzoic acid (MCPBA), oxone, sodium periodate, sodium hypochlorite or tert-butyl hypochlorite amongst many others.

A subgroup of compounds of the formula I holds a group Q defining a sulfoximine ($Q_{108}$ to $Q_{110}$) or sulfilimine ($Q_{113}$ to $Q_{115}$) functionality

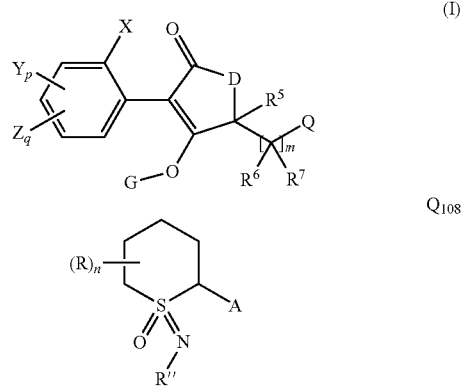

$Q_{108}$

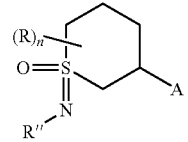

$Q_{109}$

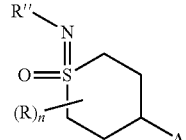

$Q_{110}$

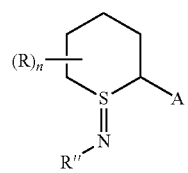

$Q_{113}$

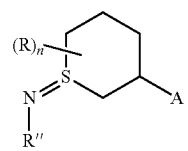

$Q_{114}$

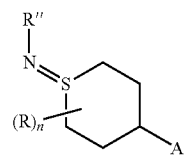

$Q_{115}$ in which X, Y, Z, p, q, m, $R^5$, $R^6$, $R^7$ and G, and wherein A, R, n and R", have the meanings assigned to them above.

Typical preparation methods of sulfoximines and/or sulfilimines, usually involving the corresponding sulfide as starting material, can be found, for example, in H. Okamura, C. Bolm, Org. Lett. 2004, 6, 1305; H. Okamura, C. Bolm, Chem. Lett. 2004, 33, 482; D. Leca, K. Song, M. Amatore, L. Fensterbank, E. Lacôte, M. Malacria, Chem. Eur. J. 2004, 10, 906; or M. Reggelin, C. Zur, Synthesis, 2000, 1.

Scheme 3

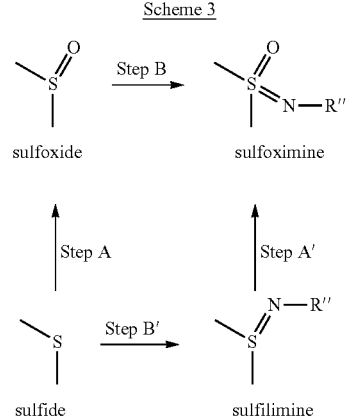

For the transformation of a sulfide to a sulfoxide or a sulfilimine to a sulfoximine (scheme 3, step A or A'), classical oxidation reagents are $KMnO_4$, mCPBA, $NaIO_4/RuO_2$, H₂O₂, oxone. For the transformation of a sulfoxide to a sulfoximine or a sulfide to a sulfilimine (scheme 3, step B or B'), typical reagents are NaN₃/H₂SO₄, O-mesitylenesulfonylhydroxylamine (MSH), or metal-catalyzed methods such as RN₃/FeCl₂, PhI=N—R/CuOTf, PhI=N—R/Cu(OTf)₂, PhI=N—R/CuPF₆, PhI(OAc)₂/R—NH₂/MgO/Ru₂(OAc)₄ or oxaziridines (e.g. 3-(4-cyano-phenyl)-oxaziridine-2-carboxylic acid tert-butyl ester). Detailed preparation conditions useful for the synthesis of such sulfoximine and/or sulfilimine compounds of formula I are given, for example, in WO2006/061200 or WO 2007/080131. These methods and reaction conditions may also be applied on any intermediates described above for the preparation of compounds of the formula I.

Compounds of the formula IV and XI, and salts thereof, are novel, have been specifically designed for the synthesis of the compounds of the formula I and as such form a further aspect of the invention. Thus compounds of the formula IV

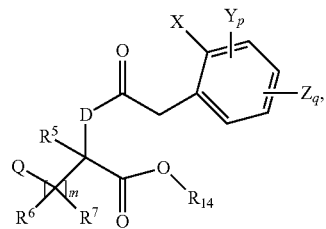

and salts thereof, wherein X, Y, Z, p, q, m, $R^5$, $R^6$, $R^7$, Q and D have the meanings assigned to them above and $R_{14}$ is $C_{1-6}$alkyl; and
compounds of the formula XI

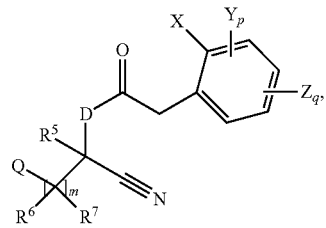

and salts thereof, wherein X, Y, Z, p, q, m, $R^5$, $R^6$, $R^7$, Q and D have the meanings assigned to them above are novel.

Compounds of the formula P1 and P2, and salts thereof, are novel, have been specifically designed for the synthesis of the compounds of the formula I and as such form a further aspect of the invention. Thus compounds of the formula P1

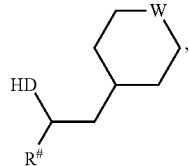

and salts thereof, wherein D is O, S or NR¹, and wherein R¹ is hydrogen or methyl, $R^\#$ is cyano, methoxycarbonyl or ethoxycarbonyl, and W is O, N—$R^{o3}$ or S, SO, SO₂, S=N—$R^{o4}$ or S(O)=N—$R^{o4}$, wherein $R^{o3}$ and $R^{o4}$, independently of each other, are hydrogen, methyl, methoxy, trifluoromethylcarbonyl or cyano; and
compounds of the formula P2

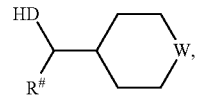

and salts thereof, wherein D is O, S or NR¹, and wherein R¹ is hydrogen or methyl, $R^\#$ is cyano, methoxycarbonyl or ethoxycarbonyl, and W is O, N—$R^{o3}$ or S, SO, SO₂, S=N—$R^{o4}$ or S(O)=N—$R^{o4}$, wherein $R^{o3}$ and $R^{o4}$, independently of each other, are hydrogen, methyl, methoxy, trifluoromethylcarbonyl or cyano are novel.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 861 below can be prepared according to the methods described above. The examples which follow are intended to illustrate the invention and show preferred compounds of formula I.

TABLE 1

This table discloses the 151 compounds T1.001 to T1.151 of the formula $I_1$:

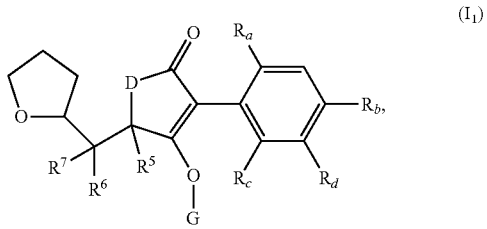

(I₁)

wherein $R^5$, $R^6$, $R^7$ and G are all hydrogen, D is NH and $R_a$, $R_b$, $R_c$, and $R_d$ are as defined below in Table T1 (Cyclo-C3 = cyclopropyl):

| No. | $R_a$ | $R_b$ | $R_c$ | $R_d$ |
|---|---|---|---|---|
| T1.001 | Br | H | H | H |
| T1.002 | Cl | H | H | H |
| T1.003 | CH₃ | H | H | H |
| T1.004 | CH₂CH₃ | H | H | H |
| T1.005 | OCH₃ | H | H | H |
| T1.006 | Br | Cl | H | H |
| T1.007 | Cl | Br | H | H |
| T1.008 | Cl | Cl | H | H |
| T1.009 | Cl | CH₃ | H | H |
| T1.010 | CH₃ | Cl | H | H |
| T1.011 | CH₃ | CH₃ | H | H |
| T1.012 | Cl | H | Cl | H |
| T1.013 | Cl | H | CH₃ | H |
| T1.014 | Cl | H | CH₂CH₃ | H |
| T1.015 | Cl | H | OCH₃ | H |
| T1.016 | CH₃ | H | CH₃ | H |
| T1.017 | CH₃ | H | CH₂CH₃ | H |
| T1.018 | CH₃ | H | OCH₃ | H |
| T1.019 | CH₂CH₃ | H | CH₂CH₃ | H |
| T1.020 | CH₂CH₃ | H | OCH₃ | H |
| T1.021 | OCH₃ | H | OCH₃ | H |
| T1.022 | Br | H | H | Cl |
| T1.023 | Br | H | H | CH₃ |
| T1.024 | Br | H | H | 4-Cl—C₆H₄ |
| T1.025 | Cl | H | H | Cl |
| T1.026 | Cl | H | H | CH₃ |
| T1.027 | Cl | H | H | 4-Cl—C₆H₄ |
| T1.028 | CH₃ | H | H | Br |
| T1.029 | CH₃ | H | H | Cl |
| T1.030 | CH₃ | H | H | CH₃ |
| T1.031 | CH₃ | H | H | C₆H₅ |
| T1.032 | CH₃ | H | H | 4-Cl—C₆H₄ |
| T1.033 | CH₂CH₃ | H | H | CH₃ |
| T1.034 | CH₂CH₃ | H | H | 4-Cl—C₆H₄ |
| T1.035 | OCH₃ | H | H | CH₃ |
| T1.036 | OCH₃ | H | H | 4-Cl—C₆H₄ |
| T1.037 | Cl | H | Cl | Br |
| T1.038 | CH₃ | H | CH₃ | Br |

TABLE 1-continued

This table discloses the 151 compounds T1.001 to T1.151 of the formula I₁:

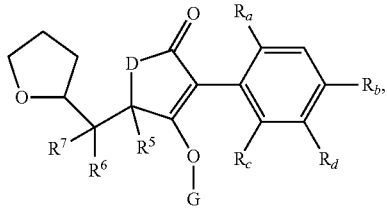

(I₁)

wherein $R^5$, $R^6$, $R^7$ and G are all hydrogen, D is NH and $R_a$, $R_b$, $R_c$, and $R_d$ are as defined below in Table T1 (Cyclo-C3 = cyclopropyl):

| No. | $R_a$ | $R_b$ | $R_c$ | $R_d$ |
|---|---|---|---|---|
| T1.039 | CH₃ | H | CH₃ | Cl |
| T1.040 | CH₃ | H | CH₃ | 4-Cl—C₆H₄ |
| T1.041 | Br | Cl | H | CH₃ |
| T1.042 | Br | CH₃ | H | CH₃ |
| T1.043 | Cl | Cl | H | Cl |
| T1.044 | Cl | Br | H | CH₃ |
| T1.045 | Cl | Cl | H | CH₃ |
| T1.046 | Cl | CH₃ | H | Cl |
| T1.047 | Cl | CH₃ | H | CH₃ |
| T1.048 | CH₃ | Br | H | CH₃ |
| T1.049 | CH₃ | Cl | H | CH₃ |
| T1.050 | CH₃ | CH₃ | H | CH₃ |
| T1.051 | CH₃ | CH₃ | H | 4-Cl—C₆H₄ |
| T1.052 | Br | Br | CH₃ | H |
| T1.053 | Br | Cl | CH₃ | H |
| T1.054 | Br | CH₃ | Br | H |
| T1.055 | Br | CH₃ | Cl | H |
| T1.056 | Cl | Br | CH₃ | H |
| T1.057 | Cl | Cl | Cl | H |
| T1.058 | Cl | Cl | CH₃ | H |
| T1.059 | Cl | CH₃ | Cl | H |
| T1.060 | Cl | CH₃ | CH₂CH₃ | H |
| T1.061 | Cl | CH₃ | OCH₃ | H |
| T1.062 | Cl | 4-Cl—C₆H₄ | Cl | H |
| T1.063 | Cl | 4-Cl—C₆H₄ | CH₃ | H |
| T1.064 | Cl | 4-Cl—C₆H₄ | CH₂CH₃ | H |
| T1.065 | Cl | 4-Cl—C₆H₄ | OCH₃ | H |
| T1.066 | CH₃ | Br | CH₃ | H |
| T1.067 | CH₃ | Cl | CH₃ | H |
| T1.068 | CH₃ | CH₃ | Br | H |
| T1.069 | CH₃ | CH₃ | Cl | H |
| T1.070 | CH₃ | CH₃ | CH₃ | H |
| T1.071 | CH₃ | CH₃ | CH₂CH₃ | H |
| T1.072 | CH₃ | CH₃ | OCH₃ | H |
| T1.073 | CH₃ | 4-Cl—C₆H₄ | CH₃ | H |
| T1.074 | CH₃ | 4-Cl—C₆H₄ | CH₂CH₃ | H |
| T1.075 | CH₃ | 4-Cl—C₆H₄ | OCH₃ | H |
| T1.076 | CH₂CH₃ | Br | Br | H |
| T1.077 | CH₂CH₃ | Br | Cl | H |
| T1.078 | CH₂CH₃ | Br | CH₃ | H |
| T1.079 | CH₂CH₃ | Br | CH₂CH₃ | H |
| T1.080 | CH₂CH₃ | Br | OCH₃ | H |
| T1.081 | CH₂CH₃ | Cl | Br | H |
| T1.082 | CH₂CH₃ | Cl | Cl | H |
| T1.083 | CH₂CH₃ | Cl | CH₃ | H |
| T1.084 | CH₂CH₃ | Cl | CH₂CH₃ | H |
| T1.085 | CH₂CH₃ | Cl | OCH₃ | H |
| T1.086 | CH₂CH₃ | CH₃ | Br | H |
| T1.087 | CH₂CH₃ | CH₃ | Cl | H |
| T1.088 | CH₂CH₃ | CH₃ | CH₂CH₃ | H |
| T1.089 | CH₂CH₃ | CH₃ | OCH₃ | H |
| T1.090 | CH₂CH₃ | CH₂CH₃ | CH₃ | H |
| T1.091 | CH₂CH₃ | CH₂CH₃ | CH₂CH₃ | H |
| T1.092 | CH₂CH₃ | 4-Cl—C₆H₄ | Br | H |
| T1.093 | CH₂CH₃ | 4-Cl—C₆H₄ | CH₂CH₃ | H |
| T1.094 | CH₂CH₃ | 4-Cl—C₆H₄ | OCH₃ | H |
| T1.095 | OCH₃ | Br | CH₃ | H |
| T1.096 | OCH₃ | Cl | CH₃ | H |
| T1.097 | OCH₃ | CH₃ | Br | H |
| T1.098 | OCH₃ | CH₃ | Cl | H |
| T1.099 | OCH₃ | CH₃ | OCH₃ | H |
| T1.100 | OCH₃ | 4-Cl—C₆H₄ | OCH₃ | H |
| T1.101 | CH₃ | CH₃ | CH₃ | F |
| T1.102 | CH₃ | CH₃ | CH₃ | Cl |
| T1.103 | CH₃ | CH₃ | CH₃ | Br |
| T1.104 | CH₃ | CH₃ | CH₃ | CH₃ |
| T1.105 | CH₃ | CH₃ | CH₃ | 4-Cl—C₆H₄ |
| T1.106 | Cl | CH₃ | CH₃ | CH₃ |
| T1.107 | CH₃ | Cl | CH₃ | CH₃ |
| T1.108 | CH₃ | CH₃ | Cl | CH₃ |
| T1.109 | CH₂CH₃ | CH₃ | CH₃ | CH₃ |
| T1.110 | OCH₃ | CH₃ | CH₃ | CH₃ |
| T1.111 | Cyclo-C3 | CH₃ | CH₃ | CH₃ |
| T1.112 | CH₃ | CH₃ | Cyclo-C3 | H |
| T1.113 | CH₃ | F | H | Br |
| T1.114 | CH₃ | CH₃ | H | Br |
| T1.115 | CH₂CH₃ | CH₃ | H | CH₃ |
| T1.116 | OCH₃ | CH₃ | H | CH₃ |
| T1.117 | Cyclo-C3 | CH₃ | H | CH₃ |
| T1.118 | CH₂CH₃ | Cl | H | CH₃ |
| T1.119 | OCH₃ | Cl | H | CH₃ |
| T1.120 | Cyclo-C3 | Cl | H | CH₃ |
| T1.121 | Cl | H | CH₃ | CH₃ |
| T1.122 | CH₃ | H | CH₃ | CH₃ |
| T1.123 | CH₂CH₃ | H | CH₃ | CH₃ |
| T1.124 | OCH₃ | H | CH₃ | CH₃ |
| T1.125 | Cyclo-C3 | H | CH₃ | CH₃ |
| T1.126 | F | H | Cl | CH₃ |
| T1.127 | Cl | H | F | CH₃ |
| T1.128 | H | CH₃ | CH₃ | CH₃ |
| T1.129 | Br | CH₃ | CH₃ | CH₃ |
| T1.130 | CH₃ | H | Cl | CH₃ |
| T1.131 | CH₃ | H | Br | CH₃ |
| T1.132 | Br | H | CH₃ | CH₃ |
| T1.133 | CH₃ | CH=CH₂ | CH₃ | H |
| T1.134 | CH₃ | CH₃ | CH=CH₂ | H |
| T1.135 | CH₃ | C≡CH | CH₃ | H |
| T1.136 | CH₃ | CH₃ | C≡CH | H |
| T1.137 | CH₃ | I | CH₃ | H |
| T1.138 | CH₃ | CH₃ | I | H |
| T1.139 | CH₃ | CH₃ | H | I |
| T1.140 | CH₃ | CF₃ | CH₃ | H |
| T1.141 | CH₃ | CH₃ | CF₃ | H |
| T1.142 | CH₃ | CHF₂ | CH₃ | H |
| T1.143 | CH₃ | CH₃ | CHF₂ | H |
| T1.144 | CH₃ | Cyclo-C3 | CH₃ | H |
| T1.145 | CH=CH₂ | CH₃ | CH=CH₂ | H |
| T1.146 | CH₃ | H | H | CF₃ |
| T1.147 | Cl | H | H | 4-Cl-3-CF₃—C₆H₃ |
| T1.148 | Cl | 4-Cl—C₆H₄ | H | H |
| T1.149 | CH₃ | CH₃ | C≡CCH₃ | H |
| T1.150 | CH₃ | C≡CCH₃ | CH₃ | H |
| T1.151 | C≡CH | CH₃ | C≡CH | H |

Table 2: This table discloses the 151 compounds T2.001 to T2.151 of the formula I₁, wherein $R^5$, $R^6$, $R^7$ and G are all hydrogen, D is NCH₃ and $R_a$, $R_b$, $R_c$ and $R_d$ are as defined in Table T1.

Table 3: This table discloses the 151 compounds T3.001 to T3.151 of the formula $I_1$, wherein $R^5$, $R^6$, $R^7$ and G are all hydrogen, D is $NCH_2CH_3$ and $R_a$, $R_b$, $R_c$ and $R_d$ are as defined in Table T1.

Table 4: This table discloses the 151 compounds T4.001 to T4.151 of the formula $I_1$, wherein $R^5$, $R^6$, $R^7$ and G are all hydrogen, D is $NCH_2CF_3$ and $R_a$, $R_b$, $R_c$ and $R_d$ are as defined in Table T1.

Table 5: This table discloses the 151 compounds T5.001 to T5.151 of the formula $I_1$, wherein $R^5$, $R^6$, $R^7$ and G are all hydrogen, D is N-allyl and $R_a$, $R_b$, $R_c$ and $R_d$ are as defined in Table T1.

Table 6: This table discloses the 151 compounds T6.001 to T6.151 of the formula $I_1$, wherein $R^5$, $R^6$, $R^7$ and G are all hydrogen, D is N-propargyl and $R_a$, $R_b$, $R_c$ and $R_d$ are as defined in Table T1.

Table 7: This table discloses the 151 compounds T7.001 to T7.151 of the formula $I_1$, wherein $R^5$, $R^6$, $R^7$ and G are all hydrogen, D is N-benzyl and $R_a$, $R_b$, $R_c$ and $R_d$ are as defined in Table T1.

Table 8: This table discloses the 151 compounds T8.001 to T8.151 of the formula $I_1$, wherein $R^5$, $R^6$, $R^7$ and G are all hydrogen, D is $NCH_2OCH_3$ and $R_a$, $R_b$, $R_c$ and $R_d$ are as defined in Table T1.

Table 9: This table discloses the 151 compounds T9.001 to T9.151 of the formula $I_1$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 10: This table discloses the 151 compounds T10.001 to T10.151 of the formula $I_1$, wherein $R^5$, $R^6$, $R^7$ and G are all hydrogen, D is NOH and $R_a$, $R_b$, $R_c$ and $R_d$ are as defined in Table T1.

Table 11: This table discloses the 151 compounds T11.001 to T11.151 of the formula $I_1$, wherein $R^5$, $R^6$, $R^7$ and G are all hydrogen, D is $NOCH_3$ and $R_a$, $R_b$, $R_c$ and $R_d$ are as defined in Table T1.

Table 12: This table discloses the 151 compounds T12.001 to T12.151 of the formula $I_1$, wherein $R^5$, $R^6$, $R^7$ and G are all hydrogen, D is $NOCH_2CH_3$ and $R_a$, $R_b$, $R_c$ and $R_d$ are as defined in Table T1.

Table 13: This table discloses the 151 compounds T13.001 to T13.151 of the formula $I_1$, wherein $R^5$, $R^6$, $R^7$ and G are all hydrogen, D is $NOCH_2CF_3$ and $R_a$, $R_b$, $R_c$ and $R_d$ are as defined in Table T1.

Table 14: This table discloses the 151 compounds T14.001 to T14.151 of the formula $I_1$, wherein $R^5$, $R^6$, $R^7$ and G are all hydrogen, D is NO-allyl and $R_a$, $R_b$, $R_c$ and $R_d$ are as defined in Table T1.

Table 15: This table discloses the 151 compounds T15.001 to T15.151 of the formula $I_1$, wherein $R^5$, $R^6$, $R^7$ and G are all hydrogen, D is NO-propargyl and $R_a$, $R_b$, $R_c$ and $R_d$ are as defined in Table T1.

Table 16: This table discloses the 151 compounds T16.001 to T16.151 of the formula $I_1$, wherein $R^5$, $R^6$, $R^7$ and G are all hydrogen, D is NO-benzyl and $R_a$, $R_b$, $R_c$ and $R_d$ are as defined in Table T1.

Table 17: This table discloses the 151 compounds T17.001 to T17.151 of the formula $I_1$, wherein $R^5$, $R^6$, $R^7$ and G are all hydrogen, D is $NOCH_2OCH_3$ and $R_a$, $R_b$, $R_c$ and $R_d$ are as defined in Table T1.

Table 18: This table discloses the 151 compounds T18.001 to T18.151 of the formula $I_1$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 19: This table discloses the 151 compounds T19.001 to T19.151 of the formula $I_1$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 20: This table discloses the 151 compounds T20.001 to T20.151 of the formula $I_1$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 21: This table discloses the 151 compounds T21.001 to T21.151 of the formula $I_1$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 22: This table discloses the 151 compounds T22.001 to T22.151 of the formula $I_1$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 23: This table discloses the 151 compounds T23.001 to T23.151 of the formula $I_1$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 24: This table discloses the 151 compounds T24.001 to T24.151 of the formula $I_1$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 25: This table discloses the 151 compounds T25.001 to T25.151 of the formula $I_1$, wherein $R^5$, $R^6$, $R^7$ and G are all hydrogen, D is NO-cyclohexyl and $R_a$, $R_b$, $R_c$ and $R_d$ are as defined in Table T1.

Table 26: This table discloses the 151 compounds T26.001 to T26.151 of the formula $I_1$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 27: This table discloses the 151 compounds T27.001 to T27.151 of the formula $I_1$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 28: This table discloses the 151 compounds T28.001 to T28.151 of the formula $I_1$, wherein $R^5$, $R^6$, $R^7$ and G are all hydrogen, D is O and $R_a$, $R_b$, $R_c$ and $R_d$ are as defined in Table T1.

Table 29: This table discloses the 151 compounds T29.001 to T29.151 of the formula $I_1$, wherein $R^5$, $R^6$, $R^7$ and G are all hydrogen, D is S and $R_a$, $R_b$, $R_c$ and $R_d$ are as defined in Table T1.

Table 30: This table discloses the 151 compounds T30.001 to T30.151 of the formula $I_2$:

wherein $R^5$, $R^6$, $R^7$ and G are all hydrogen, D is NH and $R_a$, $R_b$, $R_c$ and $R_d$ are as defined in Table T1.

Table 31: This table discloses the 151 compounds T31.001 to T31.151 of the formula $I_2$, wherein $R^5$, $R^6$, $R^7$ and G are all hydrogen, D is $NCH_3$ and $R_a$, $R_b$, $R_c$ and $R_d$ are as defined in Table T1.

Table 32: This table discloses the 151 compounds T32.001 to T32.151 of the formula $I_2$, wherein $R^5$, $R^6$, $R^7$ and G are all hydrogen, D is $NCH_2CH_3$ and $R_a$, $R_b$, $R_c$ and $R_d$ are as defined in Table T1.

Table 33: This table discloses the 151 compounds T33.001 to T33.151 of the formula I$_2$, wherein R$^5$, R$^6$, R$^7$ and G are all hydrogen, D is NCH$_2$CF$_3$ and R$_a$, R$_b$, R$_c$ and R$_d$ are as defined in Table T1.

Table 34: This table discloses the 151 compounds T34.001 to T34.151 of the formula I$_2$, wherein R$^5$, R$^6$, R$^7$ and G are all hydrogen, D is N-allyl and R$_a$, R$_b$, R$_c$ and R$_d$ are as defined in Table T1.

Table 35: This table discloses the 151 compounds T35.001 to T35.151 of the formula I$_2$, wherein R$^5$, R$^6$, R$^7$ and G are all hydrogen, D is N-propargyl and R$_a$, R$_b$, R$_c$ and R$_d$ are as defined in Table T1.

Table 36: This table discloses the 151 compounds T36.001 to T36.151 of the formula I$_2$, wherein R$^5$, R$^6$, R$^7$ and G are all hydrogen, D is N-benzyl and R$_a$, R$_b$, R$_c$ and R$_d$ are as defined in Table T1.

Table 37: This table discloses the 151 compounds T37.001 to T37.151 of the formula I$_2$, wherein R$^5$, R$^6$, R$^7$ and G are all hydrogen, D is NCH$_2$OCH$_3$ and R$_a$, R$_b$, R$_c$ and R$_d$ are as defined in Table T1.

Table 38: This table discloses the 151 compounds T38.001 to T38.151 of the formula I$_2$, wherein R$^5$, R$^6$, R$^7$ and G are all hydrogen, D is NCH$_2$CH$_2$OCH$_3$ and R$_a$, R$_b$, R$_c$ and R$_d$ are as defined in Table T1.

Table 39: This table discloses the 151 compounds T39.001 to T39.151 of the formula I$_2$, wherein R$^5$, R$^6$, R$^7$ and G are all hydrogen, D is NOH and R$_a$, R$_b$, R$_c$ and R$_d$ are as defined in Table T1.

Table 40: This table discloses the 151 compounds T40.001 to T40.151 of the formula I$_2$, wherein R$^5$, R$^6$, R$^7$ and G are all hydrogen, D is NOCH$_3$ and R$_a$, R$_b$, R$_c$ and R$_d$ are as defined in Table T1.

Table 41: This table discloses the 151 compounds T41.001 to T41.151 of the formula I$_2$, wherein R$^5$, R$^6$, R$^7$ and G are all hydrogen, D is NOCH$_2$CH$_3$ and R$_a$, R$_b$, R$_c$ and R$_d$ are as defined in Table T1.

Table 42: This table discloses the 151 compounds T42.001 to T42.151 of the formula I$_2$, wherein R$^5$, R$^6$, R$^7$ and G are all hydrogen, D is NOCH$_2$CF$_3$ and R$_a$, R$_b$, R$_c$ and R$_d$ are as defined in Table T1.

Table 43: This table discloses the 151 compounds T43.001 to T43.151 of the formula I$_2$, wherein R$^5$, R$^6$, R$^7$ and G are all hydrogen, D is NO-allyl and R$_a$, R$_b$, R$_c$ and R$_d$ are as defined in Table T1.

Table 44: This table discloses the 151 compounds T44.001 to T44.151 of the formula I$_2$, wherein R$^5$, R$^6$, R$^7$ and G are all hydrogen, D is NO-propargyl and R$_a$, R$_b$, R$_c$ and R$_d$ are as defined in Table T1.

Table 45: This table discloses the 151 compounds T45.001 to T45.151 of the formula I$_2$, wherein R$^5$, R$^6$, R$^7$ and G are all hydrogen, D is NO-benzyl and R$_a$, R$_b$, R$_c$ and R$_d$ are as defined in Table T1.

Table 46: This table discloses the 151 compounds T46.001 to T46.151 of the formula I$_2$, wherein R$^5$, R$^6$, R$^7$ and G are all hydrogen, D is NOCH$_2$OCH$_3$ and R$_a$, R$_b$, R$_c$ and R$_d$ are as defined in Table T1.

Table 47: This table discloses the 151 compounds T47.001 to T47.151 of the formula I$_2$, wherein R$^5$, R$^6$, R$^7$ and G are all hydrogen, D is NOCH$_2$CH$_2$OCH$_3$ and R$_a$, R$_b$, R$_c$ and R$_d$ are as defined in Table T1.

Table 48: This table discloses the 151 compounds T48.001 to T48.151 of the formula I$_2$, wherein R$^5$, R$^6$, R$^7$ and G are all hydrogen, D is NOCH$_2$-cyclohexyl and R$_a$, R$_b$, R$_c$ and R$_d$ are as defined in Table T1.

Table 49: This table discloses the 151 compounds T49.001 to T49.151 of the formula I$_2$, wherein R$^5$, R$^6$, R$^7$ and G are all hydrogen, D is NO-(tetrahydrofuran-2-yl) and R$_a$, R$_b$, R$_c$ and R$_d$ are as defined in Table T1.

Table 50: This table discloses the 151 compounds T50.001 to T50.151 of the formula I$_2$, wherein R$^5$, R$^6$, R$^7$ and G are all hydrogen, D is NO-(tetrahydropyran-2-yl) and R$_a$, R$_b$, R$_c$ and R$_d$ are as defined in Table T1.

Table 51: This table discloses the 151 compounds T51.001 to T51.151 of the formula I$_2$, wherein R$^5$, R$^6$, R$^7$ and G are all hydrogen, D is NO-(tetrahydrofuran-2-ylmethyl) and R$_a$, R$_b$, R$_c$ and R$_d$ are as defined in Table T1.

Table 52: This table discloses the 151 compounds T52.001 to T52.151 of the formula I$_2$, wherein R$^5$, R$^6$, R$^7$ and G are all hydrogen, D is NO-(tetrahydrofuran-3-ylmethyl) and R$_a$, R$_b$, R$_c$ and R$_d$ are as defined in Table T1.

Table 53: This table discloses the 151 compounds T53.001 to T53.151 of the formula I$_2$, wherein R$^5$, R$^6$, R$^7$ and G are all hydrogen, D is NO-(tetrahydropyran-4-ylmethyl) and R$_a$, R$_b$, R$_c$ and R$_d$ are as defined in Table T1.

Table 54: This table discloses the 151 compounds T54.001 to T54.151 of the formula I$_2$, wherein R$^5$, R$^6$, R$^7$ and G are all hydrogen, D is NO-cyclohexyl and R$_a$, R$_b$, R$_c$ and R$_d$ are as defined in Table T1.

Table 55: This table discloses the 151 compounds T55.001 to T55.151 of the formula I$_2$, wherein R$^5$, R$^6$, R$^7$ and G are all hydrogen, D is NO-(furan-2-ylmethyl) and R$_a$, R$_b$, R$_c$ and R$_d$ are as defined in Table T1.

Table 56: This table discloses the 151 compounds T56.001 to T56.151 of the formula I$_2$, wherein R$^5$, R$^6$, R$^7$ and G are all hydrogen, D is NO-(furan-3-ylmethyl) and R$_a$, R$_b$, R$_c$ and R$_d$ are as defined in Table T1.

Table 57: This table discloses the 151 compounds T57.001 to T57.151 of the formula I$_2$, wherein R$^5$, R$^6$, R$^7$ and G are all hydrogen, D is O and R$_a$, R$_b$, R$_c$ and R$_d$ are as defined in Table T1.

Table 58: This table discloses the 151 compounds T58.001 to T58.151 of the formula I$_2$, wherein R$^5$, R$^6$, R$^7$ and G are all hydrogen, D is S and R$_a$, R$_b$, R$_c$ and R$_d$ are as defined in Table T1.

Table 59: This table discloses the 151 compounds T59.001 to T59.151 of the formula I$_3$:

(I$_3$)

wherein R$^5$, R$^6$, R$^7$ and G are all hydrogen, D is NH and R$_a$, R$_b$, R$_c$ and R$_d$ are as defined in Table T1.

Table 60: This table discloses the 151 compounds T60.001 to T60.151 of the formula I$_3$, wherein R$^5$, R$^6$, R$^7$ and G are all hydrogen, D is NCH$_3$ and R$_a$, R$_b$, R$_c$ and R$_d$ are as defined in Table T1.

Table 61: This table discloses the 151 compounds T61.001 to T61.151 of the formula I$_3$, wherein R$^5$, R$^6$, R$^7$ and G are all hydrogen, D is NCH$_2$CH$_3$ and R$_a$, R$_b$, R$_c$ and R$_d$ are as defined in Table T1.

Table 62: This table discloses the 151 compounds T62.001 to T62.151 of the formula I$_3$, wherein R$^5$, R$^6$, R$^7$ and G are all hydrogen, D is NCH$_2$CF$_3$ and R$_a$, R$_b$, R$_c$ and R$_d$ are as defined in Table T1.

Table 63: This table discloses the 151 compounds T63.001 to T63.151 of the formula I$_3$, wherein R$^5$, R$^6$, R$^7$ and G are all hydrogen, D is N-allyl and R$_a$, R$_b$, R$_c$ and R$_d$ are as defined in Table T1.

Table 64: This table discloses the 151 compounds T64.001 to T64.151 of the formula I$_3$, wherein R$^5$, R$^6$, R$^7$ and G are all hydrogen, D is N-propargyl and R$_a$, R$_b$, R$_c$ and R$_d$ are as defined in Table T1.

Table 65: This table discloses the 151 compounds T65.001 to T65.151 of the formula I$_3$, wherein R$^5$, R$^6$, R$^7$ and G are all hydrogen, D is N-benzyl and R$_a$, R$_b$, R$_c$ and R$_d$ are as defined in Table T1.

Table 66: This table discloses the 151 compounds T66.001 to T66.151 of the formula I$_3$, wherein R$^5$, R$^6$, R$^7$ and G are all hydrogen, D is NCH$_2$OCH$_3$ and R$_a$, R$_b$, R$_c$ and R$_d$ are as defined in Table T1.

Table 67: This table discloses the 151 compounds T67.001 to T67.151 of the formula I$_3$, wherein R$^5$, R$^6$, R$^7$ and G are all hydrogen, D is NCH$_2$CH$_2$OCH$_3$ and R$_a$, R$_b$, R$_c$ and R$_d$ are as defined in Table T1.

Table 68: This table discloses the 151 compounds T68.001 to T68.151 of the formula I$_3$, wherein R$^5$, R$^6$, R$^7$ and G are all hydrogen, D is NOH and R$_a$, R$_b$, R$_c$ and R$_d$ are as defined in Table T1.

Table 69: This table discloses the 151 compounds T69.001 to T69.151 of the formula I$_3$, wherein R$^5$, R$^6$, R$^7$ and G are all hydrogen, D is NOCH$_3$ and R$_a$, R$_b$, R$_c$ and R$_d$ are as defined in Table T1.

Table 70: This table discloses the 151 compounds T70.001 to T70.151 of the formula I$_3$, wherein R$^5$, R$^6$, R$^7$ and G are all hydrogen, D is NOCH$_2$CH$_3$ and R$_a$, R$_b$, R$_c$ and R$_d$ are as defined in Table T1.

Table 71: This table discloses the 151 compounds T71.001 to T71.151 of the formula I$_3$, wherein R$^5$, R$^6$, R$^7$ and G are all hydrogen, D is NOCH$_2$CF$_3$ and R$_a$, R$_b$, R$_c$ and R$_d$ are as defined in Table T1.

Table 72: This table discloses the 151 compounds T72.001 to T72.151 of the formula I$_3$, wherein R$^5$, R$^6$, R$^7$ and G are all hydrogen, D is NO-allyl and R$_a$, R$_b$, R$_c$ and R$_d$ are as defined in Table T1.

Table 73: This table discloses the 151 compounds T73.001 to T73.151 of the formula I$_3$, wherein R$^5$, R$^6$, R$^7$ and G are all hydrogen, D is NO-propargyl and R$_a$, R$_b$, R$_c$ and R$_d$ are as defined in Table T1.

Table 74: This table discloses the 151 compounds T74.001 to T74.151 of the formula I$_3$, wherein R$^5$, R$^6$, R$^7$ and G are all hydrogen, D is NO-benzyl and R$_a$, R$_b$, R$_c$ and R$_d$ are as defined in Table T1.

Table 75: This table discloses the 151 compounds T75.001 to T75.151 of the formula I$_3$, wherein R$^5$, R$^6$, R$^7$ and G are all hydrogen, D is NOCH$_2$OCH$_3$ and R$_a$, R$_b$, R$_c$ and R$_d$ are as defined in Table T1.

Table 76: This table discloses the 151 compounds T76.001 to T76.151 of the formula I$_3$, wherein R$^5$, R$^6$, R$^7$ and G are all hydrogen, D is NOCH$_2$CH$_2$OCH$_3$ and R$_a$, R$_b$, R$_c$ and R$_d$ are as defined in Table T1.

Table 77: This table discloses the 151 compounds T77.001 to T77.151 of the formula I$_3$, wherein R$^5$, R$^6$, R$^7$ and G are all hydrogen, D is NOCH$_2$-cyclohexyl and R$_a$, R$_b$, R$_c$ and R$_d$ are as defined in Table T1.

Table 78: This table discloses the 151 compounds T78.001 to T78.151 of the formula I$_3$, wherein R$^5$, R$^6$, R$^7$ and G are all hydrogen, D is NO-(tetrahydrofuran-2-yl) and R$_a$, R$_b$, R$_c$ and R$_d$ are as defined in Table T1.

Table 79: This table discloses the 151 compounds T79.001 to T79.151 of the formula I$_3$, wherein R$^5$, R$^6$, R$^7$ and G are all hydrogen, D is NO-(tetrahydropyran-2-yl) and R$_a$, R$_b$, R$_c$ and R$_d$ are as defined in Table T1.

Table 80: This table discloses the 151 compounds T80.001 to T80.151 of the formula I$_3$, wherein R$^5$, R$^6$, R$^7$ and G are all hydrogen, D is NO-(tetrahydrofuran-2-ylmethyl) and R$_a$, R$_b$, R$_c$ and R$_d$ are as defined in Table T1.

Table 81: This table discloses the 151 compounds T81.001 to T81.151 of the formula I$_3$, wherein R$^5$, R$^6$, R$^7$ and G are all hydrogen, D is NO-(tetrahydrofuran-3-ylmethyl) and R$_a$, R$_b$, R$_c$ and R$_d$ are as defined in Table T1.

Table 82: This table discloses the 151 compounds T82.001 to T82.151 of the formula I$_3$, wherein R$^5$, R$^6$, R$^7$ and G are all hydrogen, D is NO-(tetrahydropyran-4-ylmethyl) and R$_a$, R$_b$, R$_c$ and R$_d$ are as defined in Table T1.

Table 83: This table discloses the 151 compounds T83.001 to T83.151 of the formula I$_3$, wherein R$^5$, R$^6$, R$^7$ and G are all hydrogen, D is NO-cyclohexyl and R$_a$, R$_b$, R$_c$ and R$_d$ are as defined in Table T1.

Table 84: This table discloses the 151 compounds T84.001 to T84.151 of the formula I$_3$, wherein R$^5$, R$^6$, R$^7$ and G are all hydrogen, D is NO-(furan-2-ylmethyl) and R$_a$, R$_b$, R$_c$ and R$_d$ are as defined in Table T1.

Table 85: This table discloses the 151 compounds T85.001 to T85.151 of the formula I$_3$, wherein R$^5$, R$^6$, R$^7$ and G are all hydrogen, D is NO-(furan-3-ylmethyl) and R$_a$, R$_b$, R$_c$ and R$_d$ are as defined in Table T1.

Table 86: This table discloses the 151 compounds T86.001 to T86.151 of the formula I$_3$, wherein R$^5$, R$^6$, R$^7$ and G are all hydrogen, D is O and R$_a$, R$_b$, R$_c$ and R$_d$ are as defined in Table T1.

Table 87: This table discloses the 151 compounds T87.001 to T87.151 of the formula I$_3$, wherein R$^5$, R$^6$, R$^7$ and G are all hydrogen, D is S and R$_a$, R$_b$, R$_c$ and R$_d$ are as defined in Table T1.

Table 88: This table discloses the 151 compounds T88.001 to T88.151 of the formula I$_4$:

wherein R$^5$, R$^6$, R$^7$ and G are all hydrogen, D is NH and R$_a$, R$_b$, R$_c$ and R$_d$ are as defined in Table T1.

Table 89: This table discloses the 151 compounds T89.001 to T89.151 of the formula I$_4$, wherein R$^5$, R$^6$, R$^7$ and G are all hydrogen, D is NCH$_3$ and R$_a$, R$_b$, R$_c$ and R$_d$ are as defined in Table T1.

Table 90: This table discloses the 151 compounds T90.001 to T90.151 of the formula I$_4$, wherein R$^5$, R$^6$, R$^7$ and G are all hydrogen, D is NCH$_2$CH$_3$ and R$_a$, R$_b$, R$_c$ and R$_d$ are as defined in Table T1.

Table 91: This table discloses the 151 compounds T91.001 to T91.151 of the formula I$_4$, wherein R$^5$, R$^6$, R$^7$ and G are all hydrogen, D is NCH$_2$CF$_3$ and R$_a$, R$_b$, R$_c$ and R$_d$ are as defined in Table T1.

Table 92: This table discloses the 151 compounds T92.001 to T92.151 of the formula I$_4$, wherein R$^5$, R$^6$, R$^7$ and G are all hydrogen, D is N-allyl and R$_a$, R$_b$, R$_c$ and R$_d$ are as defined in Table T1.

Table 93: This table discloses the 151 compounds T93.001 to T93.151 of the formula $I_4$, wherein $R^5$, $R^6$, $R^7$ and G are all hydrogen, D is N-propargyl and $R_a$, $R_b$, $R_c$ and $R_d$ are as defined in Table T1.

Table 94: This table discloses the 151 compounds T94.001 to T94.151 of the formula $I_4$, wherein $R^5$, $R^6$, $R^7$ and G are all hydrogen, D is N-benzyl and $R_a$, $R_b$, $R_c$ and $R_d$ are as defined in Table T1.

Table 95: This table discloses the 151 compounds T95.001 to T95.151 of the formula $I_4$, wherein $R^5$, $R^6$, $R^7$ and G are all hydrogen, D is $NCH_2OCH_3$ and $R_a$, $R_b$, $R_c$ and $R_d$ are as defined in Table T1.

Table 96: This table discloses the 151 compounds T96.001 to T96.151 of the formula $I_4$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 97: This table discloses the 151 compounds T97.001 to T97.151 of the formula $I_4$, wherein $R^5$, $R^6$, $R^7$ and G are all hydrogen, D is NOH and $R_a$, $R_b$, $R_c$ and $R_d$ are as defined in Table T1.

Table 98: This table discloses the 151 compounds T98.001 to T98.151 of the formula $I_4$, wherein $R^5$, $R^6$, $R^7$ and G are all hydrogen, D is $NOCH_3$ and $R_a$, $R_b$, $R_c$ and $R_d$ are as defined in Table T1.

Table 99: This table discloses the 151 compounds T99.001 to T99.151 of the formula $I_4$, wherein $R^5$, $R^6$, $R^7$ and G are all hydrogen, D is $NOCH_2CH_3$ and $R_a$, $R_b$, $R_c$ and $R_d$ are as defined in Table T1.

Table 100: This table discloses the 151 compounds T100.001 to T100.151 of the formula $I_4$, wherein $R^5$, $R^6$, $R^7$ and G are all hydrogen, D is $NOCH_2CF_3$ and $R_a$, $R_b$, $R_c$ and $R_d$ are as defined in Table T1.

Table 101: This table discloses the 151 compounds T101.001 to T101.151 of the formula $I_4$, wherein $R^5$, $R^6$, $R^7$ and G are all hydrogen, D is NO-allyl and $R_a$, $R_b$, $R_c$ and $R_d$ are as defined in Table T1.

Table 102: This table discloses the 151 compounds T102.001 to T102.151 of the formula $I_4$, wherein $R^5$, $R^6$, $R^7$ and G are all hydrogen, D is NO-propargyl and $R_a$, $R_b$, $R_c$ and $R_d$ are as defined in Table T1.

Table 103: This table discloses the 151 compounds T103.001 to T103.151 of the formula $I_4$, wherein $R^5$, $R^6$, $R^7$ and G are all hydrogen, D is NO-benzyl and $R_a$, $R_b$, $R_c$ and $R_d$ are as defined in Table T1.

Table 104: This table discloses the 151 compounds T104.001 to T104.151 of the formula $I_4$, wherein $R^5$, $R^6$, $R^7$ and G are all hydrogen, D is $NOCH_2OCH_3$ and $R_a$, $R_b$, $R_c$ and $R_d$ are as defined in Table T1.

Table 105: This table discloses the 151 compounds T105.001 to T105.151 of the formula $I_4$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 106: This table discloses the 151 compounds T106.001 to T106.151 of the formula $I_4$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 107: This table discloses the 151 compounds T107.001 to T107.101 of the formula $I_4$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 108: This table discloses the 151 compounds T108.001 to T108.151 of the formula $I_4$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 109: This table discloses the 151 compounds T109.001 to T109.151 of the formula $I_4$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 110: This table discloses the 151 compounds T110.001 to T110.151 of the formula $I_4$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 111: This table discloses the 151 compounds T111.001 to T111.151 of the formula $I_4$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 112: This table discloses the 151 compounds T112.001 to T112.151 of the formula $I_4$, wherein $R^5$, $R^6$, $R^7$ and G are all hydrogen, D is NO-cyclohexyl and $R_a$, $R_b$, $R_c$ and $R_d$ are as defined in Table T1.

Table 113: This table discloses the 151 compounds T113.001 to T113.151 of the formula $I_4$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 114: This table discloses the 151 compounds T114.001 to T114.151 of the formula $I_4$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 115: This table discloses the 151 compounds T115.001 to T115.151 of the formula $I_4$, wherein $R^5$, $R^6$, $R^7$ and G are all hydrogen, D is O and $R_a$, $R_b$, $R_c$ and $R_d$ are as defined in Table T1.

Table 116: This table discloses the 151 compounds T116.001 to T116.151 of the formula $I_4$, wherein $R^5$, $R^6$, $R^7$ and G are all hydrogen, D is S and $R_a$, $R_b$, $R_c$ and $R_d$ are as defined in Table T1.

Table 117: This table discloses the 151 compounds T117.001 to T117.151 of the formula $I_5$:

$$(I_5)$$

wherein $R^5$, $R^6$, $R^7$ and G are all hydrogen, D is NH and $R_a$, $R_b$, $R_c$ and $R_d$ are as defined in Table T1.

Table 118: This table discloses the 151 compounds T118.001 to T118.151 of the formula $I_5$, wherein $R^5$, $R^6$, $R^7$ and G are all hydrogen, D is $NCH_3$ and $R_a$, $R_b$, $R_c$ and $R_d$ are as defined in Table T1.

Table 119: This table discloses the 151 compounds T119.001 to T119.151 of the formula $I_5$, wherein $R^5$, $R^6$, $R^7$ and G are all hydrogen, D is $NCH_2CH_3$ and $R_a$, $R_b$, $R_c$ and $R_d$ are as defined in Table T1.

Table 120: This table discloses the 151 compounds T120.001 to T120.151 of the formula $I_5$, wherein $R^5$, $R^6$, $R^7$ and G are all hydrogen, D is $NCH_2CF_3$ and $R_a$, $R_b$, $R_c$ and $R_d$ are as defined in Table T1.

Table 121: This table discloses the 151 compounds T121.001 to T121.151 of the formula $I_5$, wherein $R^5$, $R^6$, $R^7$ and G are all hydrogen, D is N-allyl and $R_a$, $R_b$, $R_c$ and $R_d$ are as defined in Table T1.

Table 122: This table discloses the 151 compounds T122.001 to T122.151 of the formula $I_5$, wherein $R^5$, $R^6$, $R^7$ and G are all hydrogen, D is N-propargyl and $R_a$, $R_b$, $R_c$ and $R_d$ are as defined in Table T1.

Table 123: This table discloses the 151 compounds T123.001 to T123.151 of the formula $I_5$, wherein $R^5$, $R^6$, $R^7$ and G are all hydrogen, D is N-benzyl and $R_a$, $R_b$, $R_c$ and $R_d$ are as defined in Table T1.

Table 124: This table discloses the 151 compounds T124.001 to T124.151 of the formula $I_5$, wherein $R^5$, $R^6$, $R^7$ and G are all hydrogen, D is $NCH_2OCH_3$ and $R_a$, $R_b$, $R_c$ and $R_d$ are as defined in Table T1.

Table 125: This table discloses the 151 compounds T125.001 to T125.151 of the formula $I_5$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 126: This table discloses the 151 compounds T126.001 to T126.151 of the formula $I_5$, wherein $R^5$, $R^6$, $R^7$ and G are all hydrogen, D is NOH and $R_a$, $R_b$, $R_c$ and $R_d$ are as defined in Table T1.

Table 127: This table discloses the 151 compounds T127.001 to T127.151 of the formula $I_5$, wherein $R^5$, $R^6$, $R^7$ and G are all hydrogen, D is $NOCH_3$ and $R_a$, $R_b$, $R_c$ and $R_d$ are as defined in Table T1.

Table 128: This table discloses the 151 compounds T128.001 to T128.151 of the formula $I_5$, wherein $R^5$, $R^6$, $R^7$ and G are all hydrogen, D is $NOCH_2CH_3$ and $R_a$, $R_b$, $R_c$ and $R_d$ are as defined in Table T1.

Table 129: This table discloses the 151 compounds T129.001 to T129.151 of the formula $I_5$, wherein $R^5$, $R^6$, $R^7$ and G are all hydrogen, D is $NOCH_2CF_3$ and $R_a$, $R_b$, $R_c$ and $R_d$ are as defined in Table T1.

Table 130: This table discloses the 151 compounds T130.001 to T130.151 of the formula $I_5$, wherein $R^5$, $R^6$, $R^7$ and G are all hydrogen, D is NO-allyl and $R_a$, $R_b$, $R_c$ and $R_d$ are as defined in Table T1.

Table 131: This table discloses the 151 compounds T131.001 to T131.151 of the formula $I_5$, wherein $R^5$, $R^6$, $R^7$ and G are all hydrogen, D is NO-propargyl and $R_a$, $R_b$, $R_c$ and $R_d$ are as defined in Table T1.

Table 132: This table discloses the 151 compounds T132.001 to T132.151 of the formula $I_5$, wherein $R^5$, $R^6$, $R^7$ and G are all hydrogen, D is NO-benzyl and $R_a$, $R_b$, $R_c$ and $R_d$ are as defined in Table T1.

Table 133: This table discloses the 151 compounds T133.001 to T133.151 of the formula $I_5$, wherein $R^5$, $R^6$, $R^7$ and G are all hydrogen, D is $NOCH_2OCH_3$ and $R_a$, $R_b$, $R_c$ and $R_d$ are as defined in Table T1.

Table 134: This table discloses the 151 compounds T134.001 to T134.151 of the formula $I_5$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 135: This table discloses the 151 compounds T135.001 to T135.151 of the formula $I_5$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 136: This table discloses the 151 compounds T136.001 to T136.151 of the formula $I_5$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 137: This table discloses the 151 compounds T137.001 to T137.151 of the formula $I_5$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 138: This table discloses the 151 compounds T138.001 to T138.151 of the formula $I_5$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 139: This table discloses the 151 compounds T139.001 to T139.151 of the formula $I_5$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 140: This table discloses the 151 compounds T140.001 to T140.151 of the formula $I_5$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 141: This table discloses the 151 compounds T141.001 to T141.151 of the formula $I_5$, wherein $R^5$, $R^6$, $R^7$ and G are all hydrogen, D is NO-cyclohexyl and $R_a$, $R_b$, $R_c$ and $R_d$ are as defined in Table T1.

Table 142: This table discloses the 151 compounds T142.001 to T142.151 of the formula $I_5$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 143: This table discloses the 151 compounds T143.001 to T143.151 of the formula $I_5$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 144: This table discloses the 151 compounds T144.001 to T144.151 of the formula $I_5$, wherein $R^5$, $R^6$, $R^7$ and G are all hydrogen, D is O and $R_a$, $R_b$, $R_c$ and $R_d$ are as defined in Table T1.

Table 145: This table discloses the 151 compounds T145.001 to T145.151 of the formula $I_5$, wherein $R^5$, $R^6$, $R^7$ and G are all hydrogen, D is S and $R_a$, $R_b$, $R_c$ and $R_d$ are as defined in Table T1.

Table 146: This table discloses the 151 compounds T146.001 to T146.151 of the formula $I_6$:

$$(I_6)$$

wherein $R^5$, $R^6$, $R^7$ and G are all hydrogen, D is NH and $R_a$, $R_b$, $R_c$ and $R_d$ are as defined in Table T1.

Table 147: This table discloses the 151 compounds T147.001 to T147.151 of the formula $I_6$, wherein $R^5$, $R^6$, $R^7$ and G are all hydrogen, D is $NCH_3$ and $R_a$, $R_b$, $R_c$ and $R_d$ are as defined in Table T1.

Table 148: This table discloses the 151 compounds T148.001 to T148.151 of the formula $I_6$, wherein $R^5$, $R^6$, $R^7$ and G are all hydrogen, D is $NCH_2CH_3$ and $R_a$, $R_b$, $R_c$ and $R_d$ are as defined in Table T1.

Table 149: This table discloses the 151 compounds T149.001 to T149.151 of the formula $I_6$, wherein $R^5$, $R^6$, $R^7$ and G are all hydrogen, D is $NCH_2CF_3$ and $R_a$, $R_b$, $R_c$ and $R_d$ are as defined in Table T1.

Table 150: This table discloses the 151 compounds T150.001 to T150.151 of the formula $I_6$, wherein $R^5$, $R^6$, $R^7$ and G are all hydrogen, D is N-allyl and $R_a$, $R_b$, $R_c$ and $R_d$ are as defined in Table T1.

Table 151: This table discloses the 151 compounds T151.001 to T151.151 of the formula $I_6$, wherein $R^5$, $R^6$, $R^7$ and G are all hydrogen, D is N-propargyl and $R_a$, $R_b$, $R_c$ and $R_d$ are as defined in Table T1.

Table 152: This table discloses the 151 compounds T152.001 to T152.151 of the formula $I_6$, wherein $R^5$, $R^6$, $R^7$ and G are all hydrogen, D is N-benzyl and $R_a$, $R_b$, $R_c$ and $R_d$ are as defined in Table T1.

Table 153: This table discloses the 151 compounds T153.001 to T153.151 of the formula $I_6$, wherein $R^5$, $R^6$, $R^7$ and G are all hydrogen, D is $NCH_2OCH_3$ and $R_a$, $R_b$, $R_c$ and $R_d$ are as defined in Table T1.

Table 154: This table discloses the 151 compounds T154.001 to T154.151 of the formula $I_6$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 155: This table discloses the 151 compounds T155.001 to T155.151 of the formula $I_6$, wherein $R^5$, $R^6$, $R^7$ and G are all hydrogen, D is NOH and $R_a$, $R_b$, $R_c$ and $R_d$ are as defined in Table T1.

Table 156: This table discloses the 151 compounds T156.001 to T156.151 of the formula $I_6$, wherein $R^5$, $R^6$, $R^7$ and G are all hydrogen, D is $NOCH_3$ and $R_a$, $R_b$, $R_c$ and $R_d$ are as defined in Table T1.

Table 157: This table discloses the 151 compounds T157.001 to T157.151 of the formula $I_6$, wherein $R^5$, $R^6$, $R^7$ and G are all hydrogen, D is $NOCH_2CH_3$ and $R_a$, $R_b$, $R_c$ and $R_d$ are as defined in Table T1.

Table 158: This table discloses the 151 compounds T158.001 to T158.151 of the formula $I_6$, wherein $R^5$, $R^6$, $R^7$ and G are all hydrogen, D is $NOCH_2CF_3$ and $R_a$, $R_b$, $R_c$ and $R_d$ are as defined in Table T1.

Table 159: This table discloses the 151 compounds T159.001 to T159.151 of the formula $I_6$, wherein $R^5$, $R^6$, $R^7$ and G are all hydrogen, D is NO-allyl and $R_a$, $R_b$, $R_c$ and $R_d$ are as defined in Table T1.

Table 160: This table discloses the 151 compounds T160.001 to T160.151 of the formula $I_6$, wherein $R^5$, $R^6$, $R^7$ and G are all hydrogen, D is NO-propargyl and $R_a$, $R_b$, $R_c$ and $R_d$ are as defined in Table T1.

Table 161: This table discloses the 151 compounds T161.001 to T161.151 of the formula $I_6$, wherein $R^5$, $R^6$, $R^7$ and G are all hydrogen, D is NO-benzyl and $R_a$, $R_b$, $R_c$ and $R_d$ are as defined in Table T1.

Table 162: This table discloses the 151 compounds T162.001 to T162.151 of the formula $I_6$, wherein $R^5$, $R^6$, $R^7$ and G are all hydrogen, D is $NOCH_2OCH_3$ and $R_a$, $R_b$, $R_c$ and $R_d$ are as defined in Table T1.

Table 163: This table discloses the 151 compounds T163.001 to T163.151 of the formula $I_6$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 164: This table discloses the 151 compounds T164.001 to T164.151 of the formula $I_6$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 165: This table discloses the 151 compounds T165.001 to T165.151 of the formula $I_6$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 166: This table discloses the 151 compounds T166.001 to T166.151 of the formula $I_6$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 167: This table discloses the 151 compounds T167.001 to T167.151 of the formula $I_6$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 168: This table discloses the 151 compounds T168.001 to T168.151 of the formula $I_6$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 169: This table discloses the 151 compounds T169.001 to T169.151 of the formula $I_6$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 170: This table discloses the 151 compounds T170.001 to T170.151 of the formula $I_6$, wherein $R^5$, $R^6$, $R^7$ and G are all hydrogen, D is NO-cyclohexyl and $R_a$, $R_b$, $R_c$ and $R_d$ are as defined in Table T1.

Table 171: This table discloses the 151 compounds T171.001 to T171.151 of the formula $I_6$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 172: This table discloses the 151 compounds T172.001 to T172.151 of the formula $I_6$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 173: This table discloses the 151 compounds T173.001 to T173.151 of the formula $I_6$, wherein $R^5$, $R^6$, $R^7$ and G are all hydrogen, D is O and $R_a$, $R_b$, $R_c$ and $R_d$ are as defined in Table T1.

Table 174: This table discloses the 151 compounds T174.001 to T174.151 of the formula $I_6$, wherein $R^5$, $R^6$, $R^7$ and G are all hydrogen, D is S and $R_a$, $R_b$, $R_c$ and $R_d$ are as defined in Table T1.

Table 175: This table discloses the 151 compounds T175.001 to T175.151 of the formula $I_7$:

$$(I_7)$$

wherein $R^5$, $R^6$, $R^7$ and G are all hydrogen, D is NH and $R_a$, $R_b$, $R_c$ and $R_d$ are as defined in Table T1.

Table 176: This table discloses the 151 compounds T176.001 to T176.151 of the formula $I_7$, wherein $R^5$, $R^6$, $R^7$ and G are all hydrogen, D is $NCH_3$ and $R_a$, $R_b$, $R_c$ and $R_d$ are as defined in Table T1.

Table 177: This table discloses the 151 compounds T177.001 to T177.151 of the formula $I_7$, wherein $R^5$, $R^6$, $R^7$ and G are all hydrogen, D is $NCH_2CH_3$ and $R_a$, $R_b$, $R_c$ and $R_d$ are as defined in Table T1.

Table 178: This table discloses the 151 compounds T178.001 to T178.151 of the formula $I_7$, wherein $R^5$, $R^6$, $R^7$ and G are all hydrogen, D is $NCH_2CF_3$ and $R_a$, $R_b$, $R_c$ and $R_d$ are as defined in Table T1.

Table 179: This table discloses the 151 compounds T179.001 to T179.151 of the formula $I_7$, wherein $R^5$, $R^6$, $R^7$ and G are all hydrogen, D is N-allyl and $R_a$, $R_b$, $R_c$ and $R_d$ are as defined in Table T1.

Table 180: This table discloses the 151 compounds T180.001 to T180.151 of the formula $I_7$, wherein $R^5$, $R^6$, $R^7$ and G are all hydrogen, D is N-propargyl and $R_a$, $R_b$, $R_c$ and $R_d$ are as defined in Table T1.

Table 181: This table discloses the 151 compounds T181.001 to T181.151 of the formula $I_7$, wherein $R^5$, $R^6$, $R^7$ and G are all hydrogen, D is N-benzyl and $R_a$, $R_b$, $R_c$ and $R_d$ are as defined in Table T1.

Table 182: This table discloses the 151 compounds T182.001 to T182.151 of the formula $I_7$, wherein $R^5$, $R^6$, $R^7$ and G are all hydrogen, D is $NCH_2OCH_3$ and $R_a$, $R_b$, $R_c$ and $R_d$ are as defined in Table T1.

Table 183: This table discloses the 151 compounds T183.001 to T183.151 of the formula $I_7$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 184: This table discloses the 151 compounds T184.001 to T184.151 of the formula $I_7$, wherein $R^5$, $R^6$, $R^7$ and G are all hydrogen, D is NOH and $R_a$, $R_b$, $R_c$ and $R_d$ are as defined in Table T1.

Table 185: This table discloses the 151 compounds T185.001 to T185.151 of the formula $I_7$, wherein $R^5$, $R^6$, $R^7$ and G are all hydrogen, D is $NOCH_3$ and $R_a$, $R_b$, $R_c$ and $R_d$ are as defined in Table T1.

Table 186: This table discloses the 151 compounds T186.001 to T186.151 of the formula $I_7$, wherein $R^5$, $R^6$, $R^7$ and G are all hydrogen, D is $NOCH_2CH_3$ and $R_a$, $R_b$, $R_c$ and $R_d$ are as defined in Table T1.

Table 187: This table discloses the 151 compounds T187.001 to T187.151 of the formula $I_7$, wherein $R^5$, $R^6$, $R^7$ and G are all hydrogen, D is $NOCH_2CF_3$ and $R_a$, $R_b$, $R_c$ and $R_d$ are as defined in Table T1.

Table 188: This table discloses the 151 compounds T188.001 to T188.151 of the formula $I_7$, wherein $R^5$, $R^6$, $R^7$ and G are all hydrogen, D is NO-allyl and $R_a$, $R_b$, $R_c$ and $R_d$ are as defined in Table T1.

Table 189: This table discloses the 151 compounds T189.001 to T189.151 of the formula $I_7$, wherein $R^5$, $R^6$, $R^7$ and G are all hydrogen, D is NO-propargyl and $R_a$, $R_b$, $R_c$ and $R_d$ are as defined in Table T1.

Table 190: This table discloses the 151 compounds T190.001 to T190.151 of the formula $I_7$, wherein $R^5$, $R^6$, $R^7$ and G are all hydrogen, D is NO-benzyl and $R_a$, $R_b$, $R_c$ and $R_d$ are as defined in Table T1.

Table 191: This table discloses the 151 compounds T191.001 to T191.151 of the formula $I_7$, wherein $R^5$, $R^6$, $R^7$ and G are all hydrogen, D is $NOCH_2OCH_3$ and $R_a$, $R_b$, $R_c$ and $R_d$ are as defined in Table T1.

Table 192: This table discloses the 151 compounds T192.001 to T192.151 of the formula $I_7$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 193: This table discloses the 151 compounds T193.001 to T193.151 of the formula $I_7$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 194: This table discloses the 151 compounds T194.001 to T194.151 of the formula $I_7$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 195: This table discloses the 151 compounds T195.001 to T195.151 of the formula $I_7$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 196: This table discloses the 151 compounds T196.001 to T196.151 of the formula $I_7$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 197: This table discloses the 151 compounds T197.001 to T197.151 of the formula $I_7$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 198: This table discloses the 151 compounds T198.001 to T198.151 of the formula $I_7$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 199: This table discloses the 151 compounds T199.001 to T199.151 of the formula $I_7$, wherein $R^5$, $R^6$, $R^7$ and G are all hydrogen, D is NO-cyclohexyl and $R_a$, $R_b$, $R_c$ and $R_d$ are as defined in Table T1.

Table 200: This table discloses the 151 compounds T200.001 to T200.151 of the formula $I_7$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 201: This table discloses the 151 compounds T201.001 to T201.151 of the formula $I_7$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 202: This table discloses the 151 compounds T202.001 to T202.151 of the formula $I_7$, wherein $R^5$, $R^6$, $R^7$ and G are all hydrogen, D is O and $R_a$, $R_b$, $R_c$ and $R_d$ are as defined in Table T1.

Table 203: This table discloses the 151 compounds T203.001 to T203.151 of the formula $I_7$, wherein $R^5$, $R^6$, $R^7$ and G are all hydrogen, D is S and $R_a$, $R_b$, $R_c$ and $R_d$ are as defined in Table T1.

Table 204: This table discloses the 151 compounds T204.001 to T204.151 of the formula $I_8$:

wherein $R^5$, $R^6$, $R^7$ and G are all hydrogen, D is NH and $R_a$, $R_b$, $R_c$ and $R_d$ are as defined in Table T1.

Table 205: This table discloses the 151 compounds T205.001 to T205.151 of the formula $I_8$, wherein $R^5$, $R^6$, $R^7$ and G are all hydrogen, D is $NCH_3$ and $R_a$, $R_b$, $R_c$ and $R_d$ are as defined in Table T1.

Table 206: This table discloses the 151 compounds T206.001 to T206.151 of the formula $I_8$, wherein $R^5$, $R^6$, $R^7$ and G are all hydrogen, D is $NCH_2CH_3$ and $R_a$, $R_b$, $R_c$ and $R_d$ are as defined in Table T1.

Table 207: This table discloses the 151 compounds T207.001 to T207.151 of the formula $I_8$, wherein $R^5$, $R^6$, $R^7$ and G are all hydrogen, D is $NCH_2CF_3$ and $R_a$, $R_b$, $R_c$ and $R_d$ are as defined in Table T1.

Table 208: This table discloses the 151 compounds T208.001 to T208.151 of the formula $I_8$, wherein $R^5$, $R^6$, $R^7$ and G are all hydrogen, D is N-allyl and $R_a$, $R_b$, $R_c$ and $R_d$ are as defined in Table T1.

Table 209: This table discloses the 151 compounds T209.001 to T209.151 of the formula $I_8$, wherein $R^5$, $R^6$, $R^7$ and G are all hydrogen, D is N-propargyl and $R_a$, $R_b$, $R_c$ and $R_d$ are as defined in Table T1.

Table 210: This table discloses the 151 compounds T210.001 to T210.151 of the formula $I_8$, wherein $R^5$, $R^6$, $R^7$ and G are all hydrogen, D is N-benzyl and $R_a$, $R_b$, $R_c$ and $R_d$ are as defined in Table T1.

Table 211: This table discloses the 151 compounds T211.001 to T211.151 of the formula $I_8$, wherein $R^5$, $R^6$, $R^7$ and G are all hydrogen, D is $NCH_2OCH_3$ and $R_a$, $R_b$, $R_c$ and $R_d$ are as defined in Table T1.

Table 212: This table discloses the 151 compounds T212.001 to T212.151 of the formula $I_8$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 213: This table discloses the 151 compounds T213.001 to T213.151 of the formula $I_8$, wherein $R^5$, $R^6$, $R^7$ and G are all hydrogen, D is NOH and $R_a$, $R_b$, $R_c$ and $R_d$ are as defined in Table T1.

Table 214: This table discloses the 151 compounds T214.001 to T214.151 of the formula $I_8$, wherein $R^5$, $R^6$, $R^7$ and G are all hydrogen, D is $NOCH_3$ and $R_a$, $R_b$, $R_c$ and $R_d$ are as defined in Table T1.

Table 215: This table discloses the 151 compounds T215.001 to T215.151 of the formula $I_8$, wherein $R^5$, $R^6$, $R^7$ and G are all hydrogen, D is $NOCH_2CH_3$ and $R_a$, $R_b$, $R_c$ and $R_d$ are as defined in Table T1.

Table 216: This table discloses the 151 compounds T216.001 to T216.151 of the formula $I_8$, wherein $R^5$, $R^6$, $R^7$ and G are all hydrogen, D is $NOCH_2CF_3$ and $R_a$, $R_b$, $R_c$ and $R_d$ are as defined in Table T1.

Table 217: This table discloses the 151 compounds T217.001 to T217.151 of the formula $I_8$, wherein $R^5$, $R^6$, $R^7$ and G are all hydrogen, D is NO-allyl and $R_a$, $R_b$, $R_c$ and $R_d$ are as defined in Table T1.

Table 218: This table discloses the 151 compounds T218.001 to T218.151 of the formula $I_8$, wherein $R^5$, $R^6$, $R^7$ and G are all hydrogen, D is NO-propargyl and $R_a$, $R_b$, $R_c$ and $R_d$ are as defined in Table T1.

Table 219: This table discloses the 151 compounds T219.001 to T219.151 of the formula $I_8$, wherein $R^5$, $R^6$, $R^7$ and G are all hydrogen, D is NO-benzyl and $R_a$, $R_b$, $R_c$ and $R_d$ are as defined in Table T1.

Table 220: This table discloses the 151 compounds T220.001 to T220.151 of the formula $I_8$, wherein $R^5$, $R^6$, $R^7$ and G are all hydrogen, D is $NOCH_2OCH_3$ and $R_a$, $R_b$, $R_c$ and $R_d$ are as defined in Table T1.

Table 221: This table discloses the 151 compounds T221.001 to T221.151 of the formula $I_8$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 222: This table discloses the 151 compounds T222.001 to T222.151 of the formula $I_8$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 223: This table discloses the 151 compounds T223.001 to T223.151 of the formula $I_8$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 224: This table discloses the 151 compounds T224.001 to T224.151 of the formula $I_8$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 225: This table discloses the 151 compounds T225.001 to T225.151 of the formula $I_8$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 226: This table discloses the 151 compounds T226.001 to T226.151 of the formula $I_8$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 227: This table discloses the 151 compounds T227.001 to T227.151 of the formula $I_8$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 228: This table discloses the 151 compounds T228.001 to T228.151 of the formula $I_8$, wherein $R^5$, $R^6$, $R^7$ and G are all hydrogen, D is NO-cyclohexyl and $R_a$, $R_b$, $R_c$ and $R_d$ are as defined in Table T1.

Table 229: This table discloses the 151 compounds T229.001 to T229.151 of the formula $I_8$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 230: This table discloses the 151 compounds T230.001 to T230.151 of the formula $I_8$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 231: This table discloses the 151 compounds T231.001 to T231.151 of the formula $I_8$, wherein $R^5$, $R^6$, $R^7$ and G are all hydrogen, D is O and $R_a$, $R_b$, $R_c$ and $R_d$ are as defined in Table T1.

Table 232: This table discloses the 151 compounds T232.001 to T232.151 of the formula $I_8$, wherein $R^5$, $R^6$, $R^7$ and G are all hydrogen, D is S and $R_a$, $R_b$, $R_c$ and $R_d$ are as defined in Table T1.

Table 233: This table discloses the 151 compounds T233.001 to T233.151 of the formula $I_9$:

$$(I_9)$$

wherein $R^5$, $R^6$, $R^7$ and G are all hydrogen, D is NH and $R_a$, $R_b$, $R_c$ and $R_d$ are as defined in Table T1.

Table 234: This table discloses the 151 compounds T234.001 to T234.151 of the formula $I_9$, wherein $R^5$, $R^6$, $R^7$ and G are all hydrogen, D is $NCH_3$ and $R_a$, $R_b$, $R_c$ and $R_d$ are as defined in Table T1.

Table 235: This table discloses the 151 compounds T235.001 to T235.151 of the formula $I_9$, wherein $R^5$, $R^6$, $R^7$ and G are all hydrogen, D is $NCH_2CH_3$ and $R_a$, $R_b$, $R_c$ and $R_d$ are as defined in Table T1.

Table 236: This table discloses the 151 compounds T236.001 to T236.151 of the formula $I_9$, wherein $R^5$, $R^6$, $R^7$ and G are all hydrogen, D is $NCH_2CF_3$ and $R_a$, $R_b$, $R_c$ and $R_d$ are as defined in Table T1.

Table 237: This table discloses the 151 compounds T237.001 to T237.151 of the formula $I_9$, wherein $R^5$, $R^6$, $R^7$ and G are all hydrogen, D is N-allyl and $R_a$, $R_b$, $R_c$ and $R_d$ are as defined in Table T1.

Table 238: This table discloses the 151 compounds T238.001 to T238.151 of the formula $I_9$, wherein $R^5$, $R^6$, $R^7$ and G are all hydrogen, D is N-propargyl and $R_a$, $R_b$, $R_c$ and $R_d$ are as defined in Table T1.

Table 239: This table discloses the 151 compounds T239.001 to T239.151 of the formula $I_9$, wherein $R^5$, $R^6$, $R^7$ and G are all hydrogen, D is N-benzyl and $R_a$, $R_b$, $R_c$ and $R_d$ are as defined in Table T1.

Table 240: This table discloses the 151 compounds T240.001 to T240.151 of the formula $I_9$, wherein $R^5$, $R^6$, $R^7$ and G are all hydrogen, D is $NCH_2OCH_3$ and $R_a$, $R_b$, $R_c$ and $R_d$ are as defined in Table T1.

Table 241: This table discloses the 151 compounds T241.001 to T241.151 of the formula $I_9$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 242: This table discloses the 151 compounds T242.001 to T242.151 of the formula $I_9$, wherein $R^5$, $R^6$, $R^7$ and G are all hydrogen, D is NOH and $R_a$, $R_b$, $R_c$ and $R_d$ are as defined in Table T1.

Table 243: This table discloses the 151 compounds T243.001 to T243.151 of the formula $I_9$, wherein $R^5$, $R^6$, $R^7$ and G are all hydrogen, D is $NOCH_3$ and $R_a$, $R_b$, $R_c$ and $R_d$ are as defined in Table T1.

Table 244: This table discloses the 151 compounds T244.001 to T244.151 of the formula $I_9$, wherein $R^5$, $R^6$, $R^7$ and G are all hydrogen, D is $NOCH_2CH_3$ and $R_a$, $R_b$, $R_c$ and $R_d$ are as defined in Table T1.

Table 245: This table discloses the 151 compounds T245.001 to T245.151 of the formula $I_9$, wherein $R^5$, $R^6$, $R^7$ and G are all hydrogen, D is $NOCH_2CF_3$ and $R_a$, $R_b$, $R_c$ and $R_d$ are as defined in Table T1.

Table 246: This table discloses the 151 compounds T246.001 to T246.151 of the formula $I_9$, wherein $R^5$, $R^6$, $R^7$ and G are all hydrogen, D is NO-allyl and $R_a$, $R_b$, $R_c$ and $R_d$ are as defined in Table T1.

Table 247: This table discloses the 151 compounds T247.001 to T247.151 of the formula $I_9$, wherein $R^5$, $R^6$, $R^7$ and G are all hydrogen, D is NO-propargyl and $R_a$, $R_b$, $R_c$ and $R_d$ are as defined in Table T1.

Table 248: This table discloses the 151 compounds T248.001 to T248.151 of the formula $I_9$, wherein $R^5$, $R^6$, $R^7$ and G are all hydrogen, D is NO-benzyl and $R_a$, $R_b$, $R_c$ and $R_d$ are as defined in Table T1.

Table 249: This table discloses the 151 compounds T249.001 to T249.151 of the formula $I_9$, wherein $R^5$, $R^6$, $R^7$ and G are all hydrogen, D is $NOCH_2OCH_3$ and $R_a$, $R_b$, $R_c$ and $R_d$ are as defined in Table T1.

Table 250: This table discloses the 151 compounds T250.001 to T250.151 of the formula $I_9$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 251: This table discloses the 151 compounds T251.001 to T251.151 of the formula $I_9$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 252: This table discloses the 151 compounds T252.001 to T252.151 of the formula $I_9$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 253: This table discloses the 151 compounds T253.001 to T253.151 of the formula $I_9$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 254: This table discloses the 151 compounds T254.001 to T254.151 of the formula $I_9$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 255: This table discloses the 151 compounds T255.001 to T255.151 of the formula $I_9$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 256: This table discloses the 151 compounds T256.001 to T256.151 of the formula $I_9$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 257: This table discloses the 151 compounds T257.001 to T257.151 of the formula $I_9$, wherein $R^5$, $R^6$, $R^7$ and G are all hydrogen, D is NO-cyclohexyl and $R_a$, $R_b$, $R_c$ and $R_d$ are as defined in Table T1.

Table 258: This table discloses the 151 compounds T258.001 to T258.151 of the formula $I_9$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 259: This table discloses the 151 compounds T259.001 to T259.151 of the formula $I_9$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 260: This table discloses the 151 compounds T260.001 to T260.151 of the formula $I_9$, wherein $R^5$, $R^6$, $R^7$ and G are all hydrogen, D is O and $R_a$, $R_b$, $R_c$ and $R_d$ are as defined in Table T1.

Table 261: This table discloses the 151 compounds T261.001 to T261.151 of the formula $I_9$, wherein $R^5$, $R^6$, $R^7$ and G are all hydrogen, D is S and $R_a$, $R_b$, $R_c$ and $R_d$ are as defined in Table T1.

Table 262: This table discloses the 151 compounds T262.001 to T262.151 of the formula $I_{10}$:

$$(I_{10})$$

wherein $R^5$, $R^6$, $R^7$ and G are all hydrogen, D is NH and $R_a$, $R_b$, $R_c$ and $R_d$ are as defined in Table T1.

Table 263: This table discloses the 151 compounds T263.001 to T263.151 of the formula $I_{10}$, wherein $R^5$, $R^6$, $R^7$ and G are all hydrogen, D is $NCH_3$ and $R_a$, $R_b$, $R_c$ and $R_d$ are as defined in Table T1.

Table 264: This table discloses the 151 compounds T264.001 to T264.151 of the formula $I_{10}$, wherein $R^5$, $R^6$, $R^7$ and G are all hydrogen, D is $NCH_2CH_3$ and $R_a$, $R_b$, $R_c$ and $R_d$ are as defined in Table T1.

Table 265: This table discloses the 151 compounds T265.001 to T265.151 of the formula $I_{10}$, wherein $R^5$, $R^6$, $R^7$ and G are all hydrogen, D is $NCH_2CF_3$ and $R_a$, $R_b$, $R_c$ and $R_d$ are as defined in Table T1.

Table 266: This table discloses the 151 compounds T266.001 to T266.151 of the formula $I_{10}$, wherein $R^5$, $R^6$, $R^7$ and G are all hydrogen, D is N-allyl and $R_a$, $R_b$, $R_c$ and $R_d$ are as defined in Table T1.

Table 267: This table discloses the 151 compounds T267.001 to T267.151 of the formula $I_{10}$, wherein $R^5$, $R^6$, $R^7$ and G are all hydrogen, D is N-propargyl and $R_a$, $R_b$, $R_c$ and $R_d$ are as defined in Table T1.

Table 268: This table discloses the 151 compounds T268.001 to T268.151 of the formula $I_{10}$, wherein $R^5$, $R^6$, $R^7$ and G are all hydrogen, D is N-benzyl and $R_a$, $R_b$, $R_c$ and $R_d$ are as defined in Table T1.

Table 269: This table discloses the 151 compounds T269.001 to T269.151 of the formula $I_{10}$, wherein $R^5$, $R^6$, $R^7$ and G are all hydrogen, D is $NCH_2OCH_3$ and $R_a$, $R_b$, $R_c$ and $R_d$ are as defined in Table T1.

Table 270: This table discloses the 151 compounds T270.001 to T270.151 of the formula $I_{10}$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 271: This table discloses the 151 compounds T271.001 to T271.151 of the formula $I_{10}$, wherein $R^5$, $R^6$, $R^7$ and G are all hydrogen, D is NOH and $R_a$, $R_b$, $R_c$ and $R_d$ are as defined in Table T1.

Table 272: This table discloses the 151 compounds T272.001 to T272.151 of the formula $I_{10}$, wherein $R^5$, $R^6$, $R^7$ and G are all hydrogen, D is $NOCH_3$ and $R_a$, $R_b$, $R_c$ and $R_d$ are as defined in Table T1.

Table 273: This table discloses the 151 compounds T273.001 to T273.151 of the formula $I_{10}$, wherein $R^5$, $R^6$, $R^7$ and G are all hydrogen, D is $NOCH_2CH_3$ and $R_a$, $R_b$, $R_c$ and $R_d$ are as defined in Table T1.

Table 274: This table discloses the 151 compounds T274.001 to T274.151 of the formula $I_{10}$, wherein $R^5$, $R^6$, $R^7$ and G are all hydrogen, D is $NOCH_2CF_3$ and $R_a$, $R_b$, $R_c$ and $R_d$ are as defined in Table T1.

Table 275: This table discloses the 151 compounds T275.001 to T275.151 of the formula $I_{10}$, wherein $R^5$, $R^6$, $R^7$ and G are all hydrogen, D is NO-allyl and $R_a$, $R_b$, $R_c$ and $R_d$ are as defined in Table T1.

Table 276: This table discloses the 151 compounds T276.001 to T276.151 of the formula $I_{10}$, wherein $R^5$, $R^6$, $R^7$ and G are all hydrogen, D is NO-propargyl and $R_a$, $R_b$, $R_c$ and $R_d$ are as defined in Table T1.

Table 277: This table discloses the 151 compounds T277.001 to T277.151 of the formula $I_{10}$, wherein $R^5$, $R^6$, $R^7$ and G are all hydrogen, D is NO-benzyl and $R_a$, $R_b$, $R_c$ and $R_d$ are as defined in Table T1.

Table 278: This table discloses the 151 compounds T278.001 to T278.151 of the formula $I_{10}$, wherein $R^5$, $R^6$, $R^7$ and G are all hydrogen, D is $NOCH_2OCH_3$ and $R_a$, $R_b$, $R_c$ and $R_d$ are as defined in Table T1.

Table 279: This table discloses the 151 compounds T279.001 to T279.151 of the formula $I_{10}$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 280: This table discloses the 151 compounds T280.001 to T280.151 of the formula $I_{10}$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 281: This table discloses the 151 compounds T281.001 to T281.151 of the formula $I_{10}$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 282: This table discloses the 151 compounds T282.001 to T282.151 of the formula $I_{10}$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 283: This table discloses the 151 compounds T283.001 to T283.151 of the formula $I_{10}$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 284: This table discloses the 151 compounds T284.001 to T284.151 of the formula $I_{10}$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 285: This table discloses the 151 compounds T285.001 to T285.151 of the formula $I_{10}$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 286: This table discloses the 151 compounds T286.001 to T286.151 of the formula $I_{10}$, wherein $R^5$, $R^6$, $R^7$ and G are all hydrogen, D is NO-cyclohexyl and $R_a$, $R_b$, $R_c$ and $R_d$ are as defined in Table T1.

Table 287: This table discloses the 151 compounds T287.001 to T287.151 of the formula $I_{10}$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 288: This table discloses the 151 compounds T288.001 to T288.151 of the formula $I_{10}$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 289: This table discloses the 151 compounds T289.001 to T289.151 of the formula $I_{10}$, wherein $R^5$, $R^6$, $R^7$ and G are all hydrogen, D is O and $R_a$, $R_b$, $R_c$ and $R_d$ are as defined in Table T1.

Table 290: This table discloses the 151 compounds T290.001 to T290.151 of the formula $I_{10}$, wherein $R^5$, $R^6$, $R^7$ and G are all hydrogen, D is S and $R_a$, $R_b$, $R_c$ and $R_d$ are as defined in Table T1.

Table 291: This table discloses the 151 compounds T291.001 to T291.151 of the formula $I_{11}$:

(I<sub>11</sub>)

wherein $R^5$, $R^6$, $R^7$ and G are all hydrogen, D is NH and $R_a$, $R_b$, $R_c$ and $R_d$ are as defined in Table T1.

Table 292: This table discloses the 151 compounds T292.001 to T292.151 of the formula $I_{11}$, wherein $R^5$, $R^6$, $R^7$ and G are all hydrogen, D is $NCH_3$ and $R_a$, $R_b$, $R_c$ and $R_d$ are as defined in Table T1.

Table 293: This table discloses the 151 compounds T293.001 to T293.151 of the formula $I_{11}$, wherein $R^5$, $R^6$, $R^7$ and G are all hydrogen, D is $NCH_2CH_3$ and $R_a$, $R_b$, $R_c$ and $R_d$ are as defined in Table T1.

Table 294: This table discloses the 151 compounds T294.001 to T294.151 of the formula $I_{11}$, wherein $R^5$, $R^6$, $R^7$ and G are all hydrogen, D is $NCH_2CF_3$ and $R_a$, $R_b$, $R_c$ and $R_d$ are as defined in Table T1.

Table 295: This table discloses the 151 compounds T295.001 to T295.151 of the formula $I_{11}$, wherein $R^5$, $R^6$, $R^7$ and G are all hydrogen, D is N-allyl and $R_a$, $R_b$, $R_c$ and $R_d$ are as defined in Table T1.

Table 296: This table discloses the 151 compounds T296.001 to T296.151 of the formula $I_{11}$, wherein $R^5$, $R^6$, $R^7$ and G are all hydrogen, D is N-propargyl and $R_a$, $R_b$, $R_c$ and $R_d$ are as defined in Table T1.

Table 297: This table discloses the 151 compounds T297.001 to T297.151 of the formula $I_{11}$, wherein $R^5$, $R^6$, $R^7$ and G are all hydrogen, D is N-benzyl and $R_a$, $R_b$, $R_c$ and $R_d$ are as defined in Table T1.

Table 298: This table discloses the 151 compounds T298.001 to T298.151 of the formula $I_{11}$, wherein $R^5$, $R^6$, $R^7$ and G are all hydrogen, D is $NCH_2OCH_3$ and $R_a$, $R_b$, $R_c$ and $R_d$ are as defined in Table T1.

Table 299: This table discloses the 151 compounds T299.001 to T299.151 of the formula $I_{11}$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 300: This table discloses the 151 compounds T300.001 to T300.151 of the formula $I_{11}$, wherein $R^5$, $R^6$, $R^7$ and G are all hydrogen, D is NOH and $R_a$, $R_b$, $R_c$ and $R_d$ are as defined in Table T1.

Table 301: This table discloses the 151 compounds T301.001 to T301.151 of the formula $I_{11}$, wherein $R^5$, $R^6$, $R^7$ and G are all hydrogen, D is $NOCH_3$ and $R_a$, $R_b$, $R_c$ and $R_d$ are as defined in Table T1.

Table 302: This table discloses the 151 compounds T302.001 to T302.151 of the formula $I_{11}$, wherein $R^5$, $R^6$, $R^7$ and G are all hydrogen, D is $NOCH_2CH_3$ and $R_a$, $R_b$, $R_c$ and $R_d$ are as defined in Table T1.

Table 303: This table discloses the 151 compounds T303.001 to T303.151 of the formula $I_{11}$, wherein $R^5$, $R^6$, $R^7$ and G are all hydrogen, D is $NOCH_2CF_3$ and $R_a$, $R_b$, $R_c$ and $R_d$ are as defined in Table T1.

Table 304: This table discloses the 151 compounds T304.001 to T304.151 of the formula $I_{11}$, wherein $R^5$, $R^6$, $R^7$ and G are all hydrogen, D is NO-allyl and $R_a$, $R_b$, $R_c$ and $R_d$ are as defined in Table T1.

Table 305: This table discloses the 151 compounds T305.001 to T305.151 of the formula $I_{11}$, wherein $R^5$, $R^6$, $R^7$ and G are all hydrogen, D is NO-propargyl and $R_a$, $R_b$, $R_c$ and $R_d$ are as defined in Table T1.

Table 306: This table discloses the 151 compounds T306.001 to T306.151 of the formula $I_{11}$, wherein $R^5$, $R^6$, $R^7$ and G are all hydrogen, D is NO-benzyl and $R_a$, $R_b$, $R_c$ and $R_d$ are as defined in Table T1.

Table 307: This table discloses the 151 compounds T307.001 to T307.151 of the formula $I_{11}$, wherein $R^5$, $R^6$, $R^7$ and G are all hydrogen, D is $NOCH_2OCH_3$ and $R_a$, $R_b$, $R_c$ and $R_d$ are as defined in Table T1.

Table 308: This table discloses the 151 compounds T308.001 to T308.151 of the formula $I_{11}$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 309: This table discloses the 151 compounds T309.001 to T309.151 of the formula $I_{11}$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 310: This table discloses the 151 compounds T310.001 to T310.151 of the formula $I_{11}$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 311: This table discloses the 151 compounds T311.001 to T311.151 of the formula $I_{11}$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 312: This table discloses the 151 compounds T312.001 to T312.151 of the formula $I_{11}$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 313: This table discloses the 151 compounds T313.001 to T313.151 of the formula $I_{11}$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 314: This table discloses the 151 compounds T314.001 to T314.151 of the formula $I_{11}$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 315: This table discloses the 151 compounds T315.001 to T315.151 of the formula $I_{11}$, wherein $R^5$, $R^6$, $R^7$ and G are all hydrogen, D is NO-cyclohexyl and $R_a$, $R_b$, $R_c$ and $R_d$ are as defined in Table T1.

Table 316: This table discloses the 151 compounds T316.001 to T316.151 of the formula $I_{11}$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 317: This table discloses the 151 compounds T317.001 to T317.151 of the formula $I_{11}$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 318: This table discloses the 151 compounds T318.001 to T318.151 of the formula $I_{11}$, wherein $R^5$, $R^6$, $R^7$ and G are all hydrogen, D is O and $R_a$, $R_b$, $R_c$ and $R_d$ are as defined in Table T1.

Table 319: This table discloses the 151 compounds T319.001 to T319.151 of the formula $I_{11}$, wherein $R^5$, $R^6$, $R^7$ and G are all hydrogen, D is S and $R_a$, $R_b$, $R_c$ and $R_d$ are as defined in Table T1.

Table 320: This table discloses the 151 compounds T320.001 to T320.151 of the formula $I_{12}$:

$$(I_{12})$$

wherein $R^5$, $R^6$, $R^7$ and G are all hydrogen, D is NH and $R_a$, $R_b$, $R_c$ and $R_d$ are as defined in Table T1.

Table 321: This table discloses the 151 compounds T321.001 to T321.151 of the formula $I_{12}$, wherein $R^5$, $R^6$, $R^7$ and G are all hydrogen, D is $NCH_3$ and $R_a$, $R_b$, $R_c$ and $R_d$ are as defined in Table T1.

Table 322: This table discloses the 151 compounds T322.001 to T322.151 of the formula $I_{12}$, wherein $R^5$, $R^6$, $R^7$ and G are all hydrogen, D is $NCH_2CH_3$ and $R_a$, $R_b$, $R_c$ and $R_d$ are as defined in Table T1.

Table 323: This table discloses the 151 compounds T323.001 to T323.151 of the formula $I_{12}$, wherein $R^5$, $R^6$, $R^7$ and G are all hydrogen, D is $NCH_2CF_3$ and $R_a$, $R_b$, $R_c$ and $R_d$ are as defined in Table T1.

Table 324: This table discloses the 151 compounds T324.001 to T324.151 of the formula $I_{12}$, wherein $R^5$, $R^6$, $R^7$ and G are all hydrogen, D is N-allyl and $R_a$, $R_b$, $R_c$ and $R_d$ are as defined in Table T1.

Table 325: This table discloses the 151 compounds T325.001 to T325.151 of the formula $I_{12}$, wherein $R^5$, $R^6$, $R^7$ and G are all hydrogen, D is N-propargyl and $R_a$, $R_b$, $R_c$ and $R_d$ are as defined in Table T1.

Table 326: This table discloses the 151 compounds T326.001 to T326.151 of the formula $I_{12}$, wherein $R^5$, $R^6$, $R^7$ and G are all hydrogen, D is N-benzyl and $R_a$, $R_b$, $R_c$ and $R_d$ are as defined in Table T1.

Table 327: This table discloses the 151 compounds T327.001 to T327.151 of the formula $I_{12}$, wherein $R^5$, $R^6$, $R^7$ and G are all hydrogen, D is $NCH_2OCH_3$ and $R_a$, $R_b$, $R_c$ and $R_d$ are as defined in Table T1.

Table 328: This table discloses the 151 compounds T328.001 to T328.151 of the formula $I_{12}$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 329: This table discloses the 151 compounds T329.001 to T329.151 of the formula $I_{12}$, wherein $R^5$, $R^6$, $R^7$ and G are all hydrogen, D is NOH and $R_a$, $R_b$, $R_c$ and $R_d$ are as defined in Table T1.

Table 330: This table discloses the 151 compounds T330.001 to T330.151 of the formula $I_{12}$, wherein $R^5$, $R^6$, $R^7$ and G are all hydrogen, D is $NOCH_3$ and $R_a$, $R_b$, $R_c$ and $R_d$ are as defined in Table T1.

Table 331: This table discloses the 151 compounds T331.001 to T331.151 of the formula $I_{12}$, wherein $R^5$, $R^6$, $R^7$ and G are all hydrogen, D is $NOCH_2CH_3$ and $R_a$, $R_b$, $R_c$ and $R_d$ are as defined in Table T1.

Table 332: This table discloses the 151 compounds T332.001 to T332.151 of the formula $I_{12}$, wherein $R^5$, $R^6$, $R^7$ and G are all hydrogen, D is $NOCH_2CF_3$ and $R_a$, $R_b$, $R_c$ and $R_d$ are as defined in Table T1.

Table 333: This table discloses the 151 compounds T333.001 to T333.151 of the formula $I_{12}$, wherein $R^5$, $R^6$, $R^7$ and G are all hydrogen, D is NO-allyl and $R_a$, $R_b$, $R_c$ and $R_d$ are as defined in Table T1.

Table 334: This table discloses the 151 compounds T334.001 to T334.151 of the formula $I_{12}$, wherein $R^5$, $R^6$, $R^7$ and G are all hydrogen, D is NO-propargyl and $R_a$, $R_b$, $R_c$ and $R_d$ are as defined in Table T1.

Table 335: This table discloses the 151 compounds T335.001 to T335.151 of the formula $I_{12}$, wherein $R^5$, $R^6$, $R^7$ and G are all hydrogen, D is NO-benzyl and $R_a$, $R_b$, $R_c$ and $R_d$ are as defined in Table T1.

Table 336: This table discloses the 151 compounds T336.001 to T336.151 of the formula $I_{12}$, wherein $R^5$, $R^6$, $R^7$ and G are all hydrogen, D is $NOCH_2OCH_3$ and $R_a$, $R_b$, $R_c$ and $R_d$ are as defined in Table T1.

Table 337: This table discloses the 151 compounds T337.001 to T337.151 of the formula $I_{12}$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 338: This table discloses the 151 compounds T338.001 to T338.151 of the formula $I_{12}$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 339: This table discloses the 151 compounds T339.001 to T339.151 of the formula $I_{12}$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 340: This table discloses the 151 compounds T340.001 to T340.151 of the formula $I_{12}$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 341: This table discloses the 151 compounds T341.001 to T341.151 of the formula $I_{12}$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 342: This table discloses the 151 compounds T342.001 to T342.151 of the formula $I_{12}$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 343: This table discloses the 151 compounds T343.001 to T343.151 of the formula $I_{12}$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 344: This table discloses the 151 compounds T344.001 to T344.151 of the formula $I_{12}$, wherein $R^5$, $R^6$, $R^7$ and G are all hydrogen, D is NO-cyclohexyl and $R_a$, $R_b$, $R_c$ and $R_d$ are as defined in Table T1.

Table 345: This table discloses the 151 compounds T345.001 to T345.151 of the formula $I_{12}$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 346: This table discloses the 151 compounds T346.001 to T346.151 of the formula $I_{12}$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 347: This table discloses the 151 compounds T347.001 to T347.151 of the formula $I_{12}$, wherein $R^5$, $R^6$, $R^7$ and G are all hydrogen, D is O and $R_a$, $R_b$, $R_c$ and $R_d$ are as defined in Table T1.

Table 348: This table discloses the 151 compounds T348.001 to T348.151 of the formula $I_{12}$, wherein $R^5$, $R^6$, $R^7$ and G are all hydrogen, D is S and $R_a$, $R_b$, $R_c$ and $R_d$ are as defined in Table T1.

Table 349: This table discloses the 151 compounds T349.001 to T349.151 of the formula $I_{13}$:

$$(I_{13})$$

wherein $R^5$, $R^6$, $R^7$ and G are all hydrogen, D is NH and $R_a$, $R_b$, $R_c$ and $R_d$ are as defined in Table T1.

Table 350: This table discloses the 151 compounds T350.001 to T350.151 of the formula $I_{13}$, wherein $R^5$, $R^6$, $R^7$ and G are all hydrogen, D is $NCH_3$ and $R_a$, $R_b$, $R_c$ and $R_d$ are as defined in Table T1.

Table 351: This table discloses the 151 compounds T351.001 to T351.151 of the formula $I_{13}$, wherein $R^5$, $R^6$, $R^7$ and G are all hydrogen, D is $NCH_2CH_3$ and $R_a$, $R_b$, $R_c$ and $R_d$ are as defined in Table T1.

Table 352: This table discloses the 151 compounds T352.001 to T352.151 of the formula $I_{13}$, wherein $R^5$, $R^6$, $R^7$ and G are all hydrogen, D is $NCH_2CF_3$ and $R_a$, $R_b$, $R_c$ and $R_d$ are as defined in Table T1.

Table 353: This table discloses the 151 compounds T353.001 to T353.151 of the formula $I_{13}$, wherein $R^5$, $R^6$, $R^7$ and G are all hydrogen, D is N-allyl and $R_a$, $R_b$, $R_c$ and $R_d$ are as defined in Table T1.

Table 354: This table discloses the 151 compounds T354.001 to T354.151 of the formula $I_{13}$, wherein $R^5$, $R^6$, $R^7$ and G are all hydrogen, D is N-propargyl and $R_a$, $R_b$, $R_c$ and $R_d$ are as defined in Table T1.

Table 355: This table discloses the 151 compounds T355.001 to T355.151 of the formula $I_{13}$, wherein $R^5$, $R^6$, $R^7$ and G are all hydrogen, D is N-benzyl and $R_a$, $R_b$, $R_c$ and $R_d$ are as defined in Table T1.

Table 356: This table discloses the 151 compounds T356.001 to T356.151 of the formula $I_{13}$, wherein $R^5$, $R^6$, $R^7$ and G are all hydrogen, D is $NCH_2OCH_3$ and $R_a$, $R_b$, $R_c$ and $R_d$ are as defined in Table T1.

Table 357: This table discloses the 151 compounds T357.001 to T357.151 of the formula $I_{13}$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 358: This table discloses the 151 compounds T358.001 to T358.151 of the formula $I_{13}$, wherein $R^5$, $R^6$, $R^7$ and G are all hydrogen, D is NOH and $R_a$, $R_b$, $R_c$ and $R_d$ are as defined in Table T1.

Table 359: This table discloses the 151 compounds T359.001 to T359.151 of the formula $I_{13}$, wherein $R^5$, $R^6$, $R^7$ and G are all hydrogen, D is $NOCH_3$ and $R_a$, $R_b$, $R_c$ and $R_d$ are as defined in Table T1.

Table 360: This table discloses the 151 compounds T360.001 to T360.151 of the formula $I_{13}$, wherein $R^5$, $R^6$, $R^7$ and G are all hydrogen, D is $NOCH_2CH_3$ and $R_a$, $R_b$, $R_c$ and $R_d$ are as defined in Table T1.

Table 361: This table discloses the 151 compounds T361.001 to T361.151 of the formula $I_{13}$, wherein $R^5$, $R^6$, $R^7$ and G are all hydrogen, D is $NOCH_2CF_3$ and $R_a$, $R_b$, $R_c$ and $R_d$ are as defined in Table T1.

Table 362: This table discloses the 151 compounds T362.001 to T362.151 of the formula $I_{13}$, wherein $R^5$, $R^6$, $R^7$ and G are all hydrogen, D is NO-allyl and $R_a$, $R_b$, $R_c$ and $R_d$ are as defined in Table T1.

Table 363: This table discloses the 151 compounds T363.001 to T363.151 of the formula $I_{13}$, wherein $R^5$, $R^6$, $R^7$ and G are all hydrogen, D is NO-propargyl and $R_a$, $R_b$, $R_c$ and $R_d$ are as defined in Table T1.

Table 364: This table discloses the 151 compounds T364.001 to T364.151 of the formula $I_{13}$, wherein $R^5$, $R^6$, $R^7$ and G are all hydrogen, D is NO-benzyl and $R_a$, $R_b$, $R_c$ and $R_d$ are as defined in Table T1.

Table 365: This table discloses the 151 compounds T365.001 to T365.151 of the formula $I_{13}$, wherein $R^5$, $R^6$, $R^7$ and G are all hydrogen, D is $NOCH_2OCH_3$ and $R_a$, $R_b$, $R_c$ and $R_d$ are as defined in Table T1.

Table 366: This table discloses the 151 compounds T366.001 to T366.151 of the formula $I_{13}$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 367: This table discloses the 151 compounds T367.001 to T367.151 of the formula $I_{13}$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 368: This table discloses the 151 compounds T368.001 to T368.151 of the formula $I_{13}$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 369: This table discloses the 151 compounds T369.001 to T369.151 of the formula $I_{13}$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 370: This table discloses the 151 compounds T370.001 to T370.151 of the formula $I_{13}$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 371: This table discloses the 151 compounds T371.001 to T371.151 of the formula $I_{13}$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 372: This table discloses the 151 compounds T372.001 to T372.151 of the formula $I_{13}$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 373: This table discloses the 151 compounds T373.001 to T373.151 of the formula $I_{13}$, wherein $R^5$, $R^6$, $R^7$ and G are all hydrogen, D is NO-cyclohexyl and $R_a$, $R_b$, $R_c$ and $R_d$ are as defined in Table T1.

Table 374: This table discloses the 151 compounds T374.001 to T374.151 of the formula $I_{13}$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 375: This table discloses the 151 compounds T375.001 to T375.151 of the formula $I_{13}$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 376: This table discloses the 151 compounds T376.001 to T376.151 of the formula $I_{13}$, wherein $R^5$, $R^6$, $R^7$ and G are all hydrogen, D is O and $R_a$, $R_b$, $R_c$ and $R_d$ are as defined in Table T1.

Table 377: This table discloses the 151 compounds T377.001 to T377.151 of the formula $I_{13}$, wherein $R^5$, $R^6$, $R^7$ and G are all hydrogen, D is S and $R_a$, $R_b$, $R_c$ and $R_d$ are as defined in Table T1.

Table 378: This table discloses the 151 compounds T378.001 to T378.151 of the formula $I_{14}$:

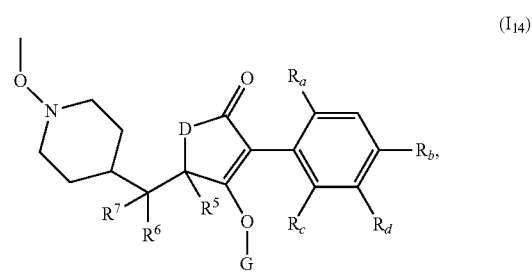

(I$_{14}$)

wherein $R^5$, $R^6$, $R^7$ and G are all hydrogen, D is NH and $R_a$, $R_b$, $R_c$ and $R_d$ are as defined in Table T1.

Table 379: This table discloses the 151 compounds T379.001 to T379.151 of the formula $I_{14}$, wherein $R^5$, $R^6$, $R^7$ and G are all hydrogen, D is $NCH_3$ and $R_a$, $R_b$, $R_c$ and $R_d$ are as defined in Table T1.

Table 380: This table discloses the 151 compounds T380.001 to T380.151 of the formula $I_{14}$, wherein $R^5$, $R^6$, $R^7$ and G are all hydrogen, D is $NCH_2CH_3$ and $R_a$, $R_b$, $R_c$ and $R_d$ are as defined in Table T1.

Table 381: This table discloses the 151 compounds T381.001 to T381.151 of the formula $I_{14}$, wherein $R^5$, $R^6$, $R^7$ and G are all hydrogen, D is $NCH_2CF_3$ and $R_a$, $R_b$, $R_c$ and $R_d$ are as defined in Table T1.

Table 382: This table discloses the 151 compounds T382.001 to T382.151 of the formula $I_{14}$, wherein $R^5$, $R^6$, $R^7$ and G are all hydrogen, D is N-allyl and $R_a$, $R_b$, $R_c$ and $R_d$ are as defined in Table T1.

Table 383: This table discloses the 151 compounds T383.001 to T383.151 of the formula $I_{14}$, wherein $R^5$, $R^6$, $R^7$ and G are all hydrogen, D is N-propargyl and $R_a$, $R_b$, $R_c$ and $R_d$ are as defined in Table T1.

Table 384: This table discloses the 151 compounds T384.001 to T384.151 of the formula $I_{14}$, wherein $R^5$, $R^6$, $R^7$ and G are all hydrogen, D is N-benzyl and $R_a$, $R_b$, $R_c$ and $R_d$ are as defined in Table T1.

Table 385: This table discloses the 151 compounds T385.001 to T385.151 of the formula $I_{14}$, wherein $R^5$, $R^6$, $R^7$ and G are all hydrogen, D is $NCH_2OCH_3$ and $R_a$, $R_b$, $R_c$ and $R_d$ are as defined in Table T1.

Table 386: This table discloses the 151 compounds T386.001 to T386.151 of the formula $I_{14}$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 387: This table discloses the 151 compounds T387.001 to T387.151 of the formula $I_{14}$, wherein $R^5$, $R^6$, $R^7$ and G are all hydrogen, D is NOH and $R_a$, $R_b$, $R_c$ and $R_d$ are as defined in Table T1.

Table 388: This table discloses the 151 compounds T388.001 to T388.151 of the formula $I_{14}$, wherein $R^5$, $R^6$, $R^7$ and G are all hydrogen, D is $NOCH_3$ and $R_a$, $R_b$, $R_c$ and $R_d$ are as defined in Table T1.

Table 389: This table discloses the 151 compounds T389.001 to T389.151 of the formula $I_{14}$, wherein $R^5$, $R^6$, $R^7$ and G are all hydrogen, D is $NOCH_2CH_3$ and $R_a$, $R_b$, $R_c$ and $R_d$ are as defined in Table T1.

Table 390: This table discloses the 151 compounds T390.001 to T390.151 of the formula $I_{14}$, wherein $R^5$, $R^6$, $R^7$ and G are all hydrogen, D is $NOCH_2CF_3$ and $R_a$, $R_b$, $R_c$ and $R_d$ are as defined in Table T1.

Table 391: This table discloses the 151 compounds T391.001 to T391.151 of the formula $I_{14}$, wherein $R^5$, $R^6$, $R^7$ and G are all hydrogen, D is NO-allyl and $R_a$, $R_b$, $R_c$ and $R_d$ are as defined in Table T1.

Table 392: This table discloses the 151 compounds T392.001 to T392.151 of the formula $I_{14}$, wherein $R^5$, $R^6$, $R^7$ and G are all hydrogen, D is NO-propargyl and $R_a$, $R_b$, $R_c$ and $R_d$ are as defined in Table T1.

Table 393: This table discloses the 151 compounds T393.001 to T393.151 of the formula $I_{14}$, wherein $R^5$, $R^6$, $R^7$ and G are all hydrogen, D is NO-benzyl and $R_a$, $R_b$, $R_c$ and $R_d$ are as defined in Table T1.

Table 394: This table discloses the 151 compounds T394.001 to T394.151 of the formula $I_{14}$, wherein $R^5$, $R^6$, $R^7$ and G are all hydrogen, D is $NOCH_2OCH_3$ and $R_a$, $R_b$, $R_c$ and $R_d$ are as defined in Table T1.

Table 395: This table discloses the 151 compounds T395.001 to T395.151 of the formula $I_{14}$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 396: This table discloses the 151 compounds T396.001 to T396.151 of the formula $I_{14}$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 397: This table discloses the 151 compounds T397.001 to T397.151 of the formula $I_{14}$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 398: This table discloses the 151 compounds T398.001 to T398.151 of the formula $I_{14}$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 399: This table discloses the 151 compounds T399.001 to T399.151 of the formula $I_{14}$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 400: This table discloses the 151 compounds T400.001 to T400.151 of the formula $I_{14}$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 401: This table discloses the 151 compounds T401.001 to T401.151 of the formula $I_{14}$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 402: This table discloses the 151 compounds T402.001 to T402.151 of the formula $I_{14}$, wherein $R^5$, $R^6$, $R^7$ and G are all hydrogen, D is NO-cyclohexyl and $R_a$, $R_b$, $R_c$ and $R_d$ are as defined in Table T1.

Table 403: This table discloses the 151 compounds T403.001 to T403.151 of the formula $I_{14}$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 404: This table discloses the 151 compounds T404.001 to T404.151 of the formula $I_{14}$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 405: This table discloses the 151 compounds T405.001 to T405.151 of the formula $I_{14}$, wherein $R^5$, $R^6$ and G are hydrogen, $R^7$ is methyl, D is NH and $R_a$, $R_b$, $R_c$ and $R_d$ are as defined in Table T1.

Table 406: This table discloses the 151 compounds T406.001 to T406.151 of the formula $I_{14}$, wherein $R^5$ and G are hydrogen, $R^6$ and $R^7$ are methyl, D is NH and $R_a$, $R_b$, $R_c$ and $R_d$ are as defined in Table T1.

Table 407: This table discloses the 151 compounds T407.001 to T407.151 of the formula $I_{14}$, wherein $R^6$, $R^7$ and G are hydrogen, $R^5$ is methyl, D is NH and $R_a$, $R_b$, $R_c$ and $R_d$ are as defined in Table T1.

Table 408: This table discloses the 151 compounds T408.001 to T408.151 of the formula $I_{14}$, wherein $R^5$, $R^6$, $R^7$ and G are all hydrogen, D is O and $R_a$, $R_b$, $R_c$ and $R_d$ are as defined in Table T1.

Table 409: This table discloses the 151 compounds T409.001 to T409.151 of the formula $I_{14}$, wherein $R^5$, $R^6$ and G are hydrogen, $R^7$ is methyl, D is O and $R_a$, $R_b$, $R_c$ and $R_d$ are as defined in Table T1.

Table 410: This table discloses the 151 compounds T410.001 to T410.151 of the formula $I_{14}$, wherein $R^5$ and G are hydrogen, $R^6$ and $R^7$ are methyl, D is O and $R_a$, $R_b$, $R_c$ and $R_d$ are as defined in Table T1.

Table 411: This table discloses the 151 compounds T411.001 to T411.151 of the formula $I_{14}$, wherein $R^6$, $R^7$ and G are hydrogen, $R^5$ is methyl, D is O and $R_a$, $R_b$, $R_c$ and $R_d$ are as defined in Table T1.

Table 412: This table discloses the 151 compounds T412.001 to T412.151 of the formula $I_{14}$, wherein $R^5$, $R^6$, $R^7$ and G are all hydrogen, D is S and $R_a$, $R_b$, $R_c$ and $R_d$ are as defined in Table T1.

Table 413: This table discloses the 151 compounds T413.001 to T413.151 of the formula $I_{14}$, wherein $R^5$, $R^6$ and G are hydrogen, $R^7$ is methyl, D is S and $R_a$, $R_b$, $R_c$ and $R_d$ are as defined in Table T1.

Table 414: This table discloses the 151 compounds T414.001 to T414.151 of the formula $I_{14}$, wherein $R^5$ and G are hydrogen, $R^6$ and $R^7$ are methyl, D is S and $R_a$, $R_b$, $R_c$ and $R_d$ are as defined in Table T1.

Table 415: This table discloses the 151 compounds T415.001 to T415.151 of the formula $I_{14}$, wherein $R^6$, $R^7$ and G are hydrogen, $R^5$ is methyl, D is S and $R_a$, $R_b$, $R_c$ and $R_d$ are as defined in Table T1.

Table 416: This table discloses the 151 compounds T416.001 to T416.151 of the formula $I_{14}$, wherein $R^5$, $R^6$ and G are hydrogen, $R^7$ is methyl, D is $NCH_3$ and $R_a$, $R_b$, $R_c$ and $R_d$ are as defined in Table T1.

Table 417: This table discloses the 151 compounds T417.001 to T417.151 of the formula $I_{14}$, wherein $R^5$ and G are hydrogen, $R^6$ and $R^7$ are methyl, D is $NCH_3$ and $R_a$, $R_b$, $R_c$ and $R_d$ are as defined in Table T1.

Table 418: This table discloses the 151 compounds T418.001 to T418.151 of the formula $I_{14}$, wherein $R^6$, $R^7$ and G are hydrogen, $R^5$ is methyl, D is $NCH_3$ and $R_a$, $R_b$, $R_c$ and $R_d$ are as defined in Table T1.

Table 419: This table discloses the 151 compounds T419.001 to T419.151 of the formula $I_{15}$:

($I_{15}$)

wherein $R^5$ and G are hydrogen, D is NH and $R_a$, $R_b$, $R_c$ and $R_d$ are as defined in Table T1.

Table 420: This table discloses the 151 compounds T420.001 to T420.151 of the formula $I_{15}$, wherein $R^5$ and G are hydrogen, D is $NCH_3$ and $R_a$, $R_b$, $R_c$ and $R_d$ are as defined in Table T1.

Table 421: This table discloses the 151 compounds T421.001 to T421.151 of the formula $I_{15}$, wherein $R^5$ and G are hydrogen, D is $NCH_2CH_3$ and $R_a$, $R_b$, $R_c$ and $R_d$ are as defined in Table T1.

Table 422: This table discloses the 151 compounds T422.001 to T422.151 of the formula $I_{15}$, wherein $R^5$ and G are hydrogen, D is $NCH_2CF_3$ and $R_a$, $R_b$, $R_c$ and $R_d$ are as defined in Table T1.

Table 423: This table discloses the 151 compounds T423.001 to T423.151 of the formula $I_{15}$, wherein $R^5$ and G are hydrogen, D is N-allyl and $R_a$, $R_b$, $R_c$ and $R_d$ are as defined in Table T1.

Table 424: This table discloses the 151 compounds T424.001 to T424.151 of the formula $I_{15}$, wherein $R^5$ and G are hydrogen, D is N-propargyl and $R_a$, $R_b$, $R_c$ and $R_d$ are as defined in Table T1.

Table 425: This table discloses the 151 compounds T425.001 to T425.151 of the formula $I_{15}$, wherein $R^5$ and G are hydrogen, D is N-benzyl and $R_a$, $R_b$, $R_c$ and $R_d$ are as defined in Table T1.

Table 426: This table discloses the 151 compounds T426.001 to T426.151 of the formula $I_{15}$, wherein $R^5$ and G are hydrogen, D is $NCH_2OCH_3$ and $R_a$, $R_b$, $R_c$ and $R_d$ are as defined in Table T1.

Table 427: This table discloses the 151 compounds T427.001 to T427.151 of the formula $I_{15}$, wherein $R^5$ and G are hydrogen, D is $NCH_2CH_2OCH_3$ and $R_a$, $R_b$, $R_c$ and $R_d$ are as defined in Table T1.

Table 428: This table discloses the 151 compounds T428.001 to T428.151 of the formula $I_{15}$, wherein $R^5$ and G are hydrogen, D is NOH and $R_a$, $R_b$, $R_c$ and $R_d$ are as defined in Table T1.

Table 429: This table discloses the 151 compounds T429.001 to T429.151 of the formula $I_{15}$, wherein $R^5$ and G are hydrogen, D is $NOCH_3$ and $R_a$, $R_b$, $R_c$ and $R_d$ are as defined in Table T1.

Table 430: This table discloses the 151 compounds T430.001 to T430.151 of the formula $I_{15}$, wherein $R^5$ and G are hydrogen, D is $NOCH_2CH_3$ and $R_a$, $R_b$, $R_c$ and $R_d$ are as defined in Table T1.

Table 431: This table discloses the 151 compounds T431.001 to T431.151 of the formula $I_{15}$, wherein $R^5$ and G are hydrogen, D is $NOCH_2CF_3$ and $R_a$, $R_b$, $R_c$ and $R_d$ are as defined in Table T1.

Table 432: This table discloses the 151 compounds T432.001 to T432.151 of the formula $I_{15}$, wherein $R^5$ and G are hydrogen, D is NO-allyl and $R_a$, $R_b$, $R_c$ and $R_d$ are as defined in Table T1.

Table 433: This table discloses the 151 compounds T433.001 to T433.151 of the formula $I_{15}$, wherein $R^5$ and G are hydrogen, D is NO-propargyl and $R_a$, $R_b$, $R_c$ and $R_d$ are as defined in Table T1.

Table 434: This table discloses the 151 compounds T434.001 to T434.151 of the formula $I_{15}$, wherein $R^5$ and G are hydrogen, D is NO-benzyl and $R_a$, $R_b$, $R_c$ and $R_d$ are as defined in Table T1.

Table 435: This table discloses the 151 compounds T435.001 to T435.151 of the formula $I_{15}$, wherein $R^5$ and G are hydrogen, D is $NOCH_2OCH_3$ and $R_a$, $R_b$, $R_c$ and $R_d$ are as defined in Table T1.

Table 436: This table discloses the 151 compounds T436.001 to T436.151 of the formula $I_{15}$, wherein $R^5$ and G are hydrogen, D is $NOCH_2CH_2OCH_3$ and $R_a$, $R_b$, $R_c$ and $R_d$ are as defined in Table T1.

Table 437: This table discloses the 151 compounds T437.001 to T437.151 of the formula $I_{15}$, wherein $R^5$ and G are hydrogen, D is $NOCH_2$-cyclohexyl and $R_a$, $R_b$, $R_c$ and $R_d$ are as defined in Table T1.

Table 438: This table discloses the 151 compounds T438.001 to T438.151 of the formula $I_{15}$, wherein $R^5$ and G are hydrogen, D is NO-(tetrahydrofuran-2-yl) and $R_a$, $R_b$, $R_c$ and $R_d$ are as defined in Table T1.

Table 439: This table discloses the 151 compounds T439.001 to T439.151 of the formula $I_{15}$, wherein $R^5$ and G are hydrogen, D is NO-(tetrahydropyran-2-yl) and $R_a$, $R_b$, $R_c$ and $R_d$ are as defined in Table T1.

Table 440: This table discloses the 151 compounds T440.001 to T440.151 of the formula $I_{15}$, wherein $R^5$ and G are hydrogen, D is NO-(tetrahydrofuran-2-ylmethyl) and $R_a$, $R_b$, $R_c$ and $R_d$ are as defined in Table T1.

Table 441: This table discloses the 151 compounds T441.001 to T441.151 of the formula $I_{15}$, wherein $R^5$ and G are hydrogen, D is NO-(tetrahydrofuran-3-ylmethyl) and $R_a$, $R_b$, $R_c$ and $R_d$ are as defined in Table T1.

Table 442: This table discloses the 151 compounds T442.001 to T442.151 of the formula $I_{15}$, wherein $R^5$ and G are hydrogen, D is NO-(tetrahydropyran-4-ylmethyl) and $R_a$, $R_b$, $R_c$ and $R_d$ are as defined in Table T1.

Table 443: This table discloses the 151 compounds T443.001 to T443.151 of the formula $I_{15}$, wherein $R^5$ and G are hydrogen, D is NO-cyclohexyl and $R_a$, $R_b$, $R_c$ and $R_d$ are as defined in Table T1.

Table 444: This table discloses the 151 compounds T444.001 to T444.151 of the formula $I_{15}$, wherein $R^5$ and G are hydrogen, D is NO-(furan-2-ylmethyl) and $R_a$, $R_b$, $R_c$ and $R_d$ are as defined in Table T1.

Table 445: This table discloses the 151 compounds T445.001 to T445.151 of the formula $I_{15}$, wherein $R^5$ and G are hydrogen, D is NO-(furan-3-ylmethyl) and $R_a$, $R_b$, $R_c$ and $R_d$ are as defined in Table T1.

Table 446: This table discloses the 151 compounds T446.001 to T446.151 of the formula $I_{15}$, wherein $R^5$ and G are hydrogen, D is O and $R_a$, $R_b$, $R_c$ and $R_d$ are as defined in Table T1.

Table 447: This table discloses the 151 compounds T447.001 to T447.151 of the formula $I_{15}$, wherein $R^5$ and G are hydrogen, D is S and $R_a$, $R_b$, $R_c$ and $R_d$ are as defined in Table T1.

Table 448: This table discloses the 151 compounds T448.001 to T448.151 of the formula $I_{16}$:

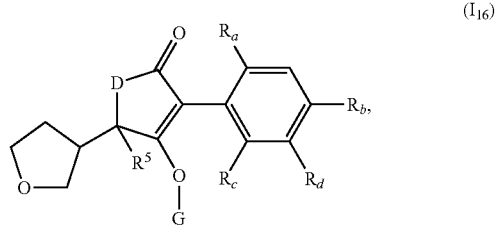

wherein $R^5$ and G are hydrogen, D is NH and $R_a$, $R_b$, $R_c$ and $R_d$ are as defined in Table T1.

Table 449: This table discloses the 151 compounds T449.001 to T449.151 of the formula $I_{16}$, wherein $R^5$ and G are hydrogen, D is $NCH_3$ and $R_a$, $R_b$, $R_c$ and $R_d$ are as defined in Table T1.

Table 450: This table discloses the 151 compounds T450.001 to T450.151 of the formula $I_{16}$, wherein $R^5$ and G are hydrogen, D is $NCH_2CH_3$ and $R_a$, $R_b$, $R_c$ and $R_d$ are as defined in Table T1.

Table 451: This table discloses the 151 compounds T451.001 to T451.151 of the formula $I_{16}$, wherein $R^5$ and G are hydrogen, D is $NCH_2CF_3$ and $R_a$, $R_b$, $R_c$ and $R_d$ are as defined in Table T1.

Table 452: This table discloses the 151 compounds T452.001 to T452.151 of the formula $I_{16}$, wherein $R^5$ and G are hydrogen, D is N-allyl and $R_a$, $R_b$, $R_c$ and $R_d$ are as defined in Table T1.

Table 453: This table discloses the 151 compounds T453.001 to T453.151 of the formula $I_{16}$, wherein $R^5$ and G are hydrogen, D is N-propargyl and $R_a$, $R_b$, $R_c$ and $R_d$ are as defined in Table T1.

Table 454: This table discloses the 151 compounds T454.001 to T454.151 of the formula $I_{16}$, wherein $R^5$ and G are hydrogen, D is N-benzyl and $R_a$, $R_b$, $R_c$ and $R_d$ are as defined in Table T1.

Table 455: This table discloses the 151 compounds T455.001 to T455.151 of the formula $I_{16}$, wherein $R^5$ and G are hydrogen, D is $NCH_2OCH_3$ and $R_a$, $R_b$, $R_c$ and $R_d$ are as defined in Table T1.

Table 456: This table discloses the 151 compounds T456.001 to T456.151 of the formula $I_{16}$, wherein $R^5$ and G are hydrogen, D is $NCH_2CH_2OCH_3$ and $R_a$, $R_b$, $R_c$ and $R_d$ are as defined in Table T1.

Table 457: This table discloses the 151 compounds T457.001 to T457.151 of the formula $I_{16}$, wherein $R^5$ and G are hydrogen, D is NOH and $R_a$, $R_b$, $R_c$ and $R_d$ are as defined in Table T1.

Table 458: This table discloses the 151 compounds T458.001 to T458.151 of the formula $I_{16}$, wherein $R^5$ and G are hydrogen, D is $NOCH_3$ and $R_a$, $R_b$, $R_c$ and $R_d$ are as defined in Table T1.

Table 459: This table discloses the 151 compounds T459.001 to T459.151 of the formula $I_{16}$, wherein $R^5$ and G are hydrogen, D is $NOCH_2CH_3$ and $R_a$, $R_b$, $R_c$ and $R_d$ are as defined in Table T1.

Table 460: This table discloses the 151 compounds T460.001 to T460.151 of the formula $I_{16}$, wherein $R^5$ and G are hydrogen, D is $NOCH_2CF_3$ and $R_a$, $R_b$, $R_c$ and $R_d$ are as defined in Table T1.

Table 461: This table discloses the 151 compounds T461.001 to T461.151 of the formula $I_{16}$, wherein $R^5$ and G are hydrogen, D is NO-allyl and $R_a$, $R_b$, $R_c$ and $R_d$ are as defined in Table T1.

Table 462: This table discloses the 151 compounds T462.001 to T462.151 of the formula $I_{16}$, wherein $R^5$ and G are hydrogen, D is NO-propargyl and $R_a$, $R_b$, $R_c$ and $R_d$ are as defined in Table T1.

Table 463: This table discloses the 151 compounds T463.001 to T463.151 of the formula $I_{16}$, wherein $R^5$ and G are hydrogen, D is NO-benzyl and $R_a$, $R_b$, $R_c$ and $R_d$ are as defined in Table T1.

Table 464: This table discloses the 151 compounds T464.001 to T464.151 of the formula $I_{16}$, wherein $R^5$ and G are hydrogen, D is $NOCH_2OCH_3$ and $R_a$, $R_b$, $R_c$ and $R_d$ are as defined in Table T1.

Table 465: This table discloses the 151 compounds T465.001 to T465.151 of the formula $I_{16}$, wherein $R^5$ and G are hydrogen, D is $NOCH_2CH_2OCH_3$ and $R_a$, $R_b$, $R_c$ and $R_d$ are as defined in Table T1.

Table 466: This table discloses the 151 compounds T466.001 to T466.151 of the formula $I_{16}$, wherein $R^5$ and G are hydrogen, D is $NOCH_2$-cyclohexyl and $R_a$, $R_b$, $R_c$ and $R_d$ are as defined in Table T1.

Table 467: This table discloses the 151 compounds T467.001 to T467.151 of the formula $I_{16}$, wherein $R^5$ and G are hydrogen, D is NO-(tetrahydrofuran-2-yl) and $R_a$, $R_b$, $R_c$ and $R_d$ are as defined in Table T1.

Table 468: This table discloses the 151 compounds T468.001 to T468.151 of the formula $I_{16}$, wherein $R^5$ and G are hydrogen, D is NO-(tetrahydropyran-2-yl) and $R_a$, $R_b$, $R_c$ and $R_d$ are as defined in Table T1.

Table 469: This table discloses the 151 compounds T469.001 to T469.151 of the formula $I_{16}$, wherein $R^5$ and G are hydrogen, D is NO-(tetrahydrofuran-2-ylmethyl) and $R_a$, $R_b$, $R_c$ and $R_d$ are as defined in Table T1.

Table 470: This table discloses the 151 compounds T470.001 to T470.151 of the formula $I_{16}$, wherein $R^5$ and G are hydrogen, D is NO-(tetrahydrofuran-3-ylmethyl) and $R_a$, $R_b$, $R_c$ and $R_d$ are as defined in Table T1.

Table 471: This table discloses the 151 compounds T471.001 to T471.151 of the formula $I_{16}$, wherein $R^5$ and G are hydrogen, D is NO-(tetrahydropyran-4-ylmethyl) and $R_a$, $R_b$, $R_c$ and $R_d$ are as defined in Table T1.

Table 472: This table discloses the 151 compounds T472.001 to T472.151 of the formula $I_{16}$, wherein $R^5$ and G are hydrogen, D is NO-cyclohexyl and $R_a$, $R_b$, $R_c$ and $R_d$ are as defined in Table T1.

Table 473: This table discloses the 151 compounds T473.001 to T473.151 of the formula $I_{16}$, wherein $R^5$ and G are hydrogen, D is NO-(furan-2-ylmethyl) and $R_a$, $R_b$, $R_c$ and $R_d$ are as defined in Table T1.

Table 474: This table discloses the 151 compounds T474.001 to T474.151 of the formula $I_{16}$, wherein $R^5$ and G are hydrogen, D is NO-(furan-3-ylmethyl) and $R_a$, $R_b$, $R_c$ and $R_d$ are as defined in Table T1.

Table 475: This table discloses the 151 compounds T475.001 to T475.151 of the formula $I_{16}$, wherein $R^5$ and G are hydrogen, D is O and $R_a$, $R_b$, $R_c$ and $R_d$ are as defined in Table T1.

Table 476: This table discloses the 151 compounds T476.001 to T476.151 of the formula $I_{16}$, wherein $R^5$ and G are hydrogen, D is S and $R_a$, $R_b$, $R_c$ and $R_d$ are as defined in Table T1.

Table 477: This table discloses the 151 compounds T477.001 to T477.151 of the formula $I_{17}$:

$$(I_{17})$$

wherein $R^5$ and G are hydrogen, D is NH and $R_a$, $R_b$, $R_c$ and $R_d$ are as defined in Table T1.

Table 478: This table discloses the 151 compounds T478.001 to T478.151 of the formula $I_{17}$, wherein $R^5$ and G are hydrogen, D is $NCH_3$ and $R_a$, $R_b$, $R_c$ and $R_d$ are as defined in Table T1.

Table 479: This table discloses the 151 compounds T479.001 to T479.151 of the formula $I_{17}$, wherein $R^5$ and G are hydrogen, D is $NCH_2CH_3$ and $R_a$, $R_b$, $R_c$ and $R_d$ are as defined in Table T1.

Table 480: This table discloses the 151 compounds T480.001 to T480.151 of the formula $I_{17}$, wherein $R^5$ and G are hydrogen, D is $NCH_2CF_3$ and $R_a$, $R_b$, $R_c$ and $R_d$ are as defined in Table T1.

Table 481: This table discloses the 151 compounds T481.001 to T481.151 of the formula $I_{17}$, wherein $R^5$ and G are hydrogen, D is N-allyl and $R_a$, $R_b$, $R_c$ and $R_d$ are as defined in Table T1.

Table 482: This table discloses the 151 compounds T482.001 to T482.151 of the formula $I_{17}$, wherein $R^5$ and G are hydrogen, D is N-propargyl and $R_a$, $R_b$, $R_c$ and $R_d$ are as defined in Table T1.

Table 483: This table discloses the 151 compounds T483.001 to T483.151 of the formula $I_{17}$, wherein $R^5$ and G are hydrogen, D is N-benzyl and $R_a$, $R_b$, $R_c$ and $R_d$ are as defined in Table T1.

Table 484: This table discloses the 151 compounds T484.001 to T484.151 of the formula $I_{17}$, wherein $R^5$ and G are hydrogen, D is $NCH_2OCH_3$ and $R_a$, $R_b$, $R_c$ and $R_d$ are as defined in Table T1.

Table 485: This table discloses the 151 compounds T485.001 to T485.151 of the formula $I_{17}$, wherein $R^5$ and G are hydrogen, D is $NCH_2CH_2OCH_3$ and $R_a$, $R_b$, $R_c$ and $R_d$ are as defined in Table T1.

Table 486: This table discloses the 151 compounds T486.001 to T486.151 of the formula $I_{17}$, wherein $R^5$ and G are hydrogen, D is NOH and $R_a$, $R_b$, $R_c$ and $R_d$ are as defined in Table T1.

Table 487: This table discloses the 151 compounds T487.001 to T487.151 of the formula $I_{17}$, wherein $R^5$ and G are hydrogen, D is $NOCH_3$ and $R_a$, $R_b$, $R_c$ and $R_d$ are as defined in Table T1.

Table 488: This table discloses the 151 compounds T488.001 to T488.151 of the formula $I_{17}$, wherein $R^5$ and G are hydrogen, D is $NOCH_2CH_3$ and $R_a$, $R_b$, $R_c$ and $R_d$ are as defined in Table T1.

Table 489: This table discloses the 151 compounds T489.001 to T489.151 of the formula $I_{17}$, wherein $R^5$ and G are hydrogen, D is $NOCH_2CF_3$ and $R_a$, $R_b$, $R_c$ and $R_d$ are as defined in Table T1.

Table 490: This table discloses the 151 compounds T490.001 to T490.151 of the formula $I_{17}$, wherein $R^5$ and G are hydrogen, D is NO-allyl and $R_a$, $R_b$, $R_c$ and $R_d$ are as defined in Table T1.

Table 491: This table discloses the 151 compounds T491.001 to T491.151 of the formula $I_{17}$, wherein $R^5$ and G are hydrogen, D is NO-propargyl and $R_a$, $R_b$, $R_c$ and $R_d$ are as defined in Table T1.

Table 492: This table discloses the 151 compounds T492.001 to T492.151 of the formula $I_{17}$, wherein $R^5$ and G are hydrogen, D is NO-benzyl and $R_a$, $R_b$, $R_c$ and $R_d$ are as defined in Table T1.

Table 493: This table discloses the 151 compounds T493.001 to T493.151 of the formula $I_{17}$, wherein $R^5$ and G are hydrogen, D is $NOCH_2OCH_3$ and $R_a$, $R_b$, $R_c$ and $R_d$ are as defined in Table T1.

Table 494: This table discloses the 151 compounds T494.001 to T494.151 of the formula $I_{17}$, wherein $R^5$ and G are hydrogen, D is $NOCH_2CH_2OCH_3$ and $R_a$, $R_b$, $R_c$ and $R_d$ are as defined in Table T1.

Table 495: This table discloses the 151 compounds T495.001 to T495.151 of the formula $I_{17}$, wherein $R^5$ and G are hydrogen, D is $NOCH_2$-cyclohexyl and $R_a$, $R_b$, $R_c$ and $R_d$ are as defined in Table T1.

Table 496: This table discloses the 151 compounds T496.001 to T496.151 of the formula $I_{17}$, wherein $R^5$ and G are hydrogen, D is NO-(tetrahydrofuran-2-yl) and $R_a$, $R_b$, $R_c$ and $R_d$ are as defined in Table T1.

Table 497: This table discloses the 151 compounds T497.001 to T497.151 of the formula $I_{17}$, wherein $R^5$ and G are hydrogen, D is NO-(tetrahydropyran-2-yl) and $R_a$, $R_b$, $R_c$ and $R_d$ are as defined in Table T1.

Table 498: This table discloses the 151 compounds T498.001 to T498.151 of the formula $I_{17}$, wherein $R^5$ and G are hydrogen, D is NO-(tetrahydrofuran-2-ylmethyl) and $R_a$, $R_b$, $R_c$ and $R_d$ are as defined in Table T1.

Table 499: This table discloses the 151 compounds T499.001 to T499.151 of the formula $I_{17}$, wherein $R^5$ and G are hydrogen, D is NO-(tetrahydrofuran-3-ylmethyl) and $R_a$, $R_b$, $R_c$ and $R_d$ are as defined in Table T1.

Table 500: This table discloses the 151 compounds T500.001 to T500.151 of the formula $I_{17}$, wherein $R^5$ and G are hydrogen, D is NO-(tetrahydropyran-4-ylmethyl) and $R_a$, $R_b$, $R_c$ and $R_d$ are as defined in Table T1.

Table 501: This table discloses the 151 compounds T501.001 to T501.151 of the formula $I_{17}$, wherein $R^5$ and G are hydrogen, D is NO-cyclohexyl and $R_a$, $R_b$, $R_c$ and $R_d$ are as defined in Table T1.

Table 502: This table discloses the 151 compounds T502.001 to T502.151 of the formula $I_{17}$, wherein $R^5$ and G are hydrogen, D is NO-(furan-2-ylmethyl) and $R_a$, $R_b$, $R_c$ and $R_d$ are as defined in Table T1.

Table 503: This table discloses the 151 compounds T503.001 to T503.151 of the formula $I_{17}$, wherein $R^5$ and G are hydrogen, D is NO-(furan-3-ylmethyl) and $R_a$, $R_b$, $R_c$ and $R_d$ are as defined in Table T1.

Table 504: This table discloses the 151 compounds T504.001 to T504.151 of the formula $I_{17}$, wherein $R^5$ and G are hydrogen, D is O and $R_a$, $R_b$, $R_c$ and $R_d$ are as defined in Table T1.

Table 505: This table discloses the 151 compounds T505.001 to T505.151 of the formula $I_{17}$, wherein $R^5$ and G are hydrogen, D is S and $R_a$, $R_b$, $R_c$ and $R_d$ are as defined in Table T1.

Table 506: This table discloses the 151 compounds T506.001 to T506.151 of the formula $I_{18}$:

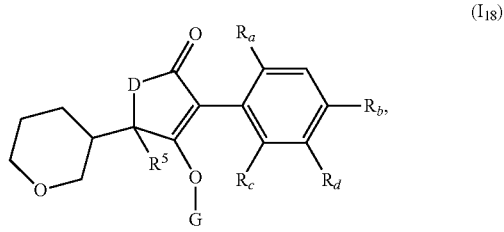

wherein $R^5$ and G are hydrogen, D is NH and $R_a$, $R_b$, $R_c$ and $R_d$ are as defined in Table T1.

Table 507: This table discloses the 151 compounds T507.001 to T507.151 of the formula $I_{18}$, wherein $R^5$ and G are hydrogen, D is $NCH_3$ and $R_a$, $R_b$, $R_c$ and $R_d$ are as defined in Table T1.

Table 508: This table discloses the 151 compounds T508.001 to T508.151 of the formula $I_{18}$, wherein $R^5$ and G are hydrogen, D is $NCH_2CH_3$ and $R_a$, $R_b$, $R_c$ and $R_d$ are as defined in Table T1.

Table 509: This table discloses the 151 compounds T509.001 to T509.151 of the formula $I_{18}$, wherein $R^5$ and G are hydrogen, D is $NCH_2CF_3$ and $R_a$, $R_b$, $R_c$ and $R_d$ are as defined in Table T1.

Table 510: This table discloses the 151 compounds T510.001 to T510.151 of the formula $I_{18}$, wherein $R^5$ and G are hydrogen, D is N-allyl and $R_a$, $R_b$, $R_c$ and $R_d$ are as defined in Table T1.

Table 511: This table discloses the 151 compounds T511.001 to T511.151 of the formula $I_{18}$, wherein $R^5$ and G are hydrogen, D is N-propargyl and $R_a$, $R_b$, $R_c$ and $R_d$ are as defined in Table T1.

Table 512: This table discloses the 151 compounds T512.001 to T512.151 of the formula $I_{18}$, wherein $R^5$ and G are hydrogen, D is N-benzyl and $R_a$, $R_b$, $R_c$ and $R_d$ are as defined in Table T1.

Table 513: This table discloses the 151 compounds T513.001 to T513.151 of the formula $I_{18}$, wherein $R^5$ and G are hydrogen, D is $NCH_2OCH_3$ and $R_a$, $R_b$, $R_c$ and $R_d$ are as defined in Table T1.

Table 514: This table discloses the 151 compounds T514.001 to T514.151 of the formula $I_{18}$, wherein $R^5$ and G are hydrogen, D is $NCH_2CH_2OCH_3$ and $R_a$, $R_b$, $R_c$ and $R_d$ are as defined in Table T1.

Table 515: This table discloses the 151 compounds T515.001 to T515.151 of the formula $I_{18}$, wherein $R^5$ and G are hydrogen, D is NOH and $R_a$, $R_b$, $R_c$ and $R_d$ are as defined in Table T1.

Table 516: This table discloses the 151 compounds T516.001 to T516.151 of the formula $I_{18}$, wherein $R^5$ and G are hydrogen, D is $NOCH_3$ and $R_a$, $R_b$, $R_c$ and $R_d$ are as defined in Table T1.

Table 517: This table discloses the 151 compounds T517.001 to T517.151 of the formula $I_{18}$, wherein $R^5$ and G are hydrogen, D is $NOCH_2CH_3$ and $R_a$, $R_b$, $R_c$ and $R_d$ are as defined in Table T1.

Table 518: This table discloses the 151 compounds T518.001 to T518.151 of the formula $I_{18}$, wherein $R^5$ and G are hydrogen, D is $NOCH_2CF_3$ and $R_a$, $R_b$, $R_c$ and $R_d$ are as defined in Table T1.

Table 519: This table discloses the 151 compounds T519.001 to T519.151 of the formula $I_{18}$, wherein $R^5$ and G are hydrogen, D is NO-allyl and $R_a$, $R_b$, $R_c$ and $R_d$ are as defined in Table T1.

Table 520: This table discloses the 151 compounds T520.001 to T520.151 of the formula $I_{18}$, wherein $R^5$ and G are hydrogen, D is NO-propargyl and $R_a$, $R_b$, $R_c$ and $R_d$ are as defined in Table T1.

Table 521: This table discloses the 151 compounds T521.001 to T521.151 of the formula $I_{18}$, wherein $R^5$ and G are hydrogen, D is NO-benzyl and $R_a$, $R_b$, $R_c$ and $R_d$ are as defined in Table T1.

Table 522: This table discloses the 151 compounds T522.001 to T522.151 of the formula $I_{18}$, wherein $R^5$ and G are hydrogen, D is $NOCH_2OCH_3$ and $R_a$, $R_b$, $R_c$ and $R_d$ are as defined in Table T1.

Table 523: This table discloses the 151 compounds T523.001 to T523.151 of the formula $I_{18}$, wherein $R^5$ and G are hydrogen, D is $NOCH_2CH_2OCH_3$ and $R_a$, $R_b$, $R_c$ and $R_d$ are as defined in Table T1.

Table 524: This table discloses the 151 compounds T524.001 to T524.151 of the formula $I_{18}$, wherein $R^5$ and G are hydrogen, D is $NOCH_2$-cyclohexyl and $R_a$, $R_b$, $R_c$ and $R_d$ are as defined in Table T1.

Table 525: This table discloses the 151 compounds T525.001 to T525.151 of the formula $I_{18}$, wherein $R^5$ and G are hydrogen, D is NO-(tetrahydrofuran-2-yl) and $R_a$, $R_b$, $R_c$ and $R_d$ are as defined in Table T1.

Table 526: This table discloses the 151 compounds T526.001 to T526.151 of the formula $I_{18}$, wherein $R^5$ and G are hydrogen, D is NO-(tetrahydropyran-2-yl) and $R_a$, $R_b$, $R_c$ and $R_d$ are as defined in Table T1.

Table 527: This table discloses the 151 compounds T527.001 to T527.151 of the formula $I_{18}$, wherein $R^5$ and G are hydrogen, D is NO-(tetrahydrofuran-2-ylmethyl) and $R_a$, $R_b$, $R_c$ and $R_d$ are as defined in Table T1.

Table 528: This table discloses the 151 compounds T528.001 to T528.151 of the formula $I_{18}$, wherein $R^5$ and G are hydrogen, D is NO-(tetrahydrofuran-3-ylmethyl) and $R_a$, $R_b$, $R_c$ and $R_d$ are as defined in Table T1.

Table 529: This table discloses the 151 compounds T529.001 to T529.151 of the formula $I_{18}$, wherein $R^5$ and G are hydrogen, D is NO-(tetrahydropyran-4-ylmethyl) and $R_a$, $R_b$, $R_c$ and $R_d$ are as defined in Table T1.

Table 530: This table discloses the 151 compounds T530.001 to T530.151 of the formula $I_{18}$, wherein $R^5$ and G are hydrogen, D is NO-cyclohexyl and $R_a$, $R_b$, $R_c$ and $R_d$ are as defined in Table T1.

Table 531: This table discloses the 151 compounds T531.001 to T531.151 of the formula $I_{18}$, wherein $R^5$ and G are hydrogen, D is NO-(furan-2-ylmethyl) and $R_a$, $R_b$, $R_c$ and $R_d$ are as defined in Table T1.

Table 532: This table discloses the 151 compounds T532.001 to T532.151 of the formula $I_{18}$, wherein $R^5$ and G are hydrogen, D is NO-(furan-3-ylmethyl) and $R_a$, $R_b$, $R_c$ and $R_d$ are as defined in Table T1.

Table 533: This table discloses the 151 compounds T533.001 to T533.151 of the formula $I_{18}$, wherein $R^5$ and G are hydrogen, D is O and $R_a$, $R_b$, $R_c$ and $R_d$ are as defined in Table T1.

Table 534: This table discloses the 151 compounds T534.001 to T534.151 of the formula $I_{18}$, wherein $R^5$ and G are hydrogen, D is S and $R_a$, $R_b$, $R_c$ and $R_d$ are as defined in Table T1.

Table 535: This table discloses the 151 compounds T535.001 to T535.151 of the formula $I_{19}$:

($I_{19}$)

wherein $R^5$ and G are hydrogen, D is NH and $R_a$, $R_b$, $R_c$ and $R_d$ are as defined in Table T1.

Table 536: This table discloses the 151 compounds T536.001 to T536.151 of the formula $I_{19}$, wherein $R^5$ and G are hydrogen, D is $NCH_3$ and $R_a$, $R_b$, $R_c$ and $R_d$ are as defined in Table T1.

Table 537: This table discloses the 151 compounds T537.001 to T537.151 of the formula $I_{19}$, wherein $R^5$ and G are hydrogen, D is $NCH_2CH_3$ and $R_a$, $R_b$, $R_c$ and $R_d$ are as defined in Table T1.

Table 538: This table discloses the 151 compounds T538.001 to T538.151 of the formula $I_{19}$, wherein $R^5$ and G are hydrogen, D is $NCH_2CF_3$ and $R_a$, $R_b$, $R_c$ and $R_d$ are as defined in Table T1.

Table 539: This table discloses the 151 compounds T539.001 to T539.151 of the formula $I_{19}$, wherein $R^5$ and G are hydrogen, D is N-allyl and $R_a$, $R_b$, $R_c$ and $R_d$ are as defined in Table T1.

Table 540: This table discloses the 151 compounds T540.001 to T540.151 of the formula $I_{19}$, wherein $R^5$ and G are hydrogen, D is N-propargyl and $R_a$, $R_b$, $R_c$ and $R_d$ are as defined in Table T1.

Table 541: This table discloses the 151 compounds T541.001 to T541.151 of the formula $I_{19}$, wherein $R^5$ and G are hydrogen, D is N-benzyl and $R_a$, $R_b$, $R_c$ and $R_d$ are as defined in Table T1.

Table 542: This table discloses the 151 compounds T542.001 to T542.151 of the formula $I_{19}$, wherein $R^5$ and G are hydrogen, D is $NCH_2OCH_3$ and $R_a$, $R_b$, $R_c$ and $R_d$ are as defined in Table T1.

Table 543: This table discloses the 151 compounds T543.001 to T543.151 of the formula $I_{19}$, wherein $R^5$ and G are hydrogen, D is $NCH_2CH_2OCH_3$ and $R_a$, $R_b$, $R_c$ and $R_d$ are as defined in Table T1.

Table 544: This table discloses the 151 compounds T544.001 to T544.151 of the formula $I_{19}$, wherein $R^5$ and G are hydrogen, D is NOH and $R_a$, $R_b$, $R_c$ and $R_d$ are as defined in Table T1.

Table 545: This table discloses the 151 compounds T545.001 to T545.151 of the formula $I_{19}$, wherein $R^5$ and G are hydrogen, D is $NOCH_3$ and $R_a$, $R_b$, $R_c$ and $R_d$ are as defined in Table T1.

Table 546: This table discloses the 151 compounds T546.001 to T546.151 of the formula $I_{19}$, wherein $R^5$ and G are hydrogen, D is $NOCH_2CH_3$ and $R_a$, $R_b$, $R_c$ and $R_d$ are as defined in Table T1.

Table 547: This table discloses the 151 compounds T547.001 to T547.151 of the formula $I_{19}$, wherein $R^5$ and G are hydrogen, D is $NOCH_2CF_3$ and $R_a$, $R_b$, $R_c$ and $R_d$ are as defined in Table T1.

Table 548: This table discloses the 151 compounds T548.001 to T548.151 of the formula $I_{19}$, wherein $R^5$ and G are hydrogen, D is NO-allyl and $R_a$, $R_b$, $R_c$ and $R_d$ are as defined in Table T1.

Table 549: This table discloses the 151 compounds T549.001 to T549.151 of the formula $I_{19}$, wherein $R^5$ and G are hydrogen, D is NO-propargyl and $R_a$, $R_b$, $R_c$ and $R_d$ are as defined in Table T1.

Table 550: This table discloses the 151 compounds T550.001 to T550.151 of the formula $I_{19}$, wherein $R^5$ and G are hydrogen, D is NO-benzyl and $R_a$, $R_b$, $R_c$ and $R_d$ are as defined in Table T1.

Table 551: This table discloses the 151 compounds T551.001 to T551.151 of the formula $I_{19}$, wherein $R^5$ and G are hydrogen, D is $NOCH_2OCH_3$ and $R_a$, $R_b$, $R_c$ and $R_d$ are as defined in Table T1.

Table 552: This table discloses the 151 compounds T552.001 to T552.151 of the formula $I_{19}$, wherein $R^5$ and G are hydrogen, D is $NOCH_2CH_2OCH_3$ and $R_a$, $R_b$, $R_c$ and $R_d$ are as defined in Table T1.

Table 553: This table discloses the 151 compounds T553.001 to T553.151 of the formula $I_{19}$, wherein $R^5$ and G are hydrogen, D is $NOCH_2$-cyclohexyl and $R_a$, $R_b$, $R_c$ and $R_d$ are as defined in Table T1.

Table 554: This table discloses the 151 compounds T554.001 to T554.151 of the formula $I_{19}$, wherein $R^5$ and G are hydrogen, D is NO-(tetrahydrofuran-2-yl) and $R_a$, $R_b$, $R_c$ and $R_d$ are as defined in Table T1.

Table 555: This table discloses the 151 compounds T555.001 to T555.151 of the formula $I_{19}$, wherein $R^5$ and G are hydrogen, D is NO-(tetrahydropyran-2-yl) and $R_a$, $R_b$, $R_c$ and $R_d$ are as defined in Table T1.

Table 556: This table discloses the 151 compounds T556.001 to T556.151 of the formula $I_{19}$, wherein $R^5$ and G are hydrogen, D is NO-(tetrahydrofuran-2-ylmethyl) and $R_a$, $R_b$, $R_c$ and $R_d$ are as defined in Table T1.

Table 557: This table discloses the 151 compounds T557.001 to T557.151 of the formula $I_{19}$, wherein $R^5$ and G are hydrogen, D is NO-(tetrahydrofuran-3-ylmethyl) and $R_a$, $R_b$, $R_c$ and $R_d$ are as defined in Table T1.

Table 558: This table discloses the 151 compounds T558.001 to T558.151 of the formula $I_{19}$, wherein $R^5$ and G are hydrogen, D is NO-(tetrahydropyran-4-ylmethyl) and $R_a$, $R_b$, $R_c$ and $R_d$ are as defined in Table T1.

Table 559: This table discloses the 151 compounds T559.001 to T559.151 of the formula $I_{19}$, wherein $R^5$ and G are hydrogen, D is NO-cyclohexyl and $R_a$, $R_b$, $R_c$ and $R_d$ are as defined in Table T1.

Table 560: This table discloses the 151 compounds T560.001 to T560.151 of the formula $I_{19}$, wherein $R^5$ and G are hydrogen, D is NO-(furan-2-ylmethyl) and $R_a$, $R_b$, $R_c$ and $R_d$ are as defined in Table T1.

Table 561: This table discloses the 151 compounds T561.001 to T561.151 of the formula $I_{19}$, wherein $R^5$ and G are hydrogen, D is NO-(furan-3-ylmethyl) and $R_a$, $R_b$, $R_c$ and $R_d$ are as defined in Table T1.

Table 562: This table discloses the 151 compounds T562.001 to T562.151 of the formula $I_{19}$, wherein $R^5$ and G are hydrogen, D is O and $R_a$, $R_b$, $R_c$ and $R_d$ are as defined in Table T1.

Table 563: This table discloses the 151 compounds T563.001 to T563.151 of the formula $I_{19}$, wherein $R^5$ and G are hydrogen, D is S and $R_a$, $R_b$, $R_c$ and $R_d$ are as defined in Table T1.

Table 564: This table discloses the 151 compounds T564.001 to T564.151 of the formula $I_{20}$:

$$(I_{20})$$

wherein $R^5$ and G are hydrogen, D is NH and $R_a$, $R_b$, $R_c$ and $R_d$ are as defined in Table T1.

Table 565: This table discloses the 151 compounds T565.001 to T565.151 of the formula $I_{20}$, wherein $R^5$ and G are hydrogen, D is $NCH_3$ and $R_a$, $R_b$, $R_c$ and $R_d$ are as defined in Table T1.

Table 566: This table discloses the 151 compounds T566.001 to T566.151 of the formula $I_{20}$, wherein $R^5$ and G are hydrogen, D is $NCH_2CH_3$ and $R_a$, $R_b$, $R_c$ and $R_d$ are defined in Table T1.

Table 567: This table discloses the 151 compounds T567.001 to T567.151 of the formula $I_{20}$, wherein $R^5$ and G are hydrogen, D is $NCH_2CF_3$ and $R_a$, $R_b$, $R_c$ and $R_d$ are as defined in Table T1.

Table 568: This table discloses the 151 compounds T568.001 to T568.151 of the formula $I_{20}$, wherein $R^5$ and G are hydrogen, D is N-allyl and $R_a$, $R_b$, $R_c$ and $R_d$ are as defined in Table T1.

Table 569: This table discloses the 151 compounds T569.001 to T569.151 of the formula $I_{20}$, wherein $R^5$ and G are hydrogen, D is N-propargyl and $R_a$, $R_b$, $R_c$ and $R_d$ are as defined in Table T1.

Table 570: This table discloses the 151 compounds T570.001 to T570.151 of the formula $I_{20}$, wherein $R^5$ and G are hydrogen, D is N-benzyl and $R_a$, $R_b$, $R_c$ and $R_d$ are as defined in Table T1.

Table 571: This table discloses the 151 compounds T571.001 to T571.151 of the formula $I_{20}$, wherein $R^5$ and G are hydrogen, D is $NCH_2OCH_3$ and $R_a$, $R_b$, $R_c$ and $R_d$ are as defined in Table T1.

Table 572: This table discloses the 151 compounds T572.001 to T572.151 of the formula $I_{20}$, wherein $R^5$ and G are hydrogen, D is $NCH_2CH_2OCH_3$ and $R_a$, $R_b$, $R_c$ and $R_d$ are as defined in Table T1.

Table 573: This table discloses the 151 compounds T573.001 to T573.151 of the formula $I_{20}$, wherein $R^5$ and G are hydrogen, D is NOH and $R_a$, $R_b$, $R_c$ and $R_d$ are as defined in Table T1.

Table 574: This table discloses the 151 compounds T574.001 to T574.151 of the formula $I_{20}$, wherein $R^5$ and G are hydrogen, D is $NOCH_3$ and $R_a$, $R_b$, $R_c$ and $R_d$ are as defined in Table T1.

Table 575: This table discloses the 151 compounds T575.001 to T575.151 of the formula $I_{20}$, wherein $R^5$ and G are hydrogen, D is $NOCH_2CH_3$ and $R_a$, $R_b$, $R_c$ and $R_d$ are as defined in Table T1.

Table 576: This table discloses the 151 compounds T576.001 to T576.151 of the formula $I_{20}$, wherein $R^5$ and G are hydrogen, D is $NOCH_2CF_3$ and $R_a$, $R_b$, $R_c$ and $R_d$ are as defined in Table T1.

Table 577: This table discloses the 151 compounds T577.001 to T577.151 of the formula $I_{20}$, wherein $R^5$ and G are hydrogen, D is NO-allyl and $R_a$, $R_b$, $R_c$ and $R_d$ are as defined in Table T1.

Table 578: This table discloses the 151 compounds T578.001 to T578.151 of the formula $I_{20}$, wherein $R^5$ and G are hydrogen, D is NO-propargyl and $R_a$, $R_b$, $R_c$ and $R_d$ are as defined in Table T1.

Table 579: This table discloses the 151 compounds T579.001 to T579.151 of the formula $I_{20}$, wherein $R^5$ and G are hydrogen, D is NO-benzyl and $R_a$, $R_b$, $R_c$ and $R_d$ are as defined in Table T1.

Table 580: This table discloses the 151 compounds T580.001 to T580.151 of the formula $I_{20}$, wherein $R^5$ and G are hydrogen, D is $NOCH_2OCH_3$ and $R_a$, $R_b$, $R_c$ and $R_d$ are as defined in Table T1.

Table 581: This table discloses the 151 compounds T581.001 to T581.151 of the formula $I_{20}$, wherein $R^5$ and G are hydrogen, D is $NOCH_2CH_2OCH_3$ and $R_a$, $R_b$, $R_c$ and $R_d$ are as defined in Table T1.

Table 582: This table discloses the 151 compounds T582.001 to T582.151 of the formula $I_{20}$, wherein $R^5$ and G are hydrogen, D is $NOCH_2$-cyclohexyl and $R_a$, $R_b$, $R_c$ and $R_d$ are as defined in Table T1.

Table 583: This table discloses the 151 compounds T583.001 to T583.151 of the formula $I_{20}$, wherein $R^5$ and G are hydrogen, D is NO-(tetrahydrofuran-2-yl) and $R_a$, $R_b$, $R_c$ and $R_d$ are as defined in Table T1.

Table 584: This table discloses the 151 compounds T584.001 to T584.151 of the formula $I_{20}$, wherein $R^5$ and G are hydrogen, D is NO-(tetrahydropyran-2-yl) and $R_a$, $R_b$, $R_c$ and $R_d$ are as defined in Table T1.

Table 585: This table discloses the 151 compounds T585.001 to T585.151 of the formula $I_{20}$, wherein $R^5$ and G are hydrogen, D is NO-(tetrahydrofuran-2-ylmethyl) and $R_a$, $R_b$, $R_c$ and $R_d$ are as defined in Table T1.

Table 586: This table discloses the 151 compounds T586.001 to T586.151 of the formula $I_{20}$, wherein $R^5$ and G are hydrogen, D is NO-(tetrahydrofuran-3-ylmethyl) and $R_a$, $R_b$, $R_c$ and $R_d$ are as defined in Table T1.

Table 587: This table discloses the 151 compounds T587.001 to T587.151 of the formula $I_{20}$, wherein $R^5$ and G are hydrogen, D is NO-(tetrahydropyran-4-ylmethyl) and $R_a$, $R_b$, $R_c$ and $R_d$ are as defined in Table T1.

Table 588: This table discloses the 151 compounds T588.001 to T588.151 of the formula $I_{20}$, wherein $R^5$ and G are hydrogen, D is NO-cyclohexyl and $R_a$, $R_b$, $R_c$ and $R_d$ are as defined in Table T1.

Table 589: This table discloses the 151 compounds T589.001 to T589.151 of the formula $I_{20}$, wherein $R^5$ and G are hydrogen, D is NO-(furan-2-ylmethyl) and $R_a$, $R_b$, $R_c$ and $R_d$ are as defined in Table T1.

Table 590: This table discloses the 151 compounds T590.001 to T590.151 of the formula $I_{20}$, wherein $R^5$ and G are hydrogen, D is NO-(furan-3-ylmethyl) and $R_a$, $R_b$, $R_c$ and $R_d$ are as defined in Table T1.

Table 591: This table discloses the 151 compounds T591.001 to T591.151 of the formula $I_{20}$, wherein $R^5$ and G are hydrogen, D is O and $R_a$, $R_b$, $R_c$ and $R_d$ are as defined in Table T1.

Table 592: This table discloses the 151 compounds T592.001 to T592.151 of the formula $I_{20}$, wherein $R^5$ and G are hydrogen, D is S and $R_a$, $R_b$, $R_c$ and $R_d$ are as defined in Table T1.

Table 593: This table discloses the 151 compounds T593.001 to T593.151 of the formula $I_{21}$:

$$(I_{21})$$

wherein $R^5$ and G are hydrogen, D is NH and $R_a$, $R_b$, $R_c$ and $R_d$ are as defined in Table T1.

Table 594: This table discloses the 151 compounds T594.001 to T594.151 of the formula $I_{21}$, wherein $R^5$ and G are hydrogen, D is $NCH_3$ and $R_a$, $R_b$, $R_c$ and $R_d$ are as defined in Table T1.

Table 595: This table discloses the 151 compounds T595.001 to T595.151 of the formula $I_{21}$, wherein $R^5$ and G are hydrogen, D is $NCH_2CH_3$ and $R_a$, $R_b$, $R_c$ and $R_d$ are as defined in Table T1.

Table 596: This table discloses the 151 compounds T596.001 to T596.151 of the formula $I_{21}$, wherein $R^5$ and G are hydrogen, D is $NCH_2CF_3$ and $R_a$, $R_b$, $R_c$ and $R_d$ are as defined in Table T1.

Table 597: This table discloses the 151 compounds T597.001 to T597.151 of the formula $I_{21}$, wherein $R^5$ and G are hydrogen, D is N-allyl and $R_a$, $R_b$, $R_c$ and $R_d$ are as defined in Table T1.

Table 598: This table discloses the 151 compounds T598.001 to T598.151 of the formula $I_{21}$, wherein $R^5$ and G are hydrogen, D is N-propargyl and $R_a$, $R_b$, $R_c$ and $R_d$ are as defined in Table T1.

Table 599: This table discloses the 151 compounds T599.001 to T599.151 of the formula $I_{21}$, wherein $R^5$ and G are hydrogen, D is N-benzyl and $R_a$, $R_b$, $R_c$ and $R_d$ are as defined in Table T1.

Table 600: This table discloses the 151 compounds T600.001 to T600.151 of the formula $I_{21}$, wherein $R^5$ and G are hydrogen, D is $NCH_2OCH_3$ and $R_a$, $R_b$, $R_c$ and $R_d$ are as defined in Table T1.

Table 601: This table discloses the 151 compounds T601.001 to T601.151 of the formula $I_{21}$, wherein $R^5$ and G are hydrogen, D is $NCH_2CH_2OCH_3$ and $R_a$, $R_b$, $R_c$ and $R_d$ are as defined in Table T1.

Table 602: This table discloses the 151 compounds T602.001 to T602.151 of the formula $I_{21}$, wherein $R^5$ and G are hydrogen, D is NOH and $R_a$, $R_b$, $R_c$ and $R_d$ are as defined in Table T1.

Table 603: This table discloses the 151 compounds T603.001 to T603.151 of the formula $I_{21}$, wherein $R^5$ and G are hydrogen, D is $NOCH_3$ and $R_a$, $R_b$, $R_c$ and $R_d$ are as defined in Table T1.

Table 604: This table discloses the 151 compounds T604.001 to T604.151 of the formula $I_{21}$, wherein $R^5$ and G are hydrogen, D is $NOCH_2CH_3$ and $R_a$, $R_b$, $R_c$ and $R_d$ are as defined in Table T1.

Table 605: This table discloses the 151 compounds T605.001 to T605.151 of the formula $I_{21}$, wherein $R^5$ and G are hydrogen, D is $NOCH_2CF_3$ and $R_a$, $R_b$, $R_c$ and $R_d$ are as defined in Table T1.

Table 606: This table discloses the 151 compounds T606.001 to T606.151 of the formula $I_{21}$, wherein $R^5$ and G are hydrogen, D is NO-allyl and $R_a$, $R_b$, $R_c$ and $R_d$ are as defined in Table T1.

Table 607: This table discloses the 151 compounds T607.001 to T607.151 of the formula $I_{21}$, wherein $R^5$ and G are hydrogen, D is NO-propargyl and $R_a$, $R_b$, $R_c$ and $R_d$ are as defined in Table T1.

Table 608: This table discloses the 151 compounds T608.001 to T608.151 of the formula $I_{21}$, wherein $R^5$ and G are hydrogen, D is NO-benzyl and $R_a$, $R_b$, $R_c$ and $R_d$ are as defined in Table T1.

Table 609: This table discloses the 151 compounds T609.001 to T609.151 of the formula $I_{21}$, wherein $R^5$ and G are hydrogen, D is $NOCH_2OCH_3$ and $R_a$, $R_b$, $R_c$ and $R_d$ are as defined in Table T1.

Table 610: This table discloses the 151 compounds T610.001 to T610.151 of the formula $I_{21}$, wherein $R^5$ and G are hydrogen, D is $NOCH_2CH_2OCH_3$ and $R_a$, $R_b$, $R_c$ and $R_d$ are as defined in Table T1.

Table 611: This table discloses the 151 compounds T611.001 to T611.151 of the formula $I_{21}$, wherein $R^5$ and G are hydrogen, D is $NOCH_2$-cyclohexyl and $R_a$, $R_b$, $R_c$ and $R_d$ are as defined in Table T1.

Table 612: This table discloses the 151 compounds T612.001 to T612.151 of the formula $I_{21}$, wherein $R^5$ and G are hydrogen, D is NO-(tetrahydrofuran-2-yl) and $R_a$, $R_b$, $R_c$ and $R_d$ are as defined in Table T1.

Table 613: This table discloses the 151 compounds T613.001 to T613.151 of the formula $I_{21}$, wherein $R^5$ and G are hydrogen, D is NO-(tetrahydropyran-2-yl) and $R_a$, $R_b$, $R_c$ and $R_d$ are as defined in Table T1.

Table 614: This table discloses the 151 compounds T614.001 to T614.151 of the formula $I_{21}$, wherein $R^5$ and G are hydrogen, D is NO-(tetrahydrofuran-2-ylmethyl) and $R_a$, $R_b$, $R_c$ and $R_d$ are as defined in Table T1.

Table 615: This table discloses the 151 compounds T615.001 to T615.151 of the formula $I_{21}$, wherein $R^5$ and G are hydrogen, D is NO-(tetrahydrofuran-3-ylmethyl) and $R_a$, $R_b$, $R_c$ and $R_d$ are as defined in Table T1.

Table 616: This table discloses the 151 compounds T616.001 to T616.151 of the formula $I_{21}$, wherein $R^5$ and G are hydrogen, D is NO-(tetrahydropyran-4-ylmethyl) and $R_a$, $R_b$, $R_c$ and $R_d$ are as defined in Table T1.

Table 617: This table discloses the 151 compounds T617.001 to T617.151 of the formula $I_{21}$, wherein $R^5$ and G are hydrogen, D is NO-cyclohexyl and $R_a$, $R_b$, $R_c$ and $R_d$ are as defined in Table T1.

Table 618: This table discloses the 151 compounds T618.001 to T618.151 of the formula $I_{21}$, wherein $R^5$ and G are hydrogen, D is NO-(furan-2-ylmethyl) and $R_a$, $R_b$, $R_c$ and $R_d$ are as defined in Table T1.

Table 619: This table discloses the 151 compounds T619.001 to T619.151 of the formula $I_{21}$, wherein $R^5$ and G are hydrogen, D is NO-(furan-3-ylmethyl) and $R_a$, $R_b$, $R_c$ and $R_d$ are as defined in Table T1.

Table 620: This table discloses the 151 compounds T620.001 to T620.151 of the formula $I_{21}$, wherein $R^5$ and G are hydrogen, D is O and $R_a$, $R_b$, $R_c$ and $R_d$ are as defined in Table T1.

Table 621: This table discloses the 151 compounds T621.001 to T621.151 of the formula $I_{21}$, wherein $R^5$ and G are hydrogen, D is S and $R_a$, $R_b$, $R_c$ and $R_d$ are as defined in Table T1.

Table 622: This table discloses the 151 compounds T622.001 to T622.151 of the formula $I_{22}$:

$$(I_{22})$$

wherein $R^5$ and G are hydrogen, D is NH and $R_a$, $R_b$, $R_c$ and $R_d$ are as defined in Table T1.

Table 623: This table discloses the 151 compounds T623.001 to T623.151 of the formula $I_{22}$, wherein $R^5$ and G are hydrogen, D is $NCH_3$ and $R_a$, $R_b$, $R_c$ and $R_d$ are as defined in Table T1.

Table 624: This table discloses the 151 compounds T624.001 to T624.151 of the formula $I_{22}$, wherein $R^5$ and G are hydrogen, D is $NCH_2CH_3$ and $R_a$, $R_b$, $R_c$ and $R_d$ are as defined in Table T1.

Table 625: This table discloses the 151 compounds T625.001 to T625.151 of the formula $I_{22}$, wherein $R^5$ and G are hydrogen, D is $NCH_2CF_3$ and $R_a$, $R_b$, $R_c$ and $R_d$ are as defined in Table T1.

Table 626: This table discloses the 151 compounds T626.001 to T626.151 of the formula $I_{22}$, wherein $R^5$ and G are hydrogen, D is N-allyl and $R_a$, $R_b$, $R_c$ and $R_d$ are as defined in Table T1.

Table 627: This table discloses the 151 compounds T627.001 to T627.151 of the formula $I_{22}$, wherein $R^5$ and G are hydrogen, D is N-propargyl and $R_a$, $R_b$, $R_c$ and $R_d$ are as defined in Table T1.

Table 628: This table discloses the 151 compounds T628.001 to T628.151 of the formula $I_{22}$, wherein $R^5$ and G are hydrogen, D is N-benzyl and $R_a$, $R_b$, $R_c$ and $R_d$ are as defined in Table T1.

Table 629: This table discloses the 151 compounds T629.001 to T629.151 of the formula $I_{22}$, wherein $R^5$ and G are hydrogen, D is $NCH_2OCH_3$ and $R_a$, $R_b$, $R_c$ and $R_d$ are as defined in Table T1.

Table 630: This table discloses the 151 compounds T630.001 to T630.151 of the formula $I_{22}$, wherein $R^5$ and G are hydrogen, D is $NCH_2CH_2OCH_3$ and $R_a$, $R_b$, $R_c$ and $R_d$ are as defined in Table T1.

Table 631: This table discloses the 151 compounds T631.001 to T631.151 of the formula $I_{22}$, wherein $R^5$ and G are hydrogen, D is NOH and $R_a$, $R_b$, $R_c$ and $R_d$ are as defined in Table T1.

Table 632: This table discloses the 151 compounds T632.001 to T632.151 of the formula $I_{22}$, wherein $R^5$ and G are hydrogen, D is $NOCH_3$ and $R_a$, $R_b$, $R_c$ and $R_d$ are as defined in Table T1.

Table 633: This table discloses the 151 compounds T633.001 to T633.151 of the formula $I_{22}$, wherein $R^5$ and G are hydrogen, D is $NOCH_2CH_3$ and $R_a$, $R_b$, $R_c$ and $R_d$ are as defined in Table T1.

Table 634: This table discloses the 151 compounds T634.001 to T634.151 of the formula $I_{22}$, wherein $R^5$ and G are hydrogen, D is $NOCH_2CF_3$ and $R_a$, $R_b$, $R_c$ and $R_d$ are as defined in Table T1.

Table 635: This table discloses the 151 compounds T635.001 to T635.151 of the formula $I_{22}$, wherein $R^5$ and G are hydrogen, D is NO-allyl and $R_a$, $R_b$, $R_c$ and $R_d$ are as defined in Table T1.

Table 636: This table discloses the 151 compounds T636.001 to T636.151 of the formula $I_{22}$, wherein $R^5$ and G are hydrogen, D is NO-propargyl and $R_a$, $R_b$, $R_c$ and $R_d$ are as defined in Table T1.

Table 637: This table discloses the 151 compounds T637.001 to T637.151 of the formula $I_{22}$, wherein $R^5$ and G are hydrogen, D is NO-benzyl and $R_a$, $R_b$, $R_c$ and $R_d$ are as defined in Table T1.

Table 638: This table discloses the 151 compounds T638.001 to T638.151 of the formula $I_{22}$, wherein $R^5$ and G are hydrogen, D is $NOCH_2OCH_3$ and $R_a$, $R_b$, $R_c$ and $R_d$ are as defined in Table T1.

Table 639: This table discloses the 151 compounds T639.001 to T639.151 of the formula $I_{22}$, wherein $R^5$ and G are hydrogen, D is $NOCH_2CH_2OCH_3$ and $R_a$, $R_b$, $R_c$ and $R_d$ are as defined in Table T1.

Table 640: This table discloses the 151 compounds T640.001 to T640.151 of the formula $I_{22}$, wherein $R^5$ and G are hydrogen, D is $NOCH_2$-cyclohexyl and $R_a$, $R_b$, $R_c$ and $R_d$ are as defined in Table T1.

Table 641: This table discloses the 151 compounds T641.001 to T641.151 of the formula $I_{22}$, wherein $R^5$ and G are hydrogen, D is NO-(tetrahydrofuran-2-yl) and $R_a$, $R_b$, $R_c$ and $R_d$ are as defined in Table T1.

Table 642: This table discloses the 151 compounds T642.001 to T642.151 of the formula $I_{22}$, wherein $R^5$ and G are hydrogen, D is NO-(tetrahydropyran-2-yl) and $R_a$, $R_b$, $R_c$ and $R_d$ are as defined in Table T1.

Table 643: This table discloses the 151 compounds T643.001 to T643.151 of the formula $I_{22}$, wherein $R^5$ and G are hydrogen, D is NO-(tetrahydrofuran-2-ylmethyl) and $R_a$, $R_b$, $R_c$ and $R_d$ are as defined in Table T1.

Table 644: This table discloses the 151 compounds T644.001 to T644.151 of the formula $I_{22}$, wherein $R^5$ and G are hydrogen, D is NO-(tetrahydrofuran-3-ylmethyl) and $R_a$, $R_b$, $R_c$ and $R_d$ are as defined in Table T1.

Table 645: This table discloses the 151 compounds T645.001 to T645.151 of the formula $I_{22}$, wherein $R^5$ and G are hydrogen, D is NO-(tetrahydropyran-4-ylmethyl) and $R_a$, $R_b$, $R_c$ and $R_d$ are as defined in Table T1.

Table 646: This table discloses the 151 compounds T646.001 to T646.151 of the formula $I_{22}$, wherein $R^5$ and G are hydrogen, D is NO-cyclohexyl and $R_a$, $R_b$, $R_c$ and $R_d$ are as defined in Table T1.

Table 647: This table discloses the 151 compounds T647.001 to T647.151 of the formula $I_{22}$, wherein $R^5$ and G are hydrogen, D is NO-(furan-2-ylmethyl) and $R_a$, $R_b$, $R_c$ and $R_d$ are as defined in Table T1.

Table 648: This table discloses the 151 compounds T648.001 to T648.151 of the formula $I_{22}$, wherein $R^5$ and G are hydrogen, D is NO-(furan-3-ylmethyl) and $R_a$, $R_b$, $R_c$ and $R_d$ are as defined in Table T1.

Table 649: This table discloses the 151 compounds T649.001 to T649.151 of the formula $I_{22}$, wherein $R^5$ and G are hydrogen, D is O and $R_a$, $R_b$, $R_c$ and $R_d$ are as defined in Table T1.

Table 650: This table discloses the 151 compounds T650.001 to T650.151 of the formula $I_{22}$, wherein $R^5$ and G are hydrogen, D is S and $R_a$, $R_b$, $R_c$ and $R_d$ are as defined in Table T1.

Table 651: This table discloses the 151 compounds T651.001 to T651.151 of the formula $I_{23}$:

$$(I_{23})$$

wherein $R^5$ and G are hydrogen, D is NH and $R_a$, $R_b$, $R_c$ and $R_d$ are as defined in Table T1.

Table 652: This table discloses the 151 compounds T652.001 to T652.151 of the formula $I_{23}$, wherein $R^5$ and G are hydrogen, D is $NCH_3$ and $R_a$, $R_b$, $R_c$ and $R_d$ are as defined in Table T1.

Table 653: This table discloses the 151 compounds T653.001 to T653.151 of the formula $I_{23}$, wherein $R^5$ and G are hydrogen, D is $NCH_2CH_3$ and $R_a$, $R_b$, $R_c$ and $R_d$ are as defined in Table T1.

Table 654: This table discloses the 151 compounds T654.001 to T654.151 of the formula $I_{23}$, wherein $R^5$ and G are hydrogen, D is $NCH_2CF_3$ and $R_a$, $R_b$, $R_c$ and $R_d$ are as defined in Table T1.

Table 655: This table discloses the 151 compounds T655.001 to T655.151 of the formula $I_{23}$, wherein $R^5$ and G are hydrogen, D is N-allyl and $R_a$, $R_b$, $R_c$ and $R_d$ are as defined in Table T1.

Table 656: This table discloses the 151 compounds T656.001 to T656.151 of the formula $I_{23}$, wherein $R^5$ and G are hydrogen, D is N-propargyl and $R_a$, $R_b$, $R_c$ and $R_d$ are as defined in Table T1.

Table 657: This table discloses the 151 compounds T657.001 to T657.151 of the formula $I_{23}$, wherein $R^5$ and G are hydrogen, D is N-benzyl and $R_a$, $R_b$, $R_c$ and $R_d$ are as defined in Table T1.

Table 658: This table discloses the 151 compounds T658.001 to T658.151 of the formula $I_{23}$, wherein $R^5$ and G are hydrogen, D is $NCH_2OCH_3$ and $R_a$, $R_b$, $R_c$ and $R_d$ are as defined in Table T1.

Table 659: This table discloses the 151 compounds T659.001 to T659.151 of the formula $I_{23}$, wherein $R^5$ and G are hydrogen, D is $NCH_2CH_2OCH_3$ and $R_a$, $R_b$, $R_c$ and $R_d$ are as defined in Table T1.

Table 660: This table discloses the 151 compounds T660.001 to T660.151 of the formula $I_{23}$, wherein $R^5$ and G are hydrogen, D is NOH and $R_a$, $R_b$, $R_c$ and $R_d$ are as defined in Table T1.

Table 661: This table discloses the 151 compounds T661.001 to T661.151 of the formula $I_{23}$, wherein $R^5$ and G are hydrogen, D is $NOCH_3$ and $R_a$, $R_b$, $R_c$ and $R_d$ are as defined in Table T1.

Table 662: This table discloses the 151 compounds T662.001 to T662.151 of the formula $I_{23}$, wherein $R^5$ and G are hydrogen, D is $NOCH_2CH_3$ and $R_a$, $R_b$, $R_c$ and $R_d$ are as defined in Table T1.

Table 663: This table discloses the 151 compounds T663.001 to T663.151 of the formula $I_{23}$, wherein $R^5$ and G are hydrogen, D is $NOCH_2CF_3$ and $R_a$, $R_b$, $R_c$ and $R_d$ are as defined in Table T1.

Table 664: This table discloses the 151 compounds T664.001 to T664.151 of the formula $I_{23}$, wherein $R^5$ and G are hydrogen, D is NO-allyl and $R_a$, $R_b$, $R_c$ and $R_d$ are as defined in Table T1.

Table 665: This table discloses the 151 compounds T665.001 to T665.151 of the formula $I_{23}$, wherein $R^5$ and G are hydrogen, D is NO-propargyl and $R_a$, $R_b$, $R_c$ and $R_d$ are as defined in Table T1.

Table 666: This table discloses the 151 compounds T666.001 to T666.151 of the formula $I_{23}$, wherein $R^5$ and G are hydrogen, D is NO-benzyl and $R_a$, $R_b$, $R_c$ and $R_d$ are as defined in Table T1.

Table 667: This table discloses the 151 compounds T667.001 to T667.151 of the formula $I_{23}$, wherein $R^5$ and G are hydrogen, D is $NOCH_2OCH_3$ and $R_a$, $R_b$, $R_c$ and $R_d$ are as defined in Table T1.

Table 668: This table discloses the 151 compounds T668.001 to T668.151 of the formula $I_{23}$, wherein $R^5$ and G are hydrogen, D is $NOCH_2CH_2OCH_3$ and $R_a$, $R_b$, $R_c$ and $R_d$ are as defined in Table T1.

Table 669: This table discloses the 151 compounds T669.001 to T669.151 of the formula $I_{23}$, wherein $R^5$ and G are hydrogen, D is $NOCH_2$-cyclohexyl and $R_a$, $R_b$, $R_c$ and $R_d$ are as defined in Table T1.

Table 670: This table discloses the 151 compounds T670.001 to T670.151 of the formula $I_{23}$, wherein $R^5$ and G are hydrogen, D is NO-(tetrahydrofuran-2-yl) and $R_a$, $R_b$, $R_c$ and $R_d$ are as defined in Table T1.

Table 671: This table discloses the 151 compounds T671.001 to T671.151 of the formula $I_{23}$, wherein $R^5$ and G are hydrogen, D is NO-(tetrahydropyran-2-yl) and $R_a$, $R_b$, $R_c$ and $R_d$ are as defined in Table T1.

Table 672: This table discloses the 151 compounds T672.001 to T672.151 of the formula $I_{23}$, wherein $R^5$ and G are hydrogen, D is NO-(tetrahydrofuran-2-ylmethyl) and $R_a$, $R_b$, $R_c$ and $R_d$ are as defined in Table T1.

Table 673: This table discloses the 151 compounds T673.001 to T673.151 of the formula $I_{23}$, wherein $R^5$ and G are hydrogen, D is NO-(tetrahydrofuran-3-ylmethyl) and $R_a$, $R_b$, $R_c$ and $R_d$ are as defined in Table T1.

Table 674: This table discloses the 151 compounds T674.001 to T674.151 of the formula $I_{23}$, wherein $R^5$ and G are hydrogen, D is NO-(tetrahydropyran-4-ylmethyl) and $R_a$, $R_b$, $R_c$ and $R_d$ are as defined in Table T1.

Table 675: This table discloses the 151 compounds T675.001 to T675.151 of the formula $I_{23}$, wherein $R^5$ and G are hydrogen, D is NO-cyclohexyl and $R_a$, $R_b$, $R_c$ and $R_d$ are as defined in Table T1.

Table 676: This table discloses the 151 compounds T676.001 to T676.151 of the formula $I_{23}$, wherein $R^5$ and G are hydrogen, D is NO-(furan-2-ylmethyl) and $R_a$, $R_b$, $R_c$ and $R_d$ are as defined in Table T1.

Table 677: This table discloses the 151 compounds T677.001 to T677.151 of the formula $I_{23}$, wherein $R^5$ and G are hydrogen, D is NO-(furan-3-ylmethyl) and $R_a$, $R_b$, $R_c$ and $R_d$ are as defined in Table T1.

Table 678: This table discloses the 151 compounds T678.001 to T678.151 of the formula $I_{23}$, wherein $R^5$ and G are hydrogen, D is O and $R_a$, $R_b$, $R_c$ and $R_d$ are as defined in Table T1.

Table 679: This table discloses the 151 compounds T679.001 to T679.151 of the formula $I_{23}$, wherein $R^5$ and G are hydrogen, D is S and $R_a$, $R_b$, $R_c$ and $R_d$ are as defined in Table T1.

Table 680: This table discloses the 151 compounds T680.001 to T680.151 of the formula $I_{24}$:

($I_{24}$)

wherein $R^5$ and G are hydrogen, D is NH and $R_a$, $R_b$, $R_c$ and $R_d$ are as defined in Table T1.

Table 681: This table discloses the 151 compounds T681.001 to T681.151 of the formula $I_{24}$, wherein $R^5$ and G are hydrogen, D is $NCH_3$ and $R_a$, $R_b$, $R_c$ and $R_d$ are as defined in Table T1.

Table 682: This table discloses the 151 compounds T682.001 to T682.151 of the formula $I_{24}$, wherein $R^5$ and G are hydrogen, D is $NCH_2CH_3$ and $R_a$, $R_b$, $R_c$ and $R_d$ are as defined in Table T1.

Table 683: This table discloses the 151 compounds T683.001 to T683.151 of the formula $I_{24}$, wherein $R^5$ and G are hydrogen, D is $NCH_2CF_3$ and $R_a$, $R_b$, $R_c$ and $R_d$ are as defined in Table T1.

Table 684: This table discloses the 151 compounds T684.001 to T684.151 of the formula $I_{24}$, wherein $R^5$ and G are hydrogen, D is N-allyl and $R_a$, $R_b$, $R_c$ and $R_d$ are as defined in Table T1.

Table 685: This table discloses the 151 compounds T685.001 to T685.151 of the formula $I_{24}$, wherein $R^5$ and G are hydrogen, D is N-propargyl and $R_a$, $R_b$, $R_c$ and $R_d$ are as defined in Table T1.

Table 686: This table discloses the 151 compounds T686.001 to T686.151 of the formula $I_{24}$, wherein $R^5$ and G are hydrogen, D is N-benzyl and $R_a$, $R_b$, $R_c$ and $R_d$ are as defined in Table T1.

Table 687: This table discloses the 151 compounds T687.001 to T687.151 of the formula $I_{24}$, wherein $R^5$ and G are hydrogen, D is $NCH_2OCH_3$ and $R_a$, $R_b$, $R_c$ and $R_d$ are as defined in Table T1.

Table 688: This table discloses the 151 compounds T688.001 to T688.151 of the formula $I_{24}$, wherein $R^5$ and G are hydrogen, D is $NCH_2CH_2OCH_3$ and $R_a$, $R_b$, $R_c$ and $R_d$ are as defined in Table T1.

Table 689: This table discloses the 151 compounds T689.001 to T689.151 of the formula $I_{24}$, wherein $R^5$ and G are hydrogen, D is NOH and $R_a$, $R_b$, $R_c$ and $R_d$ are as defined in Table T1.

Table 690: This table discloses the 151 compounds T690.001 to T690.151 of the formula $I_{24}$, wherein $R^5$ and G are hydrogen, D is $NOCH_3$ and $R_a$, $R_b$, $R_c$ and $R_d$ are as defined in Table T1.

Table 691: This table discloses the 151 compounds T691.001 to T691.151 of the formula $I_{24}$, wherein $R^5$ and G are hydrogen, D is $NOCH_2CH_3$ and $R_a$, $R_b$, $R_c$ and $R_d$ are as defined in Table T1.

Table 692: This table discloses the 151 compounds T692.001 to T692.151 of the formula $I_{24}$, wherein $R^5$ and G are hydrogen, D is $NOCH_2CF_3$ and $R_a$, $R_b$, $R_c$ and $R_d$ are as defined in Table T1.

Table 693: This table discloses the 151 compounds T693.001 to T693.151 of the formula $I_{24}$, wherein $R^5$ and G are hydrogen, D is NO-allyl and $R_a$, $R_b$, $R_c$ and $R_d$ are as defined in Table T1.

Table 694: This table discloses the 151 compounds T694.001 to T694.151 of the formula $I_{24}$, wherein $R^5$ and G are hydrogen, D is NO-propargyl and $R_a$, $R_b$, $R_c$ and $R_d$ are as defined in Table T1.

Table 695: This table discloses the 151 compounds T695.001 to T695.151 of the formula $I_{24}$, wherein $R^5$ and G are hydrogen, D is NO-benzyl and $R_a$, $R_b$, $R_c$ and $R_d$ are as defined in Table T1.

Table 696: This table discloses the 151 compounds T696.001 to T696.151 of the formula $I_{24}$, wherein $R^5$ and G are hydrogen, D is $NOCH_2OCH_3$ and $R_a$, $R_b$, $R_c$ and $R_d$ are as defined in Table T1.

Table 697: This table discloses the 151 compounds T697.001 to T697.151 of the formula $I_{24}$, wherein $R^5$ and G are hydrogen, D is $NOCH_2CH_2OCH_3$ and $R_a$, $R_b$, $R_c$ and $R_d$ are as defined in Table T1.

Table 698: This table discloses the 151 compounds T698.001 to T698.151 of the formula $I_{24}$, wherein $R^5$ and G are hydrogen, D is $NOCH_2$-cyclohexyl and $R_a$, $R_b$, $R_c$ and $R_d$ are as defined in Table T1.

Table 699: This table discloses the 151 compounds T699.001 to T699.151 of the formula $I_{24}$, wherein $R^5$ and G are hydrogen, D is NO-(tetrahydrofuran-2-yl) and $R_a$, $R_b$, $R_c$ and $R_d$ are as defined in Table T1.

Table 700: This table discloses the 151 compounds T700.001 to T700.151 of the formula $I_{24}$, wherein $R^5$ and G are hydrogen, D is NO-(tetrahydropyran-2-yl) and $R_a$, $R_b$, $R_c$ and $R_d$ are as defined in Table T1.

Table 701: This table discloses the 151 compounds T701.001 to T701.151 of the formula $I_{24}$, wherein $R^5$ and G are hydrogen, D is NO-(tetrahydrofuran-2-ylmethyl) and $R_a$, $R_b$, $R_c$ and $R_d$ are as defined in Table T1.

Table 702: This table discloses the 151 compounds T702.001 to T702.151 of the formula $I_{24}$, wherein $R^5$ and G are hydrogen, D is NO-(tetrahydrofuran-3-ylmethyl) and $R_a$, $R_b$, $R_c$ and $R_d$ are as defined in Table T1.

Table 703: This table discloses the 151 compounds T703.001 to T703.151 of the formula $I_{24}$, wherein $R^5$ and G are hydrogen, D is NO-(tetrahydropyran-4-ylmethyl) and $R_a$, $R_b$, $R_c$ and $R_d$ are as defined in Table T1.

Table 704: This table discloses the 151 compounds T704.001 to T704.151 of the formula $I_{24}$, wherein $R^5$ and G are hydrogen, D is NO-cyclohexyl and $R_a$, $R_b$, $R_c$ and $R_d$ are as defined in Table T1.

Table 705: This table discloses the 151 compounds T705.001 to T705.151 of the formula $I_{24}$, wherein $R^5$ and G are hydrogen, D is NO-(furan-2-ylmethyl) and $R_a$, $R_b$, $R_c$ and $R_d$ are as defined in Table T1.

Table 706: This table discloses the 151 compounds T706.001 to T706.151 of the formula $I_{24}$, wherein $R^5$ and G are hydrogen, D is NO-(furan-3-ylmethyl) and $R_a$, $R_b$, $R_c$ and $R_d$ are as defined in Table T1.

Table 707: This table discloses the 151 compounds T707.001 to T707.151 of the formula $I_{24}$, wherein $R^5$ and G are hydrogen, D is O and $R_a$, $R_b$, $R_c$ and $R_d$ are as defined in Table T1.

Table 708: This table discloses the 151 compounds T708.001 to T708.151 of the formula $I_{24}$, wherein $R^5$ and G are hydrogen, D is S and $R_a$, $R_b$, $R_c$ and $R_d$ are as defined in Table T1.

Table 709: This table discloses the 151 compounds T709.001 to T709.151 of the formula $I_{25}$:

$$(I_{25})$$

wherein $R^5$ and G are hydrogen, D is NH and $R_a$, $R_b$, $R_c$ and $R_d$ are as defined in Table T1.

Table 710: This table discloses the 151 compounds T710.001 to T710.151 of the formula $I_{25}$, wherein $R^5$ and G are hydrogen, D is $NCH_3$ and $R_a$, $R_b$, $R_c$ and $R_d$ are as defined in Table T1.

Table 711: This table discloses the 151 compounds T711.001 to T711.151 of the formula $I_{25}$, wherein $R^5$ and G are hydrogen, D is $NCH_2CH_3$ and $R_a$, $R_b$, $R_c$ and $R_d$ are as defined in Table T1.

Table 712: This table discloses the 151 compounds T712.001 to T712.151 of the formula $I_{25}$, wherein $R^5$ and G are hydrogen, D is $NCH_2CF_3$ and $R_a$, $R_b$, $R_c$ and $R_d$ are as defined in Table T1.

Table 713: This table discloses the 151 compounds T713.001 to T713.151 of the formula $I_{25}$, wherein $R^5$ and G are hydrogen, D is N-allyl and $R_a$, $R_b$, $R_c$ and $R_d$ are as defined in Table T1.

Table 714: This table discloses the 151 compounds T714.001 to T714.151 of the formula $I_{25}$, wherein $R^5$ and G are hydrogen, D is N-propargyl and $R_a$, $R_b$, $R_c$ and $R_d$ are as defined in Table T1.

Table 715: This table discloses the 151 compounds T715.001 to T715.151 of the formula $I_{25}$, wherein $R^5$ and G are hydrogen, D is N-benzyl and $R_a$, $R_b$, $R_c$ and $R_d$ are as defined in Table T1.

Table 716: This table discloses the 151 compounds T716.001 to T716.151 of the formula $I_{25}$, wherein $R^5$ and G are hydrogen, D is $NCH_2OCH_3$ and $R_a$, $R_b$, $R_c$ and $R_d$ are as defined in Table T1.

Table 717: This table discloses the 151 compounds T717.001 to T717.151 of the formula $I_{25}$, wherein $R^5$ and G are hydrogen, D is $NCH_2CH_2OCH_3$ and $R_a$, $R_b$, $R_c$ and $R_d$ are as defined in Table T1.

Table 718: This table discloses the 151 compounds T718.001 to T718.151 of the formula $I_{25}$, wherein $R^5$ and G are hydrogen, D is NOH and $R_a$, $R_b$, $R_c$ and $R_d$ are as defined in Table T1.

Table 719: This table discloses the 151 compounds T719.001 to T719.151 of the formula $I_{25}$, wherein $R^5$ and G are hydrogen, D is $NOCH_3$ and $R_a$, $R_b$, $R_c$ and $R_d$ are as defined in Table T1.

Table 720: This table discloses the 151 compounds T720.001 to T720.151 of the formula $I_{25}$, wherein $R^5$ and G are hydrogen, D is $NOCH_2CH_3$ and $R_a$, $R_b$, $R_c$ and $R_d$ are as defined in Table T1.

Table 721: This table discloses the 151 compounds T721.001 to T721.151 of the formula $I_{25}$, wherein $R^5$ and G are hydrogen, D is $NOCH_2CF_3$ and $R_a$, $R_b$, $R_c$ and $R_d$ are as defined in Table T1.

Table 722: This table discloses the 151 compounds T722.001 to T722.151 of the formula $I_{25}$, wherein $R^5$ and G are hydrogen, D is NO-allyl and $R_a$, $R_b$, $R_c$ and $R_d$ are as defined in Table T1.

Table 723: This table discloses the 151 compounds T723.001 to T723.151 of the formula $I_{25}$, wherein $R^5$ and G are hydrogen, D is NO-propargyl and $R_a$, $R_b$, $R_c$ and $R_d$ are as defined in Table T1.

Table 724: This table discloses the 151 compounds T724.001 to T724.151 of the formula $I_{25}$, wherein $R^5$ and G are hydrogen, D is NO-benzyl and $R_a$, $R_b$, $R_c$ and $R_d$ are as defined in Table T1.

Table 725: This table discloses the 151 compounds T725.001 to T725.151 of the formula $I_{25}$, wherein $R^5$ and G are hydrogen, D is $NOCH_2OCH_3$ and $R_a$, $R_b$, $R_c$ and $R_d$ are as defined in Table T1.

Table 726: This table discloses the 151 compounds T726.001 to T726.151 of the formula $I_{25}$, wherein $R^5$ and G are hydrogen, D is $NOCH_2CH_2OCH_3$ and $R_a$, $R_b$, $R_c$ and $R_d$ are as defined in Table T1.

Table 727: This table discloses the 151 compounds T727.001 to T727.151 of the formula $I_{25}$, wherein $R^5$ and G are hydrogen, D is $NOCH_2$-cyclohexyl and $R_a$, $R_b$, $R_c$ and $R_d$ are as defined in Table T1.

Table 728: This table discloses the 151 compounds T728.001 to T728.151 of the formula $I_{25}$, wherein $R^5$ and G are hydrogen, D is NO-(tetrahydrofuran-2-yl) and $R_a$, $R_b$, $R_c$ and $R_d$ are as defined in Table T1.

Table 729: This table discloses the 151 compounds T729.001 to T729.151 of the formula $I_{25}$, wherein $R^5$ and G are hydrogen, D is NO-(tetrahydropyran-2-yl) and $R_a$, $R_b$, $R_c$ and $R_d$ are as defined in Table T1.

Table 730: This table discloses the 151 compounds T730.001 to T730.151 of the formula $I_{25}$, wherein $R^5$ and G are hydrogen, D is NO-(tetrahydrofuran-2-ylmethyl) and $R_a$, $R_b$, $R_c$ and $R_d$ are as defined in Table T1.

Table 731: This table discloses the 151 compounds T731.001 to T731.151 of the formula $I_{25}$, wherein $R^5$ and G are hydrogen, D is NO-(tetrahydrofuran-3-ylmethyl) and $R_a$, $R_b$, $R_c$ and $R_d$ are as defined in Table T1.

Table 732: This table discloses the 151 compounds T732.001 to T732.151 of the formula $I_{25}$, wherein $R^5$ and G are hydrogen, D is NO-(tetrahydropyran-4-ylmethyl) and $R_a$, $R_b$, $R_c$ and $R_d$ are as defined in Table T1.

Table 733: This table discloses the 151 compounds T733.001 to T733.151 of the formula $I_{25}$, wherein $R^5$ and G are hydrogen, D is NO-cyclohexyl and $R_a$, $R_b$, $R_c$ and $R_d$ are as defined in Table T1.

Table 734: This table discloses the 151 compounds T734.001 to T734.151 of the formula $I_{25}$, wherein $R^5$ and G are hydrogen, D is NO-(furan-2-ylmethyl) and $R_a$, $R_b$, $R_c$ and $R_d$ are as defined in Table T1.

Table 735: This table discloses the 151 compounds T735.001 to T735.151 of the formula $I_{25}$, wherein $R^5$ and G are hydrogen, D is NO-(furan-3-ylmethyl) and $R_a$, $R_b$, $R_c$ and $R_d$ are as defined in Table T1.

Table 736: This table discloses the 151 compounds T736.001 to T736.151 of the formula $I_{25}$, wherein $R^5$ and G are hydrogen, D is O and $R_a$, $R_b$, $R_c$ and $R_d$ are as defined in Table T1.

Table 737: This table discloses the 151 compounds T737.001 to T737.151 of the formula $I_{25}$, wherein $R^5$ and G are hydrogen, D is S and $R_a$, $R_b$, $R_c$ and $R_d$ are as defined in Table T1.

Table 738: This table discloses the 151 compounds T738.001 to T738.151 of the formula $I_{26}$:

$$(I_{26})$$

wherein $R^5$ and G are hydrogen, D is NH and $R_a$, $R_b$, $R_c$ and $R_d$ are as defined in Table T1.

Table 739: This table discloses the 151 compounds T739.001 to T739.151 of the formula $I_{26}$, wherein $R^5$ and G are hydrogen, D is $NCH_3$ and $R_a$, $R_b$, $R_c$ and $R_d$ are as defined in Table T1.

Table 740: This table discloses the 151 compounds T740.001 to T740.151 of the formula $I_{26}$, wherein $R^5$ and G are hydrogen, D is $NCH_2CH_3$ and $R_a$, $R_b$, $R_c$ and $R_d$ are as defined in Table T1.

Table 741: This table discloses the 151 compounds T741.001 to T741.151 of the formula $I_{26}$, wherein $R^5$ and G are hydrogen, D is $NCH_2CF_3$ and $R_a$, $R_b$, $R_c$ and $R_d$ are as defined in Table T1.

Table 742: This table discloses the 151 compounds T742.001 to T742.151 of the formula $I_{26}$, wherein $R^5$ and G are hydrogen, D is N-allyl and $R_a$, $R_b$, $R_c$ and $R_d$ are as defined in Table T1.

Table 743: This table discloses the 151 compounds T743.001 to T743.151 of the formula $I_{26}$, wherein $R^5$ and G are hydrogen, D is N-propargyl and $R_a$, $R_b$, $R_c$ and $R_d$ are as defined in Table T1.

Table 744: This table discloses the 151 compounds T744.001 to T744.151 of the formula $I_{26}$, wherein $R^5$ and G are hydrogen, D is N-benzyl and $R_a$, $R_b$, $R_c$ and $R_d$ are as defined in Table T1.

Table 745: This table discloses the 151 compounds T745.001 to T745.151 of the formula $I_{26}$, wherein $R^5$ and G are hydrogen, D is $NCH_2OCH_3$ and $R_a$, $R_b$, $R_c$ and $R_d$ are as defined in Table T1.

Table 746: This table discloses the 151 compounds T746.001 to T746.151 of the formula $I_{26}$, wherein $R^5$ and G are hydrogen, D is $NCH_2CH_2OCH_3$ and $R_a$, $R_b$, $R_c$ and $R_d$ are as defined in Table T1.

Table 747: This table discloses the 151 compounds T747.001 to T747.151 of the formula $I_{26}$, wherein $R^5$ and G are hydrogen, D is NOH and $R_a$, $R_b$, $R_c$ and $R_d$ are as defined in Table T1.

Table 748: This table discloses the 151 compounds T748.001 to T748.151 of the formula $I_{26}$, wherein $R^5$ and G are hydrogen, D is $NOCH_3$ and $R_a$, $R_b$, $R_c$ and $R_d$ are as defined in Table T1.

Table 749: This table discloses the 151 compounds T749.001 to T749.151 of the formula $I_{26}$, wherein $R^5$ and G are hydrogen, D is $NOCH_2CH_3$ and $R_a$, $R_b$, $R_c$ and $R_d$ are as defined in Table T1.

Table 750: This table discloses the 151 compounds T750.001 to T750.151 of the formula $I_{26}$, wherein $R^5$ and G are hydrogen, D is $NOCH_2CF_3$ and $R_a$, $R_b$, $R_c$ and $R_d$ are as defined in Table T1.

Table 751: This table discloses the 151 compounds T751.001 to T751.151 of the formula $I_{26}$, wherein $R^5$ and G are hydrogen, D is NO-allyl and $R_a$, $R_b$, $R_c$ and $R_d$ are as defined in Table T1.

Table 752: This table discloses the 151 compounds T752.001 to T752.151 of the formula $I_{26}$, wherein $R^5$ and G are hydrogen, D is NO-propargyl and $R_a$, $R_b$, $R_c$ and $R_d$ are as defined in Table T1.

Table 753: This table discloses the 151 compounds T753.001 to T753.151 of the formula $I_{26}$, wherein $R^5$ and G are hydrogen, D is NO-benzyl and $R_a$, $R_b$, $R_c$ and $R_d$ are as defined in Table T1.

Table 754: This table discloses the 151 compounds T754.001 to T754.151 of the formula $I_{26}$, wherein $R^5$ and G are hydrogen, D is NOCH$_2$OCH$_3$ and $R_a$, $R_b$, $R_c$ and $R_d$ are as defined in Table T1.

Table 755: This table discloses the 151 compounds T755.001 to T755.151 of the formula $I_{26}$, wherein $R^5$ and G are hydrogen, D is NOCH$_2$CH$_2$OCH$_3$ and $R_a$, $R_b$, $R_c$ and $R_d$ are as defined in Table T1.

Table 756: This table discloses the 151 compounds T756.001 to T756.151 of the formula $I_{26}$, wherein $R^5$ and G are hydrogen, D is NOCH$_2$-cyclohexyl and $R_a$, $R_b$, $R_c$ and $R_d$ are as defined in Table T1.

Table 757: This table discloses the 151 compounds T757.001 to T757.151 of the formula $I_{26}$, wherein $R^5$ and G are hydrogen, D is NO-(tetrahydrofuran-2-yl) and $R_a$, $R_b$, $R_c$ and $R_d$ are as defined in Table T1.

Table 758: This table discloses the 151 compounds T758.001 to T758.151 of the formula $I_{26}$, wherein $R^5$ and G are hydrogen, D is NO-(tetrahydropyran-2-yl) and $R_a$, $R_b$, $R_c$ and $R_d$ are as defined in Table T1.

Table 759: This table discloses the 151 compounds T759.001 to T759.151 of the formula $I_{26}$, wherein $R^5$ and G are hydrogen, D is NO-(tetrahydrofuran-2-ylmethyl) and $R_a$, $R_b$, $R_c$ and $R_d$ are as defined in Table T1.

Table 760: This table discloses the 151 compounds T760.001 to T760.151 of the formula $I_{26}$, wherein $R^5$ and G are hydrogen, D is NO-(tetrahydrofuran-3-ylmethyl) and $R_a$, $R_b$, $R_c$ and $R_d$ are as defined in Table T1.

Table 761: This table discloses the 151 compounds T761.001 to T761.151 of the formula $I_{26}$, wherein $R^5$ and G are hydrogen, D is NO-(tetrahydropyran-4-ylmethyl) and $R_a$, $R_b$, $R_c$ and $R_d$ are as defined in Table T1.

Table 762: This table discloses the 151 compounds T762.001 to T762.151 of the formula $I_{26}$, wherein $R^5$ and G are hydrogen, D is NO-cyclohexyl and $R_a$, $R_b$, $R_c$ and $R_d$ are as defined in Table T1.

Table 763: This table discloses the 151 compounds T763.001 to T763.151 of the formula $I_{26}$, wherein $R^5$ and G are hydrogen, D is NO-(furan-2-ylmethyl) and $R_a$, $R_b$, $R_c$ and $R_d$ are as defined in Table T1.

Table 764: This table discloses the 151 compounds T764.001 to T764.151 of the formula $I_{26}$, wherein $R^5$ and G are hydrogen, D is NO-(furan-3-ylmethyl) and $R_a$, $R_b$, $R_c$ and $R_d$ are as defined in Table T1.

Table 765: This table discloses the 151 compounds T765.001 to T765.151 of the formula $I_{26}$, wherein $R^5$ and G are hydrogen, D is O and $R_a$, $R_b$, $R_c$ and $R_d$ are as defined in Table T1.

Table 766: This table discloses the 151 compounds T766.001 to T766.151 of the formula $I_{26}$, wherein $R^5$ and G are hydrogen, D is S and $R_a$, $R_b$, $R_c$ and $R_d$ are as defined in Table T1.

Table 767: This table discloses the 151 compounds T767.001 to T767.151 of the formula $I_{27}$:

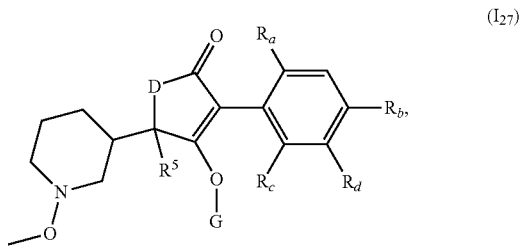

wherein $R^5$ and G are hydrogen, D is NH and $R_a$, $R_b$, $R_c$ and $R_d$ are as defined in Table T1.

Table 768: This table discloses the 151 compounds T768.001 to T768.151 of the formula $I_{27}$, wherein $R^5$ and G are hydrogen, D is NCH$_3$ and $R_a$, $R_b$, $R_c$ and $R_d$ are as defined in Table T1.

Table 769: This table discloses the 151 compounds T769.001 to T769.151 of the formula $I_{27}$, wherein $R^5$ and G are hydrogen, D is NCH$_2$CH$_3$ and $R_a$, $R_b$, $R_c$ and $R_d$ are as defined in Table T1.

Table 770: This table discloses the 151 compounds T770.001 to T770.151 of the formula $I_{27}$, wherein $R^5$ and G are hydrogen, D is NCH$_2$CF$_3$ and $R_a$, $R_b$, $R_c$ and $R_d$ are as defined in Table T1.

Table 771: This table discloses the 151 compounds T771.001 to T771.151 of the formula $I_{27}$, wherein $R^5$ and G are hydrogen, D is N-allyl and $R_a$, $R_b$, $R_c$ and $R_d$ are as defined in Table T1.

Table 772: This table discloses the 151 compounds T772.001 to T772.151 of the formula $I_{27}$, wherein $R^5$ and G are hydrogen, D is N-propargyl and $R_a$, $R_b$, $R_c$ and $R_d$ are as defined in Table T1.

Table 773: This table discloses the 151 compounds T773.001 to T773.151 of the formula $I_{27}$, wherein $R^5$ and G are hydrogen, D is N-benzyl and $R_a$, $R_b$, $R_c$ and $R_d$ are as defined in Table T1.

Table 774: This table discloses the 151 compounds T774.001 to T774.151 of the formula $I_{27}$, wherein $R^5$ and G are hydrogen, D is NCH$_2$OCH$_3$ and $R_a$, $R_b$, $R_c$ and $R_d$ are as defined in Table T1.

Table 775: This table discloses the 151 compounds T775.001 to T775.151 of the formula $I_{27}$, wherein $R^5$ and G are hydrogen, D is NCH$_2$CH$_2$OCH$_3$ and $R_a$, $R_b$, $R_c$ and $R_d$ are as defined in Table T1.

Table 776: This table discloses the 151 compounds T776.001 to T776.151 of the formula $I_{27}$, wherein $R^5$ and G are hydrogen, D is NOH and $R_a$, $R_b$, $R_c$ and $R_d$ are as defined in Table T1.

Table 777: This table discloses the 151 compounds T777.001 to T777.151 of the formula $I_{27}$, wherein $R^5$ and G are hydrogen, D is NOCH$_3$ and $R_a$, $R_b$, $R_c$ and $R_d$ are as defined in Table T1.

Table 778: This table discloses the 151 compounds T778.001 to T778.151 of the formula $I_{27}$, wherein $R^5$ and G are hydrogen, D is NOCH$_2$CH$_3$ and $R_a$, $R_b$, $R_c$ and $R_d$ are as defined in Table T1.

Table 779: This table discloses the 151 compounds T779.001 to T779.151 of the formula $I_{27}$, wherein $R^5$ and G are hydrogen, D is NOCH$_2$CF$_3$ and $R_a$, $R_b$, $R_c$ and $R_d$ are as defined in Table T1.

Table 780: This table discloses the 151 compounds T780.001 to T780.151 of the formula $I_{27}$, wherein $R^5$ and G are hydrogen, D is NO-allyl and $R_a$, $R_b$, $R_c$ and $R_d$ are as defined in Table T1.

Table 781: This table discloses the 151 compounds T781.001 to T781.151 of the formula $I_{27}$, wherein $R^5$ and G are hydrogen, D is NO-propargyl and $R_a$, $R_b$, $R_c$ and $R_d$ are as defined in Table T1.

Table 782: This table discloses the 151 compounds T782.001 to T782.151 of the formula $I_{27}$, wherein $R^5$ and G are hydrogen, D is NO-benzyl and $R_a$, $R_b$, $R_c$ and $R_d$ are as defined in Table T1.

Table 783: This table discloses the 151 compounds T783.001 to T783.151 of the formula $I_{27}$, wherein $R^5$ and G are hydrogen, D is NOCH$_2$OCH$_3$ and $R_a$, $R_b$, $R_c$ and $R_d$ are as defined in Table T1.

Table 784: This table discloses the 151 compounds T784.001 to T784.151 of the formula $I_{27}$, wherein $R^5$ and G are hydrogen, D is NOCH$_2$CH$_2$OCH$_3$ and $R_a$, $R_b$, $R_c$ and $R_d$ are as defined in Table T1.

Table 785: This table discloses the 151 compounds T785.001 to T785.151 of the formula $I_{27}$, wherein $R^5$ and G are hydrogen, D is NOCH$_2$-cyclohexyl and $R_a$, $R_b$, $R_c$ and $R_d$ are as defined in Table T1.

Table 786: This table discloses the 151 compounds T786.001 to T786.151 of the formula $I_{27}$, wherein $R^5$ and G are hydrogen, D is NO-(tetrahydrofuran-2-yl) and $R_a$, $R_b$, $R_c$ and $R_d$ are as defined in Table T1.

Table 787: This table discloses the 151 compounds T787.001 to T787.151 of the formula $I_{27}$, wherein $R^5$ and G are hydrogen, D is NO-(tetrahydropyran-2-yl) and $R_a$, $R_b$, $R_c$ and $R_d$ are as defined in Table T1.

Table 788: This table discloses the 151 compounds T788.001 to T788.151 of the formula $I_{27}$, wherein $R^5$ and G are hydrogen, D is NO-(tetrahydrofuran-2-ylmethyl) and $R_a$, $R_b$, $R_c$ and $R_d$ are as defined in Table T1.

Table 789: This table discloses the 151 compounds T789.001 to T789.151 of the formula $I_{27}$, wherein $R^5$ and G are hydrogen, D is NO-(tetrahydrofuran-3-ylmethyl) and $R_a$, $R_b$, $R_c$ and $R_d$ are as defined in Table T1.

Table 790: This table discloses the 151 compounds T790.001 to T790.151 of the formula $I_{27}$, wherein $R^5$ and G are hydrogen, D is NO-(tetrahydropyran-4-ylmethyl) and $R_a$, $R_b$, $R_c$ and $R_d$ are as defined in Table T1.

Table 791: This table discloses the 151 compounds T791.001 to T791.151 of the formula $I_{27}$, wherein $R^5$ and G are hydrogen, D is NO-cyclohexyl and $R_a$, $R_b$, $R_c$ and $R_d$ are as defined in Table T1.

Table 792: This table discloses the 151 compounds T792.001 to T792.151 of the formula $I_{27}$, wherein $R^5$ and G are hydrogen, D is NO-(furan-2-ylmethyl) and $R_a$, $R_b$, $R_c$ and $R_d$ are as defined in Table T1.

Table 793: This table discloses the 151 compounds T793.001 to T793.151 of the formula $I_{27}$, wherein $R^5$ and G are hydrogen, D is NO-(furan-3-ylmethyl) and $R_a$, $R_b$, $R_c$ and $R_d$ are as defined in Table T1.

Table 794: This table discloses the 151 compounds T794.001 to T794.151 of the formula $I_{27}$, wherein $R^5$ and G are hydrogen, D is O and $R_a$, $R_b$, $R_c$ and $R_d$ are as defined in Table T1.

Table 795: This table discloses the 151 compounds T795.001 to T795.151 of the formula $I_{27}$, wherein $R^5$ and G are hydrogen, D is S and $R_a$, $R_b$, $R_c$ and $R_d$ are as defined in Table T1.

Table 796: This table discloses the 151 compounds T796.001 to T796.151 of the formula $I_{28}$:

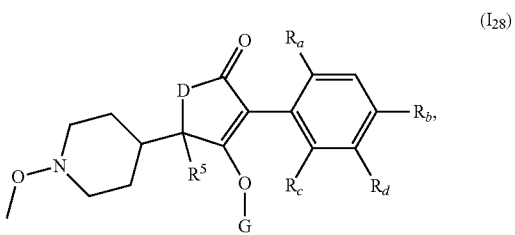

(I$_{28}$)

wherein $R^5$ and G are hydrogen, D is NH and $R_a$, $R_b$, $R_c$ and $R_d$ are as defined in Table T1.

Table 797: This table discloses the 151 compounds T797.001 to T797.151 of the formula $I_{28}$, wherein $R^5$ and G are hydrogen, D is NCH$_3$ and $R_a$, $R_b$, $R_c$ and $R_d$ are as defined in Table T1.

Table 798: This table discloses the 151 compounds T798.001 to T798.151 of the formula $I_{28}$, wherein $R^5$ and G are hydrogen, D is NCH$_2$CH$_3$ and $R_a$, $R_b$, $R_c$ and $R_d$ are as defined in Table T1.

Table 799: This table discloses the 151 compounds T799.001 to T799.151 of the formula $I_{28}$, wherein $R^5$ and G are hydrogen, D is NCH$_2$CF$_3$ and $R_a$, $R_b$, $R_c$ and $R_d$ are as defined in Table T1.

Table 800: This table discloses the 151 compounds T800.001 to T800.151 of the formula $I_{28}$, wherein $R^5$ and G are hydrogen, D is N-allyl and $R_a$, $R_b$, $R_c$ and $R_d$ are as defined in Table T1.

Table 801: This table discloses the 151 compounds T801.001 to T801.151 of the formula $I_{28}$, wherein $R^5$ and G are hydrogen, D is N-propargyl and $R_a$, $R_b$, $R_c$ and $R_d$ are as defined in Table T1.

Table 802: This table discloses the 151 compounds T802.001 to T802.151 of the formula $I_{28}$, wherein $R^5$ and G are hydrogen, D is N-benzyl and $R_a$, $R_b$, $R_c$ and $R_d$ are as defined in Table T1.

Table 803: This table discloses the 151 compounds T803.001 to T803.151 of the formula $I_{28}$, wherein $R^5$ and G are hydrogen, D is NCH$_2$OCH$_3$ and $R_a$, $R_b$, $R_c$ and $R_d$ are as defined in Table T1.

Table 804: This table discloses the 151 compounds T804.001 to T804.151 of the formula $I_{28}$, wherein $R^5$ and G are hydrogen, D is NCH$_2$CH$_2$OCH$_3$ and $R_a$, $R_b$, $R_c$ and $R_d$ are as defined in Table T1.

Table 805: This table discloses the 151 compounds T805.001 to T805.151 of the formula $I_{28}$, wherein $R^5$ and G are hydrogen, D is NOH and $R_a$, $R_b$, $R_c$ and $R_d$ are as defined in Table T1.

Table 806: This table discloses the 151 compounds T806.001 to T806.151 of the formula $I_{28}$, wherein $R^5$ and G are hydrogen, D is NOCH$_3$ and $R_a$, $R_b$, $R_c$ and $R_d$ are as defined in Table T1.

Table 807: This table discloses the 151 compounds T807.001 to T807.151 of the formula $I_{28}$, wherein $R^5$ and G are hydrogen, D is NOCH$_2$CH$_3$ and $R_a$, $R_b$, $R_c$ and $R_d$ are as defined in Table T1.

Table 808: This table discloses the 151 compounds T808.001 to T808.151 of the formula $I_{28}$, wherein $R^5$ and G are hydrogen, D is NOCH$_2$CF$_3$ and $R_a$, $R_b$, $R_c$ and $R_d$ are as defined in Table T1.

Table 809: This table discloses the 151 compounds T809.001 to T809.151 of the formula $I_{28}$, wherein $R^5$ and G are hydrogen, D is NO-allyl and $R_a$, $R_b$, $R_c$ and $R_d$ are as defined in Table T1.

Table 810: This table discloses the 151 compounds T810.001 to T810.151 of the formula $I_{28}$, wherein $R^5$ and G are hydrogen, D is NO-propargyl and $R_a$, $R_b$, $R_c$ and $R_d$ are as defined in Table T1.

Table 811: This table discloses the 151 compounds T811.001 to T811.151 of the formula $I_{28}$, wherein $R^5$ and G are hydrogen, D is NO-benzyl and $R_a$, $R_b$, $R_c$ and $R_d$ are as defined in Table T1.

Table 812: This table discloses the 151 compounds T812.001 to T812.151 of the formula $I_{28}$, wherein $R^5$ and G are hydrogen, D is $NOCH_2OCH_3$ and $R_a$, $R_b$, $R_c$ and $R_d$ are as defined in Table T1.

Table 813: This table discloses the 151 compounds T813.001 to T813.151 of the formula $I_{28}$, wherein $R^5$ and G are hydrogen, D is $NOCH_2CH_2OCH_3$ and $R_a$, $R_b$, $R_c$ and $R_d$ are as defined in Table T1.

Table 814: This table discloses the 151 compounds T814.001 to T814.151 of the formula $I_{28}$, wherein $R^5$ and G are hydrogen, D is $NOCH_2$-cyclohexyl and $R_a$, $R_b$, $R_c$ and $R_d$ are as defined in Table T1.

Table 815: This table discloses the 151 compounds T815.001 to T815.151 of the formula $I_{28}$, wherein $R^5$ and G are hydrogen, D is NO-(tetrahydrofuran-2-yl) and $R_a$, $R_b$, $R_c$ and $R_d$ are as defined in Table T1.

Table 816: This table discloses the 151 compounds T816.001 to T816.151 of the formula $I_{28}$, wherein $R^5$ and G are hydrogen, D is NO-(tetrahydropyran-2-yl) and $R_a$, $R_b$, $R_c$ and $R_d$ are as defined in Table T1.

Table 817: This table discloses the 151 compounds T817.001 to T817.151 of the formula $I_{28}$, wherein $R^5$ and G are hydrogen, D is NO-(tetrahydrofuran-2-ylmethyl) and $R_a$, $R_b$, $R_c$ and $R_d$ are as defined in Table T1.

Table 818: This table discloses the 151 compounds T818.001 to T818.151 of the formula $I_{28}$, wherein $R^5$ and G are hydrogen, D is NO-(tetrahydrofuran-3-ylmethyl) and $R_a$, $R_b$, $R_c$ and $R_d$ are as defined in Table T1.

Table 819: This table discloses the 151 compounds T819.001 to T819.151 of the formula $I_{28}$, wherein $R^5$ and G are hydrogen, D is NO-(tetrahydropyran-4-ylmethyl) and $R_a$, $R_b$, $R_c$ and $R_d$ are as defined in Table T1.

Table 820: This table discloses the 151 compounds T820.001 to T820.151 of the formula $I_{28}$, wherein $R^5$ and G are hydrogen, D is NO-cyclohexyl and $R_a$, $R_b$, $R_c$ and $R_d$ are as defined in Table T1.

Table 821: This table discloses the 151 compounds T821.001 to T821.151 of the formula $I_{28}$, wherein $R^5$ and G are hydrogen, D is NO-(furan-2-ylmethyl) and $R_a$, $R_b$, $R_c$ and $R_d$ are as defined in Table T1.

Table 822: This table discloses the 151 compounds T822.001 to T822.151 of the formula $I_{28}$, wherein $R^5$ and G are hydrogen, D is NO-(furan-3-ylmethyl) and $R_a$, $R_b$, $R_c$ and $R_d$ are as defined in Table T1.

Table 823: This table discloses the 151 compounds T823.001 to T823.151 of the formula $I_{28}$, wherein G is hydrogen, $R^5$ is methyl, D is NH and $R_a$, $R_b$, $R_c$ and $R_d$ are as defined in Table T1.

Table 824: This table discloses the 151 compounds T824.001 to T824.151 of the formula $I_{28}$, wherein $R^5$ and G are hydrogen, D is O and $R_a$, $R_b$, $R_c$ and $R_d$ are as defined in Table T1.

Table 825: This table discloses the 151 compounds T825.001 to T825.151 of the formula $I_{28}$, wherein G is hydrogen, $R^5$ is methyl, D is O and $R_a$, $R_b$, $R_c$ and $R_d$ are as defined in Table T1.

Table 826: This table discloses the 151 compounds T826.001 to T826.151 of the formula $I_{28}$, wherein $R^5$ and G are hydrogen, D is S and $R_a$, $R_b$, $R_c$ and $R_d$ are as defined in Table T1.

Table 827: This table discloses the 151 compounds T827.001 to T827.151 of the formula $I_{28}$, wherein G is hydrogen, $R^5$ is methyl, D is S and $R_a$, $R_b$, $R_c$ and $R_d$ are as defined in Table T1.

Table 828: This table discloses the 151 compounds T828.001 to T828.151 of the formula $I_{28}$, wherein G is hydrogen, $R^5$ is methyl, D is $NCH_3$ and $R_a$, $R_b$, $R_c$ and $R_d$ are as defined in Table T1.

Table 829: This table discloses the 151 compounds T829.001 to T829.151 of the formula $I_{29}$:

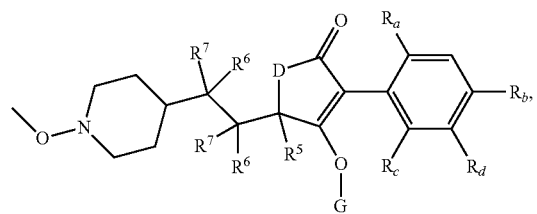

(I$_{29}$)

wherein $R^5$, $R^6$, $R^7$ and G are all hydrogen, D is NH and $R_a$, $R_b$, $R_c$ and $R_d$ are as defined in Table T1.

Table 830: This table discloses the 151 compounds T830.001 to T830.151 of the formula $I_{29}$, wherein $R^5$, $R^6$, $R^7$ and G are all hydrogen, D is $NCH_3$ and $R_a$, $R_b$, $R_c$ and $R_d$ are as defined in Table T1.

Table 831: This table discloses the 151 compounds T831.001 to T831.151 of the formula $I_{29}$, wherein $R^5$, $R^6$, $R^7$ and G are all hydrogen, D is $NCH_2CH_3$ and $R_a$, $R_b$, $R_c$ and $R_d$ are as defined in Table T1.

Table 832: This table discloses the 151 compounds T832.001 to T832.151 of the formula $I_{29}$, wherein $R^5$, $R^6$, $R^7$ and G are all hydrogen, D is $NCH_2CF_3$ and $R_a$, $R_b$, $R_c$ and $R_d$ are as defined in Table T1.

Table 833: This table discloses the 151 compounds T833.001 to T833.151 of the formula $I_{29}$, wherein $R^5$, $R^6$, $R^7$ and G are all hydrogen, D is N-allyl and $R_a$, $R_b$, $R_c$ and $R_d$ are as defined in Table T1.

Table 834: This table discloses the 151 compounds T834.001 to T834.151 of the formula $I_{29}$, wherein $R^5$, $R^6$, $R^7$ and G are all hydrogen, D is N-propargyl and $R_a$, $R_b$, $R_c$ and $R_d$ are as defined in Table T1.

Table 835: This table discloses the 151 compounds T835.001 to T835.151 of the formula $I_{29}$, wherein $R^5$, $R^6$, $R^7$ and G are all hydrogen, D is N-benzyl and $R_a$, $R_b$, $R_c$ and $R_d$ are as defined in Table T1.

Table 836: This table discloses the 151 compounds T836.001 to T836.151 of the formula $I_{29}$, wherein $R^5$, $R^6$, $R^7$ and G are all hydrogen, D is $NCH_2OCH_3$ and $R_a$, $R_b$, $R_c$ and $R_d$ are as defined in Table T1.

Table 837: This table discloses the 151 compounds T837.001 to T837.151 of the formula $I_{29}$, wherein $R^5$, $R^6$, $R^7$ and G are all hydrogen, D is $NCH_2CH_2OCH_3$ and $R_a$, $R_b$, $R_c$ and $R_d$ are as defined in Table T1.

Table 838: This table discloses the 151 compounds T838.001 to T838.151 of the formula $I_{29}$, wherein $R^5$, $R^6$, $R^7$ and G are all hydrogen, D is NOH and $R_a$, $R_b$, $R_c$ and $R_d$ are as defined in Table T1.

Table 839: This table discloses the 151 compounds T839.001 to T839.151 of the formula $I_{29}$, wherein $R^5$, $R^6$, $R^7$ and G are all hydrogen, D is $NOCH_3$ and $R_a$, $R_b$, $R_c$ and $R_d$ are as defined in Table T1.

Table 840: This table discloses the 151 compounds T840.001 to T840.151 of the formula $I_{29}$, wherein $R^5$, $R^6$, $R^7$ and G are all hydrogen, D is $NOCH_2CH_3$ and $R_a$, $R_b$, $R_c$ and $R_d$ are as defined in Table T1.

Table 841: This table discloses the 151 compounds T841.001 to T841.151 of the formula $I_{29}$, wherein $R^5$, $R^6$, $R^7$ and G are all hydrogen, D is $NOCH_2CF_3$ and $R_a$, $R_b$, $R_c$ and $R_d$ are as defined in Table T1.

Table 842: This table discloses the 151 compounds T842.001 to T842.151 of the formula $I_{29}$, wherein $R^5$, $R^6$, $R^7$ and G are all hydrogen, D is NO-allyl and $R_a$, $R_b$, $R_c$ and $R_d$ are as defined in Table T1.

Table 843: This table discloses the 151 compounds T843.001 to T843.151 of the formula $I_{29}$, wherein $R^5$, $R^6$, $R^7$ and G are all hydrogen, D is NO-propargyl and $R_a$, $R_b$, $R_c$ and $R_d$ are as defined in Table T1.

Table 844: This table discloses the 151 compounds T844.001 to T844.151 of the formula $I_{29}$, wherein $R^5$, $R^6$, $R^7$ and G are all hydrogen, D is NO-benzyl and $R_a$, $R_b$, $R_c$ and $R_d$ are as defined in Table T1.

Table 845: This table discloses the 151 compounds T845.001 to T845.151 of the formula $I_{29}$, wherein $R^5$, $R^6$, $R^7$ and G are all hydrogen, D is $NOCH_2OCH_3$ and $R_a$, $R_b$, $R_c$ and $R_d$ are as defined in Table T1.

Table 846: This table discloses the 151 compounds T846.001 to T846.151 of the formula $I_{29}$, wherein $R^5$, $R^6$, $R^7$ and G are all hydrogen, D is $NOCH_2CH_2OCH_3$ and $R_a$, $R_b$, $R_c$ and $R_d$ are as defined in Table T1.

Table 847: This table discloses the 151 compounds T847.001 to T847.151 of the formula $I_{29}$, wherein $R^5$, $R^6$, $R^7$ and G are all hydrogen, D is $NOCH_2$-cyclohexyl and $R_a$, $R_b$, $R_c$ and $R_d$ are as defined in Table T1.

Table 848: This table discloses the 151 compounds T848.001 to T848.151 of the formula $I_{29}$, wherein $R^5$, $R^6$, $R^7$ and G are all hydrogen, D is NO-(tetrahydrofuran-2-yl) and $R_a$, $R_b$, $R_c$ and $R_d$ are as defined in Table T1.

Table 849: This table discloses the 151 compounds T849.001 to T849.151 of the formula $I_{29}$, wherein $R^5$, $R^6$, $R^7$ and G are all hydrogen, D is NO-(tetrahydropyran-2-yl) and $R_a$, $R_b$, $R_c$ and $R_d$ are as defined in Table T1.

Table 850: This table discloses the 151 compounds T850.001 to T850.151 of the formula $I_{29}$, wherein $R^5$, $R^6$, $R^7$ and G are all hydrogen, D is NO-(tetrahydrofuran-2-ylmethyl) and $R_a$, $R_b$, $R_c$ and $R_d$ are as defined in Table T1.

Table 851: This table discloses the 151 compounds T851.001 to T851.151 of the formula $I_{29}$, wherein $R^5$, $R^6$, $R^7$ and G are all hydrogen, D is NO-(tetrahydrofuran-3-ylmethyl) and $R_a$, $R_b$, $R_c$ and $R_d$ are as defined in Table T1.

Table 852: This table discloses the 151 compounds T852.001 to T852.151 of the formula $I_{29}$, wherein $R^5$, $R^6$, $R^7$ and G are all hydrogen, D is NO-(tetrahydropyran-4-ylmethyl) and $R_a$, $R_b$, $R_c$ and $R_d$ are as defined in Table T1.

Table 853: This table discloses the 151 compounds T853.001 to T853.151 of the formula $I_{29}$, wherein $R^5$, $R^6$, $R^7$ and G are all hydrogen, D is NO-cyclohexyl and $R_a$, $R_b$, $R_c$ and $R_d$ are as defined in Table T1.

Table 854: This table discloses the 151 compounds T854.001 to T854.151 of the formula $I_{29}$, wherein $R^5$, $R^6$, $R^7$ and G are all hydrogen, D is NO-(furan-2-ylmethyl) and $R_a$, $R_b$, $R_c$ and $R_d$ are as defined in Table T1.

Table 855: This table discloses the 151 compounds T855.001 to T855.151 of the formula $I_{29}$, wherein $R^5$, $R^6$, $R^7$ and G are all hydrogen, D is NO-(furan-3-ylmethyl) and $R_a$, $R_b$, $R_c$ and $R_d$ are as defined in Table T1.

Table 856: This table discloses the 151 compounds T856.001 to T856.151 of the formula $I_{29}$, wherein $R^6$, $R^7$ and G are hydrogen, $R^5$ is methyl, D is NH and $R_a$, $R_b$, $R_c$ and $R_d$ are as defined in Table T1.

Table 857: This table discloses the 151 compounds T857.001 to T857.151 of the formula $I_{29}$, wherein $R^5$, $R^6$, $R^7$ and G are all hydrogen, D is O and $R_a$, $R_b$, $R_c$ and $R_d$ are as defined in Table T1.

Table 858: This table discloses the 151 compounds T858.001 to T858.151 of the formula $I_{29}$, wherein $R^6$, $R^7$ and G are hydrogen, $R^5$ is methyl, D is O and $R_a$, $R_b$, $R_c$ and $R_d$ are as defined in Table T1.

Table 859: This table discloses the 151 compounds T859.001 to T859.151 of the formula $I_{29}$, wherein $R^5$, $R^6$, $R^7$ and G are all hydrogen, D is S and $R_a$, $R_b$, $R_c$ and $R_d$ are as defined in Table T1.

Table 860: This table discloses the 151 compounds T860.001 to T860.151 of the formula $I_{29}$, wherein $R^6$, $R^7$ and G are hydrogen, $R^5$ is methyl, D is S and $R_a$, $R_b$, $R_c$ and $R_d$ are as defined in Table T1.

Table 861: This table discloses the 151 compounds T861.001 to T861.151 of the formula $I_{29}$, wherein $R^6$, $R^7$ and G are hydrogen, $R^5$ is methyl, D is $NCH_3$ and $R_a$, $R_b$, $R_c$ and $R_d$ are as defined in Table T1.

The compounds according to the invention are preventively and/or curatively valuable active ingredients in the field of pest control, even at low rates of application, which have a very favorable biocidal spectrum and are well tolerated by warm-blooded species, fish and lants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

The compounds of formula I can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula I include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. *(thrips)*, *Leptinotarsa decemlineata* (Colorado potato beetle), *Anthonomus grandis* (boll weevil), *Aonidiella* spp.

(scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus*, *Reticulitermes flavipes*, *R. speratu*, *R. virginicus*, *R. hesperus*, and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Further examples of the above mentioned pests are:

from the order Acarina, for example,

*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemLineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Diptera, for example,

*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order Heteroptera, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

from the order Homoptera, for example,

*Aleurothrixus floccosus, Aleyrodes brassicae, Aonidiella* spp., Aphididae, *Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*;

from the order Hymenoptera, for example,

*Acromyrmex, Atta* spp., *Cephus* spp., *Diprion* spp., Diprionidae, *Gilpinia polytoma, Hoplocampa* spp., *Lasius* spp., *Monomorium pharaonis, Neodiprion* spp., *Solenopsis* spp. and *Vespa* spp.;

from the order Isoptera, for example,

*Reticulitermes* spp.;

from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Periplaneta* spp. and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Frankliniella* spp., *Hercinothrips* spp., *Scirtothrips aurantii, Taeniothrips* spp., *Thrips palmi* and *Thrips tabaci*; and from the order Thysanura, for example,

*Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is also to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein CryIF for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Crops that exhibit enhanced yield or quality include those with improved flowering or fruit ripening properties (such as delayed ripening); modified oil, starch, amino acid, fatty acid, vitamin, phenolic or other content (such as Vistive™ soybean variety); enhanced nutrient utilisation (such as improved nitrogen assimilation); and enhanced quality plant product (such as higher quality cotton fibre).

Further areas of use of the compounds and compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compounds and compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds and compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore provides a method of combating and controlling insects, acarines, nematodes or molluscs which comprises applying an insecticidally, acaricidally, nematicidally or molluscicidally effective amount of a compound of formula I, or a composition containing a compound of formula I, to a pest, a locus of pest, or to a plant susceptible to attack by a pest, The compounds of formula I are preferably used against insects or acarines.

The term "plant" as used herein includes seedlings, bushes and trees.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo¬ lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propy¬ lene glycol unit. Examples which may be mentioned are nonylphenoxypolyethoxyethanol, castor oil polyglycol ether, polypropylene glycol/polyethylene oxide adducts, tributylpheno¬ xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl¬ ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl ¬ naphthalenesulfonic acid or of a naphthalenesulfonic acid/ formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl) phosphate, tris-n-octyl phosphate and tris-butoxyethyl phosphate, where tris-(2-ethylhexyl) phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037,373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

As a rule, the compositions comprise 0.1 to 99%, especially 0.1 to 95%, of active ingredient of the formula I and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 50%, more preferably 5 to 20%
surfactant: 1 to 30%, preferably 10 to 20%
solvent: 5 to 98%, preferably 70 to 85%
Dusts:
active ingredient: 0.1 to 10%, preferably 2 to 5%,
solid carrier: 99.9 to 90%, preferably 99.9 to 99%
Suspension Concentrates:
active ingredient: 5 to 75%, preferably 10 to 50%, more preferably 10 to 40%
water: 94 to 24%, preferably 88 to 30%
surfactant: 1 to 40%, preferably 2 to 30%
Oil-Based Suspension Concentrates:
active ingredient: 2 to 75%, preferably 5 to 50%, more preferably 10 to 25%
oil: 94 to 24%, preferably 88 to 30%
surfactant: 1 to 40%, preferably 2 to 30%
Wettable Powders:
active ingredient: 0.5 to 90%, preferably 1 to 80%, more preferably 25 to 75%
surfactant: 0.5 to 20%, preferably 1 to 15%
solid carrier: 5 to 99%, preferably 15 to 98%

Granulates:

active ingredient: 0.5 to 30%, preferably 3 to 25%, more preferably 3 to 15% solid carrier: 99.5 to 70%, preferably 97 to 85%

Preferably, the term "active ingredient" refers to one of the compounds selected from Tables 1 to 861 shown above. It also refers to mixtures of the compound of formula I, in particular a compound selected from said Tables 1 to 861, with other insecticides, fungicides, herbicides, safeners, adjuvants and the like, which mixtures are specifically disclosed below.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO08/017,388, which can enhance the efficacy of the inventive compounds; or other active ingredients for achieving specific effects, for example ammonium or phosphonium salts, in particular halides, (hydrogen)sulphates, nitrates, (hydrogen) carbonates, citrates, tartrates, formiates and acetates, as described in WO07/068,427 and WO07/068,428, which also can enhance the efficacy of the inventive compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

Further methods of application of the compositions according to the invention comprise drip application onto the soil, dipping of parts of plants such as roots bulbs or tubers, drenching the soil, as well as soil injection. These methods are known in the art.

In order to apply a compound of formula I as an insecticide, acaricide, nematicide or molluscicide to a pest, a locus of pest, or to a plant susceptible to attack by a pest, a compound of formula I is usually formulated into a composition which includes, in addition to the compound of formula I, a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula I. The composition is generally used for the control of pests such that a compound of formula I is applied at a rate of from 0.1 g to 10 kg per hectare, preferably from 1 g to 6 kg per hectare, more preferably from 1 g to 1 kg per hectare.

When used in a seed dressing, a compound of formula I is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula I and a suitable carrier or diluent therefor.

In a still further aspect the invention provides a method of combating and controlling pests at a locus which comprises treating the pests or the locus of the pests with an insecticidally, acaricidally, nematicidally or molluscicidally effective amount of a composition comprising a compound of formula I.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula I.

Dustable powders (DP) may be prepared by mixing a compound of formula I with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula I with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula I and one or more powdered solid diluents or carriers, or from pre-formed blank granules by absorbing a compound of formula I (or a solution thereof, in a suitable agent) in a porous granular material (such as pumice, attapulgite clays, fuller's earth, kieselguhr, diatomaceous earths or ground corn cobs) or by adsorbing a compound of formula I (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula I in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula I in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula I is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

Oil-based suspension concentrate (OD) may be prepared similarly by suspending finely divided insoluble solid particles of a compound of formula I in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, antioxidants, dyestuffs, and/or inert filler materials. An OD is intended and suitable for dilution with water before use to produce a spray solution with sufficient stability to allow spray application through appropriate equipment.

Aerosol formulations comprise a compound of formula I and a suitable propellant (for example n-butane). A compound of formula I may also be dissolved or dispersed in a suitable medium (for example water or a water miscible liquid, such as n-propanol) to provide compositions for use in non-pressurised, hand-actuated spray pumps.

A compound of formula I may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula I and, optionally, a carrier or diluent therefor. The polymeric shell may be produced by either an interfacial polycondensation reaction or by a coacervation procedure. The compositions may provide for controlled release of the compound of formula I and they may be used for seed treatment. A compound of formula I may also be formulated in a biodegradable polymeric matrix to provide a slow, controlled release of the compound.

A compound of formula I may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above. Compositions for treating seed may include an agent for assisting the adhesion of the composition to the seed (for example a mineral oil or a film-forming barrier).

A composition of the present invention may include one or more additives to improve the biological performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula I may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

A compound of formula I may be used in mixtures with fertilisers (for example nitrogen-, potassium- or phosphorus-containing fertilisers, and more particularly ammonium nitrate and/or urea fertilizers). Suitable formulation types include granules of fertiliser. The mixtures suitably contain up to 25% by weight of the compound of formula I.

The invention therefore also provides a fertiliser composition comprising a fertiliser and a compound of formula I.

The compositions of this invention may contain other compounds having biological activity, for example micronutrients or compounds having fungicidal activity or which possess plant growth regulating, herbicidal, safening, insecticidal, nematicidal or acaricidal activity.

The compound of formula I may be the sole active ingredient of the composition or it may be admixed with one or more additional active ingredients such as a pesticide (insect, acarine, mollusc and nematode pesticide), fungicide, synergist, herbicide, safener or plant growth regulator where appropriate. The activity of the compositions according to the invention may thereby be broadened considerably and may have surprising advantages which can also be described, in a wider sense, as synergistic activity. An additional active ingredient may: provide a composition having a broader spectrum of activity or increased persistence at a locus; provide a composition demonstrating better plant/crop tolerance by reducing phytotoxicity; provide a composition controlling insects in their different development stages; synergise the activity or complement the activity (for example by increasing the speed of effect or overcoming repellency) of the compound of formula I; or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, or spinosad, spinetoram or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, clothianidin, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine or pyrifluquinazon;

r) Spirotetramat, spirodiclofen or spiromesifen;

s) Flubendiamide, chloranthraliniprole, or cyanthraniliprole;

t) Cyenopyrafen or cyflumetofen; or u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorbenzilate; or growth regulators, such as hydramethylnon, cyromazine, methoprene, chlorfluazuron or diflubenzuron).

The following mixtures of the compounds of formula I with active ingredients are preferred, wherein, preferably, the term "COMPOUND OF FORMULA I" refers to a compound selected from the Tables 1 to 861:

an adjuvant selected from the group of substances consisting of an oil of vegetable or animal origin, a mineral oil, alkyl esters of such oils or mixtures of such oils, and petroleum oils (alternative name) (628)+COMPOUND OF FORMULA I, an acaricide selected from the group of substances consisting of 1,1-bis(4-chlorophenyl)-2-ethoxyethanol (IUPAC name) (910)+COMPOUND OF FORMULA I, 2,4-dichlorophenyl benzenesulfonate (IUPAC/Chemical Abstracts name) (1059)+COMPOUND OF FORMULA I, 2-fluoro-N-methyl-N-1-naphthylacetamide (IUPAC name) (1295)+COMPOUND OF FORMULA I, 4-chlorophenyl phenyl sulfone (IUPAC name) (981)+COMPOUND OF FORMULA I, abamectin (1)+COMPOUND OF FORMULA I, acequinocyl (3)+COMPOUND OF FORMULA I, acetoprole [CCN]+COMPOUND OF FORMULA I, acrinathrin (9)+COMPOUND OF FORMULA I, aldicarb (16)+COMPOUND OF FORMULA I, aldoxycarb (863)+COMPOUND OF FORMULA I, alpha-cypermethrin (202)+COMPOUND OF FORMULA I, amidithion (870)+COMPOUND OF FORMULA I, amidoflumet [CCN]+COMPOUND OF FORMULA I, amidothioate (872)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, aramite (881)+COMPOUND OF FORMULA I, arsenous oxide (882)+COMPOUND OF FORMULA I, AVI 382 (compound code)+COMPOUND OF FORMULA I, AZ 60541 (compound code)+COMPOUND OF FORMULA I, azinphos-ethyl (44)+COMPOUND OF FORMULA I, azinphos-methyl (45)+COMPOUND OF FORMULA I, azobenzene (IUPAC name) (888)+COMPOUND OF FORMULA I, azocyclotin (46)+COMPOUND OF FORMULA I, azothoate (889)+COMPOUND OF FORMULA I, benomyl (62)+COMPOUND OF FORMULA I, benoxafos (alternative name) [CCN]+COMPOUND OF FORMULA I, benzoximate (71)+COMPOUND OF FORMULA I, benzyl benzoate (IUPAC name) [CCN]+COMPOUND OF FORMULA I, bifenazate (74)+COMPOUND OF FORMULA I, bifenthrin (76)+COMPOUND OF FORMULA I, binapacryl (907)+COMPOUND OF FORMULA I, brofenvalerate (alternative name)+COMPOUND OF FORMULA I, bromocyclen (918)+COMPOUND OF FORMULA I, bromophos (920)+COMPOUND OF FORMULA I, bromophos-ethyl (921)+COMPOUND OF FORMULA I, bromopropylate (94)+COMPOUND OF FORMULA I, buprofezin (99)+COMPOUND OF FORMULA I, butocarboxim (103)+COMPOUND OF FORMULA I, butoxycarboxim (104)+COMPOUND OF FORMULA I, butylpyridaben (alternative name)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbophenothion (947)+COMPOUND OF FORMULA I, CGA 50'439 (development code) (125)+COMPOUND OF FORMULA I, chinomethionat (126)+COMPOUND OF FORMULA I, chlorbenside (959)+COMPOUND OF FORMULA I, chlordimeform (964)+COMPOUND OF FORMULA I, chlordimeform hydrochloride (964)+COMPOUND OF FORMULA I, chlorfenapyr (130)+COMPOUND OF FORMULA I, chlorfenethol (968)+COMPOUND OF FORMULA I, chlorfenson (970)+COMPOUND OF FORMULA I, chlorfensulphide (971)+COMPOUND OF FORMULA I, chlorfenvinphos (131)+COMPOUND OF FORMULA I, chlorobenzilate (975)+COMPOUND OF FORMULA I, chloromebuform (977)+COMPOUND OF FORMULA I, chloromethiuron (978)+COMPOUND OF FORMULA I, chloropropylate (983)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, cinerin 1 (696)+COMPOUND OF FORMULA I, cinerin II (696)+COMPOUND OF FORMULA I, cinerins (696)+COMPOUND OF FORMULA I, clofentezine (158)+COMPOUND OF FORMULA I, closantel (alternative name) [CCN]+COMPOUND OF FORMULA I, coumaphos (174)+COMPOUND OF FORMULA I, crotamiton (alternative name) [CCN]+COMPOUND OF FORMULA I, crotoxyphos (1010)+COMPOUND OF FORMULA I, cufraneb (1013)+COMPOUND OF FORMULA I, cyanthoate (1020)+COMPOUND OF FORMULA I, cyenopyrafen [CCN]+COMPOUND OF FORMULA I, cyflumetofen (CAS Reg. No.: 400882-07-7)+COMPOUND OF FORMULA I, cyhalothrin (196)+COMPOUND OF FORMULA I, cyhexatin (199)+COMPOUND OF FORMULA I, cypermethrin (201)+COMPOUND OF FORMULA I, DCPM (1032)+COMPOUND OF FORMULA I, DDT (219)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diazinon (227)+COMPOUND OF FORMULA I, dichlofluanid (230)+COMPOUND OF FORMULA I, dichlorvos (236)+COMPOUND OF FORMULA I, dicliphos (alternative name)+COMPOUND OF FORMULA I, dicofol (242)+COMPOUND OF FORMULA I, dicrotophos (243)+COMPOUND OF FORMULA I, dienochlor (1071)+COMPOUND OF FORMULA I, diflovidazin [CCN]+COMPOUND OF FORMULA I, dimefox (1081)+COMPOUND OF FORMULA I, dimethoate (262)+COMPOUND OF FORMULA I, dinactin (alternative name) (653)+COMPOUND OF FORMULA I, dinex (1089)+COMPOUND OF FORMULA I, dinex-diclexine (1089)+COMPOUND OF FORMULA I, dinobuton (269)+COMPOUND OF FORMULA I, dinocap (270)+COMPOUND OF FORMULA I, dinocap-4 [CCN]+COMPOUND OF FORMULA I, dinocap-6 [CCN]+COMPOUND OF FORMULA I, dinocton (1090)+COMPOUND OF FORMULA I, dinopenton (1092)+COMPOUND OF FORMULA I, dinosulfon (1097)+COMPOUND OF FORMULA I, dinoterbon (1098)+COMPOUND OF FORMULA I, dioxathion (1102)+COMPOUND OF FORMULA I, diphenyl sulfone (IUPAC name) (1103)+COMPOUND OF FORMULA I, disulfuram (alternative name) [CCN]+COMPOUND OF FORMULA I, disulfoton (278)+COMPOUND OF FORMULA I, DNOC (282)+COMPOUND OF FORMULA I, dofenapyn (1113)+COMPOUND OF FORMULA I, doramectin (alternative name) [CCN]+COMPOUND OF FORMULA I, endosulfan (294)+COMPOUND OF FORMULA I, endothion (1121)+COMPOUND OF FORMULA I, EPN (297)+COMPOUND OF FORMULA I, eprinomectin (alternative name) [CCN]+COMPOUND OF FORMULA I, ethion (309)+COMPOUND OF FORMULA I, ethoate-methyl (1134)+COMPOUND OF FORMULA I, etoxazole (320)+COMPOUND OF FORMULA I, etrimfos (1142)+COMPOUND OF FORMULA I, fenazaflor (1147)+COMPOUND OF FORMULA I, fenazaquin (328)+COMPOUND OF FORMULA I, fenbutatin oxide (330)+COMPOUND OF FORMULA I, fenothiocarb (337)+COMPOUND OF FORMULA I, fenpropathrin (342)+COMPOUND OF FORMULA I, fenpyrad (alternative name)+COMPOUND OF FORMULA I, fenpyroximate (345)+COMPOUND OF FORMULA I, fenson (1157)+COMPOUND OF FORMULA I, fentrifanil (1161)+COMPOUND OF FORMULA I, fenvalerate (349)+COMPOUND OF FORMULA I, fipronil (354)+COMPOUND OF FORMULA I, fluacrypyrim (360)+COMPOUND OF FORMULA I, fluazuron (1166)+COMPOUND OF FORMULA I, flubenzimine (1167)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, flufenoxuron (370)+COMPOUND OF FORMULA I, flumethrin (372)+COMPOUND OF FORMULA I, fluorbenside (1174)+COMPOUND OF FORMULA I, fluvalinate (1184)+COMPOUND OF FORMULA I, FMC 1137 (development code) (1185)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, gamma-HCH (430)+COMPOUND OF FORMULA I, glyodin (1205)+COMPOUND OF FORMULA I, halfenprox (424)+COMPOUND OF FORMULA I, heptenophos (432)+COMPOUND OF FORMULA I, hexadecyl cyclopropanecarboxylate (IUPAC/Chemical Abstracts name) (1216)+COMPOUND OF FORMULA I, hexythiazox (441)+COMPOUND OF FORMULA I, IKA 2002 (CAS Reg. No.: 211923-74-9)+COMPOUND OF FORMULA I, iodomethane (IUPAC name) (542)+COMPOUND OF FORMULA I, isocarbophos (alternative name) (473)+COMPOUND OF FORMULA I, isopropyl O-(methoxyaminothiophosphoryl)salicylate (IUPAC name) (473)+COMPOUND OF FORMULA I, ivermectin (alternative name) [CCN]+COMPOUND OF FORMULA I, jasmolin I (696)+COMPOUND OF FORMULA I, jasmolin II (696)+COMPOUND OF FORMULA I, jodfenphos (1248)+COMPOUND OF FORMULA I, lindane (430)+COMPOUND OF FORMULA I, lufenuron (490)+COMPOUND OF FORMULA I, malathion (492)+COMPOUND OF FORMULA I, malonoben (1254)+COMPOUND OF FORMULA I, mecarbam (502)+COMPOUND OF FORMULA I, mephosfolan (1261)+COMPOUND OF FORMULA I, mesulfen (alternative name) [CCN]+COMPOUND OF FORMULA I, methacrifos (1266)+COMPOUND OF FORMULA I, methamidophos (527)+COMPOUND OF FORMULA I, methidathion (529)+COMPOUND OF FORMULA I, methiocarb (530)+COMPOUND OF FORMULA I, methomyl (531)+COMPOUND OF FORMULA I, methyl bromide (537)+COMPOUND OF FORMULA I, metolcarb (550)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naled (567)+ COMPOUND OF FORMULA I, NC-184 (compound code)+COMPOUND OF FORMULA I, NC-512 (compound code)+COMPOUND OF FORMULA I, nifluridide (1309)+COMPOUND OF FORMULA I, nikkomycins (alternative name) [CCN]+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, omethoate (594)+COMPOUND OF FORMULA I, oxamyl (602)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, parathion (615)+COMPOUND OF FORMULA I, permethrin (626)+COMPOUND OF FORMULA I, petroleum oils (alternative name) (628)+COMPOUND OF FORMULA I, phenkapton (1330)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosphamidon (639)+COMPOUND OF FORMULA I, phoxim (642)+COMPOUND OF FORMULA I, pirimiphos-methyl (652)+COMPOUND OF FORMULA I, polychloroterpenes (traditional name) (1347)+COMPOUND OF FORMULA I, polynactins (alternative name) (653)+COMPOUND OF FORMULA I, proclonol (1350)+COMPOUND OF FORMULA I, profenofos (662)+COMPOUND OF FORMULA I, promacyl (1354)+COMPOUND OF FORMULA I, propargite (671)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothoate (1362)+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridaphenthion (701)+COMPOUND OF FORMULA I, pyrimidifen (706)+COMPOUND OF FORMULA I, pyrimitate (1370)+COMPOUND OF FORMULA I, quinalphos (711)+COMPOUND OF FORMULA I, quintiofos (1381)+COMPOUND OF FORMULA I, R-1492 (development code) (1382)+COMPOUND OF FORMULA I, RA-17 (development code) (1383)+COMPOUND OF FORMULA I, rotenone (722)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, sophamide (1402)+COMPOUND OF FORMULA I, spirodiclofen (738)+COMPOUND OF FORMULA I, spiromesifen (739)+ COMPOUND OF FORMULA I, SSI-121 (development code) (1404)+COMPOUND OF FORMULA I, sulfuram (alternative name) [CCN]+COMPOUND OF FORMULA I, sulfluramid (750)+COMPOUND OF FORMULA I, sulfotep (753)+COMPOUND OF FORMULA I, sulfur (754)+COMPOUND OF FORMULA I, SZI-121 (development code) (757)+COMPOUND OF FORMULA I, tau-fluvalinate (398)+COMPOUND OF FORMULA I, tebufenpyrad (763)+COMPOUND OF FORMULA I, TEPP (1417)+COMPOUND OF FORMULA I, terbam (alternative name)+COMPOUND OF FORMULA I, tetrachlorvinphos (777)+COMPOUND OF FORMULA I, tetradifon (786)+COMPOUND OF FORMULA I, tetranactin (alternative name) (653)+ COMPOUND OF FORMULA I, tetrasul (1425)+COMPOUND OF FORMULA I, thiafenox (alternative name)+COMPOUND OF FORMULA I, thiocarboxime (1431)+COMPOUND OF FORMULA I, thiofanox (800)+COMPOUND OF FORMULA I, thiometon (801)+COMPOUND OF FORMULA I, thioquinox (1436)+COMPOUND OF FORMULA I, thuringiensin (alternative name) [CCN]+COMPOUND OF FORMULA I, triamiphos (1441)+COMPOUND OF FORMULA I, triarathene (1443)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trifenofos (1455)+COMPOUND OF FORMULA I, trinactin (alternative name) (653)+COMPOUND OF FORMULA I, vamidothion (847)+COMPOUND OF FORMULA I, vaniliprole [CCN] and YI-5302 (compound code)+COMPOUND OF FORMULA I, an algicide selected from the group of substances consisting of bethoxazin [CCN]+COMPOUND OF FORMULA I, copper dioctanoate (IUPAC name) (170)+ COMPOUND OF FORMULA I, copper sulfate (172)+ COMPOUND OF FORMULA I, cybutryne [CCN]+ COMPOUND OF FORMULA I, dichlone (1052)+ COMPOUND OF FORMULA I, dichlorophen (232)+ COMPOUND OF FORMULA I, endothal (295)+ COMPOUND OF FORMULA I, fentin (347)+ COMPOUND OF FORMULA I, hydrated lime [CCN]+ COMPOUND OF FORMULA I, nabam (566)+ COMPOUND OF FORMULA I, quinoclamine (714)+ COMPOUND OF FORMULA I, quinonamid (1379)+ COMPOUND OF FORMULA I, simazine (730)+ COMPOUND OF FORMULA I, triphenyltin acetate (IUPAC name) (347) and triphenyltin hydroxide (IUPAC name) (347)+COMPOUND OF FORMULA I, an anthelmintic selected from the group of substances consisting of abamectin (1)+COMPOUND OF FORMULA I, crufomate (1011)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ivermectin (alternative name) [CCN]+COMPOUND OF FORMULA I, milbemycin oxime (alternative name) [CCN]+COMPOUND OF FORMULA I, moxidectin (alternative name) [CCN]+COMPOUND OF FORMULA I, piperazine [CCN]+COMPOUND OF FORMULA I, selamectin (alternative name) [CCN]+COMPOUND OF FORMULA I, spinosad (737) and thiophanate (1435)+COMPOUND OF FORMULA I, an avicide selected from the group of substances consisting of chloralose (127)+COMPOUND OF FORMULA I, endrin (1122)+COMPOUND OF FORMULA I, fenthion (346)+COMPOUND OF FORMULA I, pyridin-4-amine (IUPAC name) (23) and strychnine (745)+COMPOUND OF FORMULA I, a bactericide selected from the group of substances consisting of 1-hydroxy-1H-pyridine-2-thione (IUPAC name) (1222)+COMPOUND OF FORMULA I, 4-(quinoxalin-2-ylamino)benzenesulfonamide (IUPAC name) (748)+COMPOUND OF FORMULA I, 8-hydroxyquinoline sulfate (446)+COMPOUND OF FORMULA I, bronopol (97)+COMPOUND OF FORMULA I, copper dioctanoate (IUPAC name) (170)+COMPOUND OF FORMULA I, copper hydroxide (IUPAC name) (169)+COMPOUND OF FORMULA I, cresol [CCN]+COMPOUND OF FORMULA I, dichlorophen (232)+COMPOUND OF FORMULA I, dipyrithione (1105)+COMPOUND OF FORMULA I, dodicin (1112)+COMPOUND OF FORMULA I, fenaminosulf (1144)+COMPOUND OF FORMULA I, formaldehyde (404)+COMPOUND OF FORMULA I, hydrargaphen (alternative name) [CCN]+COMPOUND OF FORMULA I, kasugamycin (483)+COMPOUND OF FORMULA I, kasugamycin hydrochloride hydrate (483)+COMPOUND OF FORMULA I, nickel bis(dimethyldithiocarbamate) (IUPAC name) (1308)+COMPOUND OF FORMULA I, nitrapyrin (580)+COMPOUND OF FORMULA I, octhilinone (590)+COMPOUND OF FORMULA I, oxolinic acid (606)+COMPOUND OF FORMULA I, oxytetracycline (611)+COMPOUND OF FORMULA I, potassium hydroxyquinoline sulfate (446)+COMPOUND OF FORMULA I, probenazole (658)+COMPOUND OF FORMULA I, streptomycin (744)+COMPOUND OF FORMULA I, streptomycin sesquisulfate (744)+COMPOUND OF FORMULA I, tecloftalam (766)+COMPOUND OF FORMULA I, and thiomersal (alternative name) [CCN]+COMPOUND OF FORMULA I, a biological agent selected from the group of substances consisting of *Adoxophyes orana* GV (alternative name) (12)+COMPOUND OF FORMULA I, *Agrobacterium radiobacter* (alternative name) (13)+COMPOUND OF FORMULA I, *Amblyseius* spp. (alternative name) (19)+COMPOUND OF FORMULA I, *Anagrapha falcifera* NPV (alternative name) (28)+COMPOUND OF FORMULA I, *Anagrus atomus* (alternative name) (29)+COMPOUND OF FORMULA I, *Aphelinus abdominalis* (alternative name) (33)+COMPOUND OF FORMULA I, *Aphidius colemani* (alternative name) (34)+COMPOUND OF FORMULA I, *Aphidoletes aphidimyza* (alternative name) (35)+COMPOUND OF FORMULA I, *Autographa californica* NPV (alternative name) (38)+COMPOUND OF FORMULA I, *Bacillus firmus* (alternative name) (48)+COMPOUND OF FORMULA I, *Bacillus sphaericus* Neide (scientific name) (49)+COMPOUND OF FORMULA I, *Bacillus thuringiensis* Berliner (scientific name) (51)+COMPOUND OF FORMULA I, *Bacillus thuringiensis* subsp. *aizawai* (scientific name) (51)+COMPOUND OF FORMULA I, *Bacillus thuringiensis* subsp. *israelensis* (scientific name) (51)+COMPOUND OF FORMULA I, *Bacillus thuringiensis* subsp. *japonensis* (scientific name) (51)+COMPOUND OF FORMULA I, *Bacillus thuringiensis* subsp. *kurstaki* (scientific name) (51)+COMPOUND OF FORMULA I, *Bacillus thuringiensis* subsp. *tenebrionis* (scientific name) (51)+COMPOUND OF FORMULA I, *Beauveria bassiana* (alternative name) (53)+COMPOUND OF FORMULA I, *Beauveria brongniartii* (alternative name) (54)+COMPOUND OF FORMULA I, *Chrysoperla carnea* (alternative name) (151)+COMPOUND OF FORMULA I, *Cryptolaemus montrouzieri* (alternative name) (178)+COMPOUND OF FORMULA I, *Cydia pomonella* GV (alternative name) (191)+COMPOUND OF FORMULA I, *Dacnusa sibirica* (alternative name) (212)+COMPOUND OF FORMULA I, *Diglyphus isaea* (alternative name) (254)+COMPOUND OF FORMULA I, *Encarsia formosa* (scientific name) (293)+COMPOUND OF FORMULA I, *Eretmocerus eremicus* (alternative name) (300)+COMPOUND OF FORMULA I, *Helicoverpa zea* NPV (alternative name) (431)+COMPOUND OF FORMULA I, *Heterorhabditis bacteriophora* and *H. megidis* (alternative name) (433)+COMPOUND OF FORMULA I, *Hippodamia convergens* (alternative name) (442)+COMPOUND OF FORMULA I, *Leptomastix dactylopii* (alternative name) (488)+COMPOUND OF FORMULA I, *Macrolophus caliginosus* (alternative name) (491)+COMPOUND OF FORMULA I, *Mamestra brassicae* NPV (alternative name) (494)+COMPOUND OF FORMULA I, *Metaphycus helvolus* (alternative name) (522)+COMPOUND OF FORMULA I, *Metarhizium anisopliae* var. *acridum* (scientific name) (523)+COMPOUND OF FORMULA I, *Metarhizium anisopliae* var. *anisopliae* (scientific name) (523)+COMPOUND OF FORMULA I, *Neodiprion sertifer* NPV and *N. lecontei* NPV (alternative name) (575)+COMPOUND OF FORMULA I, *Orius* spp. (alternative name) (596)+COMPOUND OF FORMULA I, *Pasteuria usgae* (alternative name)+COMPOUND OF FORMULA I, *Paecilomyces fumosoroseus* (alternative name) (613)+COMPOUND OF FORMULA I, *Phytoseiulus persimilis* (alternative name) (644)+COMPOUND OF FORMULA I, *Spodoptera exigua* multicapsid nuclear polyhedrosis virus (scientific name) (741)+COMPOUND OF FORMULA I, *Steinernema bibionis* (alternative name) (742)+COMPOUND OF FORMULA I, *Steinernema carpocapsae* (alternative name) (742)+COMPOUND OF FORMULA I, *Steinernema feltiae* (alternative name) (742)+COMPOUND OF FORMULA I, *Steinernema glaseri* (alternative name) (742)+COMPOUND OF FORMULA I, *Steinernema riobrave* (alternative name) (742)+COMPOUND OF FORMULA I, *Steinernema riobravis* (alternative name) (742)+COMPOUND OF FORMULA I, *Steinernema scapterisci* (alternative name) (742)+COMPOUND OF FORMULA I, *Steinernema* spp. (alternative name) (742)+COMPOUND OF FORMULA I, *Trichoderma* spp. (alternative name)+COMPOUND OF FORMULA I, *Trichogramma* spp. (alternative name) (826)+COMPOUND OF FORMULA I, *Typhlodromus occidentalis* (alternative name) (844) and *Verticillium lecanii* (alternative name) (848)+COMPOUND OF FORMULA I, a soil sterilant selected from the group of substances consisting of dimethyl disulfide (IUPAC name)+COMPOUND OF FORMULA I, iodomethane (IUPAC name) (542) and methyl bromide (537)+COMPOUND OF FORMULA I, a chemosterilant selected from the group of substances consisting of apholate [CCN]+COMPOUND OF FORMULA I, bisazir (alternative name) [CCN]+COMPOUND OF FORMULA I, busulfan (alternative name) [CCN]+COMPOUND OF FORMULA I, diflubenzuron (250)+COMPOUND OF FORMULA I, dimatif (alternative name) [CCN]+COMPOUND OF FORMULA I, hemel [CCN]+COMPOUND OF FORMULA I, hempa [CCN]+COMPOUND OF FORMULA I, metepa [CCN]+COMPOUND OF FORMULA I, methiotepa [CCN]+COMPOUND OF FORMULA I, methyl apholate [CCN]+COMPOUND OF FORMULA I, morzid [CCN]+COMPOUND OF FORMULA I, penfluoron (alternative name) [CCN]+COMPOUND OF FORMULA I, tepa [CCN]+COMPOUND OF FORMULA I, thiohempa (alternative name) [CCN]+COMPOUND OF FORMULA I, thiotepa (alternative name) [CCN]+COMPOUND OF FORMULA I, tretamine (alternative name) [CCN] and uredepa (alternative name) [CCN]+COMPOUND OF FORMULA I, an insect pheromone selected from the group of substances consisting of (E)-dec-5-en-1-yl acetate with (E)-dec-5-en-1-ol (IUPAC name) (222)+COMPOUND OF FORMULA I, (E)-tridec-4-en-1-yl acetate (IUPAC name) (829)+COMPOUND OF FORMULA I, (E)-6-methyl-hept-2-en-4-ol (IUPAC name) (541)+COMPOUND OF FORMULA I, (E,Z)-tetradeca-4,10-dien-1-yl acetate (IUPAC name) (779)+COMPOUND OF FORMULA I, (Z)-dodec-7-en-1-yl acetate (IUPAC name) (285)+COMPOUND OF FORMULA I, (Z)-hexadec-11-enal (IUPAC name) (436)+COMPOUND OF FORMULA I, (Z)-hexadec-11-en-1-yl acetate (IUPAC name) (437)+COMPOUND OF FORMULA I, (Z)-hexadec-13-en-11-yn-1-yl acetate (IUPAC name) (438)+COMPOUND OF FORMULA I, (Z)-icos-13-en-10-one (IUPAC name) (448)+COMPOUND OF FORMULA I, (Z)-tetradec-7-en-1-al (IUPAC name) (782)+COMPOUND OF FORMULA I, (Z)-tetradec-9-en-1-ol (IUPAC name) (783)+COMPOUND OF FORMULA I, (Z)-tetradec-9-en-1-yl acetate (IUPAC name) (784)+COMPOUND OF FORMULA I, (7E,9Z)-dodeca-7,9-dien-1-yl acetate (IUPAC name) (283)+COMPOUND OF FORMULA I, (9Z,11E)-tetradeca-9,11-dien-1-yl acetate (IUPAC name) (780)+COMPOUND OF FORMULA I, (9Z,12E)-tetradeca-9,12-dien-1-yl acetate (IUPAC name) (781)+COMPOUND OF FORMULA I, 14-methyloctadec-1-ene (IUPAC name) (545)+COMPOUND OF FORMULA I, 4-methylnonan-5-ol with 4-methylnonan-5-one (IUPAC name) (544)+COMPOUND OF FORMULA I, alpha-multistriatin (alternative name) [CCN]+COMPOUND OF FORMULA I, brevicomin (alternative name) [CCN]+COMPOUND OF FORMULA I, codlelure (alternative name) [CCN]+COMPOUND OF FORMULA I, codlemone (alternative name) (167)+COMPOUND OF FORMULA I, cue-lure (alternative name) (179)+COMPOUND OF FORMULA I, disparlure (277)+COMPOUND OF FORMULA I, (E,Z)-7,9-dodecadien-1-yl acetate (IUPAC name)+COMPOUND OF FORMULA I, dodec-8-en-1-yl acetate (IUPAC name) (286)+COMPOUND OF FORMULA I, dodec-9-en-1-yl acetate (IUPAC name) (287)+COMPOUND OF FORMULA I, dodeca-8+COMPOUND OF FORMULA I, 10-dien-1-yl acetate (IUPAC name) (284)+COMPOUND OF FORMULA I, dominicalure (alternative name) [CCN]+COMPOUND OF FORMULA I, ethyl 4-methyloctanoate (IUPAC name) (317)+COMPOUND OF FORMULA I, eugenol (alternative name) [CCN]+COMPOUND OF FORMULA I, exosex SPTab (alternative name)+COMPOUND OF FORMULA I, frontalin (alternative name) [CCN]+COMPOUND OF FORMULA I, gossyplure (alternative name) (420)+COMPOUND OF FORMULA I, grandlure (421)+COMPOUND OF FORMULA I, grandlure I (alternative name) (421)+COMPOUND OF FORMULA I, grandlure II (alternative name) (421)+COMPOUND OF FORMULA I, grandlure III (alternative name) (421)+COMPOUND OF FORMULA I, grandlure IV (alternative name) (421)+COMPOUND OF FORMULA I, hexylure [CCN]+COMPOUND OF FORMULA I, imicyafos (alternative name) [CCN]+COMPOUND OF FORMULA I, ipsdienol (alternative name) [CCN]+COMPOUND OF FORMULA I, ipsenol (alternative name) [CCN]+COMPOUND OF FORMULA I, japonilure (alternative name) (481)+COMPOUND OF FORMULA I, lineatin (alternative name) [CCN]+COMPOUND OF FORMULA I, litlure (alternative name) [CCN]+COMPOUND OF FORMULA I, looplure (alternative name) [CCN]+COMPOUND OF FORMULA I, medlure [CCN]+COMPOUND OF FORMULA I, megatomoic acid (alternative name) [CCN]+COMPOUND OF FORMULA I, methyl eugenol (alternative name) (540)+COMPOUND OF FORMULA I, muscalure (563)+COMPOUND OF FORMULA I, octadeca-2,13-dien-1-yl acetate (IUPAC name) (588)+COMPOUND OF FORMULA I, octadeca-3,13-dien-1-yl acetate (IUPAC name) (589)+COMPOUND OF FORMULA I, orfralure (alternative name) [CCN]+COMPOUND OF FORMULA I, oryctalure (alternative name) (317)+COMPOUND OF FORMULA I, ostramone (alternative name) [CCN]+COMPOUND OF FORMULA I, siglure [CCN]+COMPOUND OF FORMULA I, sordidin (alternative name) (736)+COMPOUND OF FORMULA I, sulcatol (alternative name) [CCN]+COMPOUND OF FORMULA I, tetradec-11-en-1-yl acetate (IUPAC name) (785)+COMPOUND OF FORMULA I, trimedlure (839)+COMPOUND OF FORMULA I, trimedlure A (alternative name) (839)+COMPOUND OF FORMULA I, trimedlure $B_1$ (alternative name) (839)+COMPOUND OF FORMULA I, trimedlure $B_2$ (alternative name) (839)+COMPOUND OF FORMULA I, trimedlure C (alternative name) (839) and trunc-call (alternative name) [CCN]+COMPOUND OF FORMULA I, an insect repellent selected from the group of substances consisting of 2-(octylthio)ethanol (IUPAC name) (591)+COMPOUND OF FORMULA I, butopyronoxyl (933)+COMPOUND OF FORMULA I, butoxy (polypropylene glycol) (936)+COMPOUND OF FORMULA I, dibutyl adipate (IUPAC name) (1046)+COMPOUND OF FORMULA I, dibutyl phthalate (1047)+COMPOUND OF FORMULA I, dibutyl succinate (IUPAC name) (1048)+COMPOUND OF FORMULA I, diethyltoluamide [CCN]+COMPOUND OF FORMULA I, dimethyl carbate [CCN]+COMPOUND OF FORMULA I, dimethyl phthalate [CCN]+COMPOUND OF FORMULA I, ethyl hexanediol (1137)+COMPOUND OF FORMULA I, hexamide [CCN]+COMPOUND OF FORMULA I, methoquin-butyl (1276)+COMPOUND OF FORMULA I, methylneodecanamide [CCN]+COMPOUND OF FORMULA I, oxamate [CCN] and picaridin [CCN]+COMPOUND OF FORMULA I, an insecticide selected from the group of substances consisting of 1-dichloro-1-nitroethane (IUPAC/Chemical Abstracts name) (1058)+COMPOUND OF FORMULA I, 1,1-dichloro-2,2-bis(4-ethylphenyl)ethane (IUPAC name) (1056), +COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1-bromo-2-chloroethane (IUPAC/Chemical Abstracts name) (916)+COMPOUND OF FORMULA I, 2,2,2-trichloro-1-(3,4-dichlorophenyl)ethyl acetate (IUPAC name) (1451)+COMPOUND OF FORMULA I, 2,2-dichlorovinyl 2-ethylsulfinylethyl methyl phosphate (IUPAC name) (1066)+COMPOUND OF FORMULA I, 2-(1,3-dithiolan-2-yl)phenyl dimethylcarbamate (IUPAC/Chemical Abstracts name) (1109)+COMPOUND OF FORMULA I, 2-(2-butoxyethoxy)ethyl thiocyanate (IUPAC/Chemical Abstracts name) (935)+COMPOUND OF FORMULA I, 2-(4,5-dimethyl-1,3-dioxolan-2-yl)phenyl methylcarbamate (IUPAC/Chemical Abstracts name) (1084)+COMPOUND OF FORMULA I, 2-(4-chloro-3,5-xylyloxy)ethanol (IUPAC name) (986)+COMPOUND OF FORMULA I, 2-chlorovinyl diethyl phosphate (IUPAC name) (984)+COMPOUND OF FORMULA I, 2-imidazolidone (IUPAC name) (1225)+COMPOUND OF FORMULA I, 2-isovalerylindan-1,3-dione (IUPAC name) (1246)+COMPOUND OF FORMULA I, 2-methyl(prop-2-ynyl)aminophenyl methylcarbamate (IUPAC name) (1284)+COMPOUND OF FORMULA I, 2-thiocyanatoethyl laurate (IUPAC name) (1433)+COMPOUND OF FORMULA I, 3-bromo-1-chloroprop-1-ene (IUPAC name) (917)+COMPOUND OF FORMULA I, 3-methyl-1-phenylpyrazol-5-yl dimethylcarbamate (IUPAC name) (1283)+COMPOUND OF FORMULA I, 4-methyl(prop-2-ynyl)amino-3,5-xylyl methylcarbamate (IUPAC name) (1285)+COMPOUND OF FORMULA I, 5,5-dimethyl-3-oxocyclohex-1-enyl dimethylcarbamate (IUPAC name) (1085)+COMPOUND OF FORMULA I, abamectin (1)+COMPOUND OF FORMULA I, acephate (2)+COMPOUND OF FORMULA I, acetamiprid (4)+COMPOUND OF FORMULA I, acethion (alternative name) [CCN]+COMPOUND OF FORMULA I, acetoprole [CCN]+COMPOUND OF FORMULA I, acrinathrin (9)+COMPOUND OF FORMULA I, acrylonitrile (IUPAC name) (861)+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, aldrin (864)+COMPOUND OF FORMULA I, allethrin (17)+COMPOUND OF FORMULA I, allosamidin (alternative name) [CCN]+COMPOUND OF FORMULA I, allyxycarb (866)+COMPOUND OF FORMULA I, alpha-cypermethrin (202)+COMPOUND OF FORMULA I, alpha-ecdysone (alternative name) [CCN]+COMPOUND OF FORMULA I, alpha-endosulfan [CCN]+COMPOUND OF FORMULA I, aluminium phosphide (640)+COMPOUND OF FORMULA I, amidithion (870)+COMPOUND OF FORMULA I, amidothioate (872)+COMPOUND OF FORMULA I, aminocarb (873)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, anabasine (877)+COMPOUND OF FORMULA I, athidathion (883)+COMPOUND OF FORMULA I, AVI 382 (compound code)+COMPOUND OF FORMULA I, AZ 60541 (compound code)+COMPOUND OF FORMULA I, azadirachtin (alternative name) (41)+COMPOUND OF FORMULA I, azamethiphos (42)+COMPOUND OF FORMULA I, azinphos-ethyl (44)+COMPOUND OF FORMULA I, azinphos-methyl (45)+COMPOUND OF FORMULA I, azothoate (889)+COMPOUND OF FORMULA I, *Bacillus thuringiensis* delta endotoxins (alternative name) (52)+COMPOUND OF FORMULA I, barium hexafluorosilicate (alternative name) [CCN]+COMPOUND OF FORMULA I, barium polysulfide (IUPAC/Chemical Abstracts name) (892)+COMPOUND OF FORMULA I, barthrin [CCN]+COMPOUND OF FORMULA I, Bayer 22/190 (development code) (893)+COMPOUND OF FORMULA I, Bayer 22408 (development code) (894)+COMPOUND OF FORMULA I, bendiocarb (58)+COMPOUND OF FORMULA I, benfuracarb (60)+COMPOUND OF FORMULA I, bensultap (66)+COMPOUND OF FORMULA I, beta-cyfluthrin (194)+COMPOUND OF FORMULA I, beta-cypermethrin (203)+COMPOUND OF FORMULA I, bifenthrin (76)+COMPOUND OF FORMULA I, bioallethrin (78)+COMPOUND OF FORMULA I, bioallethrin S-cyclopentenyl isomer (alternative name) (79)+COMPOUND OF FORMULA I, bioethanomethrin [CCN]+COMPOUND OF FORMULA I, biopermethrin (908)+COMPOUND OF FORMULA I, bioresmethrin (80)+COMPOUND OF FORMULA I, bis(2-chloroethyl)ether (IUPAC name) (909)+COMPOUND OF FORMULA I, bistrifluoron (83)+COMPOUND OF FORMULA I, borax (86)+COMPOUND OF FORMULA I, brofenvalerate (alternative name)+COMPOUND OF FORMULA I, bromfenvinfos (914)+COMPOUND OF FORMULA I, bromocyclen (918)+COMPOUND OF FORMULA I, bromo-DDT (alternative name) [CCN]+COMPOUND OF FORMULA I, bromophos (920)+COMPOUND OF FORMULA I, bromophos-ethyl (921)+COMPOUND OF FORMULA I, bufencarb (924)+COMPOUND OF FORMULA I, buprofezin (99)+COMPOUND OF FORMULA I, butacarb (926)+COMPOUND OF FORMULA I, butathiofos (927)+COMPOUND OF FORMULA I, butocarboxim (103)+COMPOUND OF FORMULA I, butonate (932)+COMPOUND OF FORMULA I, butoxycarboxim (104)+COMPOUND OF FORMULA I, butylpyridaben (alternative name)+COMPOUND OF FORMULA I, cadusafos (109)+COMPOUND OF FORMULA I, calcium arsenate [CCN]+COMPOUND OF FORMULA I, calcium cyanide (444)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbon disulfide (IUPAC/Chemical Abstracts name) (945)+COMPOUND OF FORMULA I, carbon tetrachloride (IUPAC name) (946)+COMPOUND OF FORMULA I, carbophenothion (947)+COMPOUND OF FORMULA I, carbosulfan (119)+COMPOUND OF FORMULA I, cartap (123)+COMPOUND OF FORMULA I, cartap hydrochloride (123)+COMPOUND OF FORMULA I, celangulin (alternative name)+COMPOUND OF FORMULA I, cevadine (alternative name) (725)+COMPOUND OF FORMULA I, chlorantraniliprole [CCN]+COMPOUND OF FORMULA I, chlorbicyclen (960)+COMPOUND OF FORMULA I, chlordane (128)+COMPOUND OF FORMULA I, chlordecone (963)+COMPOUND OF FORMULA I, chlordimeform (964)+COMPOUND OF FORMULA I, chlordimeform hydrochloride (964)+COMPOUND OF FORMULA I, chlorethoxyfos (129)+COMPOUND OF FORMULA I, chlorfenapyr (130)+COMPOUND OF FORMULA I, chlorfenvinphos (131)+COMPOUND OF FORMULA I, chlorfluazuron (132)+COMPOUND OF FORMULA I, chlormephos (136)+COMPOUND OF FORMULA I, chloroform [CCN]+COMPOUND OF FORMULA I, chloropicrin (141)+COMPOUND OF FORMULA I, chlorphoxim (989)+COMPOUND OF FORMULA I, chlorprazophos (990)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, chromafenozide (150)+COMPOUND OF FORMULA I, cinerin I (696)+COMPOUND OF FORMULA I, cinerin II (696)+COMPOUND OF FORMULA I, cinerins (696)+COMPOUND OF FORMULA I, cis-resmethrin (alternative name)+COMPOUND OF FORMULA I, cismethrin (80)+COMPOUND OF FORMULA I, clocythrin (alternative name)+COMPOUND OF FORMULA I, cloethocarb (999)+COMPOUND OF FORMULA I, closantel (alternative name) [CCN]+COMPOUND OF FORMULA I, clothianidin (165)+COMPOUND OF FORMULA I, copper acetoarsenite [CCN]+COMPOUND OF FORMULA I, copper arsenate [CCN]+COMPOUND OF FORMULA I, copper oleate [CCN]+COMPOUND OF FORMULA I, coumaphos (174)+COMPOUND OF FORMULA I, coumithoate (1006)+COMPOUND OF FORMULA I, crotamiton (alternative name) [CCN]+COMPOUND OF FORMULA I, crotoxyphos (1010)+COMPOUND OF FORMULA I, crufomate (1011)+COMPOUND OF FORMULA I, cryolite (alternative name) (177)+COMPOUND OF FORMULA I, CS 708 (development code) (1012)+COMPOUND OF FORMULA I, cyanofenphos (1019)+COMPOUND OF FORMULA I, cyanophos (184)+COMPOUND OF FORMULA I, cyanthoate (1020)+COMPOUND OF FORMULA I, cyantraniliprole [CCN]+COMPOUND OF FORMULA I, cyclethrin [CCN]+COMPOUND OF FORMULA I, cycloprothrin (188)+COMPOUND OF FORMULA I, cyfluthrin (193)+COMPOUND OF FORMULA I, cyhalothrin (196)+COMPOUND OF FORMULA I, cypermethrin (201)+COMPOUND OF FORMULA I, cyphenothrin (206)+COMPOUND OF FORMULA I, cyromazine (209)+COMPOUND OF FORMULA I, cythioate (alternative name) [CCN]+COMPOUND OF FORMULA I, d-limonene (alternative name) [CCN]+COMPOUND OF FORMULA I, d-tetramethrin (alternative name) (788)+COMPOUND OF FORMULA I, DAEP (1031)+COMPOUND OF FORMULA I, dazomet (216)+COMPOUND OF FORMULA I, DDT (219)+COMPOUND OF FORMULA I, decarbofuran (1034)+COMPOUND OF FORMULA I, deltamethrin (223)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diamidafos (1044)+COMPOUND OF FORMULA I, diazinon (227)+COMPOUND OF FORMULA I, dicapthon (1050)+COMPOUND OF FORMULA I, dichlofenthion (1051)+COMPOUND OF FORMULA I, dichlorvos (236)+COMPOUND OF FORMULA I, dicliphos (alternative name)+COMPOUND OF FORMULA I, dicresyl (alternative name) [CCN]+COMPOUND OF FORMULA I, dicrotophos (243)+COMPOUND OF FORMULA I, dicyclanil (244)+COMPOUND OF FORMULA I, dieldrin (1070)+COMPOUND OF FORMULA I, diethyl 5-methylpyrazol-3-yl phosphate (IUPAC name) (1076)+COMPOUND OF FORMULA I, diflubenzuron (250)+COMPOUND OF FORMULA I, dilor (alternative name) [CCN]+COMPOUND OF FORMULA I, dimefluthrin [CCN]+COMPOUND OF FORMULA I, dimefox (1081)+COMPOUND OF FORMULA I, dimetan (1085)+COMPOUND OF FORMULA I, dimethoate (262)+COMPOUND OF FORMULA I, dimethrin (1083)+COMPOUND OF FORMULA I, dimethylvinphos (265)+COMPOUND OF FORMULA I, dimetilan (1086)+COMPOUND OF FORMULA I, dinex (1089)+COMPOUND OF FORMULA I, dinex-diclexine (1089)+COMPOUND OF FORMULA I, dinoprop (1093)+COMPOUND OF FORMULA I, dinosam (1094)+COMPOUND OF FORMULA I, dinoseb (1095)+COMPOUND OF FORMULA I, dinotefuran (271)+COMPOUND OF FORMULA I, diofenolan (1099)+COMPOUND OF FORMULA I, dioxabenzofos (1100)+COMPOUND OF FORMULA I, dioxacarb (1101)+COMPOUND OF FORMULA I, dioxathion (1102)+COMPOUND OF FORMULA I, disulfoton (278)+COMPOUND OF FORMULA I, dithicrofos (1108)+COMPOUND OF FORMULA I, DNOC (282)+COMPOUND OF FORMULA I, doramectin (alternative name) [CCN]+COMPOUND OF FORMULA I, DSP (1115)+COMPOUND OF FORMULA I, ecdysterone (alternative name) [CCN]+COMPOUND OF FORMULA I, EI 1642 (development code) (1118)+COMPOUND OF FORMULA I, emamectin (291)+COMPOUND OF FORMULA I, emamectin benzoate (291)+COMPOUND OF FORMULA I, EMPC (1120)+COMPOUND OF FORMULA I, empenthrin (292)+COMPOUND OF FORMULA I, endosulfan (294)+COMPOUND OF FORMULA I, endothion (1121)+COMPOUND OF FORMULA I, endrin (1122)+COMPOUND OF FORMULA I, EPBP (1123)+COMPOUND OF FORMULA I, EPN (297)+COMPOUND OF FORMULA I, epofenonane (1124)+COMPOUND OF FORMULA I, eprinomectin (alternative name) [CCN]+COMPOUND OF FORMULA I, eremophilone oil+COMPOUND OF FORMULA I, esfenvalerate (302)+COMPOUND OF FORMULA I, etaphos (alternative name) [CCN]+COMPOUND OF FORMULA I, ethiofencarb (308)+COMPOUND OF FORMULA I, ethion (309)+COMPOUND OF FORMULA I, ethiprole (310)+COMPOUND OF FORMULA I, ethoate-methyl (1134)+COMPOUND OF FORMULA I, ethoprophos (312)+COMPOUND OF FORMULA I, ethyl formate (IUPAC name) [CCN]+COMPOUND OF FORMULA I, ethyl-DDD (alternative name) (1056)+COMPOUND OF FORMULA I, ethylene dibromide (316)+COMPOUND OF FORMULA I, ethylene dichloride (chemical name) (1136)+COMPOUND OF FORMULA I, ethylene oxide [CCN]+COMPOUND OF FORMULA I, etofenprox (319)+COMPOUND OF FORMULA I, etrimfos (1142)+COMPOUND OF FORMULA I, EXD (1143)+COMPOUND OF FORMULA I, famphur (323)+COMPOUND OF FORMULA I, fenamiphos (326)+COMPOUND OF FORMULA I, fenazaflor (1147)+COMPOUND OF FORMULA I, fenchlorphos (1148)+COMPOUND OF FORMULA I, fenethacarb (1149)+COMPOUND OF FORMULA I, fenfluthrin (1150)+COMPOUND OF FORMULA I, fenitrothion (335)+COMPOUND OF FORMULA I, fenobucarb (336)+COMPOUND OF FORMULA I, fenoxacrim (1153)+COMPOUND OF FORMULA I, fenoxycarb (340)+COMPOUND OF FORMULA I, fenpirithrin (1155)+COMPOUND OF FORMULA I, fenpropathrin (342)+COMPOUND OF FORMULA I, fenpyrad (alternative name)+COMPOUND OF FORMULA I, fensulfothion (1158)+COMPOUND OF FORMULA I, fenthion (346)+COMPOUND OF FORMULA I, fenthion-ethyl [CCN]+COMPOUND OF FORMULA I, fenvalerate (349)+COMPOUND OF FORMULA I, fipronil (354)+COMPOUND OF FORMULA I, flometoquin [CCN]+COMPOUND OF FORMULA I, flonicamid (358)+COMPOUND OF FORMULA I, flubendiamide (CAS. Reg. No.: 272451-65-7)+COMPOUND OF FORMULA I, flucofuron (1168)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, fluensulfon [CCN]+COMPOUND OF FORMULA I, flufenerim [CCN]+COMPOUND OF FORMULA I, flufenoxuron (370)+COMPOUND OF FORMULA I, flufenprox (1171)+COMPOUND OF FORMULA I, flufiprole [CCN]+COMPOUND OF FORMULA I, flumethrin (372)+COMPOUND OF FORMULA I, flupyradifurone [CCN]+COMPOUND OF FORMULA I, fluvalinate (1184)+COMPOUND OF FORMULA I, FMC 1137 (development code) (1185)+COMPOUND OF FORMULA I, fonofos (1191)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, fosmethilan (1194)+COMPOUND OF FORMULA I, fospirate (1195)+COMPOUND OF FORMULA I, fosthiazate (408)+COMPOUND OF FORMULA I, fosthietan (1196)+COMPOUND OF FORMULA I, furathiocarb (412)+COMPOUND OF FORMULA I, furethrin (1200)+COMPOUND OF FORMULA I, gamma-cyhalothrin (197)+COMPOUND OF FORMULA I, gamma-HCH (430)+COMPOUND OF FORMULA I, guazatine (422)+COMPOUND OF FORMULA I, guazatine acetates (422)+COMPOUND OF FORMULA I, GY-81 (development code) (423)+COMPOUND OF FORMULA I, halfenprox (424)+COMPOUND OF FORMULA I, halofenozide (425)+COMPOUND OF FORMULA I, HCH (430)+COMPOUND OF FORMULA I, HEOD (1070)+COMPOUND OF FORMULA I, heptachlor (1211)+COMPOUND OF FORMULA I, heptenophos (432)+COMPOUND OF FORMULA I, heterophos [CCN]+COMPOUND OF FORMULA I, hexaflumuron (439)+COMPOUND OF FORMULA I, HHDN (864)+COMPOUND OF FORMULA I, hydramethylnon (443)+COMPOUND OF FORMULA I, hydrogen cyanide (444)+COMPOUND OF FORMULA I, hydroprene (445)+COMPOUND OF FORMULA I, hyquincarb (1223)+COMPOUND OF FORMULA I, imidacloprid (458)+COMPOUND OF FORMULA I, imiprothrin (460)+COMPOUND OF FORMULA I, indoxacarb (465)+COMPOUND OF FORMULA I, iodomethane (IUPAC name) (542)+COMPOUND OF FORMULA I, IPPA-152004 (compound code)+COMPOUND OF FORMULA I, IPSP (1229)+COMPOUND OF FORMULA I, isazofos (1231)+COMPOUND OF FORMULA I, isobenzan (1232)+COMPOUND OF FORMULA I, isocarbophos (alternative name) (473)+COMPOUND OF FORMULA I, isodrin (1235)+COMPOUND OF FORMULA I, isofenphos (1236)+COMPOUND OF FORMULA I, isolane (1237)+COMPOUND OF FORMULA I, isoprocarb (472)+COMPOUND OF FORMULA I, isopropyl 0-(methoxyaminothiophosphoryl)salicylate (IUPAC name) (473)+COMPOUND OF FORMULA I, isoprothiolane (474)+COMPOUND OF FORMULA I, isothioate (1244)+COMPOUND OF FORMULA I, isoxathion (480)+COMPOUND OF FORMULA I, ivermectin (alternative name) [CCN]+COMPOUND OF FORMULA I, jasmolin 1 (696)+COMPOUND OF FORMULA I, jasmolin II (696)+COMPOUND OF FORMULA I, jodfenphos (1248)+COMPOUND OF FORMULA I, juvenile hormone I (alternative name) [CCN]+COMPOUND OF FORMULA I, juvenile hormone II (alternative name) [CCN]+COMPOUND OF FORMULA I, juvenile hormone III (alternative name) [CCN]+COMPOUND OF FORMULA I, kelevan (1249)+COMPOUND OF FORMULA I, kinoprene (484)+COMPOUND OF FORMULA I, lambda-cyhalothrin (198)+COMPOUND OF FORMULA I, lead arsenate [CCN]+COMPOUND OF FORMULA I, lepimectin (CCN)+COMPOUND OF FORMULA I, leptophos (1250)+COMPOUND OF FORMULA I, lindane (430)+COMPOUND OF FORMULA I, lirimfos (1251)+COMPOUND OF FORMULA I, lufenuron (490)+COMPOUND OF FORMULA I, lythidathion (1253)+COMPOUND OF FORMULA I, m-cumenyl methylcarbamate (IUPAC name) (1014)+COMPOUND OF FORMULA I, magnesium phosphide (IUPAC name) (640)+COMPOUND OF FORMULA I, malathion (492)+COMPOUND OF FORMULA I, malonoben (1254)+COMPOUND OF FORMULA I, mazidox (1255)+COMPOUND OF FORMULA I, mecarbam (502)+COMPOUND OF FORMULA I, mecarphon (1258)+COMPOUND OF FORMULA I, menazon (1260)+COMPOUND OF FORMULA I, mephosfolan (1261)+COMPOUND OF FORMULA I, mercurous chloride (513)+COMPOUND OF FORMULA I, mesulfenfos (1263)+COMPOUND OF FORMULA I, metaflumizone (CCN)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methacrifos (1266)+COMPOUND OF FORMULA I, methamidophos (527)+COMPOUND OF FORMULA I, methanesulfonyl fluoride (IUPAC/Chemical Abstracts name) (1268)+COMPOUND OF FORMULA I, methidathion (529)+COMPOUND OF FORMULA I, methiocarb (530)+COMPOUND OF FORMULA I, methocrotophos (1273)+COMPOUND OF FORMULA I, methomyl (531)+COMPOUND OF FORMULA I, methoprene (532)+COMPOUND OF FORMULA I, methoquin-butyl (1276)+COMPOUND OF FORMULA I, methothrin (alternative name) (533)+COMPOUND OF FORMULA I, methoxychlor (534)+COMPOUND OF FORMULA I, methoxyfenozide (535)+COMPOUND OF FORMULA I, methyl bromide (537)+COMPOUND OF FORMULA I, methyl isothiocyanate (543)+COMPOUND OF FORMULA I, methylchloroform (alternative name) [CCN]+COMPOUND OF FORMULA I, methylene chloride [CCN]+COMPOUND OF FORMULA I, metofluthrin [CCN]+COMPOUND OF FORMULA I, metolcarb (550)+COMPOUND OF FORMULA I, metoxadiazone (1288)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, mirex (1294)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naftalofos (alternative name) [CCN]+COMPOUND OF FORMULA I, naled (567)+COMPOUND OF FORMULA I, naphthalene (IUPAC/Chemical Abstracts name) (1303)+COMPOUND OF FORMULA I, NC-170 (development code) (1306)+COMPOUND OF FORMULA I, NC-184 (compound code)+COMPOUND OF FORMULA I, nicotine (578)+COMPOUND OF FORMULA I, nicotine sulfate (578)+COMPOUND OF FORMULA I, nifluridide (1309)+COMPOUND OF FORMULA I, nitenpyram (579)+COMPOUND OF FORMULA I, nithiazine (1311)+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, nornicotine (traditional name) (1319)+COMPOUND OF FORMULA I, novaluron (585)+COMPOUND OF FORMULA I, noviflumuron (586)+COMPOUND OF FORMULA I, O-5-dichloro-4-iodophenyl O-ethyl ethylphosphonothioate (IUPAC name) (1057)+COMPOUND OF FORMULA I, O,O-diethyl O-4-methyl-2-oxo-2H-chromen-7-yl phosphorothioate (IUPAC name) (1074)+COMPOUND OF FORMULA I, O,O-diethyl O-6-methyl-2-propylpyrimidin-4-yl phosphorothioate (IUPAC name) (1075)+COMPOUND OF FORMULA I, O,O,O',O'-tetrapropyl dithiopyrophosphate (IUPAC name) (1424)+COMPOUND OF FORMULA I, oleic acid (IUPAC name) (593)+COMPOUND OF FORMULA I, omethoate (594)+COMPOUND OF FORMULA I, oxamyl (602)+COMPOUND OF FORMULA I, oxydemeton-methyl (609)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, para-dichlorobenzene [CCN]+COMPOUND OF FORMULA I, parathion (615)+COMPOUND OF FORMULA I, parathion-methyl (616)+COMPOUND OF FORMULA I, penfluoron (alternative name) [CCN]+COMPOUND OF FORMULA I, pentachlorophenol (623)+COMPOUND OF FORMULA I, pentachlorophenyl laurate (IUPAC name) (623)+COMPOUND OF FORMULA I, permethrin (626)+COMPOUND OF FORMULA I, petroleum oils (alternative name) (628)+COMPOUND OF FORMULA I, PH 60-38 (development code) (1328)+COMPOUND OF FORMULA I, phenkapton (1330)+COMPOUND OF FORMULA I, phenothrin (630)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosnichlor (1339)+COMPOUND OF FORMULA I, phosphamidon (639)+COMPOUND OF FORMULA I, phosphine (IUPAC name) (640)+COMPOUND OF FORMULA I, phoxim (642)+COMPOUND OF FORMULA I, phoxim-methyl (1340)+COMPOUND OF FORMULA I, pirimetaphos (1344)+COMPOUND OF FORMULA I, pirimicarb (651)+COMPOUND OF FORMULA I, pirimiphos-ethyl (1345)+COMPOUND OF FORMULA I, pirimiphos-methyl (652)+COMPOUND OF FORMULA I, polychlorodicyclopentadiene isomers (IUPAC name) (1346)+COMPOUND OF FORMULA I, polychloroterpenes (traditional name) (1347)+COMPOUND OF FORMULA I, potassium arsenite [CCN]+COMPOUND OF FORMULA I, potassium thiocyanate [CCN]+COMPOUND OF FORMULA I, prallethrin (655)+COMPOUND OF FORMULA I, precocene I (alternative name) [CCN]+COMPOUND OF FORMULA I, precocene II (alternative name) [CCN]+COMPOUND OF FORMULA I, precocene III (alternative name) [CCN]+COMPOUND OF FORMULA I, primidophos (1349)+COMPOUND OF FORMULA I, profenofos (662)+COMPOUND OF FORMULA I, profluthrin [CCN]+COMPOUND OF FORMULA I, promacyl (1354)+COMPOUND OF FORMULA I, promecarb (1355)+COMPOUND OF FORMULA I, propaphos (1356)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothiofos (686)+COMPOUND OF FORMULA I, prothoate (1362)+COMPOUND OF FORMULA I, protrifenbute [CCN]+COMPOUND OF FORMULA I, pymetrozine (688)+COMPOUND OF FORMULA I, pyraclofos (689)+COMPOUND OF FORMULA I, pyrafluprole [CCN]+COMPOUND OF FORMULA I, pyrazophos (693)+COMPOUND OF FORMULA I, pyresmethrin (1367)+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridalyl (700)+COMPOUND OF FORMULA I, pyridaphenthion (701)+COMPOUND OF FORMULA I, pyrifluquinazon [CCN]+COMPOUND OF FORMULA I, pyrimidifen (706)+COMPOUND OF FORMULA I, pyrimitate (1370)+COMPOUND OF FORMULA I, pyriprole [CCN]+COMPOUND OF FORMULA I, pyriproxyfen (708)+COMPOUND OF FORMULA I, quassia (alternative name) [CCN]+COMPOUND OF FORMULA I, quinalphos (711)+COMPOUND OF FORMULA I, quinalphos-methyl (1376)+COMPOUND OF FORMULA I, quinothion (1380)+COMPOUND OF FORMULA I, quintiofos (1381)+COMPOUND OF FORMULA I, R-1492 (development code) (1382)+COMPOUND OF FORMULA I, rafoxanide (alternative name) [CCN]+COMPOUND OF FORMULA I, resmethrin (719)+COMPOUND OF FORMULA I, rotenone (722)+COMPOUND OF FORMULA I, RU 15525 (development code) (723)+COMPOUND OF FORMULA I, RU 25475 (development code) (1386)+COMPOUND OF FORMULA I, ryania (alternative name)

(1387)+COMPOUND OF FORMULA I, ryanodine (traditional name) (1387)+COMPOUND OF FORMULA I, sabadilla (alternative name) (725)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, SI-0205 (compound code)+COMPOUND OF FORMULA I, SI-0404 (compound code)+COMPOUND OF FORMULA I, SI-0405 (compound code)+COMPOUND OF FORMULA I, silafluofen (728)+COMPOUND OF FORMULA I, SN 72129 (development code) (1397)+COMPOUND OF FORMULA I, sodium arsenite [CCN]+COMPOUND OF FORMULA I, sodium cyanide (444)+COMPOUND OF FORMULA I, sodium fluoride (IUPAC/Chemical Abstracts name) (1399)+COMPOUND OF FORMULA I, sodium hexafluorosilicate (1400)+COMPOUND OF FORMULA I, sodium pentachlorophenoxide (623)+COMPOUND OF FORMULA I, sodium selenate (IUPAC name) (1401)+COMPOUND OF FORMULA I, sodium thiocyanate [CCN]+COMPOUND OF FORMULA I, sophamide (1402)+COMPOUND OF FORMULA I, spinetoram [CCN]+COMPOUND OF FORMULA I, spinosad (737)+COMPOUND OF FORMULA I, spiromesifen (739)+COMPOUND OF FORMULA I, spirotetramat [CCN]+COMPOUND OF FORMULA I, sulcofuron (746)+COMPOUND OF FORMULA I, sulcofuron-sodium (746)+COMPOUND OF FORMULA I, sulfluramid (750)+COMPOUND OF FORMULA I, sulfotep (753)+COMPOUND OF FORMULA I, sulfoxaflor [CCN]+COMPOUND OF FORMULA I, sulfuryl fluoride (756)+COMPOUND OF FORMULA I, sulprofos (1408)+COMPOUND OF FORMULA I, tar oils (alternative name) (758)+COMPOUND OF FORMULA I, tau-fluvalinate (398)+COMPOUND OF FORMULA I, tazimcarb (1412)+COMPOUND OF FORMULA I, TDE (1414)+COMPOUND OF FORMULA I, tebufenozide (762)+COMPOUND OF FORMULA I, tebufenpyrad (763)+COMPOUND OF FORMULA I, tebupirimfos (764)+COMPOUND OF FORMULA I, teflubenzuron (768)+COMPOUND OF FORMULA I, tefluthrin (769)+COMPOUND OF FORMULA I, temephos (770)+COMPOUND OF FORMULA I, TEPP (1417)+COMPOUND OF FORMULA I, terallethrin (1418)+COMPOUND OF FORMULA I, terbam (alternative name)+COMPOUND OF FORMULA I, terbufos (773)+COMPOUND OF FORMULA I, tetrachloroethane [CCN]+COMPOUND OF FORMULA I, tetrachlorvinphos (777)+COMPOUND OF FORMULA I, tetramethrin (787)+COMPOUND OF FORMULA I, tetramethylfluthrin (CAS. Reg. No.: 84937-88-2)+COMPOUND OF FORMULA I, theta-cypermethrin (204)+COMPOUND OF FORMULA I, thiacloprid (791)+COMPOUND OF FORMULA I, thiafenox (alternative name)+COMPOUND OF FORMULA I, thiamethoxam (792)+COMPOUND OF FORMULA I, thicrofos (1428)+COMPOUND OF FORMULA I, thiocarboxime (1431)+COMPOUND OF FORMULA I, thiocyclam (798)+COMPOUND OF FORMULA I, thiocyclam hydrogen oxalate (798)+COMPOUND OF FORMULA I, thiodicarb (799)+COMPOUND OF FORMULA I, thiofanox (800)+COMPOUND OF FORMULA I, thiometon (801)+COMPOUND OF FORMULA I, thionazin (1434)+COMPOUND OF FORMULA I, thiosultap (803)+COMPOUND OF FORMULA I, thiosultap-sodium (803)+COMPOUND OF FORMULA I, thuringiensin (alternative name) [CCN]+COMPOUND OF FORMULA I, tolfenpyrad (809)+COMPOUND OF FORMULA I, tralomethrin (812)+COMPOUND OF FORMULA I, transfluthrin (813)+COMPOUND OF FORMULA I, transpermethrin (1440)+COMPOUND OF FORMULA I, triamiphos (1441)+COMPOUND OF FORMULA I, triazamate (818)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trichlormetaphos-3 (alternative name) [CCN]+COMPOUND OF FORMULA I, trichloronat (1452)+COMPOUND OF FORMULA I, trifenofos (1455)+COMPOUND OF FORMULA I, triflumuron (835)+COMPOUND OF FORMULA I, trimethacarb (840)+COMPOUND OF FORMULA I, triprene (1459)+COMPOUND OF FORMULA I, vamidothion (847)+COMPOUND OF FORMULA I, vaniliprole [CCN]+COMPOUND OF FORMULA I, veratridine (alternative name) (725)+COMPOUND OF FORMULA I, veratrine (alternative name) (725)+COMPOUND OF FORMULA I, XMC (853)+COMPOUND OF FORMULA I, xylylcarb (854)+COMPOUND OF FORMULA I, YI-5302 (compound code)+COMPOUND OF FORMULA I, zeta-cypermethrin (205)+COMPOUND OF FORMULA I, zetamethrin (alternative name)+COMPOUND OF FORMULA I, zinc phosphide (640)+COMPOUND OF FORMULA I, zolaprofos (1469), ZJ0967 (development code)+COMPOUND OF FORMULA I, ZJ3757 (development code)+COMPOUND OF FORMULA I, and ZXI 8901 (development code) (858)+COMPOUND OF FORMULA I, a molluscicide selected from the group of substances consisting of bis(tributyltin) oxide (IUPAC name) (913)+COMPOUND OF FORMULA I, bromoacetamide [CCN]+COMPOUND OF FORMULA I, calcium arsenate [CCN]+COMPOUND OF FORMULA I, cloethocarb (999)+COMPOUND OF FORMULA I, copper acetoarsenite [CCN]+COMPOUND OF FORMULA I, copper sulfate (172)+COMPOUND OF FORMULA I, fentin (347)+COMPOUND OF FORMULA I, ferric phosphate (IUPAC name) (352)+COMPOUND OF FORMULA I, metaldehyde (518)+COMPOUND OF FORMULA I, methiocarb (530)+COMPOUND OF FORMULA I, niclosamide (576)+COMPOUND OF FORMULA I, niclosamide-olamine (576)+COMPOUND OF FORMULA I, pentachlorophenol (623)+COMPOUND OF FORMULA I, sodium pentachlorophenoxide (623)+COMPOUND OF FORMULA I, tazimcarb (1412)+COMPOUND OF FORMULA I, thiodicarb (799)+COMPOUND OF FORMULA I, tralopyril [CCN]+COMPOUND OF FORMULA I, tributyltin oxide (913)+COMPOUND OF FORMULA I, trifenmorph (1454)+COMPOUND OF FORMULA I, trimethacarb (840)+COMPOUND OF FORMULA I, triphenyltin acetate (IUPAC name) (347) and triphenyltin hydroxide (IUPAC name) (347)+COMPOUND OF FORMULA I, a nematicide selected from the group of substances consisting of AKD-3088 (compound code)+COMPOUND OF FORMULA I, 1,2-dibromo-3-chloropropane (IUPAC/Chemical Abstracts name) (1045)+COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1,3-dichloropropene (233)+COMPOUND OF FORMULA I, 3,4-dichlorotetrahydrothiophene 1,1-dioxide (IUPAC/Chemical Abstracts name) (1065)+COMPOUND OF FORMULA I, 3-(4-chlorophenyl)-5-methylrhodanine (IUPAC name) (980)+COMPOUND OF FORMULA I, 5-methyl-6-thioxo-1,3,5-thiadiazinan-3-ylacetic acid (IUPAC name) (1286)+COMPOUND OF FORMULA I, 6-isopentenylaminopurine (alternative name) (210)+COMPOUND OF FORMULA I, abamectin (1)+COMPOUND OF FORMULA I, acetoprole [CCN]+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, AZ 60541 (compound code)+COMPOUND OF FORMULA I, benclothiaz [CCN]+COMPOUND OF FORMULA I, benomyl (62)+COMPOUND OF FORMULA I, butylpyridaben (alternative name)+COMPOUND OF FORMULA I, cadusafos (109)+COMPOUND OF FORMULA I, carbofuran (118)+COMPOUND OF FORMULA I, carbon disulfide (945)+COMPOUND OF FORMULA I, carbosulfan (119)+COMPOUND OF FORMULA I, chloropicrin (141)+COMPOUND OF FORMULA I, chlorpyrifos (145)+COMPOUND OF FORMULA I, cloethocarb (999)+COMPOUND OF FORMULA I, cytokinins (alternative name) (210)+COMPOUND OF FORMULA I, dazomet (216)+COMPOUND OF FORMULA I, DBCP (1045)+COMPOUND OF FORMULA I, DCIP (218)+COMPOUND OF FORMULA I, diamidafos (1044)+COMPOUND OF FORMULA I, dichlofenthion (1051)+COMPOUND OF FORMULA I, dicliphos (alternative name)+COMPOUND OF FORMULA I, dimethoate (262)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ethoprophos (312)+COMPOUND OF FORMULA I, ethylene dibromide (316)+COMPOUND OF FORMULA I, fenamiphos (326)+COMPOUND OF FORMULA I, fenpyrad (alternative name)+COMPOUND OF FORMULA I, fensulfothion (1158)+COMPOUND OF FORMULA I, fluensulfone (CAS. Reg. No.: 318290-98-1)+COMPOUND OF FORMULA I, fosthiazate (408)+COMPOUND OF FORMULA I, fosthietan (1196)+COMPOUND OF FORMULA I, furfural (alternative name) [CCN]+COMPOUND OF FORMULA I, GY-81 (development code) (423)+COMPOUND OF FORMULA I, heterophos [CCN]+COMPOUND OF FORMULA I, imicyafos [CCN]+COMPOUND OF FORMULA I, imicyafos (alternative name) [CCN]+COMPOUND OF FORMULA I, iodomethane (IUPAC name) (542)+COMPOUND OF FORMULA I, isamidofos (1230)+COMPOUND OF FORMULA I, isazofos (1231)+COMPOUND OF FORMULA I, ivermectin (alternative name) [CCN]+COMPOUND OF FORMULA I, kinetin (alternative name) (210)+COMPOUND OF FORMULA I, mecarphon (1258)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methyl bromide (537)+COMPOUND OF FORMULA I, methyl isothiocyanate (543)+COMPOUND OF FORMULA I, milbemycin oxime (alternative name) [CCN]+COMPOUND OF FORMULA I, moxidectin (alternative name) [CCN]+COMPOUND OF FORMULA I, *Myrothecium verrucaria* composition (alternative name) (565)+COMPOUND OF FORMULA I, NC-184 (compound code)+COMPOUND OF FORMULA I, oxamyl (602)+COMPOUND OF FORMULA I, phorate (636)+COMPOUND OF FORMULA I, phosphamidon (639)+COMPOUND OF FORMULA I, phosphocarb [CCN]+COMPOUND OF FORMULA I, sebufos (alternative name)+COMPOUND OF FORMULA I, selamectin (alternative name) [CCN]+COMPOUND OF FORMULA I, spinosad (737)+COMPOUND OF FORMULA I, terbam (alternative name)+COMPOUND OF FORMULA I, terbufos (773)+COMPOUND OF FORMULA I, tetrachlorothiophene (IUPAC/Chemical Abstracts name) (1422)+COMPOUND OF FORMULA I, thiafenox (alternative name)+COMPOUND OF FORMULA I, thionazin (1434)+COMPOUND OF FORMULA I, triazophos (820)+COMPOUND OF FORMULA I, triazuron (alternative name)+COMPOUND OF FORMULA I, xylenols [CCN]+COMPOUND OF FORMULA I, YI-5302 (compound code) and zeatin (alternative name) (210)+COMPOUND OF FORMULA I, a nitrification inhibitor selected from the group of substances consisting of potassium ethylxanthate [CCN] and nitrapyrin (580)+COMPOUND OF FORMULA I, a plant activator selected from the group of substances consisting of acibenzolar (6)+COMPOUND OF FORMULA I, acibenzolar-5-methyl (6)+COMPOUND OF FORMULA I, probenazole (658) and *Reynoutria sachalinensis* extract (alternative name) (720)+COMPOUND OF FORMULA I, a rodenticide selected from the group of substances consisting of 2-isovalerylindan-1,3-dione (IUPAC name) (1246)+COMPOUND OF FORMULA I, 4-(quinoxalin-2-ylamino)benzenesulfonamide (IUPAC name) (748)+COMPOUND OF FORMULA I, alpha-chlorohydrin [CCN]+COMPOUND OF FORMULA I, aluminium phosphide (640)+COMPOUND OF FORMULA I, antu (880)+COMPOUND OF FORMULA I, arsenous oxide (882)+COMPOUND OF FORMULA I, barium carbonate (891)+COMPOUND OF FORMULA I, bisthiosemi (912)+COMPOUND OF FORMULA I, brodifacoum (89)+COMPOUND OF FORMULA I, bromadiolone (91)+COMPOUND OF FORMULA I, bromethalin (92)+COMPOUND OF FORMULA I, calcium cyanide (444)+COMPOUND OF FORMULA I, chloralose (127)+COMPOUND OF FORMULA I, chlorophacinone (140)+COMPOUND OF FORMULA I, cholecalciferol (alternative name) (850)+COMPOUND OF FORMULA I, coumachlor (1004)+COMPOUND OF FORMULA I, coumafuryl (1005)+COMPOUND OF FORMULA I, coumatetralyl (175)+COMPOUND OF FORMULA I, crimidine (1009)+COMPOUND OF FORMULA I, difenacoum (246)+COMPOUND OF FORMULA I, difethialone (249)+COMPOUND OF FORMULA I, diphacinone (273)+COMPOUND OF FORMULA I, ergocalciferol (301)+COMPOUND OF FORMULA I, flocoumafen (357)+COMPOUND OF FORMULA I, fluoroacetamide (379)+COMPOUND OF FORMULA I, flupropadine (1183)+COMPOUND OF FORMULA I, flupropadine hydrochloride (1183)+COMPOUND OF FORMULA I, gamma-HCH (430)+COMPOUND OF FORMULA I, HCH (430)+COMPOUND OF FORMULA I, hydrogen cyanide (444)+COMPOUND OF FORMULA I, iodomethane (IUPAC name) (542)+COMPOUND OF FORMULA I, lindane (430)+COMPOUND OF FORMULA I, magnesium phosphide (IUPAC name) (640)+COMPOUND OF FORMULA I, methyl bromide (537)+COMPOUND OF FORMULA I, norbormide (1318)+COMPOUND OF FORMULA I, phosacetim (1336)+COMPOUND OF FORMULA I, phosphine (IUPAC name) (640)+COMPOUND OF FORMULA I, phosphorus [CCN]+COMPOUND OF FORMULA I, pindone (1341)+COMPOUND OF FORMULA I, potassium arsenite [CCN]+COMPOUND OF FORMULA I, pyrinuron (1371)+COMPOUND OF FORMULA I, scilliroside (1390)+COMPOUND OF FORMULA I, sodium arsenite [CCN]+COMPOUND OF FORMULA I, sodium cyanide (444)+COMPOUND OF FORMULA I, sodium fluoroacetate (735)+COMPOUND OF FORMULA I, strychnine (745)+COMPOUND OF FORMULA I, thallium sulfate [CCN]+COMPOUND OF FORMULA I, warfarin (851) and zinc phosphide (640)+COMPOUND OF FORMULA I, a synergist selected from the group of substances consisting of 2-(2-butoxyethoxy)ethyl piperonylate (IUPAC name) (934)+COMPOUND OF FORMULA I, 5-(1,3-benzodioxol-5-yl)-3-hexylcyclohex-2-enone (IUPAC name) (903)+COMPOUND OF FORMULA I, farnesol with nerolidol (alternative name) (324)+COMPOUND OF FORMULA I, MB-599 (development code) (498)+COMPOUND OF FORMULA I, MGK 264 (development code) (296)+COMPOUND OF FORMULA I, piperonyl butoxide (649)+COMPOUND OF FORMULA I, piprotal (1343)+COMPOUND OF FORMULA I, propyl isomer (1358)+COMPOUND OF FORMULA I, S421 (development code) (724)+COMPOUND OF FORMULA I, sesamex (1393)+COMPOUND OF FORMULA I, sesasmolin (1394) and sulfoxide (1406)+COMPOUND OF FORMULA I, an animal repellent selected from the group of substances consisting of anthraquinone (32)+COMPOUND OF FORMULA I, chloralose (127)+COMPOUND OF FORMULA I, copper naphthenate [CCN]+COMPOUND OF FORMULA I, copper oxychloride (171)+COMPOUND OF FORMULA I, diazinon (227)+COMPOUND OF FORMULA I, dicyclopentadiene (chemical name) (1069)+COMPOUND OF FORMULA I, guazatine (422)+COMPOUND OF FORMULA I, guazatine acetates (422)+COMPOUND OF FORMULA I, methiocarb (530)+COMPOUND OF FORMULA I, pyridin-4-amine (IUPAC name) (23)+COMPOUND OF FORMULA I, thiram (804)+COMPOUND OF FORMULA I, trimethacarb (840)+COMPOUND OF FORMULA I, zinc naphthenate [CCN] and ziram (856)+COMPOUND OF FORMULA I, a virucide selected from the group of substances consisting of imanin (alternative name) [CCN] and ribavirin (alternative name) [CCN]+COMPOUND OF FORMULA I, a wound protectant selected from the group of substances consisting of mercuric oxide (512)+COMPOUND OF FORMULA I, octhilinone (590) and thiophanate-methyl (802)+COMPOUND OF FORMULA I, an insecticide selected from the group consisting of the compound of the formula A-1

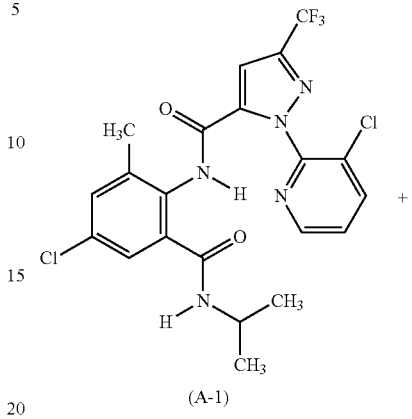

(A-1)

COMPOUND OF FORMULA I, the formula A-2

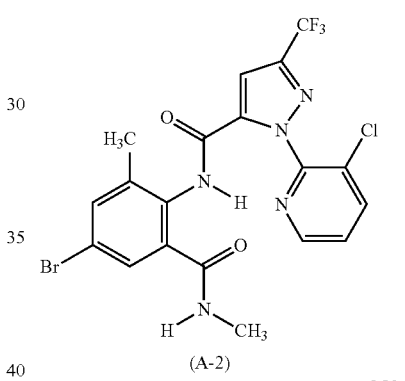

(A-2)

COMPOUND OF FORMULA I, the formula A-3

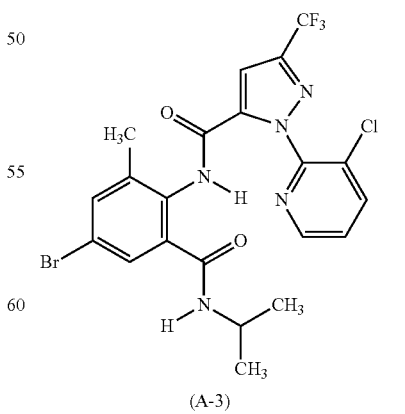

(A-3)

COMPOUND OF FORMULA I, the formula A-4
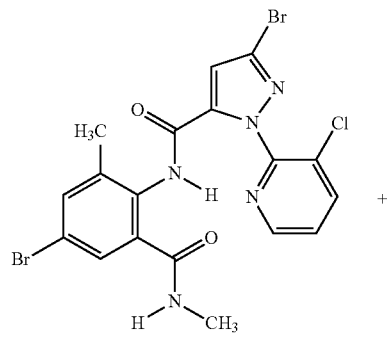
(A-4)
COMPOUND OF FORMULA I,
the formula A-5
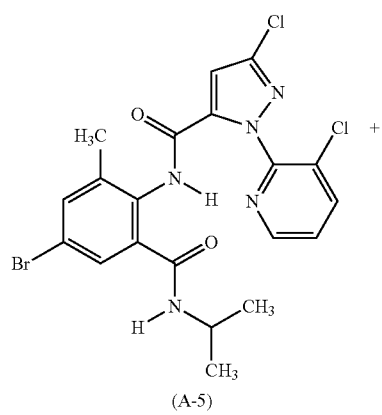
(A-5)
COMPOUND OF FORMULA I,
the formula A-6
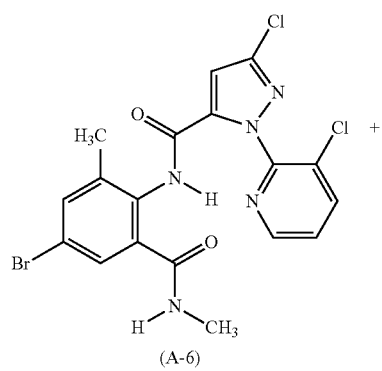
(A-6)
COMPOUND OF FORMULA I,
the formula A-7
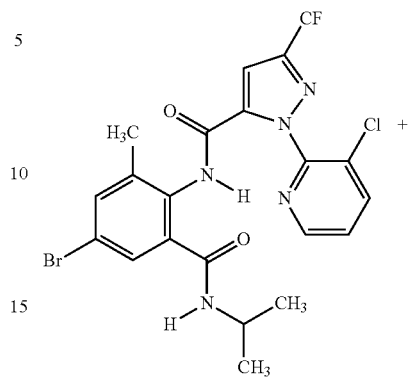
(A-7)
COMPOUND OF FORMULA I,
the formula A-8
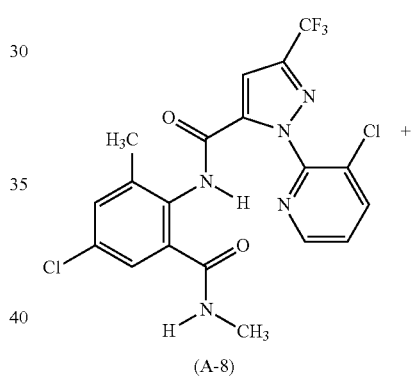
(A-8)
COMPOUND OF FORMULA I,
the formula A-9
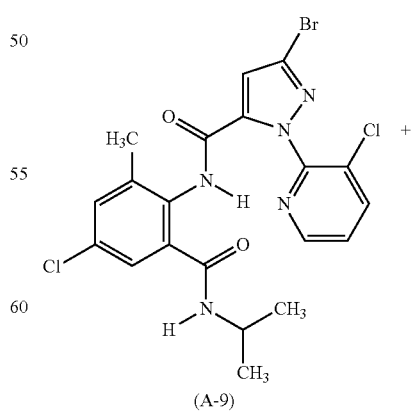
(A-9)
COMPOUND OF FORMULA I, the formula A-10
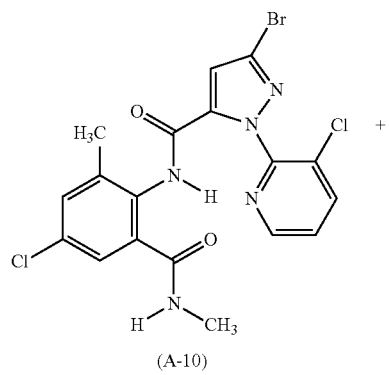
(A-10)
COMPOUND OF FORMULA I,
the formula A-11
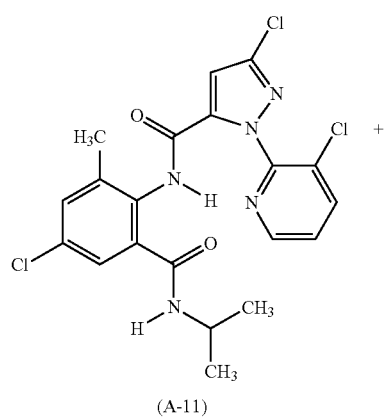
(A-11)
COMPOUND OF FORMULA I,
the formula A-12
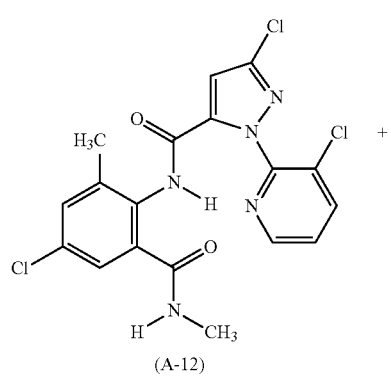
(A-12)
COMPOUND OF FORMULA I,
the formula A-13
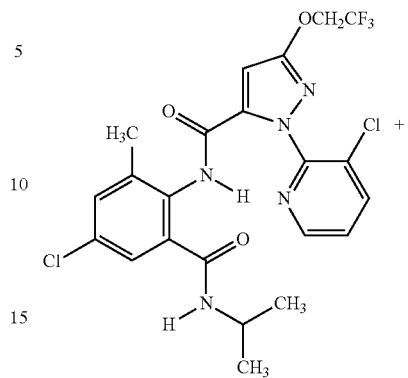
(A-13)
COMPOUND OF FORMULA I,
the formula A-14
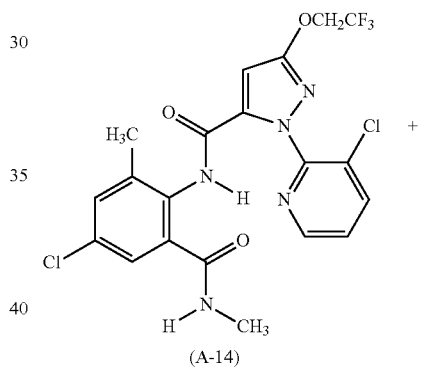
(A-14)
COMPOUND OF FORMULA I,
the formula A-15
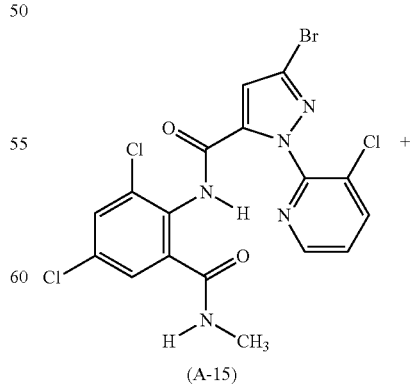
(A-15)
COMPOUND OF FORMULA I, the formula A-16
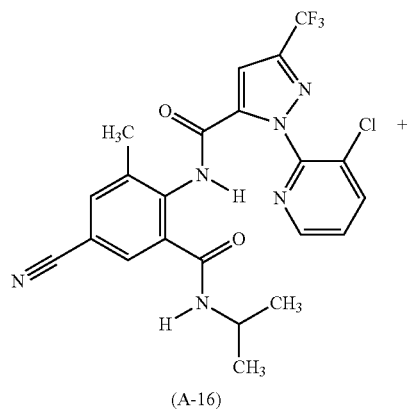
(A-16)
the formula A-17
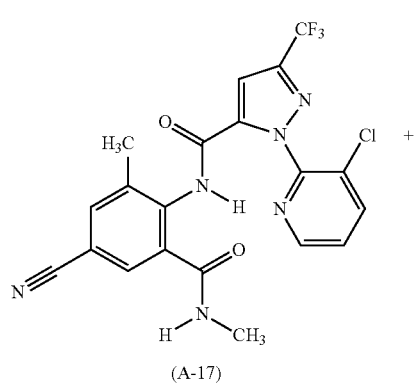
(A-17)
the formula A-18
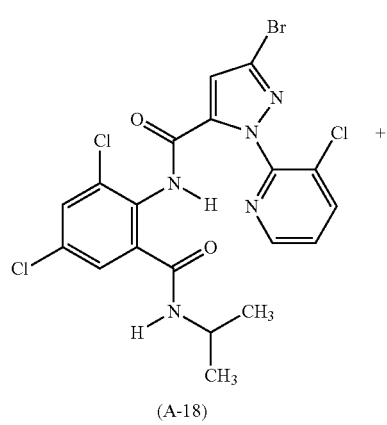
(A-18)
COMPOUND OF FORMULA I,
the formula A-19
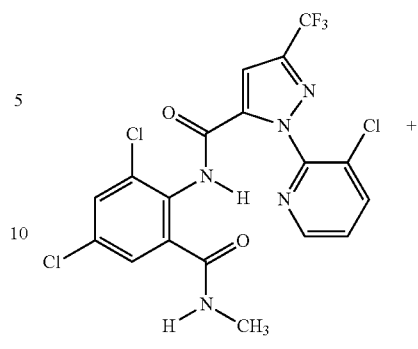
(A-19)
COMPOUND OF FORMULA I,
the formula A-20
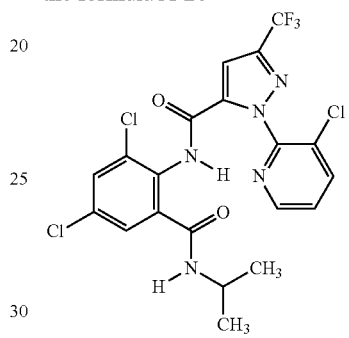
(A-20)
+ COMPOUND OF FORMULA I,
the formula A-21
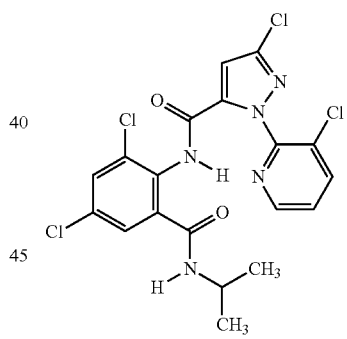
(A-21)
+ COMPOUND OF FORMULA I,
the formula A-22
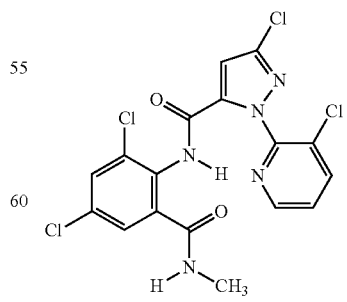
(A-22)
+ COMPOUND OF FORMULA I, the formula A-23

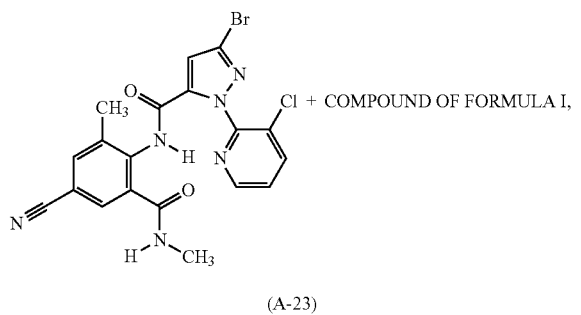

(A-23)

+ COMPOUND OF FORMULA I, the formula A-24

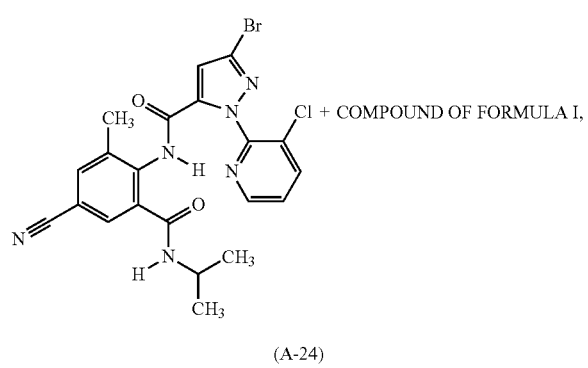

(A-24)

+ COMPOUND OF FORMULA I, the formula A-25

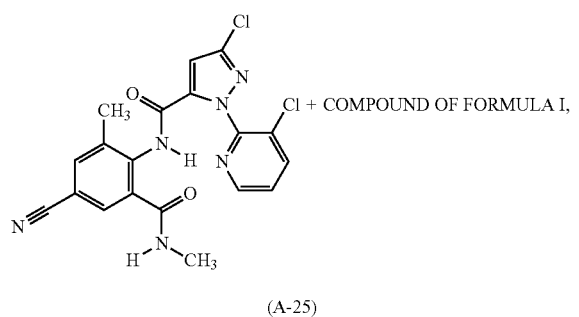

(A-25)

+ COMPOUND OF FORMULA I, the formula A-26

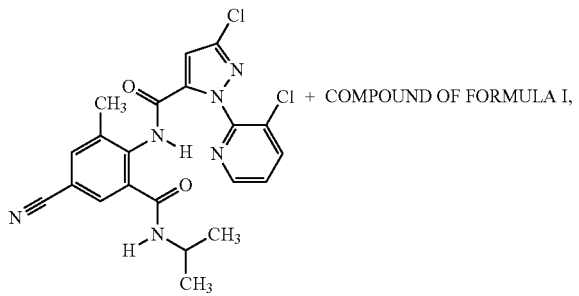

(A-26)

+ COMPOUND OF FORMULA I, and the formula A-27

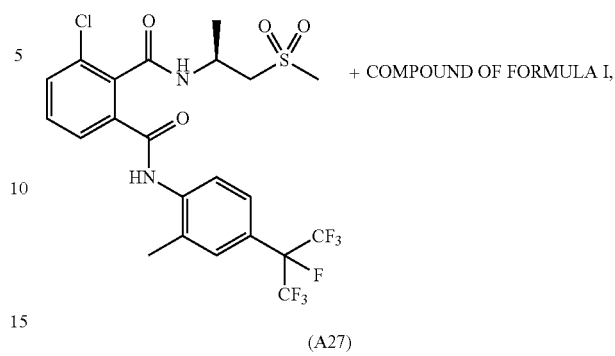

(A27)

+ COMPOUND OF FORMULA I, an insecticide selected from the group consisting of the compound of the formula A-28

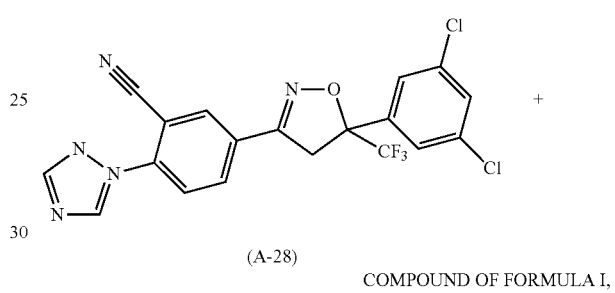

(A-28)

+ COMPOUND OF FORMULA I, and the formula A-29

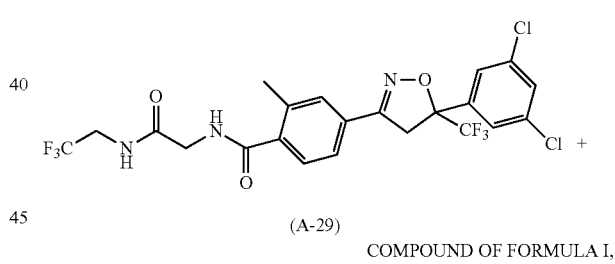

(A-29)

+ COMPOUND OF FORMULA I, and the formula A-30

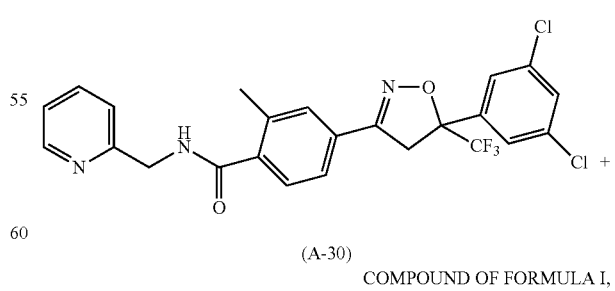

(A-30)

+ COMPOUND OF FORMULA I, an insecticide selected from the group consisting of the compound of the formula A-31 [BYI2960 (development code)]

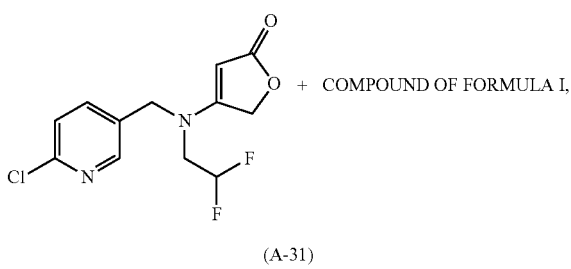

(A-31) + COMPOUND OF FORMULA I, the formula A-32

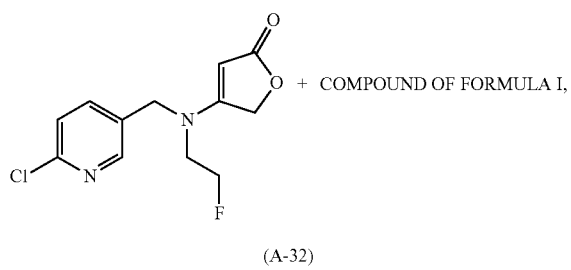

(A-32) + COMPOUND OF FORMULA I, the formula A-33

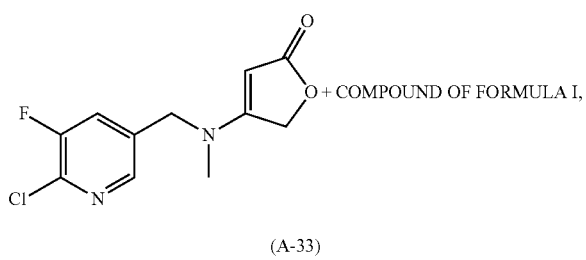

(A-33) + COMPOUND OF FORMULA I, and an insecticide of the formula A-34 [SYN 876 (compound code)]

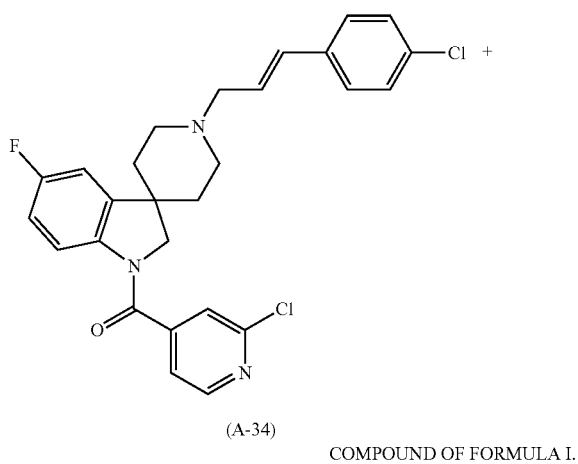

(A-34) + COMPOUND OF FORMULA I.

The references in brackets behind the active ingredients, e.g. [3878-19-1] refer to the Chemical Abstracts Registry number. The compounds of the formula A-1 to A-26 are described in WO 03/015518 or in WO 04/067528. The compound of the formula A-27 is described in WO 06/022225 and in WO 07/112,844. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright© 1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The compounds of formula I according to the invention can also be used in combination with one or more fungicides. In particular, in the following mixtures of the compounds of formula I with fungicides, the term COMPOUND OF FORMULA I preferably refers to a compound selected from one of the Tables 1 to 861:

COMPOUND OF FORMULA I+(E)-N-methyl-2-[2-(2,5-dimethylphenoxymethyl)phenyl]-2-methoxy-iminoacetamide (SSF-129), COMPOUND OF FORMULA I+4-bromo-2-cyano-N,N-dimethyl-6-trifluoromethylbenzimidazole-1-sulphonamide, COMPOUND OF FORMULA I+α-[N-(3-chloro-2,6-xylyl)-2-methoxyacetamido]-γ-butyrolactone, COMPOUND OF FORMULA I+4-chloro-2-cyano-N,N-dimethyl-5-p-tolylimidazole-1-sulfonamide (IKF-916, cyamidazosulfamid), COMPOUND OF FORMULA I+3-5-dichloro-N-(3-chloro-1-ethyl-1-methyl-2-oxopropyl)-4-methylbenzamide (RH-7281, zoxamide), COMPOUND OF FORMULA I+N-allyl-4,5,-dimethyl-2-trimethylsilylthiophene-3-carboxamide (MON65500), COMPOUND OF FORMULA I+N-(1-cyano-1,2-dimethylpropyl)-2-(2,4-dichlorophenoxy)propionamide (AC382042), COMPOUND OF FORMULA I+N-(2-methoxy-5-pyridyl)-cyclopropane carboxamide, COMPOUND OF FORMULA I+acibenzolar, COMPOUND OF FORMULA I+alanycarb, COMPOUND OF FORMULA I+aldimorph, COMPOUND OF FORMULA I+ametoctradin, COMPOUND OF FORMULA I+amisulbrom, COMPOUND OF FORMULA I+anilazine, COMPOUND OF FORMULA I+azaconazole, COMPOUND OF FORMULA I+azoxystrobin, COMPOUND OF FORMULA I+benalaxyl, COMPOUND OF FORMULA I+benalaxyl-M, COMPOUND OF FORMULA I+benomyl, COMPOUND OF FORMULA I+benthiavalicarb, COMPOUND OF FORMULA I+benzodiflupyr, COMPOUND OF FORMULA I+benzovindiflupyr, COMPOUND OF FORMULA I+biloxazol, COMPOUND OF FORMULA I+bitertanol, COMPOUND OF FORMULA I+bixafen, COMPOUND OF FORMULA I+blasticidin S, COMPOUND OF FORMULA I+boscalid, COMPOUND OF FORMULA I+bromuconazole, COMPOUND OF FORMULA I+bupirimate, COMPOUND OF FORMULA I+captafol, COMPOUND OF FORMULA I+captan, COMPOUND OF FORMULA I+carbendazim, COMPOUND OF FORMULA I+carbendazim chlorhydrate, COMPOUND OF FORMULA I+carboxin, COMPOUND OF FORMULA I+carpropamid, carvone, COMPOUND OF FORMULA I+CGA41396, COMPOUND OF FORMULA I+CGA41397, COMPOUND OF FORMULA I+chinomethionate, COMPOUND OF FORMULA I+chlazafenone, COMPOUND OF FORMULA I+chlorodincarb, COMPOUND OF FORMULA I+chlorothalonil, COMPOUND OF FORMULA I+chlorozolinate, COMPOUND OF FORMULA I+clozylacon, COMPOUND OF FORMULA I+copper containing compounds such as copper oxychloride, copper oxyquinolate, copper sulphate, copper tallate and Bordeaux mixture, COMPOUND OF FORMULA I+coumoxystrobin, COMPOUND OF FORMULA I+cyazofamid, COMPOUND OF FORMULA I+cyflufenamid, COMPOUND OF FORMULA I+cymoxanil, COMPOUND OF FORMULA I+cyproconazole, COMPOUND OF FORMULA I+cyprodinil, COMPOUND OF FORMULA I+debacarb, COMPOUND OF FORMULA I+di-2-pyridyl disulphide 1,1'-dioxide, COMPOUND OF FORMULA I+dicloaminstrobin, COMPOUND OF FORMULA I+diclofenoxystrobin, COMPOUND OF FORMULA I+dichlofluanid, COMPOUND OF FORMULA I+diclomezine, COMPOUND OF FORMULA I+dicloran, COMPOUND OF FORMULA I+diethofencarb, COMPOUND OF FORMULA I+difenoconazole, COMPOUND OF FORMULA I+difenzoquat, COMPOUND OF FORMULA I+diflumetorim, COMPOUND OF FORMULA I+O, O-di-iso-propyl-5-benzyl thiophosphate, COMPOUND OF FORMULA I+dimefluazole, COMPOUND OF FORMULA I+dimetconazole, COMPOUND OF FORMULA I+dimethomorph, COMPOUND OF FORMULA I+dimethirimol, COMPOUND OF FORMULA I+dimoxystrobin, COMPOUND OF FORMULA I+diniconazole, COMPOUND OF FORMULA I+dinocap, COMPOUND OF FORMULA I+dithianon, COMPOUND OF FORMULA I+dodecyl dimethyl ammonium chloride, COMPOUND OF FORMULA I+dodemorph, COMPOUND OF FORMULA I+dodine, COMPOUND OF FORMULA I+doguadine, COMPOUND OF FORMULA I+edifenphos, COMPOUND OF FORMULA I+enoxastrobin, COMPOUND OF FORMULA I+epoxiconazole, COMPOUND OF FORMULA I+ethirimol, COMPOUND OF FORMULA I+ethyl(Z)—N-benzyl-N([methyl(methyl-thioethylideneaminooxycarbonyl)amino]thio)-β-alaninate, COMPOUND OF FORMULA I+etridiazole, COMPOUND OF FORMULA I+famoxadone, COMPOUND OF FORMULA I+fenamidone (RPA407213), COMPOUND OF FORMULA I+fenaminstrobin, COMPOUND OF FORMULA I+fenarimol, COMPOUND OF FORMULA I+fenbuconazole, COMPOUND OF FORMULA I+fenfuram, COMPOUND OF FORMULA I+fenhexamid (KBR2738), COMPOUND OF FORMULA I+fenoxanil, COMPOUND OF FORMULA I+fenoxystrobin, COMPOUND OF FORMULA I+fenpiclonil, COMPOUND OF FORMULA I+fenpropidin, COMPOUND OF FORMULA I+fenpropimorph, COMPOUND OF FORMULA I+fenpyrazamine, COMPOUND OF FORMULA I+fenpyrazamine/ipfenpyrazolone, COMPOUND OF FORMULA I+fentin acetate, COMPOUND OF FORMULA I+fentin hydroxide, COMPOUND OF FORMULA I+ferbam, COMPOUND OF FORMULA I+ferimzone, COMPOUND OF FORMULA I+fluazinam, COMPOUND OF FORMULA I+fludioxonil, COMPOUND OF FORMULA I+flufenoxystrobin, COMPOUND OF FORMULA I+flumetover, COMPOUND OF FORMULA I+flumorph, COMPOUND OF FORMULA I+fluopicolide, COMPOUND OF FORMULA I+fluopyram, COMPOUND OF FORMULA I+fluoxastrobin, COMPOUND OF FORMULA I+fluoroimide, COMPOUND OF FORMULA I+fluquinconazole, COMPOUND OF FORMULA I+flusilazole, COMPOUND OF FORMULA I+flutianil, COMPOUND OF FORMULA I+flutolanil, COMPOUND OF FORMULA I+flutriafol, COMPOUND OF FORMULA I+fluxapyroxad, COMPOUND OF FORMULA I+folpet, COMPOUND OF FORMULA I+fosetyl, COMPOUND OF FORMULA I+fosetyl-aluminium, COMPOUND OF FORMULA I+fuberidazole, COMPOUND OF FORMULA I+furalaxyl, COMPOUND OF FORMULA I+furametpyr, COMPOUND OF FORMULA I+guazatine, COMPOUND OF FORMULA I+hexaconazole, COMPOUND OF FORMULA I+hydroxyisoxazole, COMPOUND OF FORMULA I+hymexazole, COMPOUND OF FORMULA I+imazalil, COMPOUND OF FORMULA I+imibenconazole, COMPOUND OF FORMULA I+iminoctadine, COMPOUND OF FORMULA I+iminoctadine triacetate, COMPOUND OF FORMULA I+ipconazole, COMPOUND OF FORMULA I+iprobenfos, COMPOUND OF FORMULA I+iprodione, COMPOUND OF FORMULA I+iprovalicarb (SZX0722), COMPOUND OF FORMULA I+isopropanyl butyl carbamate, COMPOUND OF FORMULA I+isoprothiolane, COMPOUND OF FORMULA I+isopyrazam, COMPOUND OF FORMULA I+isotianil, COMPOUND OF FORMULA I+kasugamycin, COMPOUND OF FORMULA I+kresoxim-methyl, COMPOUND OF FORMULA I+LY186054, COMPOUND OF FORMULA I+LY211795, COMPOUND OF FORMULA I+LY248908, COMPOUND OF FORMULA I+mancozeb, COMPOUND OF FORMULA I+mandipropamid, COMPOUND OF FORMULA I+maneb, COMPOUND OF FORMULA I+mefenoxam, COMPOUND OF FORMULA I+mepanipyrim, COMPOUND OF FORMULA I+mepronil, COMPOUND OF FORMULA I+meptyldinocap, COMPOUND OF FORMULA I+metalaxyl, COMPOUND OF FORMULA I+metconazole, COMPOUND OF FORMULA I+metiram, COMPOUND OF FORMULA I+metiram-zinc, COMPOUND OF FORMULA I+metominostrobin, COMPOUND OF FORMULA I+metrafenone, COMPOUND OF FORMULA I+myclobutanil, COMPOUND OF FORMULA I+neoasozin, COMPOUND OF FORMULA I+nickel dimethyldithiocarbamate, COMPOUND OF FORMULA I+nicobifen, COMPOUND OF FORMULA I+nitrothal-isopropyl, COMPOUND OF FORMULA I+nuarimol, COMPOUND OF FORMULA I+ofurace, COMPOUND OF FORMULA I+organomercury compounds, COMPOUND OF FORMULA I+orysastrobin, COMPOUND OF FORMULA I+oxadixyl, COMPOUND OF FORMULA I+oxasulfuron, COMPOUND OF FORMULA I+oxolinic acid, COMPOUND OF FORMULA I+oxpoconazole, COMPOUND OF FORMULA I+oxycarboxin, COMPOUND OF FORMULA I+pefurazoate, COMPOUND OF FORMULA I+penconazole, COMPOUND OF FORMULA I+pencycuron, COMPOUND OF FORMULA I+penflufen, COMPOUND OF FORMULA I+penthiopyrad, COMPOUND OF FORMULA I+phenazin oxide, COMPOUND OF FORMULA I+phosetyl-Al, COMPOUND OF FORMULA I+phosphorus acids, COMPOUND OF FORMULA I+phthalide, COMPOUND OF FORMULA I+picoxystrobin (ZA1963), COMPOUND OF FORMULA I+polyoxin D, COMPOUND OF FORMULA I+polyram, COMPOUND OF FORMULA I+probenazole, COMPOUND OF FORMULA I+prochloraz, COMPOUND OF FORMULA I+procymidone, COMPOUND OF FORMULA I+propamocarb, COMPOUND OF FORMULA I+propiconazole, COM- POUND OF FORMULA I+propineb, COMPOUND OF FORMULA I+propionic acid, COMPOUND OF FORMULA I+proquinazid, COMPOUND OF FORMULA I+prothioconazole, COMPOUND OF FORMULA I+pyraclostrobin, COMPOUND OF FORMULA I+pyraoxystrobin, COMPOUND OF FORMULA I+pyrazophos, COMPOUND OF FORMULA I+pyribencarb, COMPOUND OF FORMULA I+pyrifenox, COMPOUND OF FORMULA I+pyrimethanil, COMPOUND OF FORMULA I+pyrisoxazole, COMPOUND OF FORMULA I+pyroquilon, COMPOUND OF FORMULA I+pyroxyfur, COMPOUND OF FORMULA I+pyrroInitrin, COMPOUND OF FORMULA I+quaternary ammonium compounds, COMPOUND OF FORMULA I+quinomethionate, COMPOUND OF FORMULA I+quinoxyfen, COMPOUND OF FORMULA I+quintozene, COMPOUND OF FORMULA I+sedaxane, COMPOUND OF FORMULA I+sipconazole (F-155), COMPOUND OF FORMULA I+sodium pentachlorophenate, COMPOUND OF FORMULA I+spiroxamine, COMPOUND OF FORMULA I+streptomycin, COMPOUND OF FORMULA I+sulphur, COMPOUND OF FORMULA I+tebuconazole, COMPOUND OF FORMULA I+tecloftalam, COMPOUND OF FORMULA I+tecnazene, COMPOUND OF FORMULA I+terbufloquin, COMPOUND OF FORMULA I+tetraconazole, COMPOUND OF FORMULA I+thiabendazole, COMPOUND OF FORMULA I+thifluzamid, COMPOUND OF FORMULA I+2-(thiocyanomethylthio)benzothiazole, COMPOUND OF FORMULA I+thiophanate-methyl, COMPOUND OF FORMULA I+thiram, COMPOUND OF FORMULA I+tiadinil, COMPOUND OF FORMULA I+timibenconazole, COMPOUND OF FORMULA I+tolclofos-methyl, COMPOUND OF FORMULA I+tolylfluanid, COMPOUND OF FORMULA I+triadimefon, COMPOUND OF FORMULA I+triadimenol, COMPOUND OF FORMULA I+triazbutil, COMPOUND OF FORMULA I+triazoxide, COMPOUND OF FORMULA I+triclopyricarb, COMPOUND OF FORMULA I+tricyclazole, COMPOUND OF FORMULA I+tridemorph, COMPOUND OF FORMULA I+trifloxystrobin, COMPOUND OF FORMULA I+triforine, COMPOUND OF FORMULA I+triflumizole, COMPOUND OF FORMULA I+triticonazole, COMPOUND OF FORMULA I+validamycin A, COMPOUND OF FORMULA I+valiphenal, COMPOUND OF FORMULA I+vapam, COMPOUND OF FORMULA I+vinclozolin, COMPOUND OF FORMULA I+zineb and COMPOUND OF FORMULA I+ziram.

The compounds of formula I may be mixed with soil, peat or other rooting media for the protection of plants against seed-borne, soil-borne or foliar fungal diseases.

The compounds of formula I according to the invention can also be used in combination with one or more other synergists. In particular, the following mixtures of the COMPOUND OF FORMULA I, where this term preferably refers to a compound selected from one of the Tables 1 to 861, are important:
COMPOUND OF FORMULA I+piperonyl butoxide, COMPOUND OF FORMULA I+sesamex, COMPOUND OF FORMULA I+safroxan and COMPOUND OF FORMULA I+dodecyl imidazole.

The compounds of formula I according to the invention can also be used in combination with one or more other herbicides. In particular, the following mixtures of the COMPOUND OF FORMULA I, where this term preferably refers to a compound selected from one of the Tables 1 to 861, are important:
COMPOUND OF FORMULA I+acetochlor, COMPOUND OF FORMULA I+acifluorfen, COMPOUND OF FORMULA I+acifluorfen-sodium, COMPOUND OF FORMULA I+aclonifen, COMPOUND OF FORMULA I+acrolein, COMPOUND OF FORMULA I+alachlor, COMPOUND OF FORMULA I+alloxydim, COMPOUND OF FORMULA I+allyl alcohol, COMPOUND OF FORMULA I+ametryn, COMPOUND OF FORMULA I+amicarbazone, COMPOUND OF FORMULA I+amidosulfuron, COMPOUND OF FORMULA I+aminocyclopyrachlor, COMPOUND OF FORMULA I+aminopyralid, COMPOUND OF FORMULA I+amitrole, COMPOUND OF FORMULA I+ammonium sulfamate, COMPOUND OF FORMULA I+anilofos, COMPOUND OF FORMULA I+asulam, COMPOUND OF FORMULA I+ataton, COMPOUND OF FORMULA I+atrazine, COMPOUND OF FORMULA I+azimsulfuron, COMPOUND OF FORMULA I+BCPC, COMPOUND OF FORMULA I+beflubutamid, COMPOUND OF FORMULA I+benazolin, COMPOUND OF FORMULA I+bencarbazone, COMPOUND OF FORMULA I+benfluralin, COMPOUND OF FORMULA I+benfuresate, COMPOUND OF FORMULA I+bensulfuron, COMPOUND OF FORMULA I+bensulfuron-methyl, COMPOUND OF FORMULA I+bensulide, COMPOUND OF FORMULA I+bentazone, COMPOUND OF FORMULA I+benzfendizone, COMPOUND OF FORMULA I+benzobicyclon, COMPOUND OF FORMULA I+benzofenap, COMPOUND OF THE FORMULA I+bicyclopyrone, COMPOUND OF FORMULA I+bifenox, COMPOUND OF FORMULA I+bilanafos, COMPOUND OF FORMULA I+bispyribac, COMPOUND OF FORMULA I+bispyribac-sodium, COMPOUND OF FORMULA I+borax, COMPOUND OF FORMULA I+bromacil, COMPOUND OF FORMULA I+bromobutide, COMPOUND OF FORMULA I+bromoxynil, COMPOUND OF FORMULA I+butachlor, COMPOUND OF FORMULA I+butafenacil, COMPOUND OF FORMULA I+butamifos, COMPOUND OF FORMULA I+butralin, COMPOUND OF FORMULA I+butroxydim, COMPOUND OF FORMULA I+butylate, COMPOUND OF FORMULA I+cacodylic acid, COMPOUND OF FORMULA I+calcium chlorate, COMPOUND OF FORMULA I+cafenstrole, COMPOUND OF FORMULA I+carbetamide, COMPOUND OF FORMULA I+carfentrazone, COMPOUND OF FORMULA I+carfentrazone-ethyl, COMPOUND OF FORMULA I+CDEA, COMPOUND OF FORMULA I+CEPC, COMPOUND OF FORMULA I+chlorflurenol, COMPOUND OF FORMULA I+chlorflurenol-methyl, COMPOUND OF FORMULA I+chloridazon, COMPOUND OF FORMULA I+chlorimuron, COMPOUND OF FORMULA I+chlorimuron-ethyl, COMPOUND OF FORMULA I+chloroacetic acid, COMPOUND OF FORMULA I+chlorotoluron, COMPOUND OF FORMULA I+chlorpropham, COMPOUND OF FORMULA I+chlorsulfuron, COMPOUND OF FORMULA I+chlorthal, COMPOUND OF FORMULA I+chlorthal-dimethyl, COMPOUND OF FORMULA I+cinidon-ethyl, COMPOUND OF FORMULA I+cinmethylin, COMPOUND OF FORMULA I+cinosulfuron, COMPOUND OF FORMULA I+cisanilide, COMPOUND OF FORMULA I+clethodim, COMPOUND OF FORMULA I+clodinafop, COMPOUND OF FORMULA I+clodinafop-propargyl, COMPOUND OF FORMULA I+clomazone, COMPOUND OF FORMULA I+clomeprop, COMPOUND OF FORMULA I+clopyralid, COMPOUND OF FORMULA I+cloransulam, COMPOUND OF FORMULA I+cloransulam-methyl, COMPOUND OF FORMULA I+CMA, COMPOUND OF FORMULA I+4-CPB, COMPOUND OF FORMULA I+CPMF, COMPOUND OF FORMULA I+4-CPP, COMPOUND OF FORMULA I+CPPC, COMPOUND OF FORMULA I+cresol, COMPOUND OF FORMULA I+cumyluron, COMPOUND OF FORMULA I+cyanamide, COMPOUND OF FORMULA I+cyanazine, COMPOUND OF FORMULA I+cycloate, COMPOUND OF FORMULA I+cyclosulfamuron, COMPOUND OF FORMULA I+cycloxydim, COMPOUND OF FORMULA I+cyhalofop, COMPOUND OF FORMULA I+cyhalofop-butyl, COMPOUND OF FORMULA I+2,4-D, COMPOUND OF FORMULA I+3,4-DA, COMPOUND OF FORMULA I+daimuron, COMPOUND OF FORMULA I+dalapon, COMPOUND OF FORMULA I+dazomet, COMPOUND OF FORMULA I+2,4-DB, COMPOUND OF FORMULA I+3,4-DB, COMPOUND OF FORMULA I+2,4-DEB, COMPOUND OF FORMULA I+desmedipham, COMPOUND OF FORMULA I+dicamba, COMPOUND OF FORMULA I+dichlobenil, COMPOUND OF FORMULA I+ortho-dichlorobenzene, COMPOUND OF FORMULA I+para-dichlorobenzene, COMPOUND OF FORMULA I+dichlorprop, COMPOUND OF FORMULA I+dichlorprop-P, COMPOUND OF FORMULA I+diclofop, COMPOUND OF FORMULA I+diclofop-methyl, COMPOUND OF FORMULA I+diclosulam, COMPOUND OF FORMULA I+difenzoquat, COMPOUND OF FORMULA I+difenzoquat metilsulfate, COMPOUND OF FORMULA I+diflufenican, COMPOUND OF FORMULA I+diflufenzopyr, COMPOUND OF FORMULA I+dimefuron, COMPOUND OF FORMULA I+dimepiperate, COMPOUND OF FORMULA I+dimethachlor, COMPOUND OF FORMULA I+dimethametryn, COMPOUND OF FORMULA I+dimethenamid, COMPOUND OF FORMULA I+dimethenamid-P, COMPOUND OF FORMULA I+dimethipin, COMPOUND OF FORMULA I+dimethylarsinic acid, COMPOUND OF FORMULA I+dinitramine, COMPOUND OF FORMULA I+dinoterb, COMPOUND OF FORMULA I+diphenamid, COMPOUND OF FORMULA I+diquat, COMPOUND OF FORMULA I+diquat dibromide, COMPOUND OF FORMULA I+dithiopyr, COMPOUND OF FORMULA I+diuron, COMPOUND OF FORMULA I+DNOC, COMPOUND OF FORMULA I+3,4-DP, COMPOUND OF FORMULA I+DSMA, COMPOUND OF FORMULA I+EBEP, COMPOUND OF FORMULA I+endothal, COMPOUND OF FORMULA I+EPTC, COMPOUND OF FORMULA I+esprocarb, COMPOUND OF FORMULA I+ethalfluralin, COMPOUND OF FORMULA I+ethametsulfuron, COMPOUND OF FORMULA I+ethametsulfuron-methyl, COMPOUND OF FORMULA I+ethofumesate, COMPOUND OF FORMULA I+ethoxyfen, COMPOUND OF FORMULA I+ethoxysulfuron, COMPOUND OF FORMULA I+etobenzanid, COMPOUND OF FORMULA I+fenoxaprop-P, COMPOUND OF FORMULA I+fenoxaprop-P-ethyl, COMPOUND OF FORMULA I+fentrazamide, COMPOUND OF FORMULA I+ferrous sulfate, COMPOUND OF FORMULA I+flamprop-M, COMPOUND OF FORMULA I+flazasulfuron, COMPOUND OF FORMULA I+florasulam, COMPOUND OF FORMULA I+fluazifop, COMPOUND OF FORMULA I+fluazifop-butyl, COMPOUND OF FORMULA I+fluazifop-P, COMPOUND OF FORMULA I+fluazifop-P-butyl, COMPOUND OF FORMULA I+flucarbazone, COMPOUND OF FORMULA I+flucarbazone-sodium, COMPOUND OF FORMULA I+flucetosulfuron, COMPOUND OF FORMULA I+fluchloralin, COMPOUND OF FORMULA I+flufenacet, COMPOUND OF FORMULA I+flufenpyr, COMPOUND OF FORMULA I+flufenpyr-ethyl, COMPOUND OF FORMULA I+flumetsulam, COMPOUND OF FORMULA I+flumiclorac, COMPOUND OF FORMULA I+flumiclorac-pentyl, COMPOUND OF FORMULA I+flumioxazin, COMPOUND OF FORMULA I+flumeturon, COMPOUND OF FORMULA I+fluoroglycofen, COMPOUND OF FORMULA I+fluoroglycofen-ethyl, COMPOUND OF FORMULA I+flupropanate, COMPOUND OF FORMULA I+flupyrsulfuron, COMPOUND OF FORMULA I+flupyrsulfuron-methyl-sodium, COMPOUND OF FORMULA I+flurenol, COMPOUND OF FORMULA I+fluridone, COMPOUND OF FORMULA I+fluorochloridone, COMPOUND OF FORMULA I+fluoroxypyr, COMPOUND OF FORMULA I+flurtamone, COMPOUND OF FORMULA I+fluthiacet, COMPOUND OF FORMULA I+fluthiacet-methyl, COMPOUND OF FORMULA I+fomesafen, COMPOUND OF FORMULA I+foramsulfuron, COMPOUND OF FORMULA I+fosamine, COMPOUND OF FORMULA I+glufosinate, COMPOUND OF FORMULA I+glufosinate-ammonium, COMPOUND OF FORMULA I+glufosinate-P, COMPOUND OF FORMULA I+glyphosate, COMPOUND OF FORMULA I+glyphosate-trimesium, COMPOUND OF FORMULA I+halosulfuron, COMPOUND OF FORMULA I+halosulfuron-methyl, COMPOUND OF FORMULA I+haloxyfop, COMPOUND OF FORMULA I+haloxyfop-P, COMPOUND OF FORMULA I+HC-252, COMPOUND OF FORMULA I+hexazinone, COMPOUND OF FORMULA I+imazamethabenz, COMPOUND OF FORMULA I+imazamethabenz-methyl, COMPOUND OF FORMULA I+imazamox, COMPOUND OF FORMULA I+imazapic, COMPOUND OF FORMULA I+imazapyr, COMPOUND OF FORMULA I+imazaquin, COMPOUND OF FORMULA I+imazethapyr, COMPOUND OF FORMULA I+imazosulfuron, COMPOUND OF FORMULA I+indanofan, COMPOUND OF FORMULA I+indaziflam, COMPOUND OF FORMULA I+iodomethane, COMPOUND OF FORMULA I+iodosulfuron, COMPOUND OF FORMULA I+iodosulfuron-methyl-sodium, COMPOUND OF FORMULA I+iofensulfuron, COMPOUND OF FORMULA I+ioxynil, COMPOUND OF FORMULA I+ipfencarbazone, COMPOUND OF FORMULA I+isoproturon, COMPOUND OF FORMULA I+isouron, COMPOUND OF FORMULA I+isoxaben, COMPOUND OF FORMULA I+isoxachlortole, COMPOUND OF FORMULA I+isoxaflutole, COMPOUND OF FORMULA I+karbutilate, COMPOUND OF FORMULA I+lactofen, COMPOUND OF FORMULA I+lenacil, COMPOUND OF FORMULA I+linuron, COMPOUND OF FORMULA I+MAA, COMPOUND OF FORMULA I+MAMA, COMPOUND OF FORMULA I+MCPA, COMPOUND OF FORMULA I+MCPA-thioethyl, COMPOUND OF FORMULA I+MCPB, COMPOUND OF FORMULA I+mecoprop, COMPOUND OF FORMULA I+mecoprop-P, COMPOUND OF FORMULA I+mefenacet, COMPOUND OF FORMULA I+mefluidide, COMPOUND OF FORMULA I+mesosulfuron, COMPOUND OF FORMULA I+mesosulfuron-methyl, COMPOUND OF FORMULA I+mesotrione, COMPOUND OF FORMULA I+metam, COMPOUND OF FORMULA I+metamifop, COMPOUND OF FORMULA I+metamitron, COMPOUND OF FORMULA I+metazachlor, COMPOUND OF FORMULA I+methabenzthiazuron, COMPOUND OF FORMULA I+methylarsonic acid, COMPOUND OF FORMULA I+methyldymron, COMPOUND OF FORMULA I+methyl isothiocyanate, COMPOUND OF FORMULA I+metiozolin, COMPOUND OF FORMULA I+metobenzuron, COMPOUND OF FORMULA I+metolachlor, COMPOUND OF FORMULA I+S-metolachlor, COMPOUND OF FORMULA I+metosulam, COMPOUND OF FORMULA I+metoxuron, COMPOUND OF FORMULA I+metribuzin, COMPOUND OF FORMULA I+metsulfuron, COMPOUND OF FORMULA I+metsulfuron-methyl, COMPOUND OF FORMULA I+MK-616, COMPOUND OF FORMULA I+molinate, COMPOUND OF FORMULA I+monolinuron, COMPOUND OF FORMULA I+MSMA, COMPOUND OF FORMULA I+naproanilide, COMPOUND OF FORMULA I+napropamide, COMPOUND OF FORMULA I+naptalam, COMPOUND OF FORMULA I+neburon, COMPOUND OF FORMULA I+nicosulfuron, COMPOUND OF FORMULA I+nonanoic acid, COMPOUND OF FORMULA I+norflurazon, COMPOUND OF FORMULA I+oleic acid (fatty acids), COMPOUND OF FORMULA I+orbencarb, COMPOUND OF FORMULA I+orthosulfamuron, COMPOUND OF FORMULA I+oryzalin, COMPOUND OF FORMULA I+oxadiargyl, COMPOUND OF FORMULA I+oxadiazon, COMPOUND OF FORMULA I+oxasulfuron, COMPOUND OF FORMULA I+oxaziclomefone, COMPOUND OF FORMULA I+oxyfluorfen, COMPOUND OF FORMULA I+paraquat, COMPOUND OF FORMULA I+paraquat dichloride, COMPOUND OF FORMULA I+pebulate, COMPOUND OF FORMULA I+pendimethalin, COMPOUND OF FORMULA I+penoxsulam, COMPOUND OF FORMULA I+pentachlorophenol, COMPOUND OF FORMULA I+pentanochlor, COMPOUND OF FORMULA I+pentoxazone, COMPOUND OF FORMULA I+pethoxamid, COMPOUND OF FORMULA I+petrolium oils, COMPOUND OF FORMULA I+phenmedipham, COMPOUND OF FORMULA I+phenmedipham-ethyl, COMPOUND OF FORMULA I+picloram, COMPOUND OF FORMULA I+picolinafen, COMPOUND OF FORMULA I+pinoxaden, COMPOUND OF FORMULA I+piperophos, COMPOUND OF FORMULA I+potassium arsenite, COMPOUND OF FORMULA I+potassium azide, COMPOUND OF FORMULA I+pretilachlor, COMPOUND OF FORMULA I+primisulfuron, COMPOUND OF FORMULA I+primisulfuron-methyl, COMPOUND OF FORMULA I+prodiamine, COMPOUND OF FORMULA I+profluazol, COMPOUND OF FORMULA I+profoxydim, COMPOUND OF FORMULA I+prometon, COMPOUND OF FORMULA I+prometryn, COMPOUND OF FORMULA I+propachlor, COMPOUND OF FORMULA I+propanil, COMPOUND OF FORMULA I+propaquizafop, COMPOUND OF FORMULA I+propazine, COMPOUND OF FORMULA I+propham, COMPOUND OF FORMULA I+propisochlor, COMPOUND OF FORMULA I+propoxycarbazone, COMPOUND OF FORMULA I+propoxycarbazone-sodium, COMPOUND OF FORMULA I+propyrisulfuron, COMPOUND OF FORMULA I+propyzamide, COMPOUND OF FORMULA I+prosulfocarb, COMPOUND OF FORMULA I+prosulfuron, COMPOUND OF FORMULA I+pyraclonil, COMPOUND OF FORMULA I+pyraflufen, COMPOUND OF FORMULA I+pyraflufen-ethyl, COMPOUND OF FORMULA I+pyrasulfutole, COMPOUND OF FORMULA I+pyrazolynate, COMPOUND OF FORMULA I+pyrazosulfuron, COMPOUND OF FORMULA I+pyrazosulfuron-ethyl, COMPOUND OF FORMULA I+pyrazoxyfen, COMPOUND OF FORMULA I+pyribenzoxim, COMPOUND OF FORMULA I+pyributicarb, COMPOUND OF FORMULA I+pyridafol, COMPOUND OF FORMULA I+pyridate, COMPOUND OF FORMULA I+pyriftalid, COMPOUND OF FORMULA I+pyriminobac, COMPOUND OF FORMULA I+pyriminobac-methyl, COMPOUND OF FORMULA I+pyrimisulfan, COMPOUND OF FORMULA I+pyrithiobac, COMPOUND OF FORMULA I+pyrithiobac-sodium, COMPOUND OF FORMULA I+pyroxsulam, COMPOUND OF FORMULA I+pyroxasulfone, COMPOUND OF FORMULA I+quinclorac, COMPOUND OF FORMULA I+quinmerac, COMPOUND OF FORMULA I+quinoclamine, COMPOUND OF FORMULA I+quizalofop, COMPOUND OF FORMULA I+quizalofop-P, COMPOUND OF FORMULA I+rimsulfuron, COMPOUND OF FORMULA I+saflufenacil, COMPOUND OF FORMULA I+sethoxydim, COMPOUND OF FORMULA I+siduron, COMPOUND OF FORMULA I+simazine, COMPOUND OF FORMULA I+simetryn, COMPOUND OF FORMULA I+SMA, COMPOUND OF FORMULA I+sodium arsenite, COMPOUND OF FORMULA I+sodium azide, COMPOUND OF FORMULA I+sodium chlorate, COMPOUND OF FORMULA I+sulcotrione, COMPOUND OF FORMULA I+sulfentrazone, COMPOUND OF FORMULA I+sulfometuron, COMPOUND OF FORMULA I+sulfometuron-methyl, COMPOUND OF FORMULA I+sulfosate, COMPOUND OF FORMULA I+sulfosulfuron, COMPOUND OF FORMULA I+sulfuric acid, COMPOUND OF FORMULA I+tar oils, COMPOUND OF FORMULA I+2,3,6-TBA, COMPOUND OF FORMULA I+TCA, COMPOUND OF FORMULA I+TCA-sodium, COMPOUND OF FORMULA I+tebuthiuron, COMPOUND OF FORMULA I+tefuryltrione, COMPOUND OF FORMULA I+tembotrione, COMPOUND OF FORMULA I+tepraloxydim, COMPOUND OF FORMULA I+terbacil, COMPOUND OF FORMULA I+terbumeton, COMPOUND OF FORMULA I+terbuthylazine, COMPOUND OF FORMULA I+terbutryn, COMPOUND OF FORMULA I+thenylchlor, COMPOUND OF FORMULA I+thiazopyr, COMPOUND OF FORMULA I+thiencarbazone, COMPOUND OF FORMULA I+thiencarbazone-methyl, COMPOUND OF FORMULA I+thifensulfuron, COMPOUND OF FORMULA I+thifensulfuron-methyl, COMPOUND OF FORMULA I+thiobencarb, COMPOUND OF FORMULA I+tiocarbazil, COMPOUND OF FORMULA I+topramezone, COMPOUND OF FORMULA I+tralkoxydim, COMPOUND OF FORMULA I+triafamone, COMPOUND OF FORMULA I+tri-allate, COMPOUND OF FORMULA I+triasulfuron, COMPOUND OF FORMULA I+triaziflam, COMPOUND OF FORMULA I+tribenuron, COMPOUND OF FORMULA I+tribenuron-methyl, COMPOUND OF FORMULA I+tricamba, COMPOUND OF FORMULA I+triclopyr, COMPOUND OF FORMULA I+trietazine, COMPOUND OF FORMULA I+trifloxysulfuron, COMPOUND OF FORMULA I+trifloxysulfuron-sodium, COMPOUND OF FORMULA I+trifluralin, COMPOUND OF FORMULA I+triflusulfuron, COMPOUND OF FORMULA I+triflusulfuron-methyl, COMPOUND OF FORMULA I+trihydroxytriazine, COMPOUND OF FORMULA I+tritosulfuron, COMPOUND OF FORMULA I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), COMPOUND OF FORMULA I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), COMPOUND OF FORMULA I+BAY747 (CAS RN 335104-84-2), COMPOUND OF FORMULA I+topramezone (CAS RN 210631-68-8), COMPOUND OF FORMULA I+4-hydroxy-3-[[2-[(2-methoxyethoxy)methyl]-6-(trifluoromethyl)-3-pyridinyl]-carbonyl]bicyclo[3.2.1]oct-3-en-2-one (CAS RN 352010-68-5), COMPOUND OF FORMULA I+4-hydroxy-3-[[2-(3-methoxypropyl)-6-(difluoromethyl)-3-pyridinyl]carbonyl]-bicyclo[3.2.1]oct-3-en-2-one and COMPOUND OF FORMULA I+ZJ0273.

The compounds of formula (I) according to the invention can also be used in combination with safeners. Preferably, in these mixtures, the compound of the formula (I) is one of those compounds listed in Tables 1 to 861 above. The following mixtures with safeners, especially, come into consideration:

compound of formula (I)+cloquintocet-mexyl, compound of formula (I)+cloquintocet acid and salts thereof, compound of formula (I)+cyprosulfamide, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecopropand compound of the formula (I)+mecoprop-P.

The mixing partners of the compound of formula I may also be in the form of esters or salts, as mentioned e.g. in The Pesticide Manual, 12th Edition (BCPC), 2000.

In the above different lists of active ingredients to be mixed with a COMPOUND OF FORMULA I, the compound of the formula I is preferably a compound of Tables 1 to 861, whereby G can be hydrogen, C(O)OEt or C(O)OiPr.

In the above-mentioned mixtures of compounds of formula I, in particular a compound selected from said Tables 1 to 861, with other insecticides, fungicides, herbicides, safeners, adjuvants and the like, the mixing ratios can vary over a large range and are, preferably 100:1 to 1:6000, especially 50:1 to 1:50, more especially 20:1 to 1:20, even more especially 10:1 to 1:10. Those mixing ratios are understood to include, on the one hand, ratios by weight and also, on other hand, molar ratios.

The mixtures can advantageously be used in the above-mentioned formulations (in which case "active ingredient" relates to the respective mixture of compound of formula I with the mixing partner).

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The mixtures comprising a compound of formula I selected from Tables 1 to 861 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 861 and the active ingredients as described above is not essential for working the present invention.

The invention is illustrated by the following preparation examples. The H-NMR data of certain compounds of this invention show line broadening at room temperature, suggesting the existence of plural conformational isomers due to, for example keto-enol tautomerism, hindered rotation, ring inversion in the piperidine moitey or nitrogen inversion at the piperidine N—OR center. Broad signals have been labeled with 'br' accordingly.

EXAMPLE 1

Preparation of carbonic acid 4-(2,5-dimethyl-phenyl)-2-(1-methoxy-piperidin-4-ylmethyl)-5-oxo-2,5-dihydro-1H-pyrrol-3-yl ester ethyl ester (Compound P1.1)

Step 1: Preparation of (1-methoxy-piperidin-4-ylidene)-acetic acid ethyl ester

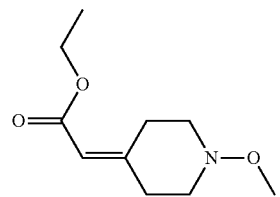

A solution of triethyl phosphonoacetate (13.4 g, 60 mmol) in 20 ml of THF was added dropwise to a suspension of NaH (60%, 2.4 g, 60 mmol) in 100 ml of THF at 0° C. under nitrogen. After the addition, the mixture was stirred at 0° C. for 0.5 h. Then, 1-methoxy-piperidin-4-one [prepared according to Journal of Organic Chemistry (1961), 26, 1867-74] (7.0 g, 54.2 mmol) in 20 ml of THF was added dropwise to the mixture and the mixture was kept for 2 h at room temperature. The resulting mixture was poured into 500 ml of ice water and extracted with EtOAc three times. The combined organic layers were dried over sodium sulfate, filtered and concentrated in vacuum. The residue was purified by column chromatography on silica gel. Yield: 9.7 g of (1-methoxy-piperidin-4-ylidene)-acetic acid ethyl ester as an oil.

$^1$H-NMR (300 MHz, CDCl$_3$): δ 1.21 (t, 3H), 2.33-3.48 (m, 8H), 3.49 (s, 3H), 4.07 (q, 2H), 5.59 (s, 1H).

Step 2: Preparation of (1-methoxy-piperidin-4-yl)-acetic acid ethyl ester

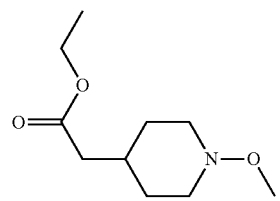

To a solution of (1-methoxy-piperidin-4-ylidene)-acetic acid ethyl ester (597 mg, 3 mmol) in 20 ml of methanol was added 10% Pd/C (100 mg). The mixture was hydrogenated for 2 h and filtered. The filtrate was concentrated under reduced pressure to give the crude product, which was directly used in the next step without further purification. Yield: 500 mg of (1-methoxy-piperidin-4-yl)-acetic acid ethyl ester as an oil.

Step 3: Preparation of
2-(1-methoxy-piperidin-4-yl)-ethanol

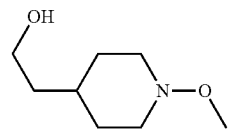

A solution of (1-methoxy-piperidin-4-yl)-acetic acid ethyl ester (16.7 g, 83 mmol) in 50 ml of THF was added dropwise to a suspension of lithium aluminum hydride (6.3 g, 166 mmol) in 150 ml of THF at 0° C. under nitrogen. After the addition, the mixture was warmed to room temperature for 2 h. Then, the resulting mixture was poured into 500 ml of ice water and extracted with CH$_2$Cl$_2$ three times. The combined organic layers were dried over sodium sulfate, filtered and evaporated under reduced pressure. The residue was purified by column chromatography on silica gel. Yield: 12.0 g of 2-(1-methoxy-piperidin-4-yl)-ethanol as an oil.

$^1$H-NMR (300 MHz, CDCl$_3$): δ 1.15-1.36 (m, 5H), 1.65-1.69 (m, 2H), 2.18-2.25 (m, 2H), 2.77 (br s, 1H), 3.23-3.26 (m, 2H), 3.42 (s, 3H), 3.53 (t, 2H).

Step 4: Preparation of
(1-methoxy-piperidin-4-yl)-acetaldehyde

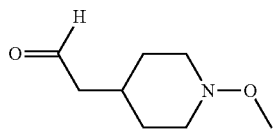

To a cooled (−78° C.) solution of oxalyl chloride (23.8 g, 189 mmol) in 100 ml of methylene chloride, DMSO (29.6 g, 380 mmol) was added slowly and the mixture was stirred for 0.5 h at the same temperature. Then, a solution of 2-(1-methoxy-piperidin-4-yl)-ethanol (12 g, 75 mmol) in 50 ml of methylene chloride was added. After stirring for 30 minutes, triethylamine (44 g, 430 mmol) was added to the mixture. After the addition, the reaction mixture was warmed to room temperature and diluted with methylene chloride. The organic solution was washed with water and aqueous NaHCO$_3$. The organic layers was dried over sodium sulfate, filtered and concentrated in vacuo. The residue was purified by chromatography on silica gel. Yield: 11.5 g of (1-methoxy-piperidin-4-yl)-acetaldehyde as an oil.

$^1$H-NMR (300 MHz, CDCl$_3$): δ 1.21-1.34 (m, 2H), 1.75-1.78 (m, 3H), 2.32-2.34 (m, 4H), 3.29-3.32 (m, 2H), 3.47 (s, 3H), 9.71 (s, 1H).

Step 5: Preparation of
2-amino-3-(1-methoxy-piperidin-4-yl)-propionitrile

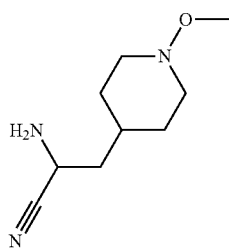

(1-Methoxy-piperidin-4-yl)-acetaldehyde (1.7 g, 10.8 mmol) was added dropwise to a mixture of KCN (910 mg, 14 mmol) and NH$_4$Cl (795 mg, 15 mmol) in 10 ml of 33% aqueous ammonia and 10 ml of water at room temperature. After stirring at room temperature for 30 minutes, the reaction mixture was diluted with 20 ml of water and extracted with CH$_2$Cl$_2$ three times. The combined organic layers were dried over sodium sulfate, filtered and concentrated under vacuum. The crude product was purified by column chromatography on silica gel. Yield: 1.0 g of 2-amino-3-(1-methoxy-piperidin-4-yl)-propionitrile as an oil.

$^1$H-NMR (300 MHz, CDCl$_3$): δ 0.79-0.85 (m, 2H), 1.22-1.32 (m, 3H), 1.61-1.75 (m, 4H), 2.28-2.31 (m, 2H), 3.32-3.34 (m, 2H), 3.49 (s, 3H), 3.61-3.75 (m, 1H).

Step 6: Preparation of
2-amino-3-(1-methoxy-piperidin-4-yl)-propionic
acid methyl ester

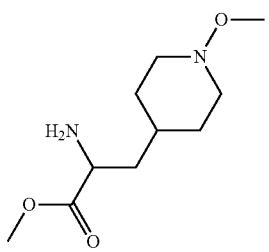

A mixture of 2-amino-3-(1-methoxy-piperidin-4-yl)-propionitrile (240 mg, 1.3 mmol) in 10 ml of concentrated hydrochloric acid was refluxed for 10 h and the mixture was evaporated under reduced pressure to dryness to give the crude 2-amino-3-(1-methoxy-piperidin-4-yl)-propionic acid (320 mg, 1.3 mmol), which was soluted in 10 ml of methanol. To the mixture, was added dropwise SOCl$_2$ (316 mg, 2.6 mmol). After the addition, the mixture was refluxed for 5 h and cooled to room temperature. Then, it was poured into 40 ml of water and adjusted to pH 8-9 with aqueous K$_2$CO$_3$. The resulting mixture was extracted with CH$_2$Cl$_2$ three times and the collected organic layers were dried over sodium sulfate, filtered and concentrated under reduced pressure. The residue was purified by flash chromatography on silica gel. Yield: 80 mg of 2-amino-3-(1-methoxy-piperidin-4-yl)-propionic acid methyl ester as an oil.

$^1$H-NMR (300 MHz, CDCl$_3$): δ 1.21-1.75 (m, 11H), 3.31-3.32 (m, 2H), 3.41-3.45 (m, 1H), 3.48 (s, 3H), 3.68 (s, 3H).
LC/MS (ES+): 217 (M+H)$^+$, 239 (M+Na)$^+$.

Step 7: Preparation of 2-[2-(2,5-dimethyl-phenyl)-acetylamino]-3-(1-methoxy-piperidin-4-yl)-propionic acid methyl ester

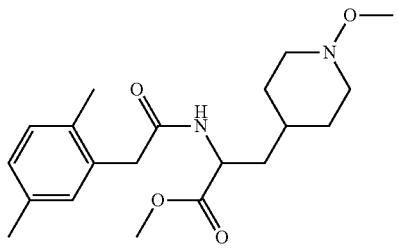 [SMILES: COC(=O)C(CC1CCN(OC)CC1)NC(=O)Cc1cc(C)ccc1C]

2,5-Dimethylphenylacetyl chloride (2.1 g, 11.5 mmol) was added dropwise to a mixture of 2-amino-3-(1-methoxy-piperidin-4-yl)-propionic acid methyl ester (1.7 g, 7.8 mmol) and K$_2$CO$_3$ (2.1 g, 15.2 mmol) in 50 mL of THF at room temperature. After the addition, the mixture was stirred for 0.5 h and diluted with 50 ml of water. The mixture was extracted with EtOAc five times and the combined organic layers were dried over sodium sulfate, filtered and concentrated under vacuum. The residue was purified by column chromatography on silica gel. Yield: 1.2 g of 2-[2-(2,5-dimethyl-phenyl)-acetylamino]-3-(1-methoxy-piperidin-4-yl)-propionic acid methyl ester as a solid.

$^1$H-NMR (300 MHz, CDCl$_3$): δ 1.15-1.74 (m, 7H), 2.15-2.19 (m, 2H), 2.24 (s, 3H), 2.31 (s, 3H), 3.29-3.30 (m, 2H), 3.50 (s, 3H), 3.55 (s, 2H), 3.68 (s, 3H), 4.60-4.62 (m, 1H), 5.64 (d, 1H), 7.00-7.11 (m, 3H).

LC/MS (ES+): 385 (M+Na)$^+$.

Step 8: Preparation of 3-(2,5-dimethyl-phenyl)-4-hydroxy-5-(1-methoxy-piperidin-4-ylmethyl)-1,5-dihydro-pyrrol-2-one (Compound P2.2)

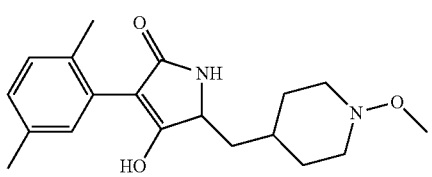 [SMILES: CON1CCC(CC2NC(=O)C(c3cc(C)ccc3C)=C2O)CC1]

Under nitrogen, t-BuOK (1.8 g, 16.0 mmol) was added to a stirred solution of 2-[2-(2,5-dimethyl-phenyl)-acetylamino]-3-(1-methoxy-piperidin-4-yl)-propionic acid methyl ester (2.6 g, 8.0 mmol) in 15 ml of THF at 60° C. and the mixture was stirred at the same temperature for another 30 min. Then, the mixture was poured into diluted hydrochloric acid (50 ml) and extracted with ethyl acetate five times. The combined organic layers were dried over sodium sulfate, filtered and concentrated in vacuum. The residue was purified by flash chromatography on silica gel. Yield: 500 mg of 3-(2,5-dimethyl-phenyl)-4-hydroxy-5-(1-methoxy-piperidin-4-ylmethyl)-1,5-dihydro-pyrrol-2-one (compound P2.2) as a solid, mp 116-119° C.

$^1$H-NMR (300 MHz, CD$_3$OD): δ 1.28-1.98 (m, 9H), 2.16 (s, 3H), 2.28 (s, 3H), 2.32-2.40 (m, 2H), 3.31-3.55 (m, 2H), 3.52 (s, 3H), 4.12-4.14 (m, 1H), 6.93-7.11 (m, 3H).

LC/MS (ES+): 331 (M+H)$^+$.

Step 9: Preparation of carbonic acid 4-(2,5-dimethyl-phenyl)-2-(1-methoxy-piperidin-4-ylmethyl)-5-oxo-2,5-dihydro-1H-pyrrol-3-yl ester ethyl ester (Title Compound P1.1)

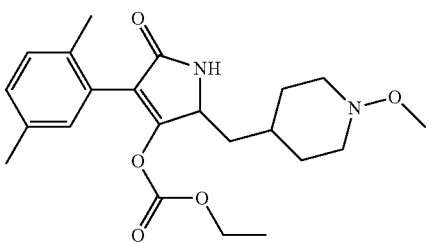 [SMILES: CCOC(=O)OC1=C(c2cc(C)ccc2C)C(=O)NC1CC1CCN(OC)CC1]

Ethyl chloroformate (72 mg, 0.67 mmol) was added dropwise to a solution of 3-(2,5-dimethyl-phenyl)-4-hydroxy-5-(1-methoxy-piperidin-4-ylmethyl)-1,5-dihydro-pyrrol-2-one (220 mg, 0.67 mmol), Et$_3$N (94 mg, 0.9 mmol) and DMAP (30 mg, 0.25 mmol) in 10 ml of THF at room temperature. The mixture was stirred for 30 min and concentrated to dryness in vacuo. The residue was purified by column chromatography on silica gel. Yield: 150 mg of carbonic acid 4-(2,5-dimethyl-phenyl)-2-(1-methoxy-piperidin-4-ylmethyl)-5-oxo-2,5-dihydro-1H-pyrrol-3-yl ester ethyl ester (title compound P1.1) as a gum.

$^1$H-NMR (300 MHz, CDCl$_3$): δ 1.20 (t, 3H), 1.34-1.89 (m, 7H), 2.20 (s, 3H), 2.29 (s, 3H), 2.25-2.35 (m, 2H), 3.31-3.40 (m, 2H), 3.50 (s, 3H), 4.12 (q, 2H), 4.61-4.63 (m, 1H), 6.97 (s, 1H), 7.03-7.12 (m, 2H), 7.52 (br s, 1H).

LC/MS (ES+): 403 (M+H)$^+$, 425 (M+Na)$^+$, 457 (M+Na+MeOH)$^+$.

EXAMPLE 2

Preparation of 3-(1-methoxy-piperidin-4-yl)-2-[2-(2,4,6-trimethyl-phenyl)-acetylamino]-propionic acid methyl ester (Compound P3.9)

Step 1: Preparation of N-[1-cyano-2-(1-methoxy-piperidin-4-yl)-ethyl]-2-(2,4,6-trimethyl-phenyl)-acetamide

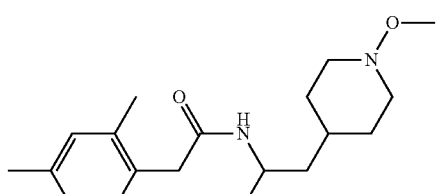

At room temperature, (2,4,6-trimethyl-phenyl)-acetyl chloride (10.6 g, 54 mmol) was added dropwise to a mixture of 2-amino-3-(1-methoxy-piperidin-4-yl)-propionitrile (6.6 g, 36 mmol) and K$_2$CO$_3$ (9.9 g, 72 mmol) in 100 ml of THF. After the addition, the mixture was stirred for 0.5 h. The reaction mixture was diluted with 50 ml of water and extracted with EtOAc five times. The combined organic layers were dried over sodium sulfate, filtered and concentrated under vacuum. The residue was purified by flash chromatography on silica gel Yield: 10.6 g of N-[1-cyano-2-(1-methoxy-piperidin-4-yl)-ethyl]-2-(2,4,6-trimethyl-phenyl)-acetamide as a solid.

LC/MS (ES+): 344 (M+H)$^+$, 366 (M+Na)$^+$.

Step 2: Preparation of 3-(1-methoxy-piperidin-4-yl)-2-[2-(2,4,6-trimethyl-phenyl)-acetylamino]-propionic acid methyl ester (Title Compound P3.9)

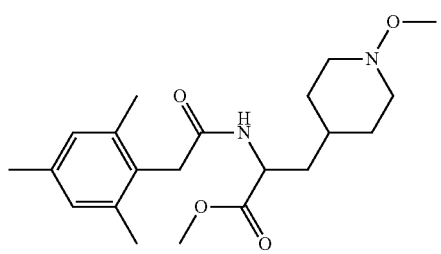

Hydrogen chloride gas was introduced to a solution of N-[1-cyano-2-(1-methoxy-piperidin-4-yl)-ethyl]-2-(2,4,6-trimethyl-phenyl)-acetamide (10.6 g, 31 mmol) in 200 ml of methanol at room temperature for 2 h and the mixture was refluxed for 1 h. The reaction mixture was concentrated under reduced pressure. The residue was diluted with 50 ml of water and adjusted to pH 8-9 with aqueous Na$_2$CO$_3$. The resulting mixture was extracted with CH$_2$Cl$_2$ five times. The collected organic layers were dried over sodium sulfate, filtered and concentrated in vacuo. The residue was purified by chromatography on silica gel. Yield: 9.1 g of 3-(1-methoxy-piperidin-4-yl)-2-[2-(2,4,6-trimethyl-phenyl)-acetylamino]-propionic acid methyl ester (title compound P3.9) as a solid.

$^1$H-NMR (300 MHz, CDCl$_3$): δ 1.13-1.76 (m, 7H), 2.20-2.24 (m, 2H), 2.28 (s, 6H), 2.30 (s, 3H), 3.30-3.33 (m, 2H), 3.52 (s, 3H), 3.62 (s, 2H), 3.69 (s, 3H), 4.63-4.65 (m, 1H), 5.60 (d, 1H), 6.92 (s, 2H).

LC/MS (ES+): 377 (M+H)$^+$, 399 (M+Na)$^+$.

EXAMPLE 3

Preparation of 3-(1-methoxy-piperidin-4-yl)-2-methylamino-propionitrile (Compound P4.11)

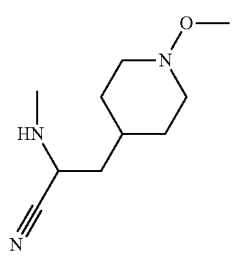

1-Methoxy-piperidin-4-yl)-acetaldehyde (2.0 g, 12.7 mmol) was added dropwise to a stirred mixture of KCN (1.1 g, 16.9 mmol), methylamine hydrochloride (1.23 g, 18.4 mmol) in 33% aqueous methylamine (7 ml) and water (5 mL) at room temperature and the reaction mixture was stirred for another 10 hours at room temperature. Then, the reaction mixture was diluted with 50 mL of water and extracted with CH$_2$Cl$_2$ three times. The combined organic layers were dried over sodium sulfate, filtered and concentrated under vacuum. The crude product was purified by column chromatography on silica gel. Yield: 650 mg of 3-(1-methoxy-piperidin-4-yl)-2-methylamino-propionitrile (title compound P4.11) as an oil.

$^1$H-NMR (300 MHz, CDCl$_3$): δ 1.22-1.32 (m, 3H), 1.60-1.62 (m, 3H), 1.74-1.77 (m, 2H), 2.27-2.30 (m, 2H), 2.50 (s, 3H), 3.31-3.33 (m, 2H), 3.45-3.46 (m, 1H), 3.48 (s, 3H).

EXAMPLE 4

Preparation of 3-(1-methoxy-piperidin-4-yl)-2-[2-(2,4,6-trimethyl-phenyl)-acetoxy]-propionic acid methyl ester (Compound P3.12)

Step 1: Preparation of 2-hydroxy-3-(1-methoxy-piperidin-4-yl)-propionitrile

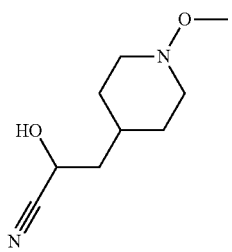

A mixture of (1-methoxy-piperidin-4-yl)-acetaldehyde (10 g, 63 mmol) and NaHSO$_3$ (8.6 g, 83 mmol) in 210 ml of water was stirred at room temperature for 30 min. Then, a solution of KCN (6.2 g, 95 mmol) in 50 ml of water was added to the mixture. After the addition, the mixture was stirred at room temperature for another 10 h. The resulting mixture was extracted with CH$_2$Cl$_2$ five times. The combined organic layers were dried over sodium sulfate, filtered and concentrated under vacuum. The residue was purified by flash chromatography on silica gel. Yield: 2.1 g of 2-hydroxy-3-(1-methoxy-piperidin-4-yl)-propionitrile as a solid.

Step 2: Preparation of 2-hydroxy-3-(1-methoxy-piperidin-4-yl)-propionic acid methyl ester

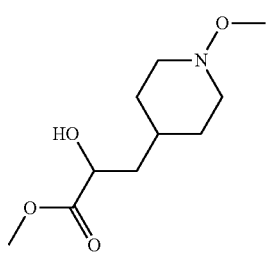

Hydrogen chloride gas was introduced to a solution of 2-hydroxy-3-(1-methoxy-piperidin-4-yl)-propionitrile (2.1 g, 11.4 mmol) in 50 ml of methanol at room temperature for 2 h and the mixture was refluxed for 1 h. The reaction mixture was concentrated under reduced pressure. The residue was diluted with 100 ml of water and adjusted to pH 8-9 with aqueous Na$_2$CO$_3$. The mixture was extracted with CH$_2$Cl$_2$ five times. The combined organic layers were dried over sodium sulfate, filtered and concentrated in vacuo. The residue was purified by column chromatography on silica gel. Yield: 900 mg of 2-hydroxy-3-(1-methoxy-piperidin-4-yl)-propionic acid methyl ester as an oil.

Step 3: Preparation of 3-(1-methoxy-piperidin-4-yl)-2-[2-(2,4,6-trimethyl-phenyl)-acetoxy]-propionic acid methyl ester (Title Compound P3.12)

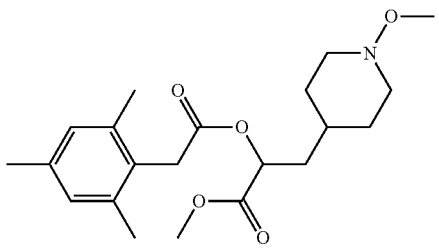

A mixture of 2-hydroxy-3-(1-methoxy-piperidin-4-yl)-propionic acid methyl ester (700 mg, 3.5 mmol) and (2,4,6-trimethyl-phenyl)-acetyl chloride (700 mg, 3.6 mmol) in 10 ml of toluene was refluxed for 6 h. Then, the reaction mixture was concentrated under vacuum to dryness and the residue was purified by column chromatography on silica gel. Yield: 520 mg of 3-(1-methoxy-piperidin-4-yl)-2-[2-(2,4,6-trimethyl-phenyl)-acetoxy]-propionic acid methyl ester (title compound P3.12) as a oil.

$^1$H-NMR (300 MHz, CDCl$_3$): δ 1.22-1.28 (m, 3H), 1.62-1.80 (m, 4H), 2.10-2.17 (m, 2H), 2.18 (s, 3H), 2.29 (s, 6H), 3.26-3.29 (m, 2H), 3.50 (s, 3H), 3.70 (s, 3H), 3.72 (s, 2H), 4.99-5.04 (m, 1H), 6.85 (s, 2H).

LC/MS (ES+): 378 (M+H)$^+$, 400 (M+Na)$^+$.

EXAMPLE 5

Preparation of carbonic acid 4-(2,5-dimethyl-phenyl)-5-oxo-2-[1-oxo-1-(2,2,2-trifluoro-acetylimino)-hexahydro-1λ$^6$-thiopyran-4-ylmethyl]-2,5-dihydro-1H-pyrrol-3-yl ester ethyl ester (Compounds P1.6 and P1.7)

Step 1: Preparation of carbonic acid 4-(2,5-dimethyl-phenyl)-5-oxo-2-(1-oxo-hexahydro-1λ$^4$-thiopyran-4-ylmethyl)-2,5-dihydro-1H-pyrrol-3-yl ester ethyl ester (Compound P1.4)

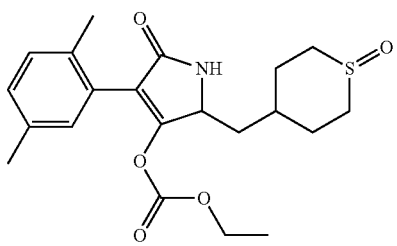 [SMILES: CCOC(=O)OC1=C(c2cc(C)ccc2C)C(=O)NC1CC1CCS(=O)CC1]

A solution of m-CPBA (189 mg, 1.1 mmol) in 5 ml of CH$_2$Cl$_2$ was added slowly to a stirred solution of carbonic acid 4-(2,5-dimethyl-phenyl)-5-oxo-2-(tetrahydro-thiopyran-4-ylmethyl)-2,5-dihydro-1H-pyrrol-3-yl ester ethyl ester (compound P1.2) (390 mg, 1.0 mmol) in 10 ml CH$_2$Cl$_2$ and the reaction mixture was stirred at room temperature for 1 h. Then, the resulting mixture was washed with saturated NaHCO$_3$ (aq) and aqueous Na$_2$S$_2$O$_3$, respectively. The organic layer was dried over sodium sulfate, filtered and concentrated under reduce pressure. The residue was purified by chromatography on silica gel. Yield: 100 mg of carbonic acid 4-(2,5-dimethyl-phenyl)-5-oxo-2-(1-oxo-hexahydro-1λ$^4$-thiopyran-4-ylmethyl)-2,5-dihydro-1H-pyrrol-3-yl ester ethyl ester (compound P1.4) as a solid, mp 103-106° C.

$^1$H-NMR (300 MHz, CD$_3$OD): δ 1.17-1.25 (m, 3H), 1.46-1.84 (m, 8H), 2.19 (s, 3H), 2.30 (s, 3H), 2.62-2.75 (m, 2H), 3.01-3.08 (m, 1H), 3.31-3.42 (m, 1H), 4.11-4.21 (m, 2H), 4.66-4.76 (m, 1H), 6.93 (s, 1H), 7.07-7.16 (m, 2H).

LC/MS (ES+): 428 (M+Na)$^+$.

Step 2: Preparation of carbonic acid 4-(2,5-dimethyl-phenyl)-5-oxo-2-[1-oxo-1-(2,2,2-trifluoro-acetylimino)-hexahydro-1λ$^6$-thiopyran-4-ylmethyl]-2,5-dihydro-1H-pyrrol-3-yl ester ethyl ester (Title Compounds P1.6 and P1.7)

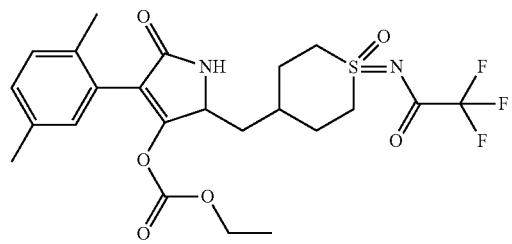 [SMILES: CCOC(=O)OC1=C(c2cc(C)ccc2C)C(=O)NC1CC1CCS(=O)(=NC(=O)C(F)(F)F)CC1]

A mixture of carbonic acid 4-(2,5-dimethyl-phenyl)-5-oxo-2-(1-oxo-hexahydro-1λ$^4$-thiopyran-4-ylmethyl)-2,5-dihydro-1H-pyrrol-3-yl ester ethyl ester (191 mg, 0.47 mmol), trifluoro-acetamide (104 mg, 0.92 mmol), (diacetoxyiodo)benzene (246 mg, 0.76 mmol), MgO (75 mg, 1.8 mmol) and rhodium acetate (10 mg, 0.023 mmol) in 10 ml of CH$_2$Cl$_2$ was stirred at room temperature for 2 h. Then, it was filtered and the filtrate was concentrated under vacuum. The residue was purified by column chromatography on silica gel. Yield: 80 mg of carbonic acid 4-(2,5-dimethyl-phenyl)-5-oxo-2-[1-oxo-1-(2,2,2-trifluoro-acetylimino)-hexahydro-1λ$^6$-thiopyran-4-ylmethyl]-2,5-dihydro-1H-pyrrol-3-yl ester ethyl ester (isomer A, compound P1.6) as a solid, mp 91-93° C. and 40 mg of carbonic acid 4-(2,5-dimethyl-phenyl)-5-oxo-2-[1-oxo-1-(2,2,2-trifluoro-acetylimino)-hexahydro-1λ$^6$-thiopyran-4-ylmethyl]-2,5-dihydro-1H-pyrrol-3-yl ester ethyl ester (isomer B, compound P1.7) as a solid, mp 87-89° C.

Isomer A (Compound P1.6):

$^1$H-NMR (300 MHz, d$_6$-DMSO) δ 1.11 (t, 3H), 1.42-1.73 (m, 1H). 1.74-1.87 (m, 4H), 1.90-2.05 (m, 2H), 2.10 (s, 3H), 2.25 (s, 3H), 3.51-3.82 (m, 4H), 4.10 (q, 2H), 4.56 (d, 1H), 6.88 (s, 1H), 7.05-7.14 (m, 2H), 8.58 (s, 1H).

LC/MS (ES+): 539 (M+Na)$^+$;

Isomer B (Compound P1.7):

$^1$H-NMR (300 MHz, d$_6$-DMSO) δ 1.11 (t, 3H), 1.4-1.90 (m, 5H), 2.10 (s, 3H), 2.14-2.30 (m, 2H), 2.24 (s, 3H), 3.52-3.96 (m, 4H), 4.09 (q, 2H), 4.55 (d, 1H), 6.87 (s, 1H), 7.05-7.14 (m, 2H), 8.57 (s, 1H).

LC/MS (ES+): 539 (M+Na)$^+$.

EXAMPLE 6

Preparation of 3-(2,5-dimethyl-phenyl)-5-(1,1-dioxo-hexahydro-1λ⁶-thiopyran-4-ylmethyl)-4-hydroxy-1,5-dihydro-pyrrol-2-one (Compound P2.6)

Step 1: Preparation of 4-benzyloxy-3-(2,5-dimethyl-phenyl)-5-(tetrahydro-thiopyran-4-ylmethyl)-1,5-dihydro-pyrrol-2-one

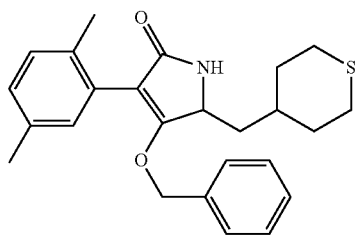 [SMILES: Cc1ccc(C)c(C2=C(OCc3ccccc3)C(CC3CCSCC3)NC2=O)c1]

A solution of 3-(2,5-dimethyl-phenyl)-4-hydroxy-5-(tetrahydro-thiopyran-4-ylmethyl)-1,5-dihydro-pyrrol-2-one (compound P2.5) (1.0 g, 3.15 mmol), potassium carbonate (0.87 g, 6.3 mmol) and benzyl bromide (0.81 g, 4.7 mmol) in 10 ml of acetone was refluxed for 2 h. Then, the reaction mixture was filtered and the filtrate was concentrated under vacuum. The residue was purified by chromatography on silica gel. Yield: 640 mg of 4-benzyloxy-3-(2,5-dimethyl-phenyl)-5-(tetrahydro-thiopyran-4-ylmethyl)-1,5-dihydro-pyrrol-2-one as a solid.

¹H-NMR (300 MHz, CD₃OD): δ 1.25-1.75 (m, 4H), 1.80-2.05 (m, 2H). 2.09 (s, 3H), 2.10-2.15 (m, 1H), 2.30 (s, 3H), 2.58-2.70 (m, 4H), 4.27-4.29 (m, 1H), 4.81-4.88 (m, 2H), 6.93 (s, 1H), 7.01-7.06 (m, 2H), 7.11-7.13 (m, 2H), 7.28-7.31 (m, 3H).

LC/MS (ES+): 408 (M+H)⁺, 430 (M+Na)⁺.

Step 2: Preparation of 4-benzyloxy-3-(2,5-dimethyl-phenyl)-5-(1,1-dioxo-hexahydro-1λ⁶-thiopyran-4-ylmethyl)-1,5-dihydro-pyrrol-2-one

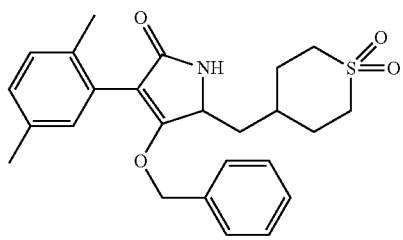 [SMILES: Cc1ccc(C)c(C2=C(OCc3ccccc3)C(CC3CCS(=O)(=O)CC3)NC2=O)c1]

A solution of m-CPBA (676 mg, 3.9 mmol) in 10 ml of CH₂Cl₂ was added to a solution of 4-benzyloxy-3-(2,5-dimethyl-phenyl)-5-(tetrahydro-thiopyran-4-ylmethyl)-1,5-dihydro-pyrrol-2-one (640 mg, 1.57 mmol) in 15 ml of CH₂Cl₂ at room temperature and the mixture was stirred for 0.5 h. Then, the resulting mixture was washed with aqueous NaHCO₃ and aqueous Na₂S₂O₃, respectively. The organic layer was dried over sodium sulfate, filtered and concentrated under vacuum. The residue was purified by flash chromatography on silica gel. Yield: 280 mg of 4-benzyloxy-3-(2,5-dimethyl-phenyl)-5-(1,1-dioxo-hexahydro-1λ⁶-thiopyran-4-ylmethyl)-1,5-dihydro-pyrrol-2-one as a solid.

Step 3: Preparation of 3-(2,5-dimethyl-phenyl)-5-(1,1-dioxo-hexahydro-1λ⁶-thiopyran-4-ylmethyl)-4-hydroxy-1,5-dihydro-pyrrol-2-one (Title Compound P2.6)

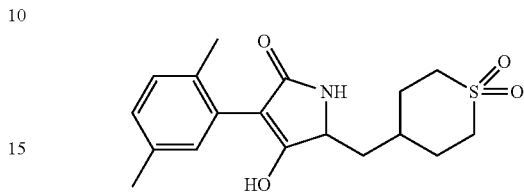

10% Pd/C (50 mg) was added to a solution of 4-benzyloxy-3-(2,5-dimethyl-phenyl)-5-(1,1-dioxo-hexahydro-1λ⁶-thiopyran-4-ylmethyl)-1,5-dihydro-pyrrol-2-one (280 mg, 0.64 mmol) in 20 ml of methanol and the mixture was hydrogenated for 2 h. Then, the resulting mixture was filtered and the filtrate was evaporated in vacuo. The residue was purified by flash chromatography on silica gel. Yield: 200 mg of 3-(2,5-dimethyl-phenyl)-5-(1,1-dioxo-hexahydro-1λ⁶-thiopyran-4-ylmethyl)-4-hydroxy-1,5-dihydro-pyrrol-2-one (title compound P2.6) as a solid, mp 244-246° C.

¹H-NMR (300 MHz, CD₃OD): δ 1.59-1.93 (m, 5H), 1.94-2.18 (m, 2H), 2.19 (s, 3H), 2.31 (s, 3H), 3.07-3.14 (m, 4H), 4.16-4.20 (m, 1H), 6.97 (s, 1H), 7.02-7.05 (m, 1H), 7.12-7.14 (m, 1H).

LC/MS (ES+): 372 (M+Na)⁺.

EXAMPLE 7

Preparation of N-{4-[3-benzyloxy-4-(2,5-dimethyl-phenyl)-5-oxo-2,5-dihydro-1H-pyrrol-2-ylmethyl]-1-oxo-hexahydro-1λ⁶-thiopyran-1-ylidene}-2,2,2-trifluoro-acetamide

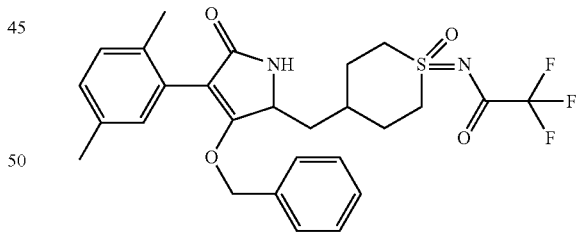

A mixture of 4-benzyloxy-3-(2,5-dimethyl-phenyl)-5-(1-oxo-hexahydro-1λ⁴-thiopyran-4-ylmethyl)-1,5-dihydro-pyrrol-2-one (200 mg, 0.47 mmol), trifluoroacetamide (104 mg, 0.92 mmol), (diacetoxyiodo)benzene (246 mg, 0.76 mmol), MgO (75 mg, 1.8 mmol) and rhodium acetate (10 mg, 0.02 mmol) in 100 ml CH₂Cl₂ was stirred at room temperature for 2 h. Then, it was filtered and the filtrate was concentrated under vacuum. The residue was purified by column chromatography on silica gel. Yield: 127 mg of N-{4-[3-benzyloxy-4-(2,5-dimethyl-phenyl)-5-oxo-2,5-dihydro-1H-pyrrol-2-ylmethyl]-1-oxo-hexahydro-1λ⁶-thiopyran-1-ylidene}-2,2,2-trifluoro-acetamide (isomer A, title compound) as a solid and 43 mg of N-{4-[3-benzyloxy-4-(2,5-dimethyl-phenyl)-5- oxo-2,5-dihydro-1H-pyrrol-2-ylmethyl]-1-oxo-hexahydro-1λ⁶-thiopyran-1-ylidene}-2,2,2-trifluoro-acetamide (isomer B, title compound) as a solid.

N-{4-[3-benzyloxy-4-(2,5-dimethyl-phenyl)-5-oxo-2,5-dihydro-1H-pyrrol-2-ylmethyl]-1-oxo-hexahydro-1λ⁶-thiopyran-1-ylidene}-2,2,2-trifluoro-acetamide (isomer A):

¹H-NMR (300 MHz, CDCl₃): δ 2.10-2.15 (m, 1H), 2.90-2.98 (m, 1H), 3.17-3.33 (m, 4H), 3.39 (s, 3H), 3.54 (s, 3H), 4.14-4.15 (m, 1H), 4.75-5.02 (m, 4H), 5.59-5.63 (m, 1H), 6.14 (s, 2H), 8.26 (s, 1H), 8.30-8.35 (m, 2H), 8.39-8.43 (m, 2H), 8.55-8.68 (m, 3H), 8.68 (br s, 1H). LC/MS (ES+): 557 (M+Na)⁺;

N-{4-[3-benzyloxy-4-(2,5-dimethyl-phenyl)-5-oxo-2,5-dihydro-1H-pyrrol-2-ylmethyl]-1-oxo-hexahydro-1λ⁶-thiopyran-1-ylidene}-2,2,2-trifluoro-acetamide (isomer B):

¹H-NMR (300 MHz, CDCl₃): δ 2.10-2.14 (m, 1H), 2.90-2.98 (m, 1H), 3.17-3.34 (m, 4H), 3.35 (s, 3H), 3.55 (s, 3H), 4.14-4.15 (m, 1H), 4.65-4.72 (m, 2H), 5.50-5.52 (m, 2H), 5.55-5.59 (m, 1H), 6.13 (s, 2H), 8.27 (s, 1H), 8.31-8.40 (m, 4H), 8.55-8.58 (m, 3H), 8.86 (br s, 1H).

LC/MS (ES+): 557 (M+Na)⁺.

EXAMPLE 8

Preparation of carbonic acid 2-(1-cyanoimino-hexahydro-1λ⁴-thiopyran-4-ylmethyl)-4-(2,5-dimethyl-phenyl)-5-oxo-2,5-dihydro-1H-pyrrol-3-yl ester ethyl ester (Compound P1.9)

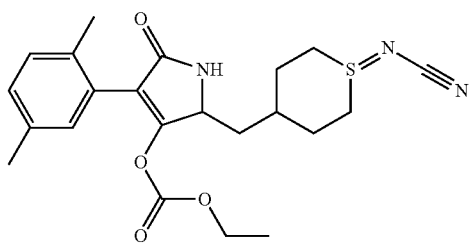 [SMILES: CCOC(=O)OC1=C(c2cc(C)ccc2C)C(=O)NC1CC1CCS(=NC#N)CC1]

A mixture of carbonic acid 4-(2,5-dimethyl-phenyl)-5-oxo-2-(tetrahydro-thiopyran-4-ylmethyl)-2,5-dihydro-1H-pyrrol-3-yl ester ethyl ester (compound P1.2) (184 mg, 0.47 mmol), NH₂CN (40 mg, 0.95 mmol), (diacetoxyiodo)benzene (247 mg, 0.76 mmol), MgO (75 mg, 1.87 mmol) and rhodium acetate (10 mg, 0.02 mmol) in 10 ml of CH₂Cl₂ was stirred at room temperature for 2 h. Then, the mixture was filtered and the filtrate was concentrated under vacuum. The residue was purified by chromatography on silica gel. Yield: 110 mg of carbonic acid 2-(1-cyanoimino-hexahydro-1λ⁴-thiopyran-4-ylmethyl)-4-(2,5-dimethyl-phenyl)-5-oxo-2,5-dihydro-1H-pyrrol-3-yl ester ethyl ester (title compound P1.9) as a solid, mp 103-105° C.

¹H-NMR (300 MHz, CD₃OD): δ 1.17 (t, 3H), 1.53-1.70 (m, 3H), 1.81-1.85 (m, 2H), 2.16 (s, 3H), 2.30 (s, 3H), 2.31-2.45 (m, 2H), 3.01-3.10 (m, 2H), 3.50-3.56 (m, 2H), 4.12 (q, 2H), 4.65-4.69 (m, 1H), 6.93 (s, 1H), 7.10-7.16 (m, 2H).

LC/MS (ES+): 452 (M+Na)⁺.

EXAMPLE 9

Preparation of carbonic acid ethyl ester 2-(1-methoxy-piperidin-4-yl)-5-oxo-4-(2,4,6-trimethyl-phenyl)-2,5-dihydro-1H-pyrrol-3-yl ester (Compound P1.12)

Step 1: Preparation of 1-methoxy-4-methoxymethylene-piperidine

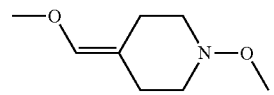

A mixture of (methoxymethyl)triphenylphosphonium chloride (35.8 g, 104 mmol) in THF (160 mL) was cooled to −60° C. and treated with a 2.5M solution of n-BuLi in hexane (42 mL, 105 mmol). After 20 min, a solution of 1-methoxy-piperidin-4-one [prepared according to Journal of Organic Chemistry (1961), 26, 1867-74] (9 g, 70 mmol) in THF (80 mL) was added, and the reaction mixture was allowed to warm to 10° C. over 2 h. The reaction was quenched with saturated ammonium chloride, and the solvent was removed under reduced pressure. The residue was partitioned between water and chloroform and the organic layer dried with sodium sulfate and evaporated. The residue was purified by column chromatography on silica gel. Yield: 9.2 g of 1-methoxy-4-methoxymethylene-piperidine as an oil.

¹H-NMR (300 MHz, CDCl₃): δ 1.85-2.09 (m, 1H), 2.11-2.20 (m, 2H), 2.30-2.50 (m, 2H), 2.66-2.79 (m, 1H), 3.25-3.40 (m, 2H), 3.55 (s, 3H), 3.56 (s, 3H), 5.80 (s, 1H).

Step 2: Preparation of 1-methoxy-piperidine-4-carbaldehyde

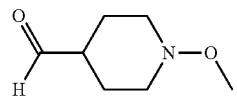

Concentrated hydrochloric acid (7 mL) was added to a solution of 1-methoxy-4-methoxymethylene-piperidine (9.2 g, 58 mmol) in THF (100 mL), and the mixture was stirred at room temperature for 4 h. The organic solvent was removed under reduced pressure, and the reaction mixture was partitioned between methylene chloride and water. The separated organic layer was dried over sodium sulfate, filtered and concentrated in vacuum. The crude product was purified by column chromatography on silica gel. Yield: 7.5 g of 1-methoxy-piperidine-4-carbaldehyde as an oil.

¹H-NMR (300 MHz, DMSO-d₆): δ 1.26-1.77 (m, 2H), 1.84-2.01 (m, 2H), 2.15-2.36 (m, 2H), 2.40-3.08 (m, 2H), 3.15-3.33 (m, 1H), 3.39 (s, 3H), 9.56 (s, 1H).

Step 3: Preparation of amino-(1-methoxy-piperidin-4-yl)-acetonitrile

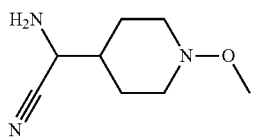

1-Methoxy-piperidine-4-carbaldehyde (2.86 g, 20 mmol) was added to a mixture of KCN (1.95 g, 30 mmol) and NH$_4$Cl (2.2 g, 41 mmol) in H$_2$O (20 ml) and NH$_3$.H$_2$O (20 ml). The mixture was stirred at room temperature for 12 h and then was extracted with CH$_2$Cl$_2$ (5×50 ml). The combined organic layers were dried with Na$_2$SO$_4$, filtered and evaporated under reduced pressure. The residue was purified by chromatography on silica gel. Yield: 2.0 g of amino-(1-methoxy-piperidin-4-yl)-acetonitrile as an oil.

Step 4: Preparation of N-[cyano-(1-methoxy-piperidin-4-yl)-methyl]-2-(2,4,6-trimethyl-phenyl)-acetamide

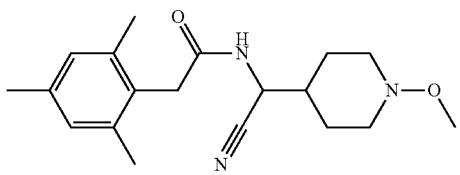

To a stirred mixture of amino-(1-methoxy-piperidin-4-yl)-acetonitrile (500 mg, 2.95 mmol) and Et$_3$N (610 mg, 6.02 mmol) in THF (15 ml), was added (2,4,6-trimethyl-phenyl)-acetyl chloride (581 mg, 2.95 mmol). After the addition, the mixture was stirred at room temperature for 0.5 h. Then, the mixture was poured into water (100 ml) and extracted with CH$_2$Cl$_2$ (3×50 ml). The combined organic layers were dried over Na$_2$SO$_4$, filtered and evaporated under vacuum. The residue was purified by chromatography on silica gel. Yield: 700 mg of N-[cyano-(1-methoxy-piperidin-4-yl)-methyl]-2-(2,4,6-trimethyl-phenyl)-acetamide as a solid.

$^1$H-NMR (300 MHz, CDCl$_3$): δ 1.33-1.74 (m, 5H), 2.26 (s, 6H), 2.28-2.30 (m, 2H), 2.32 (s, 3H), 3.37-3.82 (m, 2H), 3.52 (s, 3H), 3.73 (s, 2H), 4.78-4.81 (m, 1H), 5.53 (d, 1H), 6.95 (s, 2H).

LC/MS (ES+): 330 (M+H)$^+$, 352 (M+Na)$^+$.

Step 5: Preparation of (1-methoxy-piperidin-4-yl)-[2-(2,4,6-trimethyl-phenyl)-acetylamino]-acetic acid methyl ester

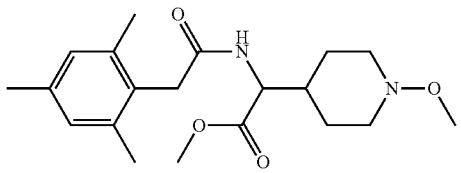

To a stirred solution of N-[cyano-(1-methoxy-piperidin-4-yl)-methyl]-2-(2,4,6-trimethyl-phenyl)-acetamide (400 mg, 1.21 mmol) in MeOH (10 ml) was introduced dry hydrogen chloride gas for 2 h and the mixture was reflux for 10 h. Then, the solvent was evaporated to dryness and water (25 ml) was added. The resulting mixture was extracted with CH$_2$Cl$_2$ three times. The collected organic layers were dried over Na$_2$SO$_4$, filtered and evaporated under reduced pressure. The crude product was purified by chromatography on silica gel.

Yield: 270 mg of (1-methoxy-piperidin-4-yl)-[2-(2,4,6-trimethyl-phenyl)-acetylamino]-acetic acid methyl ester as a solid.

$^1$H-NMR (300 MHz, CDCl$_3$): δ 1.28-1.60 (m, 5H), 2.22-2.28 (m, 2H), 2.29 (s, 6H), 2.31 (s, 3H), 3.30-3.42 (m, 2H), 3.51 (s, 3H), 3.63 (s, 2H), 3.71 (s, 3H), 4.53-4.58 (m, 1H), 5.78 (d, 1H), 6.94 (s, 2H).

LC/MS (ES+): 363 (M+H)$^+$, 385 (M+Na)$^+$.

Step 6: Preparation of 4-hydroxy-5-(1-methoxy-piperidin-4-yl)-3-(2,4,6-trimethyl-phenyl)-1,5-dihydro-pyrrol-2-one (Compound P2.12)

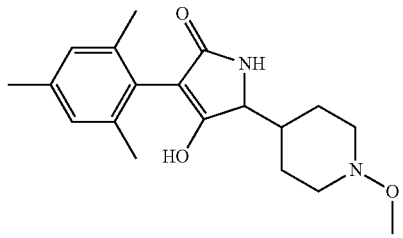

To a solution of (1-methoxy-piperidin-4-yl)-[2-(2,4,6-trimethyl-phenyl)-acetylamino]-acetic acid methyl ester (1.217 g, 3.36 mmol) in DMF (6 ml) at 90° C. under nitrogen was added t-BuOK (1.12 g, 10 mmol), the mixture was stirred for 10 min. Then the reaction mixture was poured into diluted hydrochloric acid and concentrated in vacuum. The crude product was purified by column chromatography on silica gel. Yield: 960 mg of 4-hydroxy-5-(1-methoxy-piperidin-4-yl)-3-(2,4,6-trimethyl-phenyl)-1,5-dihydro-pyrrol-2-one (compound P2.12) as a solid, mp 206-209° C.

$^1$H-NMR (300 Mz, CD$_3$OD): δ 1.69-2.08 (m, 2H), 2.15 (d, 6H), 2.20-2.38 (m, 2H), 2.27 (s, 3H), 3.45-3.59 (m, 1H), 3.87-4.07 (m, 2H), 3.98 (s, 3H), 4.24-4.27 (m, 1H), 6.93 (m, 2H).

ESI-MS (−): 329 (M−H)$^−$.

Step 7: Preparation of carbonic acid ethyl ester 2-(1-methoxy-piperidin-4-yl)-5-oxo-4-(2,4,6-trimethyl-phenyl)-2,5-dihydro-1H-pyrrol-3-yl ester (Title Compound P1.12)

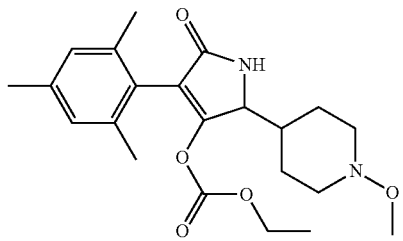

Ethyl chloroformate (216 mg, 2 mmol) was added dropwise to a mixture of 4-hydroxy-5-(1-methoxy-piperidin-4-yl)-3-(2,4,6-trimethyl-phenyl)-1,5-dihydro-pyrrol-2-one (400 mg, 1.2 mmol), Et$_3$N (606 mg, 6 mmol) and DMAP (60 mg, 0.5 mmol) in acetone (20 ml). The mixture was stirred for 15 min and concentrated under vacuum to dryness. The residue was purified by column chromatography on silica gel. Yield: 260 mg of carbonic acid ethyl ester 2-(1-methoxypiperidin-4-yl)-5-oxo-4-(2,4,6-trimethyl-phenyl)-2,5-dihydro-1H-pyrrol-3-yl ester (title compound P1.12) as a solid, mp 154-155° C.

$^1$H-NMR (300 MHz, CD$_3$OD): δ 1.11 (t, 3H), 1.43-1.70 (m, 3H), 1.72-1.88 (m, 2H), 2.05 (s, 3H), 2.10 (s, 3H), 2.21 (s, 3H), 2.26-2.40 (m, 2H), 3.36 (t, 2H), 3.45 (s, 3H), 4.06 (q, 2H), 4.50 (s, 1H), 6.84 (s, 2H).

ESI-MS (−): 401 (M−H)$^-$.

EXAMPLE 10

Preparation of (1-methoxy-piperidin-4-yl)-[2-(2,4,6-trimethyl-phenyl)-acetoxy]-acetic acid methyl ester (Compound P3.13)

Step 1: Preparation of hydroxy-(1-methoxy-piperidin-4-yl)-acetonitrile

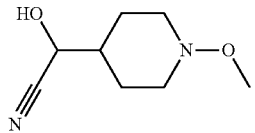

NaHSO$_3$ (11.4 g, 110 mmol) was added to a solution of 1-methoxy-piperidine-4-carbaldehyde (7.5 g, 52.4 mmol) in water (200 mL). After the mixture was stirred at room temperature for 3 h, a solution of KCN (7.2 g, 110 mmol) in water (100 mL) was added to the mixture. The reaction mixture was stirred for 2 h. Then the mixture was extracted with ethyl acetate three times. The combined organic layers were dried over sodium sulfate, concentrated under vacuum to dryness and the residue was purified by column chromatography on silica gel. Yield: 6.2 g of hydroxy-(1-methoxy-piperidin-4-yl)-acetonitrile as an oil.

$^1$H-NMR (300 MHz, DMSO-d$_6$): δ 1.28-1.47 (m, 2H), 1.49-1.68 (m, 1H), 1.69-1.85 (m, 2H), 2.13-2.32 (m, 2H), 3.23-3.36 (m, 2H), 3.39 (s, 3H), 4.36 (t, 1H), 6.38 (d, 1H).

Step 2: Preparation of (2,4,6-trimethyl-phenyl)-acetic acid cyano-(1-methoxy-piperidin-4-yl)-methyl ester

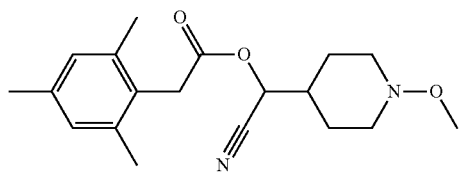

(2,4,6-Trimethyl-phenyl)-acetyl chloride (588 mg, 3 mmol) was added slowly to a mixture of hydroxy-(1-methoxy-piperidin-4-yl)-acetonitrile (390 mg, 2.3 mmol) and Et$_3$N (505 mg, 5 mmol) in THF (10 ml) at 0° C. After the addition was completed, the mixture was stirred at room temperature for 16 h. Then, the mixture was concentrated under vacuum to dryness, the residue was purified by column chromatography on silica.

Yield: 516 mg of (2,4,6-trimethyl-phenyl)-acetic acid cyano-(1-methoxy-piperidin-4-yl)-methyl ester as a solid.

$^1$H-NMR (300 MHz, CD$_3$OD): δ 1.36-1.66 (m, 2H), 1.68-1.99 (m, 3H), 2.24 (s, 3H), 2.27 (s, 6H), 2.24-2.46 (m, 2H), 3.26-3.44 (m, 2H), 3.50 (s, 3H), 3.79 (s, 2H), 5.60 (d, 1H), 6.88 (s, 2H).

LC/MS (ES+): 331 (M+H)$^+$, 353 (M+Na)$^+$, 385 (M+Na+CH$_3$OH)$^+$.

Step 3: Preparation of (1-methoxy-piperidin-4-yl)-[2-(2,4,6-trimethyl-phenyl)-acetoxy]-acetic acid ethyl ester (Title Compound P3.13)

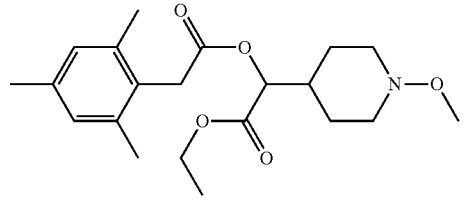

To a solution of (2,4,6-trimethyl-phenyl)-acetic acid cyano-(1-methoxy-piperidin-4-yl)-methyl ester (200 mg, 0.6 mmol) in 10 mL of ethanol was introduced hydrogen chloride gases at room temperature for about two hours, then the solvent was evaporated at 40° C. under vacuum and ice was added to the residue. Then, the aqueous phase was extracted with ethyl acetate three times. The combined organic layers were washed with brine, dried over Na$_2$SO$_4$ and concentrated in vacuo to dryness. The residue was purified by careful chromatography on silica gel. Yield: 164 mg of (1-methoxy-piperidin-4-yl)-[2-(2,4,6-trimethyl-phenyl)-acetoxy]-acetic acid ethyl ester (title compound P3.13) as a solid.

$^1$H-NMR (300 MHz, DMSO-d$_6$): δ 1.13 (t, 3H), 1.33-1.90 (m, 5H), 2.19 (s, 3H), 2.22 (s, 6H), 2.12-2.27 (m, 2H), 3.22-3.33 (m, 2H), 3.38 (s, 3H), 3.63-3.78 (q, 2H), 3.99-4.12 (q, 2H), 4.74 (d, 1H), 6.83 (s, 2H).

LC/MS (ES+): 378 (M+H)$^+$, 400 (M+Na)$^+$.

Compounds of the formula I from Table P1, compounds of the formula II from Table P2 and intermediates listed in Table P3 and Table 4 can be prepared by analogous procedures. Either one of the following LC-MS methods was used to characterize the compounds:

Method A

MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC: HP 1100 HPLC from Agilent: solvent degasser, quaternary pump (ZCQ)/binary pump (ZDQ), heated column compartment and diode-array detector. Column: Phenomenex Gemini C18, 3 μm particle size, 110 Angström, 30×3 mm, Temp: 60° C.; DAD Wavelength range (nm): 200 to 500; Solvent gradient: A=water+0.05% v/v HCOOH, B=Acetonitril/Methanol (4:1, v/v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B

MS: ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.

LC: HP 1100 HPLC from Agilent: solvent degasser, binary pump, heated column compartment and diode-array detector. Column: Phenomenex Gemini C18, 3 μm particle size, 110 Angström, 30×3 mm, Temp: 60° C.; DAD Wavelength range (nm): 200 to 500; Solvent gradient: A=water+0.05% v/v HCOOH, B=Acetonitril/Methanol (4:1, v:v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method C

MS: Aquiety SQD Mass Spectrometer from Waters (Single quadrupole mass spectrometer); Ionisation method: Electrospray; Polarity: positive ions; Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700; Mass range: 100 to 800 Da.

LC: Method Waters ACQUITY UPLC. Column: Waters ACQUITY UPLC HSS T3, column length: 30 mm, internal column diameter: 2.1 mm, particle size: 1.8 micron, temperature: 60° C.; DAD Wavelength range (nm): 210 to 400; HPLC gradient conditions: Solvent A: Water/Methanol (9:1, v/v)+0.1% (v/v) formic acid and Solvent B: Acetonitrile+0.1% (v/v) formic acid.

| Time (min) | A % | B % | Flow (ml/min) |
|---|---|---|---|
| 0.00 | 100.0 | 0.0 | 1.50 |
| 0.10 | 100.0 | 0.0 | 1.50 |
| 0.20 | 100.0 | 0.0 | 0.75 |
| 1.20 | 0.0 | 100.0 | 0.75 |
| 1.40 | 0.0 | 100.0 | 0.75 |
| 1.45 | 100.0 | 0.0 | 0.75 |

Method D

MS: ACQUITY SQD Mass Spectrometer from Waters (Single quadrupole mass spectrometer); Ionisation method: Electrospray; Polarity: positive ions; Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 Mass range: 100 to 800 Da.

LC: Method Waters ACQUITY UPLC. Column: Waters ACQUITY UPLC HSS T3, column length: 30 mm, internal column diameter: 2.1 mm, particle size: 1.8 micron, temperature: 60° C.; DAD Wavelength range (nm): 210 to 400; HPLC gradient conditions: Solvent A: Water/Methanol (9:1, v/v)+0.1% (v/v) formic acid and Solvent B: Acetonitrile+0.1% (v/v) formic acid.

| Time (min) | A % | B % | Flow (ml/min) |
|---|---|---|---|
| 0.00 | 80.0 | 20.0 | 1.50 |
| 0.10 | 75.0 | 25.0 | 1.50 |
| 0.20 | 70.0 | 30.0 | 0.75 |
| 1.20 | 0.0 | 100.0 | 0.75 |
| 1.40 | 0.0 | 100.0 | 0.75 |
| 1.45 | 80.0 | 20.0 | 0.75 |

Method E

MS: Instrument model: Shimadzu LCMS-2010EV; ESI (+)/ESI(−) scan mode; Nebulizer gas: 1.5 ml/min; CDL temperature: 250° C.; Interface Voltage: 3.5 kV; Detector Voltage: 1.5 kV.

HPLC: Instrument model: Shimadzu LC-20AD; UV wavelength: 254 nm; Flow rate: 1 ml/min; Column temperature: 40° C.; Mobile phase: Acetonitrile/water; Column condition: Inertsil ODS-SP C18, 4.6×150 mm, 5 μm; Gradient elution:

| Time (min) | 0 | 15 | 25 |
|---|---|---|---|
| Acetonitrile % | 10 | 100 | 100 |

The characteristic values obtained for each compound were the retention time ("$R_t$", recorded in minutes) and the molecular ion as listed in Table P1, Table P2, Table 3 and in Table P4.

TABLE P1

Physical data of compounds of formula I:

| Compound No. | Structures | Melting Point | MS/NMR |
|---|---|---|---|
| P1.1 | 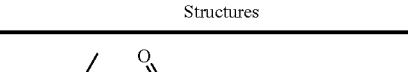<br>EXAMPLE 1, step 9 | gum | $^1$H-NMR (300 MHz, CDCl$_3$): δ 1.20 (t, 3H), 1.34-1.89 (m, 7H), 2.20 (s, 3H), 2.29 (s, 3H), 2.25-2.35 (m, 2H), 3.31-3.40 (m, 2H), 3.50 (s, 3H), 4.12 (q, 2H), 4.61-4.63 (m, 1H), 6.97 (s, 1H), 7.03-7.12 (m, 2H), 7.52 (br s, 1H). LC/MS (ES+): 403 (M + H)$^+$, 425 (M + Na)$^+$, 457 (M + Na + MeOH)$^+$. |

TABLE P1-continued

Physical data of compounds of formula I:

| Compound No. | Structures | Melting Point | MS/NMR |
|---|---|---|---|
| P1.2 | 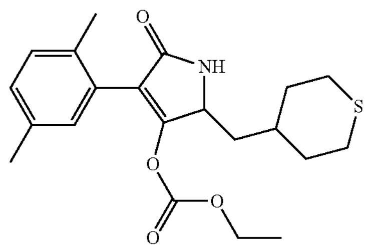 [SMILES: CCOC(=O)OC1=C(c2cc(C)ccc2C)C(=O)NC1CC1CCSCC1] | 75-76° C. | $^1$H-NMR (300 MHz, CD$_3$OD): δ 1.20 (t, 3H), 1.24-2.23 (m, 7H), 2.19 (s, 3H), 2.30 (s, 3H), 2.60-2.72 (m, 4H), 4.13 (q, 2H), 4.65-4.72 (m, 1H), 6.93 (s, 1H), 7.03-7.13 (m, 2H). LC/MS (ES+): 390 (M + H)$^+$, 412 (M + Na)$^+$, 444 (M + Na + MeOH)$^+$. |
| P1.3 | 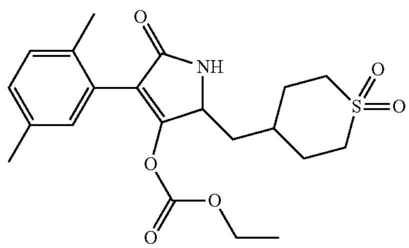 [SMILES: CCOC(=O)OC1=C(c2cc(C)ccc2C)C(=O)NC1CC1CCS(=O)(=O)CC1] | 97-101° C. | $^1$H-NMR (300 MHz, CD$_3$OD): δ 1.18 (t, 3H), 1.57-2.25 (m, 7H), 2.19 (s, 3H), 2.30 (s, 3H), 3.01-3.15 (m, 4H), 4.16 (q, 2H), 4.65-4.68 (m, 1H), 6.94 (s, 1H), 7.09-7.14 (m, 2H). LC/MS (ES+): 422 (M + H)$^+$, 444 (M + Na)$^+$, 476 (M + Na + MeOH)$^+$. |
| P1.4 | EXAMPLE 5, step 1 | 103-106° C. | $^1$H-NMR (300 MHz, CD$_3$OD): δ 1.17-1.25 (m, 3H), 1.46-1.84 (m, 8H), 2.19 (s, 3H), 2.30 (s, 3H), 2.62-2.75 (m, 2H), 3.01-3.08 (m, 1H), 3.31-3.42 (m, 1H), 4.11-4.21 (m, 2H), 4.66-4.76 (m, 1H), 6.93 (s, 1H), 7.07-7.16 (m, 2H). LC/MS (ES+): 428 (M + Na)$^+$. |
| P1.5 | 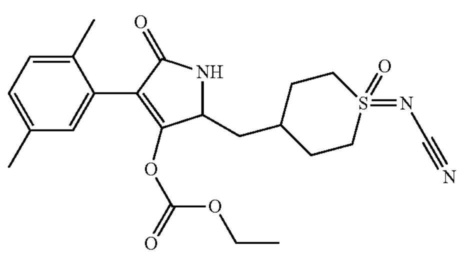 [SMILES: CCOC(=O)OC1=C(c2cc(C)ccc2C)C(=O)NC1CC1CCS(=O)(=NC#N)CC1] | 93-95° C. | $^1$H-NMR (300 MHz, CD$_3$OD): δ 1.18 (t, 3H), 1.37-2.41 (m, 7H), 2.18 (s, 3H), 2.28 (s, 3H), 3.42-3.70 (m, 4H), 4.13 (q, 2H), 4.65-4.75 (m, 1H), 6.92 (s, 1H), 7.05-7.15 (m, 2H). LC/MS (ES+): 468 (M + Na)$^+$. |
| P1.6 | Isomer A EXAMPLE 5, step 2 | 91-93° C. | $^1$H-NMR (300 MHz, DMSO-d$_6$): δ 1.11 (t, 3H), 1.42-1.73 (m, 1H), 1.74-1.87 (m, 4H), 1.90-2.05 (m, 2H), 2.10 (s, 3H), 2.25 (s, 3H), 3.51-3.82 (m, 4H), 4.10 (q, 2H), 4.56 (d, 1H), 6.88 (s, 1H), 7.05-7.14 (m, 2H), 8.58 (s, 1H). LC/MS (ES+): 539 (M + Na)$^+$. |

TABLE P1-continued

Physical data of compounds of formula I:

| Compound No. | Structures | Melting Point | MS/NMR |
|---|---|---|---|
| P1.7 | Isomer B EXAMPLE 5, step 2 | 87-89° C. | $^1$H-NMR (300 MHz, DMSO-d$_6$): δ 1.11 (t, 3H), 1.4-1.90 (m, 5H), 2.10 (s, 3H), 2.14-2.30 (m, 2H), 2.24 (s, 3H), 3.52-3.96 (m, 4H), 4.09 (q, 2H), 4.55 (d, 1H), 6.87 (s, 1H), 7.05-7.14 (m, 2H), 8.57 (s, 1H). LC/MS (ES+): 539 (M + Na)$^+$. |
| P1.8 | 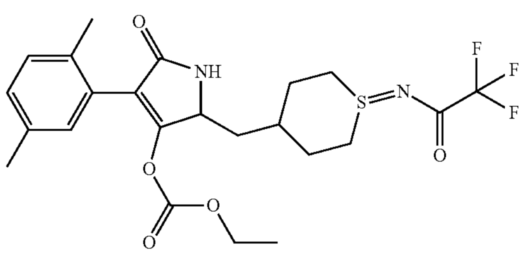 [SMILES: CCOC(=O)OC1=C(c2cc(C)ccc2C)C(=O)NC1CC1CCS(=NC(=O)C(F)(F)F)CC1] | 190-192° C. | $^1$H-NMR (300 MHz, DMSO-d$_6$): δ 1.11 (t, 3H), 1.35-2.25 (m, 7H), 2.09 (s, 3H), 2.24 (s, 3H), 2.88-2.95 (m, 2H), 3.51-3.58 (m, 2H), 4.13 (q, 2H), 4.58 (d, 1H), 6.87 (s, 1H), 7.05-7.14 (m, 2H), 8.60 (s, 1H). LC/MS (ES+): 501 (M + H)$^+$, 523 (M + Na)$^+$. |
| P1.9 | EXAMPLE 8 | 103-105° C. | $^1$H-NMR (300 MHz, CD$_3$OD): δ 1.17 (t, 3H), 1.53-1.70 (m, 3H), 1.81-1.85 (m, 2H), 2.16 (s, 3H), 2.30 (s, 3H), 2.31-2.45 (m, 2H), 3.01-3.10 (m, 2H), 3.50-3.56 (m, 2H), 4.12 (q, 2H), 4.65-4.69 (m, 1H), 6.93 (s, 1H), 7.10-7.16 (m, 2H). LC/MS (ES+): 452 (M + Na)$^+$. |
| P1.10 | 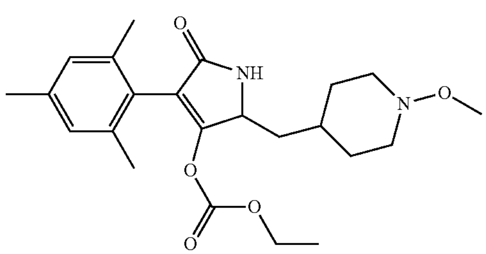 | solid | $^1$H-NMR (300 MHz, CD$_3$OD): δ 1.17 (t, 3H), 1.25-2.01 (m, 7H), 2.12 (s, 3H), 2.14 (s, 3H), 2.28 (s, 3H), 2.30-2.41 (m, 2H), 3.30-3.45 (m, 2H), 3.53 (s, 3H), 4.14 (q, 2H), 4.62-4.68 (m, 1H), 6.91 (s, 2H). ESI-MS (−): 417 (M + H)$^+$, 439 (M + Na)$^+$. |
| P1.11 | 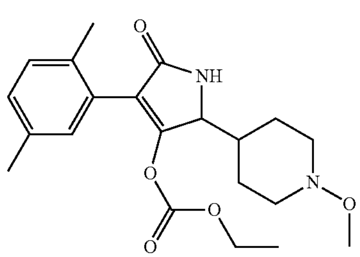 [SMILES: CCOC(=O)OC1=C(c2cc(C)ccc2C)C(=O)NC1C1CCN(OC)CC1] | 166-168° C. | $^1$H-NMR (300 MHz, CDCl$_3$): δ 1.18 (t, 3H), 1.57-1.88 (m, 5H), 2.21 (s, 3H), 2.33 (s, 3H), 2.34-3.42 (m, 2H), 3.38-3.44 (m, 2H), 3.52 (s, 3H), 4.13 (q, 2H), 4.52 (s, 1H), 6.59 (s, 1H), 6.96 (s, 1H), 7.04-7.13 (m, 2H). LC/MS (ES+): 389 (M + H)$^+$, 411 (M + Na)$^+$, 443 (M + Na + MeOH)$^+$. |

TABLE P1-continued

Physical data of compounds of formula I:

| Compound No. | Structures | Melting Point | MS/NMR |
|---|---|---|---|
| P1.12 | EXAMPLE 9, step 7 | 154-155° C. | $^1$H NMR (300 MHz, CD$_3$OD): δ 1.11 (t, 3H), 1.43-1.70 (m, 3H), 1.72-1.88 (m, 2H), 2.05 (s, 3H), 2.10 (s, 3H), 2.21 (s, 3H), 2.26-2.40 (m, 2H), 3.36 (t, 2H), 3.45 (s, 3H), 4.06 (q, 2H), 4.50 (s, 1H), 6.84 (s, 2H); ESI-MS (−): 401 (M − H)$^-$. |
| P1.13 | 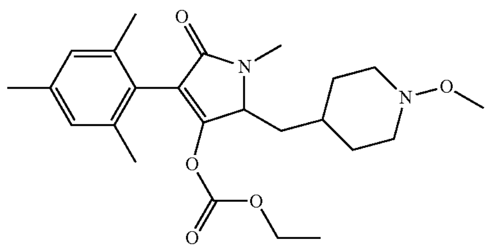 | gum | $^1$H NMR (300 MHz, CDCl$_3$): δ 1.25 (t, 3H), 1.43-1.85 (m, 7H), 2.15 (s, 3H), 2.18 (s, 3H), 2.30 (s, 3H), 2.38-2.42 (m, 2H), 3.06 (s, 3H), 3.35-3.38 (m, 2H), 3.55 (s, 3H), 4.14 (q, 2H), 4.57 (t, 1H), 6.91 (s, 2H). ESI-MS (+): 431 (M + H)$^+$, 453 (M + Na)$^+$, 485 (M + MeOH + Na)$^+$. |
| P1.14 | 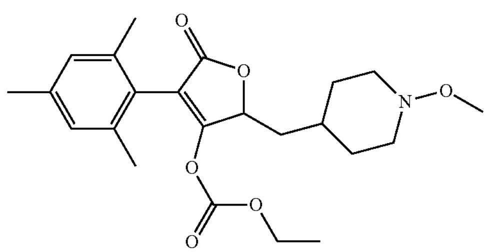 | gum | $^1$H NMR (300 MHz, CDCl$_3$): δ 1.25 (t, 3H), 1.34-2.01 (m, 7H), 2.16 (s, 6H), 2.29 (s, 3H), 2.38-2.42 (m, 2H), 3.38-3.43 (m, 2H), 3.55 (s, 3H), 4.17 (q, 2H), 5.48 (d, 1H), 6.91 (s, 2H). ESI-MS (+): 418 (M + H)$^+$, 440 (M + Na)$^+$. |
| P1.15 | 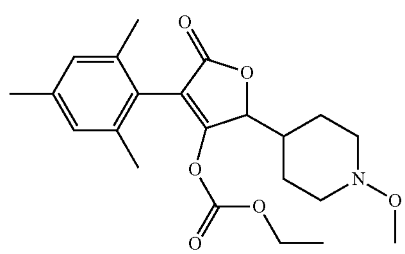 | gum | $^1$H NMR (300 MHz, CDCl$_3$): δ 1.54-1.78 (m, 2H), 1.80-1.99 (m, 3H), 2.13 (s, 3H), 2.17 (s, 3H), 2.26 (s, 3H), 2.32-2.48 (m, 2H), 3.38-3.50 (m, 2H), 3.54 (s, 3H), 5.30 (s, 1H), 6.90 (s, 2H); ESI-MS (+): 404 (M + H)$^+$, 426 (M + Na)$^+$, 458 (M + MeOH + Na)$^+$. |
| P1.16 | 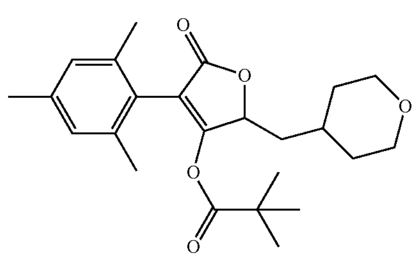 [SMILES: Cc1cc(C)c(C2=C(OC(=O)C(C)(C)C)C(CC3CCOCC3)OC2=O)c(C)c1] | solid | |
| P1.17 | 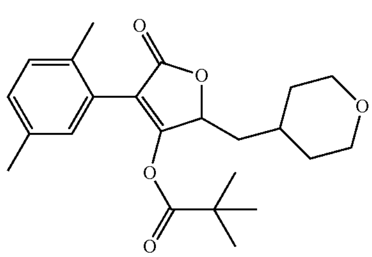 [SMILES: Cc1ccc(C)c(C2=C(OC(=O)C(C)(C)C)C(CC3CCOCC3)OC2=O)c1] | solid | |

TABLE P1-continued

Physical data of compounds of formula I:

| Compound No. | Structures | Melting Point | MS/NMR |
|---|---|---|---|
| P1.18 | 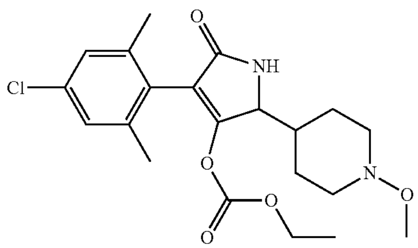 [SMILES: CCOC(=O)OC1=C(c2c(C)cc(Cl)cc2C)C(=O)NC1C1CCN(OC)CC1] | 178-180° C. | LC/MS: 423/425 (M + H)+<br>$R_t$ = 1.75 min |
| P1.19 | 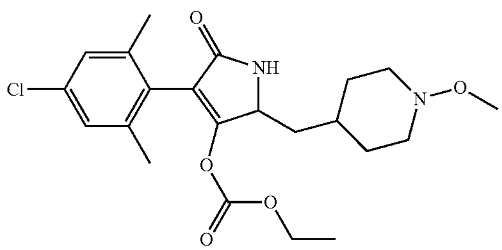 [SMILES: CCOC(=O)OC1=C(c2c(C)cc(Cl)cc2C)C(=O)NC1CC1CCN(OC)CC1] | 93-95° C. | LC/MS: 437/439 (M + H)+<br>$R_t$ = 1.78 min |

TABLE P2

Physical data of compounds of formula II:

| Compound No. | Structures | Melting Point | MS/NMR |
|---|---|---|---|
| P2.1 | 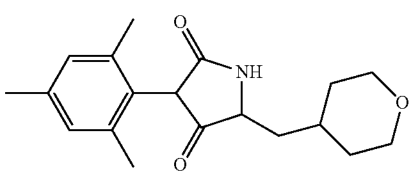 [SMILES: Cc1cc(C)c(C2C(=O)NC(CC3CCOCC3)C2=O)c(C)c1] | gum | — |
| P2.2 | (EXAMPLE 1, step 8) | 116-119° C. | $^1$H-NMR (300 MHz, CD$_3$OD): δ 1.28-1.98 (m, 9H), 2.16 (s, 3H), 2.28 (s, 3H), 2.32-2.40 (m, 2H), 3.31-3.55 (m, 2H), 3.52 (s, 3H), 4.12-4.14 (m, 1H), 6.93-7.11 (m, 3H).<br>LC/MS (ES+): 331 (M + H)+ |
| P2.3 | 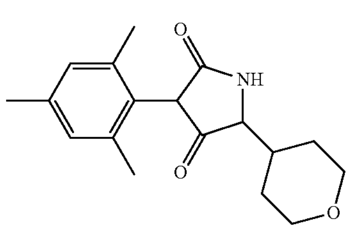 [SMILES: Cc1cc(C)c(C2C(=O)NC(C3CCOCC3)C2=O)c(C)c1] | gum | — |

TABLE P2-continued

Physical data of compounds of formula II:

| Compound No. | Structures | Melting Point | MS/NMR |
|---|---|---|---|
| P2.4 | 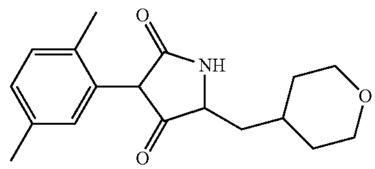 [SMILES: Cc1ccc(C)c(C2C(=O)NC(CC3CCOCC3)C2=O)c1] | 114-116° C. | ¹H NMR (300 MHz, DMSO-d₆): δ 1.13-1.78 (m, 7H), 2.10 (s, 3H), 2.24 (s, 3H), 3.22-3.30 (m, 2H), 3.80-3.86 (m, 2H), 4.01-4.04 (m, 1H), 6.88 (s, 1H), 6.98 (d, 1H), 7.07 (d, 1H), 7.65 (s, 1H), 10.72 (s, 1H). ESI-MS: 302 (M + 1)⁺, 324 (M + Na)⁺, 356 (M + Na + MeOH)⁺. |
| P2.5 | 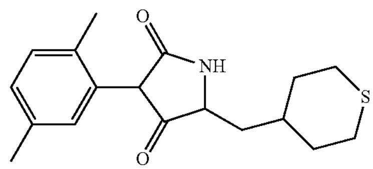 [SMILES: Cc1ccc(C)c(C2C(=O)NC(CC3CCSCC3)C2=O)c1] | 108-111° C. | ¹H-NMR (300 MHz, CD₃OD): δ 1.35-2.05 (m, 5H), 2.18-2.25 (m, 2H), 2.17 (s, 3H), 2.28 (s, 3H), 2.58-2.71 (m, 4H), 4.15-4.18 (m, 1H), 6.93 (s, 1H), 7.02 (d, 1H), 7.09 (d, 1H). LC/MS (ES−): 316 (M − H)⁻. |
| P2.6 | EXAMPLE 6, step 3 | 244-246° C. | ¹H-NMR (300 MHz, CD₃OD): δ 1.59-1.93 (m, 5H), 1.94-2.18 (m, 2H), 2.19 (s, 3H), 2.31 (s, 3H), 3.07-3.14 (m, 4H), 4.16-4.20 (m, 1H), 6.97 (s, 1H), 7.02-7.05 (m, 1H), 7.12-7.14 (m, 1H). LC/MS (ES+): 372 (M + Na)⁺ |
| P2.7 | Isomer A | 150-153° C. | ¹H-NMR (300 MHz, CD₃OD): δ 1.60-2.01 (m, 5H), 2.19 (s, 3H), 2.30 (s, 3H), 2.20-2.35 (m, 2H), 3.45-3.60 (m, 2H), 3.70-3.80 (m, 2H), 4.18-4.22 (m, 1H), 6.97 (s, 1H), 7.02 (d, 1H), 7.12 (s, 1H). ESI-MS (+): 467 (M + Na)⁺. |
| P2.8 | Isomer B | 158-161° C. | ¹H-NMR (300 MHz, CD₃OD): δ 1.50-2.01 (m, 5H), 2.19 (s, 3H), 2.29 (s, 3H), 2.20-2.35 (m, 2H), 3.40-3.52 (m, 2H), 3.80-3.92 (m, 2H), 4.01-4.05 (m, 1H), 6.98 (s, 1H), 7.01 (d, 1H), 7.09 (s, 1H). ESI-MS (+): 467 (M + Na)⁺. |
| P2.9 | 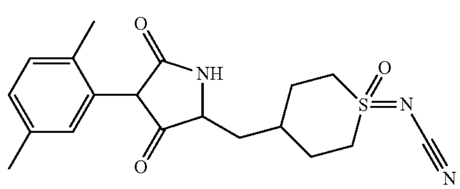 [SMILES: Cc1ccc(C)c(C2C(=O)NC(CC3CCS(=O)(=NC#N)CC3)C2=O)c1] | 189-191° C. | ¹H-NMR (300 MHz, CD₃OD): δ 1.50-1.98 (m, 5H), 2.19 (s, 3H), 2.29 (s, 3H), 2.20-2.35 (m, 2H), 3.41-3.64 (m, 4H), 4.02 (d, 1H), 6.98 (s, 1H), 7.01 (d, 1H), 7.10 (d, 1H). ESI-MS (+): 396 (M + Na)⁺. |
| P2.10 | 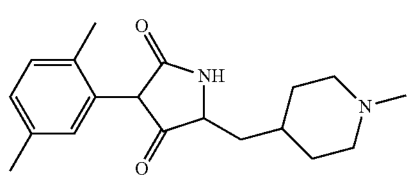 [SMILES: Cc1ccc(C)c(C2C(=O)NC(CC3CCN(C)CC3)C2=O)c1] | 142-145° C. | ¹H-NMR (300 MHz, CD₃OD): δ 1.52-2.32 (m, 7H), 2.18 (s, 3H), 2.30 (s, 3H), 2.86 (s, 3H), 2.90-3.10 (m, 2H), 3.51-3.56 (m, 2H), 4.21-4.30 (m, 1H), 6.96 (s, 1H), 7.06 (d, 1H), 7.12 (d, 1H). |

TABLE P2-continued

Physical data of compounds of formula II:

| Compound No. | Structures | Melting Point | MS/NMR |
|---|---|---|---|
| P2.11 | 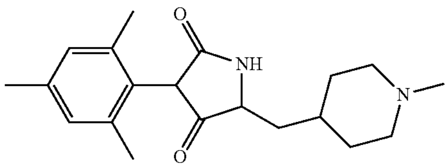 | 133-136° C. | $^1$H-NMR (300 MHz, CD$_3$OD): δ 1.52-2.31 (m, 7H), 2.13 (s, 3H), 2.14 (s, 3H), 2.27 (s, 3H), 2.86 (s, 3H), 2.90-3.01 (m, 2H), 3.50-3.54 (m, 2H), 4.22-4.26 (m, 1H), 6.91 (s, 2H). ESI-MS (+): 329 (M + H)$^+$. |
| P2.12 EXAMPLE 9, step 6 | | 206-209° C. | $^1$H-NMR (300 Mz, CD$_3$OD): δ 1.69-2.08 (m, 2H), 2.15 (d, 6H), 2.20-2.38 (m, 2H), 2.27 (s, 3H), 3.45-3.59 (m, 1H), 3.87-4.07 (m, 2H), 3.98 (s, 3H), 4.24-4.27 (m, 1H), 6.93 (m, 2H). ESI-MS (−): 329 (M − H)$^-$. |
| P2.13 | 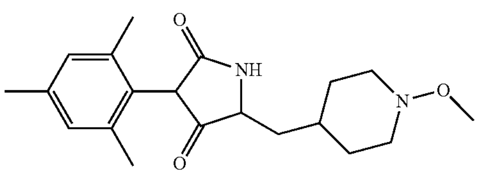 | 133-135° C. | $^1$H-NMR (300 MHz, CD$_3$OD): δ 1.25-2.05 (m, 7H), 2.14 (s, 6H), 2.27 (s, 3H), 2.32-2.41 (m, 2H), 3.31-3.45 (m, 2H), 3.53 (s, 3H), 4.18-4.21 (m, 1H), 6.91 (s, 2H). ESI-MS (+): 345 (M + H)$^+$. |
| P2.14 | 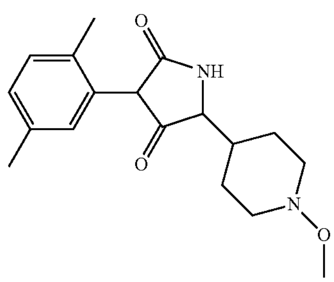 [SMILES: CON1CCC(C2NC(=O)C(c3cc(C)ccc3C)C2=O)CC1] | 128-131° C. | $^1$H-NMR (300 MHz, CD$_3$OD): δ 1.61-1.85 (m, 5H), 2.18 (s, 3H), 2.30 (s, 3H), 2.31-2.38 (m, 2H), 3.38-3.42 (m, 2H), 3.59 (s, 3H), 4.07 (d, 1H), 6.95 (s, 1H), 7.05 (d, 1H), 7.11 (d, 1H). ESI-MS (+): 317 (M + H)$^+$, 339 (M + Na)$^+$. |
| P2.15 | 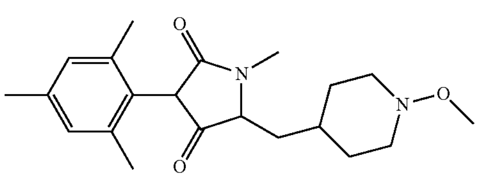 | 165-170° C. | $^1$H-NMR (300 MHz, DMSO-d$_6$): δ 1.28-1.85 (m, 7H), 2.14 (s, 6H), 2.25-2.31 (m, 2H), 2.29 (s, 3H), 2.93 (s, 3H), 3.31-3.34 (m, 2H), 3.52 (s, 3H), 3.87 (t, 1H), 6.91 (s, 2H). ESI-MS (+): 346 (M + H)$^+$. |
| P2.16 | 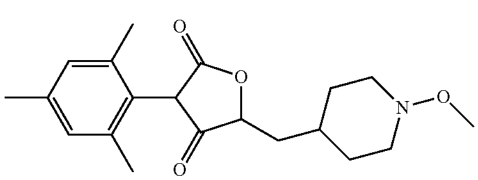 | 125-130° C. | $^1$H-NMR (300 MHz, DMSO-d$_6$): δ 1.22-1.95 (m, 7H), 2.04 (s, 3H), 2.06 (s, 3H), 2.22-2.31 (m, 2H), 2.23 (s, 3H), 3.30-3.35 (m, 2H), 3.40 (s, 3H), 4.96 (t, 1H), 6.87 (s, 2H). ESI-MS (+): 346 (M + H)$^+$. |

TABLE P2-continued

Physical data of compounds of formula II:

| Compound No. | Structures | Melting Point | MS/NMR |
|---|---|---|---|
| P2.17 | 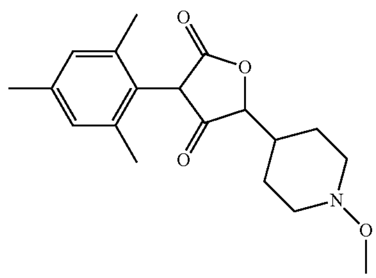 | 109-110° C. | ¹H-NMR (300 MHz, CD$_3$OD): δ 1.35-2.01 (m, 5H), 2.13 (s, 3H), 2.14 (s, 3H), 2.27 (s, 3H), 3.35-3.50 (m, 2H), 3.52 (s, 3H), 4.81-4.83 (m, 1H), 6.92 (s, 2H). ESI-MS (−): 330 (M − H)⁻. |
| P2.18 | 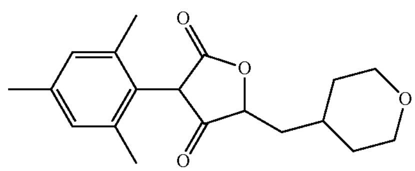 [SMILES: Cc1cc(C)c(C2C(=O)OC(CC3CCOCC3)C2=O)c(C)c1] | gum | |
| P2.19 | 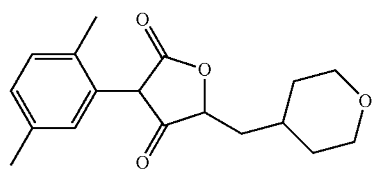 [SMILES: Cc1ccc(C)c(C2C(=O)OC(CC3CCOCC3)C2=O)c1] | gum | |
| P2.20 | 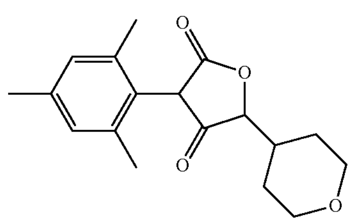 [SMILES: Cc1cc(C)c(C2C(=O)OC(C3CCOCC3)C2=O)c(C)c1] | solid | |
| P2.21 | 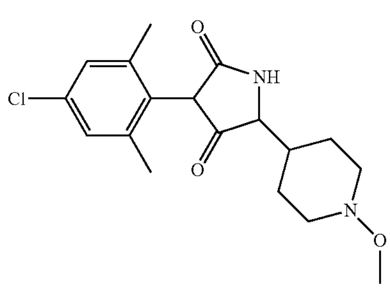 [SMILES: CON1CCC(C2NC(=O)C(c3c(C)cc(Cl)cc3C)C2=O)CC1] | 211-213° C. | LC/MS: 351/353 (M + H)⁺ R$_t$ = 1.38 min |
| P2.22 | 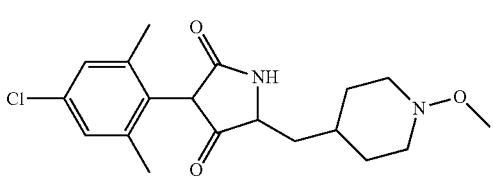 [SMILES: CON1CCC(CC2NC(=O)C(c3c(C)cc(Cl)cc3C)C2=O)CC1] | 123-125° C. | LC/MS: 365/367 (M + H)⁺ R$_t$ = 1.40 min |

Intermediates of the formula IV or XI from Table P3 can be prepared by analogous procedures.

TABLE P3

Physical data of intermediates of formula IV or XI:

| Compound No. | Structures | Melting Point | MS/NMR |
|---|---|---|---|
| P3.1 | 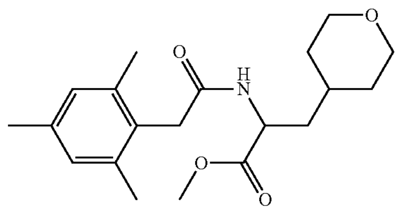 [SMILES: COC(=O)C(CC1CCOCC1)NC(=O)Cc1c(C)cc(C)cc1C] | — | |
| P3.2 | EXAMPLE 1, step 7 | Solid | ¹H NMR (300 MHz, CDCl₃): δ 1.15-1.74 (m, 7H), 2.15-2.19 (m, 2H), 2.24 (s, 3H), 2.31 (s, 3H), 3.29-3.30 (m, 2H), 3.50 (s, 3H), 3.55 (s, 2H), 3.68 (s, 3H), 4.60-4.62 (m, 1H), 5.64 (d, 1H), 7.00-7.11 (m, 3H). LC/MS (ES+): 385 (M + Na)⁺ |
| P3.3 | 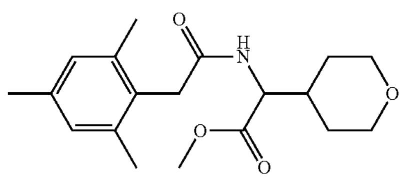 [SMILES: COC(=O)C(NC(=O)Cc1c(C)cc(C)cc1C)C1CCOCC1] | — | |
| P3.4 | 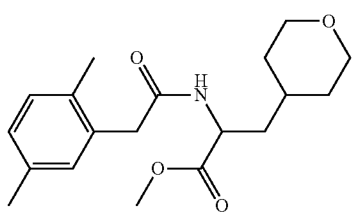 [SMILES: COC(=O)C(CC1CCOCC1)NC(=O)Cc1cc(C)ccc1C] | Solid | ¹H NMR (300 MHz, CDCl₃): δ 1.18-1.71 (m, 7H), 2.25 (s, 3H), 2.32 (s, 3H), 3.23-3.32 (m, 2H), 3.57 (s, 2H), 3.70 (s, 3H), 3.88-3.92 (m, 2H), 4.64-4.68 (m, 1H), 5.69 (d, 1H), 6.98-7.12 (m, 3H). ESI-MS (+): 334 (M + H)⁺, 356 (M + Na)⁺. |
| P3.5 | 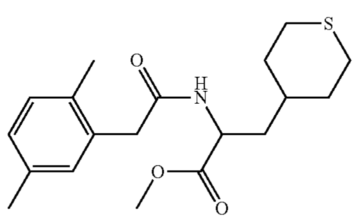 [SMILES: COC(=O)C(CC1CCSCC1)NC(=O)Cc1cc(C)ccc1C] | Solid | ¹H NMR (300 MHz, CDCl₃): δ 1.22-1.99 (m, 7H), 2.24 (s, 3H), 2.31 (s, 3H), 2.53-2.55 (m, 4H), 3.55 (s, 2H), 3.68 (s, 3H), 4.61-4.68 (m, 1H), 5.65 (d, 1H), 7.00-7.11 (m, 3H). ESI-MS (+): 372 (M + Na)⁺. |
| P3.6 | 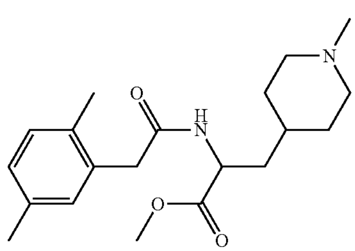 [SMILES: COC(=O)C(CC1CCN(C)CC1)NC(=O)Cc1cc(C)ccc1C] | Solid | ¹H-NMR (300 MHz, CDCl₃): δ 1.16-2.07 (m, 9H), 2.26 (s, 3H), 2.30 (s, 3H), 2.33 (s, 3H), 2.85-2.88 (m, 2H), 3.57 (s, 2H), 3.70 (s, 3H), 4.61-4.68 (m, 1H), 5.67 (d, 1H), 7.02-7.13 (m, 2H). LC/MS (ES+): 347 (M + H)⁺. |

TABLE P3-continued

Physical data of intermediates of formula IV or XI:

| Compound No. | Structures | Melting Point | MS/NMR |
|---|---|---|---|
| P3.7 | 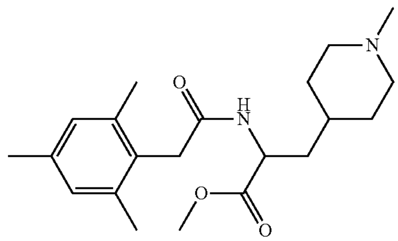 | Solid | $^1$H-NMR (300 MHz, CDCl$_3$): δ 1.15-2.01 (m, 9H), 2.27 (s, 6H), 2.29 (s, 3H), 2.33 (s, 3H), 2.89-2.92 (m, 2H), 3.61 (s, 2H), 3.69 (s, 3H), 4.61-4.68 (m, 1H), 5.62 (d, 1H), 6.92 (s, 2H). LC/MS (ES+): 361 (M + H)$^+$. |
| P3.8 EXAMPLE 9, step 5 | | Solid | $^1$H-NMR (300 MHz, CDCl$_3$): δ 1.28-1.60 (m, 5H), 2.22-2.28 (m, 2H), 2.29 (s, 6H), 2.31 (s, 3H), 3.30-3.42 (m, 2H), 3.51 (s, 3H), 3.63 (s, 2H), 3.71 (s, 3H), 4.53-4.58 (m, 1H), 5.78 (d, 1H), 6.94 (s, 2H). LC/MS (ES+): 363 (M + H)$^+$, 385 (M + Na)$^+$. |
| P3.9 EXAMPLE 2, step 2 | | Solid | $^1$H-NMR (300 MHz, CDCl$_3$): δ 1.13-1.76 (m, 7H), 2.20-2.24 (m, 2H), 2.28 (s, 6H), 2.30 (s, 3H), 3.30-3.33 (m, 2H), 3.52 (s, 3H), 3.62 (s, 2H), 3.69 (s, 3H), 4.63-4.65 (m, 1H), 5.60 (d, 1H), 6.92 (s, 2H). LC/MS (ES+): 377 (M + H)$^+$, 399 (M + Na)$^+$. |
| P3.10 | 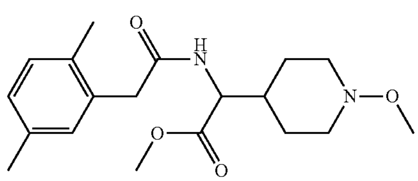 [SMILES: COC(=O)C(NC(=O)Cc1cc(C)ccc1C)C1CCN(OC)CC1] | Solid | $^1$H-NMR (300 MHz, CDCl$_3$): δ 1.26-1.75 (m, 5H), 2.25-2.33 (m, 2H), 2.25 (s, 3H), 2.33 (s, 3H), 3.32-3.35 (m, 2H), 3.49 (s, 3H), 3.58 (s, 2H), 3.71 (s, 3H), 4.56-4.58 (m, 1H), 6.01 (d, 1H), 7.03-7.13 (m, 3H). LC/MS (ES+): 349 (M + H)$^+$, 371 (M + Na)$^+$. |
| P3.11 | 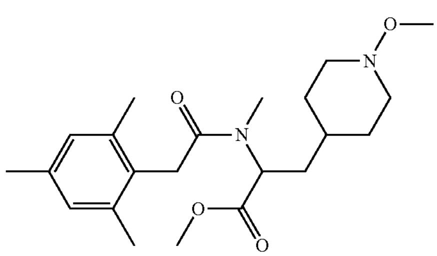 | Solid | $^1$H NMR (300 MHz, CDCl$_3$): δ 0.85-1.95 (m, 7H), 2.10-2.31 (m, 2H), 2.22 (s, 6H), 2.26 (s, 3H), 3.07 (s, 3H), 3.32-3.35 (m, 2H), 3.53 (s, 3H), 3.67 (s, 2H), 3.77 (s, 3H), 5.42 (t, 1H), 6.86 (s, 2H). |
| P3.12 EXAMPLE 4, step 3 | | Oil | $^1$H-NMR (300 MHz, CDCl$_3$): δ 1.22-1.28 (m, 3H), 1.62-1.80 (m, 4H), 2.10-2.17 (m, 2H), 2.18 (s, 3H), 2.29 (s, 6H), 3.26-3.29 (m, 2H), 3.50 (s, 3H), 3.70 (s, 3H), 3.72 (s, 2H), 4.99-5.04 (m, 1H), 6.85 (s, 2H). LC/MS (ES+): 378 (M + H)$^+$, 400 (M + Na)$^+$. |

TABLE P3-continued

Physical data of intermediates of formula IV or XI:

| Compound No. | Structures | Melting Point | MS/NMR |
|---|---|---|---|
| P3.13 | EXAMPLE 10, step 3 | Oil | ¹H-NMR (300 MHz, DMSO-d₆): δ 1.13 (t, 3H), 1.33-1.90 (m, 5H), 2.19 (s, 3H), 2.22 (s, 6H), 2.12-2.27 (m, 2H), 3.22-3.33 (m, 2H), 3.38 (s, 3H), 3.63-3.78 (q, 2H), 3.99-4.12 (q, 2H), 4.74 (d, 1H), 6.83 (s, 2H); LC/MS (ES+): 378 (M + H)⁺, 400 (M + Na)⁺. |
| P3.14 | 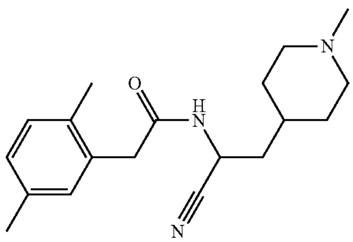 [SMILES: Cc1ccc(C)c(CC(=O)NC(C#N)CC2CCN(C)CC2)c1] | Solid | ¹H-NMR (300 MHz, DMSO-d₆): δ 1.25-1.66 (m, 7H), 1.89-2.01 (s, 2H), 2.22 (s, 3H), 2.28 (s, 3H), 2.33 (s, 3H), 2.81-2.89 (m, 2H), 3.58 (s, 2H), 4.90 (q, 1H), 5.61 (d, 1H), 6.98 (s, 1H), 7.05-7.13 (m, 2H). LC/MS (ES+): 313 (M + H)⁺, 336 (M + Na)⁺. |
| P3.15 | 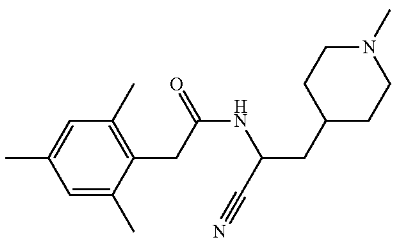 | Solid | |
| P3.16 | EXAMPLE 2, step 1 | Solid | LC/MS (ES+): 344 (M + H)⁺, 366 (M + Na)⁺. |
| P3.17 | EXAMPLE 9, step 4 | Solid | ¹H-NMR (300 MHz, CDCl₃): δ 1.33-1.74 (m, 5H), 2.26 (s, 6H), 2.28-2.30 (m, 2H), 2.32 (s, 3H), 3.37-3.82 (m, 2H), 3.52 (s, 3H), 3.73 (s, 2H), 4.78-4.81 (m, 1H), 5.53 (d, 1H), 6.95 (s, 2H). LC/MS (ES+): 330 (M + H)⁺, 352 (M + Na)⁺. |
| P3.18 | 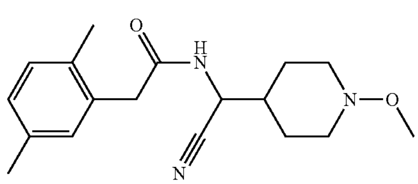 [SMILES: CON1CCC(C(C#N)NC(=O)Cc2cc(C)ccc2C)CC1] | Solid | ¹H-NMR (300 MHz, CDCl₃): δ 1.33-1.74 (m, 5H), 2.23 (s, 6H), 2.24-2.32 (m, 2H), 2.35 (s, 3H), 3.34-3.41 (m, 2H), 3.52 (s, 3H), 3.61 (s, 2H), 4.77-4.83 (m, 1H), 5.54 (d, 1H), 6.99 (s, 1H), 7.09-7.15 (m, 2H). LC/MS (ES+): 316 (M + H)⁺, 338 (M + Na)⁺. |

TABLE P3-continued

Physical data of intermediates of formula IV or XI:

| Compound No. | Structures | Melting Point | MS/NMR |
|---|---|---|---|
| P3.19 | 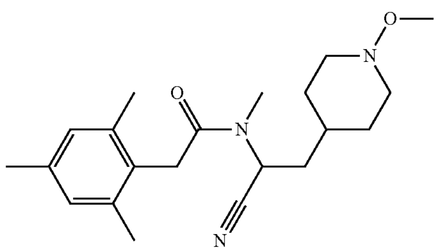 | Oil | ¹H-NMR (300 MHz, CDCl$_3$): δ 1.20-1.82 (m, 7H), 2.09-2.70 (m, 2H), 2.09 (s, 6H), 2.68 (s, 3H), 3.13 (s, 3H), 3.24-3.31 (m, 2H), 3.45 (s, 3H), 3.58 (s, 2H), 5.75 (t, 1H), 6.81 (s, 2H). LC/MS (ES+): 358 (M + H)$^+$, 380 (M + Na)$^+$. |
| P3.20 | EXAMPLE 10, step 2 | solid | ¹H-NMR (300 MHz, CD$_3$OD): δ 1.36-1.66 (m, 2H), 1.68-1.99 (m, 3H), 2.24 (s, 3H), 2.27 (s, 6H), 2.24-2.46 (m, 2H), 3.26-3.44 (m, 2H), 3.50 (s, 3H), 3.79 (s, 2H), 5.60 (d, 1H), 6.88 (s, 2H). LC/MS (ES+): 331 (M + H)$^+$, 353 (M + Na)$^+$, 385 (M + Na + MeOH)$^+$. |
| P3.21 | 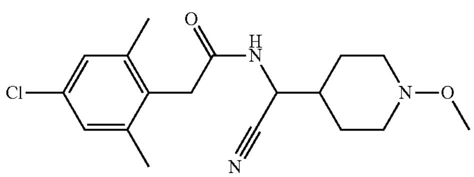 [SMILES: CON1CCC(C(C#N)NC(=O)Cc2c(C)cc(Cl)cc2C)CC1] | 189-191° C. | LC/MS: 350/352 (M + H)$^+$ R$_t$ = 1.65 min |
| P3.22 | 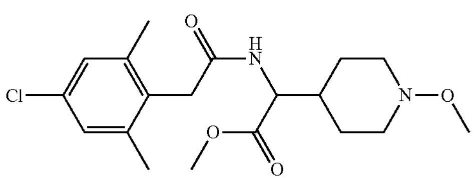 [SMILES: COC(=O)C(NC(=O)Cc1c(C)cc(Cl)cc1C)C1CCN(OC)CC1] | solid | LC/MS: 383/385 (M + H)$^+$ R$_t$ = 1.68 min |
| P3.23 | 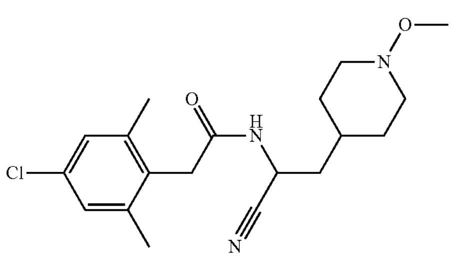 [SMILES: CON1CCC(CC(C#N)NC(=O)Cc2c(C)cc(Cl)cc2C)CC1] | solid | LC/MS: 364/366 (M + H)$^+$ R$_t$ = 1.65 min |
| P3.24 | 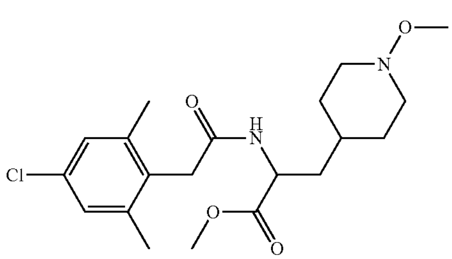 [SMILES: COC(=O)C(CC1CCN(OC)CC1)NC(=O)Cc1c(C)cc(Cl)cc1C] | solid | LC/MS: 397/399 (M + H)$^+$ R$_t$ = 1.66 min |

Intermediates of the formula V, VII or VIII from Table P4 can be prepared by analogous procedures.

TABLE P4

Physical data of intermediates of formula V, VII or VIII:

| Compound No. | Structures | Melting Point | MS/NMR/IR |
|---|---|---|---|
| P4.1 | (structure: H₂N, CN, CH₂-tetrahydropyran-4-yl) | Solid | $^1$H NMR (300 MHz, CDCl$_3$): δ 1.24 (m, 2H), 1.59-1.69 (m, 6H), 1.82-1.84 (m, 1H), 3.38 (t, 2H), 3.73 (t, 1H), 3.92-3.97 (m, 2H). |
| P4.2 | (structure: methyl 2-amino-3-(tetrahydropyran-4-yl)propanoate) | Oil | |
| P4.3 | (structure: H₂N, CN, CH₂-tetrahydrothiopyran-4-yl) | Solid | $^1$H NMR (300 MHz, CDCl$_3$): δ 1.39-1.42 (m, 2H), 1.60-1.66 (m, 5H), 1.99-2.03 (m, 2H), 2.57-2.74 (m, 4H), 3.72-.377 (m, 1H). |
| P4.4 | (structure: methyl 2-amino-3-(tetrahydrothiopyran-4-yl)propanoate) | Oil | $^1$H NMR (300 MHz, CDCl$_3$): δ 1.24-1.76 (m, 6H), 2.57-2.67 (m, 2H), 3.34-3.42 (m, 3H), 3.58-3.59 (m, 1H), 3.73 (s, 3H), 3.92-3.95 (m, 2H). |
| P4.5 | (structure: H₂N, CN, CH₂-(1-methoxypiperidin-4-yl))<br>EXAMPLE 1, step 5 | Oil | $^1$H-NMR (300 MHz, CDCl$_3$): δ 0.79-0.85 (m, 2H), 1.22-1.32 (m, 3H), 1.61-1.75 (m, 4H), 2.28-2.31 (m, 2H), 3.32-3.34 (m, 2H), 3.49 (s, 3H), 3.61-3.75 (m, 1H). |
| P4.6 | (structure: methyl 2-amino-3-(1-methoxypiperidin-4-yl)propanoate)<br>EXAMPLE 1, step 6 | Oil | $^1$H-NMR (300 MHz, CDCl$_3$): δ 1.21-1.75 (m, 11H), 3.31-3.32 (m, 2H), 3.41-3.45 (m, 1H), 3.48 (s, 3H), 3.68 (s, 3H).<br>LC/MS (ES+): 217 (M + H)$^+$, 239 (M + Na)$^+$. |

TABLE P4-continued

Physical data of intermediates of formula V, VII or VIII:

| Compound No. | Structures | Melting Point | MS/NMR/IR |
|---|---|---|---|
| P4.7 | (structure) | Oil | $^1$H-NMR (300 MHz, CDCl$_3$): δ 0.82-1.24 (m, 2H), 1.25-1.71 (m, 5H), 1.89-1.96 (m, 2H), 2.25 (s, 3H), 2.81-2.85 (m, 2H), 3.74 (t, 1H). LC/MS (ES+): 168 (M + H)$^+$. |
| P4.8 | (structure) EXAMPLE 9, step 3 | Oil | |
| P4.9 | (structure) EXAMPLE 10, step 1 | Oil | $^1$H NMR (300 Mz, DMSO-d$_6$): δ 1.28-1.47 (m, 2H), 1.49-1.68 (m, 1H), 1.69-1.85 (m, 2H), 2.13-2.32 (m, 2H), 3.23-3.36 (m, 2H), 3.39 (s, 3H), 4.36 (t, 1H), 6.38 (d, 1H). |
| P4.10 | (structure) | | |
| P4.11 | (structure) EXAMPLE 3 | Oil | $^1$H-NMR (300 MHz, CDCl$_3$): δ 1.22-1.32 (m, 3H), 1.60-1.62 (m, 3H), 1.74-1.77 (m, 2H), 2.27-2.30 (m, 2H), 2.50 (s, 3H), 3.31-3.33 (m, 2H), 3.45-3.46 (m, 1H), 3.48 (s, 3H). |
| P4.12 | (structure) EXAMPLE 4, step 1 | Solid | |

TABLE P4-continued

Physical data of intermediates of formula V, VII or VIII:

| Compound No. | Structures | Melting Point | MS/NMR/IR |
|---|---|---|---|
| P4.13 | (structure shown) EXAMPLE 4, step 2 | Oil | |

FORMULATION EXAMPLES

%=Percent by Weight

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

| Example F8a: Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |

| Example F8a: Suspension concentrate | |
|---|---|
| 37% aqueous formaldehyde solution | 0.2% |
| Silicone oil (75% aqueous emulsion) | 0.8% |
| Water | 32% |

| Example F8b: Suspension concentrate | |
|---|---|
| Active ingredient | 10% |
| Naphthalenesulfonic acid, sodium salt condensed with formaldehyde | 2% |
| Solution of an acrylic graft copolymer in water and propyleneglycole | 8% |
| Silicone antifoam emulsion | 0.5% |
| DL-propanediol-(1,2) | 3% |
| Heteropolysaccharide | 0.5% |
| 1,2-Benzisothiazol-3-one | 0.2% |
| Water | 75.8% |

The finely ground active ingredient is mixed intimately with the additives. Suspensions of any desired concentration can be prepared from the thus resulting suspension concentrate by dilution with water.

| Example F9: Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Example F10: Flowable concentrate for seed treatment | |
|---|---|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Example F11a: Oil-based suspension concentrate (based on a vegetable oil) | |
|---|---|
| Active ingredient | 10% |
| Tristyrylphenole with 16 moles EO | 10% |
| Block copolymer of polyhydroxystearic acid and polyalkylene glycols | 2% |
| AEROSIL 200 | 1% |

| Example F11a: Oil-based suspension concentrate (based on a vegetable oil) | |
|---|---|
| Rape seed oil methyl ester | 12% |
| Oleic acid | 65% |

| Example F11b: Oil-based suspension concentrate (based on a mineral oil) | |
|---|---|
| Active ingredient | 10% |
| Ethoxylated alcohols, C16-18 and C18-unsatd | 5% |
| Dodecyl-benzene sulfonic acid Ca-salt linear | 2.5% |
| 2-Pyrrolidinone, 1-ethenylhexadecyl-, homopolymer | 1% |
| Organophilic clay | 1% |
| Mixture of petroleum | 80.5% |

The finely ground active ingredient is mixed intimately with the additives. Suspensions of any desired concentration can be prepared from the thus resulting suspension concentrate by dilution with water.

Preferably, the term "active ingredient" used above refers to one of the compounds selected from Tables 1 to 861 shown above. It also refers to mixtures of the compound of formula I, in particular a compound selected from said Tables 1 to 861, with other insecticides, fungicides, herbicides, safeners, adjuvants and the like, which mixtures are specifically disclosed above.

BIOLOGICAL EXAMPLES

These examples illustrate the pesticidal/insecticidal properties of compounds of formula I.

EXAMPLE B1

Activity Against *Myzus persicae* (Green Peach Aphid)

(Mixed Population, Feeding/Residual Contact Activity, Preventive)

Sunflower leaf discs are placed on agar in a 24-well microtiter plate and sprayed with test solutions. After drying, the leaf discs are infested with an aphid population of mixed ages. After an incubation period of 6 days, samples are checked for mortality and special effects (e.g. phytotoxicity).

In this test, compounds listed in the tables above show good activity. In particular compounds P1.1, P1.5, P1.10, P1.12, P1.13, P1.15, P1.16, P1.18, P2.1, P2.2, P2.13, P2.15, P2.16, P2.17, P2.21 and P2.22 show an activity of over 80% at a concentration of 400 ppm.

EXAMPLE B2

Activity Against *Myzus persicae* (Green Peach Aphid)

(Mixed Population, Systemic/Feeding Activity, Curative)

Roots of pea seedlings, infested with an aphid population of mixed ages, are placed directly in the test solutions. 6 days after introduction, samples are checked for mortality and special effects on the plant.

In this test, compounds listed in the tables above show good activity. In particular compounds P1.10, P1.11, P1.12, P1.14, P1.15, P1.19, P2.13, P2.16, P2.17 and P2.21 show an activity of over 80% at a concentration of 400 ppm.

EXAMPLE B3

Activity Against *Thrips tabaci* (Onion *Thrips*)

(Mixed Population, Feeding/Residual Contact Activity, Preventive)

Sunflower leaf discs are placed on agar in a 24-well microtiter plate and sprayed with test solutions. After drying, the leaf discs are infested with a *thrips* population of mixed ages. After an incubation period of 6 days, samples are checked for mortality and special effects (e.g. phytotoxicity).

In this test, compounds listed in the tables above show good activity. In particular compounds P1.13, P2.3 and P2.13 show an activity of over 80% at a concentration of 400 ppm.

EXAMPLE B4

Activity Against *Tetranychus urticae* (Two-Spotted Spider Mite)

(Mixed Population, Feeding/Residual Contact Activity, Preventive)

Bean leaf discs on agar in 24-well microtiter plates are sprayed with test solutions. After drying, the leaf discs are infested with mite populations of mixed ages. 8 days later, discs are checked for egg mortality, larval mortality, and adult mortality.

In this test, compounds listed in the tables above show good activity. In particular compounds P1.12, P2.2, P2.3, P2.8 and P2.13 show an activity of over 80% at a concentration of 400 ppm.

EXAMPLE B5

Activity Against *Myzus persicae* (Green Peach Aphid)

(Mixed Population, Feeding/Residual Contact Activity, Plant Damage Evaluation)

Cabbage plants infested with a mixed population of *Myzus persicae* are treated with diluted test solutions of the compounds in a spray chamber. 6 days after treatment, samples are checked for mortality and for plant damage (phytotoxicity), visual assessment being made using a 0-100% rating scale (100%=total damage to plant; 0%=no damage to plant).

In this test, compounds listed in the tables above show good activity against *Myzus persicae* and acceptable plant compatibility. For example compounds P1.1, P1.10, P1.11, P1.12, P1.13, P1.14, P1.15, P2.13, P2.14, P2.15, P2.16, P2.17, P2.21 and P2.22 show an activity of greater or equal to 80% against *Myzus persicae* and damage to cabbage plants less or equal to 10% at a concentration of 200 ppm.

EXAMPLE B6

Activity Against *Nilaparvata lugens* (Brown Rice Planthopper)

(Larvicide, Feeding/Contact)

Rice seedlings are treated with the diluted test solutions in a spray chamber. After drying, they are infested with 20 $N_3$ nymphs (2 replicates). 6-12 days after the treatment samples are checked for mortality, growth regulation, and effects on the $F_1$ generation.

In this test, compounds listed in the tables above show good activity. For example compounds P1.10, P1.12, P1.15, P2.2 and P2.17 show an activity of over 80% at a concentration of 400 ppm.

EXAMPLE B7

Activity Against *Aphis Craccivora* (Cowpea Aphid)

(Mixed Population, Contact/Feeding)

Pea seedlings, infested with an aphid population of mixed ages, are treated (2 replicates) with diluted test solutions in a spray chamber. 6 days after treatment, samples are checked for mortality.

In this test, compounds listed in the tables above show good activity. For example compounds P1.10, P1.15 and P2.17 show an activity of over 80% at a concentration of 400 ppm.

EXAMPLE B8

Activity Against *Aphis Craccivora* (Cowpea Aphid)

(Mixed Population, Systemic/Feeding)

Roots of pea seedlings, infested with an aphid population of mixed ages, are placed (2 replicates) directly in the test solution. 6 days later, samples are checked for mortality.

In this test, compounds listed in the tables above show good activity. For example compounds P1.10, P1.15, P2.2 and P2.17 show an activity of over 80% at a concentration of 25 ppm.

EXAMPLE B9

Translaminar Activity Against *Aphis* Craccivora (Cowpea Aphid)

French bean leaves (*Phaseolus vulgaris*) are infested with about 20 mixed age individuals on the lower leaf side using clip cages. 1 day after the infestation, the upper side of the leaves is treated with the test solution by painting. 5 days later, samples are checked for mortality.

In this test, compounds listed in the tables above show good activity. For example compounds P1.10, P1.12, P1.15, P2.2 and P2.17 show an activity of over 80% at a concentration of 400 ppm.

EXAMPLE B10

Drench Activity Against *Myzus persicae* (Green Peach Aphid)

Pea seedlings cultivated in field soil are treated as drench application and infested with a mixed population of *M. persicae*. 7 days after infestation, samples are checked for mortality.

In this test, compounds listed in the tables above show good activity. For example compounds P1.10, P1.15, P2.2 and P2.17 show an activity of over 80% at a concentration of 25 ppm.

EXAMPLE B11

Activity Against *Bemisia tabaci* (Tobacco White Fly)

(Larvicide, Contact/Feeding)

Bean plants are infested with 20-30 adults that were removed after a 4 day egg-laying period. After another 7 days, bean plants with hatched nymphs (N-2) are treated (2 replicates) with the test solutions in a spray chamber. Three weeks later, samples are checked for number of emerged adults. Efficacy was calculated by comparing number of emerged adults in treated and non treated samples.

In this test, compounds listed in the tables above show good activity. For example compounds P1.10, P1.15 and P2.17 show an activity of over 80% at a concentration of 200 ppm.

The invention claimed is:
1. A compound of the formula I

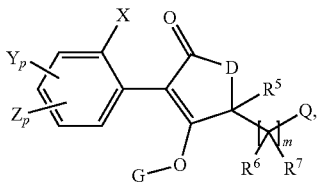

wherein
X, Y and Z independently of each other are $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl, halogen, phenyl or phenyl substituted by $C_{1-4}$alkyl, $C_{1-4}$haloalkyl, halogen or cyano;
p and q, independently of each other, are 0, 1, 2 or 3, where p+q is 0, 1, 2 or 3;
G is hydrogen, a metal, ammonium, sulfonium or a latentiating group;
D is O, S, $NR^1$ or $NOR^1$, wherein $R^1$ is hydrogen, $C_{1-6}$alkyl, $C_{1-6}$haloalkyl, $C_{3-6}$cycloalkyl or $C_{3-6}$cycloalkyl, wherein a methylene group is replaced by O, S or $NR^{00}$, where $R^{00}$ is $C_{1-6}$alkyl or $C_{1-6}$alkoxy, or $R^1$ is $C_{3-6}$cycloalkyl($C_{1-4}$)alkyl or $C_{3-6}$cycloalkyl($C_{1-4}$)alkyl, where in the cycloalkyl moiety a methylene group is replaced by O, S or $NR^{01}$, where $R^{01}$ is $C_{1-6}$alkyl or $C_{1-6}$alkoxy, or $R^1$ is $C_{2-6}$alkenyl, $C_{2-6}$haloalkenyl, $C_{3-6}$alkynyl, $C_{1-6}$cyanoalkyl, benzyl, furanyl-($C_{1-4}$)alkyl, $C_{1-4}$alkoxy($C_{1-4}$)alkyl, $C_{1-4}$alkoxy($C_{1-4}$)alkoxy($C_{1-4}$)alkyl, $C_{1-4}$alkylthio($C_{1-4}$)alkyl, $C_{1-4}$alkylsulfinyl($C_{1-4}$)alkyl or $C_{1-4}$alkylsulfonyl($C_{1-4}$)alkyl;
$R^5$, $R^6$ and $R^7$, independently of each other, are hydrogen;
Q is a saturated ring of the formula $Q_{86}$, $Q_{87}$, $Q_{88}$, $Q_{89}$, or $Q_{90}$:

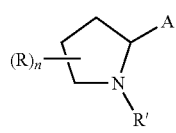
$Q_{86}$

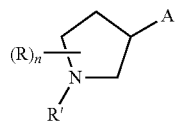
$Q_{87}$

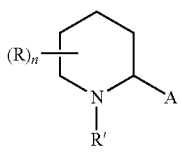
$Q_{88}$

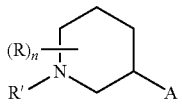
$Q_{89}$

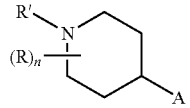
$Q_{90}$ wherein:
R is hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl;
R' is hydrogen, hydroxy, $C_1$-$C_6$alkyl, $C_1$-$C_6$haloalkyl, $C_3$-$C_7$cycloalkyl, $C_1$-$C_6$alkoxy, $C_1$-$C_6$haloalkoxy, $C_2$-$C_6$alkenyloxy, $C_2$-$C_6$haloalkenyloxy, $C_3$-$C_6$alkynyloxy, benzyloxy, $C_{1-4}$alkoxy($C_{1-4}$)alkyoxy, $C_1$-$C_6$alkylsulfinyl, $C_1$-$C_6$alkylsulfonyl, $C_1$-$C_6$alkylcarbonyl, $C_1$-$C_6$haloalkylcarbonyl, $C_1$-$C_6$alkoxycarbonyl, $C_1$-$C_6$alkylaminocarbonyl, $C_2$-$C_8$dialkylaminocarbonyl, $C_6$-$C_{10}$arylsulfonyl, $C_6$-$C_{10}$arylcarbonyl, $C_6$-$C_{10}$arylaminocarbonyl, $C_7$-$C_{16}$arylalkylaminocarbonyl, $C_1$-$C_9$heteroarylsulfonyl, $C_1$-$C_9$heteroarylcarbonyl, $C_1$-$C_9$heteroarylaminocarbonyl, or $C_2$-$C_{15}$heteroarylalkylaminocarbonyl;
n is 0, 1 or 2; and
A denotes the position of attachment to the —$(CR^6R^7)_m$— moiety in the compound of formula (I);
and wherein
m is 0 or 1,
where, when m is 0, Q is directly attached to the —C(D)$R^5$— moiety through a bond;
and wherein, when G is a latentiating group, then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;
wherein $X^a$, $X^b$, $X^c$, $X^d$, $X^e$ and $X^f$ are independently of each other oxygen or sulfur;
and wherein
$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-

$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro; or heteroaryl or heteroaryl substituted by $C_1$-$C_3$ alkyl, $C_{1-3}$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O or S; and $R^e$ is $C_1$-$C_{10}$ alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$ alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

or an agrochemically acceptable salt or an N-oxide thereof.

2. A compound according to the formula I of claim 1 wherein

X, Y and Z independently of each other are $C_{1-4}$alkyl or halogen;

p and q, independently of each other, are 1 or 2;

G is hydrogen or a latentiating group;

D is O, NR$^1$ or NOR$^1$, wherein R$^1$ is hydrogen or $C_{1-6}$alkyl;

Q is a saturated heterocyclyl ring as defined in claim 1 containing one heteroatom being N, which heterocyclyl is unsubstituted or substituted at a carbon or N atom by a residue of formula $C_{1-4}$alkyl, $C_{1-4}$haloalkyl, $C_{3-6}$cycloalkyl, or $C_{1-4}$alkoxy; and m is 0 or 1.

3. A compound according to the formula I of claim 1 wherein

X is a $C_{1-4}$alkyl, Y and Z independently of each other are $C_{1-4}$alkyl or halogen;

p and q, independently of each other, are 1 or 2;

G is hydrogen or a latentiating group;

D is O, NR$^1$ or NOR$^1$, wherein R$^1$ is hydrogen or $C_{1-6}$alkyl;

Q is a saturated heterocyclyl ring as defined in claim 1 containing one heteroatom being N, which heterocyclyl is unsubstituted or substituted at a carbon or N atom by a residue of formula $C_{1-4}$alkyl or $C_{1-4}$alkoxy; and m is 0 or 1.

4. A pesticidal composition comprising a pesticidal effective amount of at least one compound of formula I according to claim 1.

5. A pesticidal composition according to claim 4, which, in addition to comprising the compound of formula I, comprises formulation adjuvants.

6. A pesticidal composition according to claim 4, further comprising at least one additional insecticide, acaricide, nemacitide or molluscicide or at least one additional fungicide, herbicide, safener or plant growth regulator.

7. A method of combating and controlling pests which comprises applying to a pest, to a locus of a pest, or to a plant susceptible to attack by a pest a pesticidally effective amount of a compound of formula I according to claim 1 or a pesticidal composition according to claim 4.

8. A compound according to claim 1, wherein D is O, $NR^1$ or $NOR^1$.

9. A compound according to claim 1, wherein D is $NR^1$ or $NOR^1$; wherein $R^1$ is hydrogen, methyl, ethyl, isopropyl, trifluoromethyl, 2,2,2-trifluoroethyl, 2,2-difluoroethyl, 2-fluoroethyl, cyclopropyl, cyclobutyl, cyclopentyl, cyclohexyl, cyclopropylmethyl, cyclobutyl-methyl, cyclopentylmethyl, cyclohexylmethyl, allyl, propargyl, benzyl, methoxymethyl, ethoxymethyl, methoxyethyl, methoxypropyl, methoxyethoxymethyl, methoxymethoxyethyl, oxetan-3-yl, tetrahydrofuran-2-yl, tetrahydropyran-2-yl, tetrahydrofuran-3-yl, tetrahydropyran-4-yl, tetrahydrothiopyran-4-yl, 1-methoxy-piperidin-4-yl, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, methylthioethyl, 2-methanesulfinyl-ethyl, 2-methanesulfonyl-ethyl, furan-2-ylmethyl, furan-3-ylmethyl, or tetrahydro-thiopyran-4-ylmethyl.

10. A compound according to claim 8, wherein X, Y and Z denote $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl or halogen.

11. A compound according to claim 1, wherein X, Y and Z denote methyl, ethyl, isopropyl, cyclopropyl, trifluoromethyl, methoxy, vinyl, ethynyl, fluoro, bromo, iodo or chloro.

12. A compound according to claim 1, wherein p+q is 1-2.

13. A compound according to claim 10, wherein p+q is 1-2.

14. A compound according to claim 1, wherein:
m is 0.

15. A compound according to claim 13, wherein:
m is 1.

16. A compound according to claim 1, wherein, when G is a latentiating group, then G is a group $—C(X^a)—R^a$ or $—C(X^b)—X^c—R^b$, and the meanings of $X^a$, $R^a$, $X^b$, $X^c$ and $R^b$ are as defined in claim 1.

17. A compound according to claim 1, wherein R and R', independently of each other, are hydrogen, $C_1$-$C_4$alkyl, $C_1$-$C_4$haloalkyl, $C_1$-$C_4$alkoxy or $C_1$-$C_4$haloalkoxy.

18. A compound according to claim 1, wherein Q is a group of the formula $Q_{90}$ as defined in claim 1, and wherein n is 0.

19. A compound according to claim 18, wherein, in the group $Q_{90}$, the substituent R' is hydroxy, methyl, methoxy, ethoxy, propoxy, isopropoxy, 2,2,2-trifluoroethoxy, allyloxy, propargyloxy, benzyloxy, methoxymethoxy, ethoxymethoxy or methoxyethoxy.

* * * * *